United States Patent
Ubbesen

(10) Patent No.: US 11,910,998 B2
(45) Date of Patent: Feb. 27, 2024

(54) MEDICAL VISUALISATION SYSTEM INCLUDING A MONITOR AND A GRAPHICAL USER INTERFACE THEREFORE

(71) Applicant: AMBU A/S, Ballerup (DK)

(72) Inventor: Line Sandahl Ubbesen, Holte (DK)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 17/875,731

(22) Filed: Jul. 28, 2022

(65) Prior Publication Data

US 2022/0369897 A1     Nov. 24, 2022

Related U.S. Application Data

(63) Continuation of application No. 17/179,232, filed on Feb. 18, 2021, now Pat. No. 11,426,055.

(30) Foreign Application Priority Data

Feb. 21, 2020 (DK) ............................. PA 2020 70108
Feb. 21, 2020 (DK) ............................. PA 2020 70109
(Continued)

(51) Int. Cl.
*A61B 1/00* (2006.01)
*A61B 1/05* (2006.01)

(52) U.S. Cl.
CPC ........ *A61B 1/0005* (2013.01); *A61B 1/00009* (2013.01); *A61B 1/00034* (2013.01);
(Continued)

(58) Field of Classification Search
CPC .............. A61B 1/0005; A61B 1/00009; A61B 1/00034; A61B 1/00045; A61B 1/05; A61B 2560/0487
See application file for complete search history.

(56) References Cited

U.S. PATENT DOCUMENTS 5,099,210 A   3/1992   Fortney et al.
5,654,623 A   8/1997   Shiga et al.
(Continued)

FOREIGN PATENT DOCUMENTS

EP   1736094 A1   12/2006
EP   2722002 A1   4/2014
(Continued)

OTHER PUBLICATIONS

Bq27542-G1 Single Cell Li-Ion Battery Fuel Gauge for Battery Pack Integration, Texas Instruments Incorporated, Apr. 2015, 38 pages.
(Continued)

*Primary Examiner* — Anh Tuan T Nguyen
*Assistant Examiner* — Shankar Raj Ghimire
(74) *Attorney, Agent, or Firm* — Faegre Drinker Biddle & Reath LLP

(57) ABSTRACT

A monitor device and a method of using the monitor device in a medical visualisation system including a visualisation device having an image sensor configured to generate image data indicative of a view, the monitor device configured to operate in a first interface orientation mode and a second interface orientation mode, wherein in the first interface orientation mode, a second portion is between a fourth housing side and a first portion, and wherein in the second interface orientation mode, the second portion is between a third housing side and the first portion.

18 Claims, 56 Drawing Sheets

(30) Foreign Application Priority Data

Feb. 21, 2020 (DK) .......................... PA 2020 70110
Feb. 21, 2020 (DK) .......................... PA 2020 70111
Feb. 21, 2020 (DK) .......................... PA 2020 70112

(52) U.S. Cl.
CPC ............ *A61B 1/00045* (2013.01); *A61B 1/05* (2013.01); *A61B 2560/0487* (2013.01)

(56) References Cited

U.S. PATENT DOCUMENTS

| | | | |
|---|---|---|---|
| 6,106,457 | A | 8/2000 | Perkins et al. |
| 6,236,214 | B1 | 5/2001 | Camp et al. |
| 6,494,827 | B1 | 12/2002 | Matsumoto et al. |
| 6,636,254 | B1 | 10/2003 | Onishi et al. |
| 7,946,981 | B1 | 5/2011 | Cubb |
| 8,182,416 | B1 | 5/2012 | Hosaka et al. |
| 9,179,831 | B2 | 11/2015 | McGrail et al. |
| 9,459,326 | B2 | 10/2016 | McGrath et al. |
| 9,883,787 | B2 | 2/2018 | Kasumi et al. |
| 11,547,481 | B2* | 1/2023 | Begg ................ A61B 1/00009 |
| 2002/0118279 | A1 | 8/2002 | Spoonhower et al. |
| 2003/0088156 | A1 | 5/2003 | Berci et al. |
| 2003/0114899 | A1 | 6/2003 | Woods et al. |
| 2004/0098222 | A1 | 5/2004 | Pehrsson et al. |
| 2005/0174473 | A1* | 8/2005 | Morgan ............... H05B 45/355 348/370 |
| 2006/0017692 | A1* | 1/2006 | Wehrenberg .......... G06F 1/1694 700/302 |
| 2006/0022953 | A1 | 2/2006 | Franttila |
| 2006/0152516 | A1 | 7/2006 | Plummer |
| 2006/0220614 | A1 | 10/2006 | Abe |
| 2007/0030344 | A1 | 2/2007 | Miyamoto et al. |
| 2007/0106121 | A1 | 5/2007 | Yokota et al. |
| 2007/0260119 | A1* | 11/2007 | Otawara ............... A61B 5/0071 600/176 |
| 2008/0064928 | A1* | 3/2008 | Otawara ................ A61B 1/051 600/129 |
| 2008/0108884 | A1 | 5/2008 | Kiani |
| 2008/0167529 | A1* | 7/2008 | Otawara .................. A61B 1/07 600/168 |
| 2008/0242983 | A1 | 10/2008 | Hibi |
| 2009/0096919 | A1 | 4/2009 | Wang et al. |
| 2009/0131750 | A1* | 5/2009 | Amano ............. A61B 1/00042 600/109 |
| 2009/0198111 | A1 | 8/2009 | Nearman et al. |
| 2009/0225159 | A1 | 9/2009 | Schneider et al. |
| 2009/0253966 | A1* | 10/2009 | Ichimura ............ A61B 1/00181 600/158 |
| 2010/0053218 | A1 | 3/2010 | Risher-Kelly |
| 2010/0145146 | A1 | 6/2010 | Melder |
| 2011/0193704 | A1* | 8/2011 | Harper ................. A61B 5/7445 340/573.1 |
| 2011/0245609 | A1 | 10/2011 | Laser |
| 2011/0275896 | A1* | 11/2011 | Tanaka ................ A61B 1/0052 600/118 |
| 2012/0119873 | A1 | 5/2012 | Ramsdell et al. |
| 2012/0256009 | A1 | 10/2012 | Mucignat et al. |
| 2013/0066153 | A1 | 3/2013 | McGrath et al. |
| 2013/0079594 | A1* | 3/2013 | Motoki .............. G02B 23/2484 600/109 |
| 2014/0276207 | A1 | 9/2014 | Ouyang et al. |
| 2014/0288460 | A1 | 9/2014 | Ouyang et al. |
| 2014/0316193 | A1 | 10/2014 | Taniguchi |
| 2015/0029224 | A1 | 1/2015 | Ise et al. |
| 2016/0041597 | A1* | 2/2016 | Graham ................ G06F 1/3212 713/323 |
| 2016/0077159 | A1 | 3/2016 | Petrucelli |
| 2016/0198093 | A1 | 7/2016 | Ito et al. |
| 2016/0278611 | A1 | 9/2016 | Power |
| 2016/0317035 | A1* | 11/2016 | Hendriks ............. A61B 1/2676 |
| 2017/0010771 | A1 | 1/2017 | Bernstein et al. |
| 2017/0139012 | A1 | 5/2017 | Smith |
| 2018/0351379 | A1 | 12/2018 | Garbus et al. |
| 2019/0033571 | A1* | 1/2019 | Maule .................. H04N 17/002 |
| 2019/0142262 | A1* | 5/2019 | Inglis ................ A61B 1/00042 600/188 |
| 2019/0147721 | A1 | 5/2019 | Avitan et al. |
| 2019/0159656 | A1* | 5/2019 | Hale ....................... G06F 3/038 |
| 2019/0238791 | A1 | 8/2019 | Ingle |
| 2019/0320879 | A1 | 10/2019 | Langell et al. |
| 2019/0350440 | A1 | 11/2019 | Leong et al. |
| 2019/0369711 | A1 | 12/2019 | Wang et al. |
| 2021/0259517 | A1 | 8/2021 | Ubbesen |
| 2022/0369897 | A1* | 11/2022 | Ubbesen ............ A61B 1/00009 |

FOREIGN PATENT DOCUMENTS

| | | |
|---|---|---|
| EP | 3420969 A2 | 1/2019 |
| GB | 2431539 A | 4/2007 |
| JP | 11-023678 A | 1/1999 |
| JP | 2009-042392 A | 2/2009 |
| JP | 2009-112644 A | 5/2009 |
| JP | 2016-218322 A | 12/2016 |
| JP | 2019-042392 A | 3/2019 |
| WO | 2008/060897 A1 | 5/2008 |
| WO | 2012/033936 A2 | 3/2012 |
| WO | 2014/070396 A1 | 5/2014 |
| WO | 2019/117926 A1 | 6/2019 |

OTHER PUBLICATIONS

First Examination Report issued by the Danish Patent and Trademark Office, dated Jun. 11, 2020 in Danish Patent Application No. PA 2020 70108, 10 pages.
First Examination Report issued by the Danish Patent and Trademark Office, dated May 14, 2020 in Danish Patent Application No. PA 2020 70112, 8 pages.
First Examination Report issued by the Danish Patent and Trademark Office, dated Jun. 15, 2020 in Danish Patent Application No. PA 2020 70109, 11 pages.
First Examination Report issued by the Danish Patent and Trademark Office, dated May 19, 2020 in Danish Patent Application No. PA 2020 70111, 10 pages.
First Examination Report issued by the Danish Patent and Trademark Office, dated Jun. 11, 2020, for Danish Application No. PA 2020 70110; 8 pages.
Keller et al., "Getting the most battery life from portable systems," Texas Instruments Incorporated, 2008, 9 pages.
Search Report and Written Opinion issued in PCT/EP2021/053960, dated Apr. 23, 2021.
Search Report and Written Opinion issued in PCT/EP2021/053961, dated Apr. 30, 2021.
Search Report and Written Opinion issued in PCT/EP2021/053962, dated Apr. 28, 2021.
Search Report and Written Opinion issued in PCT/EP2021/053963, dated Apr. 5, 2021.
Search Report and Written Opinion issued in PCT/EP2021/053964, dated May 10, 2021.
Second Examination Report issued by the Danish Patent and Trademark Office, dated May 13, 2020 in Danish Patent Application No. PA 2020 70109, 5 pages.
Second Examination Report issued by the Danish Patent and Trademark Office, dated Jan. 21, 2021 in Danish Patent Application No. PA 2020 70108, 3 pages.
Second Examination Report issued by the Danish Patent and Trademark Office, dated Oct. 28, 2020 in Danish Patent Application No. PA 2020 70112, 5 pages.
Verathon; Glidescope Core, Operations & Maintenance Manual, Effective Jul. 20, 2020; 62 pages; https://www.verathon.com/wp-content/uploads/product_docs/0900-5017-xx- 61.pdf?doc=1591705360.
Verathon; Glidescope Core, "See More and Do More with the New GlideScope Care Airway Visulization System," GlidescopeVL; Jan. 3, 2019, Youtube video (https://www.youtube.corn/watch?v=2CKOvBjVjxU).

(56) References Cited

OTHER PUBLICATIONS

Second Examination Report issued by the Danish Patent and Trademark Office, dated Oct. 21, 2020, for Danish Application No. PA 2020 70110; 3 pages.
Screenshots of Ambu aScope 4 Demonstration; Paediatric Emergencies; Mar. 19, 2018 at https://www.youtube.com/watch?v=QEE3M7waKzk, and aView datasheet dated Jan. 2017.

* cited by examiner

MEDICAL VISUALISATION SYSTEM INCLUDING A MONITOR AND A GRAPHICAL USER INTERFACE THEREFORE

CROSS-REFERENCE TO RELATED APPLICATIONS

The present application is a continuation of U.S. patent application Ser. No. 17/179,232, filed Feb. 18, 2021, which claims priority from and the benefit of Danish Patent Application Nos. PA 2020 70108, PA 2020 70109, PA 2020 70110, PA 2020 70111, and PA 2020 70112, all filed Feb. 21, 2020, which are incorporated by reference herein in their entirety.

TECHNICAL FIELD

The present disclosure relates to a visualization device, such as an endoscope and a medical visualization system, such as an endoscope system, comprising a visualization device. More specifically the present disclosure relates to a graphical user interface and a monitor device having such graphical user interface for interacting with the medical visualization system.

BACKGROUND

A visualization device may be utilized to visually examine certain areas of the body of a person, such as inside a body cavity of the person. For example, a visualization device may be used to inspect the airways, the digestive tract, or the intestines.

A visualization device may be provided with a camera and be attached to a monitor device, such as a monitor with a display screen, a video output from the camera of the visualization device may be received and displayed at the monitor device, thereby allowing an operator to control the visualization device to inspect an area of interest.

For example, a visualization device may be an endoscope, such as a disposable endoscope. An endoscope comprises an operating handle at the proximal end and an insertion tube extending from the handle towards the distal end. The handle is configured to be held by an operator and inter alia comprises externally protruding operating members connected to internal control means allowing the operator to control the movement of a bending section at the distal end of the insertion tube, while advancing the distal end of the insertion tube to a desired location e.g. within a body cavity of a person. By means of an attached monitor device, such as a monitor with a display screen, the location to which the distal end has been advanced may be inspected using the endoscope.

The monitor device of a medical visualization system may be provided with some functionality, such as ability to save still images and/or video sequences of the view from the attached visualization device. Furthermore, the monitor device may comprise some image processing capabilities, and may be configured to output a video or image output, e.g. to an external display.

In some procedures it may be desirous to use a plurality of visualization devices, e.g. a video laryngoscope and an endoscope simultaneously, e.g. to inspect different positions within a body cavity of the person. For example, the video laryngoscope may be used to visually aid the operator in inserting an endoscope into the airways. In another example, a second inserted visualization device may be used to confirm the anticipated position of a first inserted visualization device.

SUMMARY

The present disclosure relates to a visualization device, such as an endoscope, and a visualization system, such as an endoscope system. Particularly, but not exclusively the visualization device may be a disposable camera endoscope. Alternatively, the visualization device may be a video laryngoscope, an endotracheal tube and/or a laryngeal mask. The visualization system may further comprise a monitor device for being connected to the visualization device, e.g. the monitor device may be configured to receive image data from the visualization device. The present disclosure further relates to a graphical user interface for such monitor device of a medical visualization system.

It is an object of the present disclosure to provide a solution which at least improves the solutions of the prior art. Particularly, it is an object of the present disclosure to provide a graphical user interface for a medical visualization system which facilitates and enhances human interaction with the system.

It is a further object of the present disclosure to provide a system and method facilitating enhanced control and usability of a medical visualization system.

Accordingly, a medical visualization system and a method performed at a monitor device of the medical visualization system are disclosed.

The medical visualization system comprises a visualization device, such as an endoscope, such as a disposable endoscope. Alternatively, the visualization device may be a video laryngoscope, an endotracheal tube and/or a laryngeal mask. The visualization device has an image sensor configured to generate image data indicative of a view from the visualization device. The medical visualization system may comprise a plurality of visualization devices each having an image sensor configured to generate image data indicative of a view from the visualization device. The plurality of visualization devices may include a first visualization device and/or a second visualization device. The first visualization device may comprise a first image sensor configured to generate image data indicative of a view from the first visualization device. The second visualization device may comprise a second image sensor configured to generate image data indicative of a view from the second visualization device. The image sensor(s) may be any sensor capable of detecting and conveying information used to make an image. For example, the image sensor(s) may comprise a CCD or CMOS sensor, or similar. The image sensor(s) may generate image data corresponding to a square image, i.e. having equal height and width. For example, the image data generated by the image sensors may correspond to a 300×300 pixel image, or a 400×400 pixel image, or a 600×600 pixel image, or a 800×800 pixel image. Alternatively or additionally, the image sensor may generate image data corresponding to a non-square image, which is cropped to form a square image, such as a square image having 300×300 pixels, 400×400 pixels, 600×600 pixels, or 800×800 pixels.

The medical visualization system further comprises a monitor device receiving and/or being operable to receive the image data generated by the image sensor. The monitor device may receive and/or be operable to receive the image data, e.g. as the image data is being generated, e.g. within limitation of the hardware. The monitor device comprises a first housing extending in a first direction from a first housing side to a second housing side and in a second direction perpendicular to the first direction from a third housing side to a fourth housing side. The monitor device comprises a display, e.g. a touch sensitive display. The display may be accommodated in the first housing. The display may have a first length in the first direction and a second length in the second direction. The second length may be longer than the first length, e.g. the display may be a 16:9 or 16:10 display. Alternatively, the first length may be longer than the second length, or the first length and the second length may be substantially the same. The touch sensitive display may be any suitable type of touch display, e.g. capacitive touch display or resistive touch display.

The monitor device may comprise one or more connection ports configured to receive a connector of the visualization device. The connection ports and the corresponding connector of the visualization device may be a proprietary plug and socket connectors, or any standard connector capable of transmitting therethrough at least the image data from the image sensor. Furthermore, the connector and connection ports may be configured to supply power to the components of the visualization device.

The one or more connection ports may be arranged on the first housing. The one or more connection ports may be provided on the third housing side, and/or on the fourth housing side. The monitor device may comprise an on/off button. The on/off button may be arranged on the first housing. The on/off button may be provided on the third housing side or on the fourth housing side. The one or more connection ports may be provided on the third housing side and the on/off button may be provided on the fourth housing side.

The monitor device may establish connection to a visualization device, such as the first visualization device and/or the second visualization device. Establishing connection to the visualization device may include receiving a device connector of the respective visualization device in a connection port of the one or more connection ports of the monitor device. Establishing connection to a visualization device may include obtaining device identifier information from a device identifier (e.g. EPROM, QR-code, NFC, RFID or similar) of the visualization device. For example, establishing connection to the first visualization device may include obtaining first device identifier information from a first device identifier of the first visualization device and/or establishing connection to the second visualization device may include obtaining second device identifier information from a second device identifier of the second visualization device.

The monitor device may comprise a processing unit and memory. The processing unit and/or the memory may be accommodated in the first housing. Alternatively, the monitor device may comprise a second housing, and the processing unit and/or the memory may be accommodated in the second housing. The monitor device may comprise an orientation sensor, e.g. for determining the orientation of the monitor device, such as of the first housing, relative to gravity. The orientation sensor may comprise one or more accelerometers and/or a gyroscope. The orientation sensor may be accommodated in the first housing. The processing unit may be connected to the touch sensitive display to control display of information with the touch sensitive display, and the processing unit may be adapted to receive a signal from the touch sensitive display indicative of touch inputs on the touch sensitive display. Thereby, the monitor device may detect user inputs, e.g. in the form of touch inputs, with the touch sensitive display. Touch inputs may, for example, comprise single tap(s), double tap(s), or swipe (s) on the touch sensitive display. The processing unit may be connected to the orientation sensor to receive an orientation signal indicative of the orientation of the monitor device, such as of the first housing of the monitor device. The processing unit may be connected to the memory and be adapted to read and write data from and to the memory.

The monitor device may comprise a power unit for powering the monitor device. The power unit may comprise a rechargeable battery and/or a power connection for connecting the power unit to an external power supply, such as a conventional AC power socket. The power unit may be accommodated in the first housing. Alternatively, the power unit may be accommodated in the second housing.

The monitor device may comprise a graphical user interface. The monitor device and/or the processing unit of the monitor device may display with the touch sensitive display the graphical user interface. The graphical user interface may comprise one or more portions, such as a plurality of portions. The portions may be non-overlapping portions, such as a plurality of non-overlapping portions. The portions may include a first portion and/or a second portion. The portions may further include a third portion and/or a fourth portion. The second portion and/or the fourth portion may be designated as background portions, e.g. the second portion may be a first background portion and/or the fourth portion may be a second background portion. Each of the plurality of portions may extend substantially throughout the first length in the first direction. The first portion may be arranged between the fourth portion and the second portion along the second direction. The fourth portion may be arranged between the third portion and the first portion along the second direction. The third portion may be arranged between a side of the first housing, e.g. the third housing side, and the fourth portion along the second direction. The second portion may be arranged between another side of the first housing, e.g. the fourth housing side, and the first portion along the second direction. The first portion and the fourth portion may be arranged between the second portion and the third portion along the second direction. The first portion of the graphical user interface may be square. The first portion of the graphical user interface may occupy the center of the touch sensitive display. The first portion of the graphical user interface may be larger along the second direction than the second portion, the third portion and/or the fourth portion, individually and/or collectively. The first portion of the graphical user interface may extend throughout more than 40% of the second length in the second direction, such as more than 50% of the second length in the second direction, such as more than 60% of the second length in the second direction.

The monitor device may display a live representation of the image data, e.g. within the first portion of the graphical user interface. The live representation of the image data may be displayed, e.g. by the processing unit, with the touch sensitive display, e.g. within the first portion of the graphical user interface.

The visualization device, e.g. an endoscope, may comprise a handle and an elongated flexible member extending from the handle to a distal end. The image sensor may be arranged at the distal end of the elongated flexible member. The image data may be indicative of a view from the distal end of the elongated flexible member. The handle may comprise a control button adapted to receive an input in a first input direction and/or in a second input direction. The first input direction and the second input direction may be opposite. The touch input in the first input direction may cause a distal portion of the elongated flexible member to bend in a first bending direction and/or may cause movement of the image sensor in a first image sensor direction. The touch input in the second input direction may cause the distal portion of the elongated flexible member to bend in a second bending direction and/or may cause movement of the image sensor in a second image sensor direction. The live representation of the image data may have directions corresponding to directions of the image sensor generating the image data. The first bending direction may correspond to a first image direction of a representation of the image data, such as the live representation of the image data. The second bending direction may correspond to a second image direction of the representation of the image data, such as the live representation of the image data. The first image direction and/or the second image direction may be parallel to the first direction of the first housing.

The monitor device may provide one or more actionable items. One or more actionable items may be displayed, e.g. by the processing unit, with the touch sensitive display, e.g. within the second portion of the graphical user interface. One or more actionable menu items may be displayed, e.g. by the processing unit, with the touch sensitive display, e.g. within the third portion of the graphical user interface. A battery indicator may be displayed, e.g. by the processing unit, with the touch sensitive display, e.g. within the third portion of the graphical user interface. A time indicator may be displayed, e.g. by the processing unit, with the touch sensitive display, e.g. within the third portion of the graphical user interface.

The one or more actionable items, e.g. displayed within the second portion of the graphical user interface of the monitor device, may comprise an image capture button and/or a video capture button. In response to activation of the image capture button, e.g. by a user providing a touch input, e.g. a single tap, at the respective location of the touch sensitive display, an image data file corresponding to the image data received when the image capture button was activated may be stored, e.g. in memory of the monitor device. In response to activation of the video capture button, e.g. by a user providing a touch input, e.g. a single tap, at the respective location of the touch sensitive display, a video sequence of image data corresponding to the image data received when the video capture button was activated may be stored, e.g. in memory of the monitor device. A first activation of the video capture button may start collection of image data for the video sequence, and a second activation of the video capture button (subsequent to the first activation of the video capture button) may stop the collection of image data for the video sequence. The stored video sequence may correspond to the image data received between the first activation and the second activation of the video capture button. The video capture button may be displayed in a first appearance prior to the first activation and after the second activation. The video capture button may be displayed in a second appearance after the first activation and before the second activation.

The monitor device may be adapted to establish connection to a first visualization device of a plurality of visualization devices. The plurality of visualization devices may be a plurality of visualization devices being substantially similar, or the plurality of visualization devices may comprise visualization devices of different types. For example, the first visualization device may be an endoscope and a second visualization device may be a laryngoscope. Alternatively, the first visualization device may be an endoscope and the second visualization device may be an endoscope. Alternatively, the first visualization device may be a laryngoscope and the second visualization device may be an endoscope. Alternatively, the first visualization device may be a medical airway device such as an endotracheal tube or a laryngeal mask and the second visualization device may be an endoscope. Alternatively, the first visualization device may be an endoscope and the second visualization device may be a medical airway device such as an endotracheal tube or a laryngeal mask.

In response to establishing the connection to the first visualization device, the monitor device may display, e.g. with the touch sensitive display, within the first portion of the graphical user interface, a first live representation of first image data generated by a first image sensor of the first visualization device.

While the first visualization device is connected to the monitor device, the monitor device may be further adapted to establish connection to a second visualization device of the plurality of visualization devices.

In response to establishing the connection to the second visualization device the monitor device concurrently displays a second live representation of second image data generated by a second image sensor of the second visualization device and the first live representation of first image data generated by the first image sensor of the first visualization device. The second live representation is displayed in the fourth portion and extending into the first portion of the graphical user interface. The first live representation is displayed in the second portion and extending into the first portion of the graphical user interface. The first live representation is displayed in reduced size compared to the second live representation.

Accordingly, a monitor device for an endoscope system and a method are disclosed, which allows handling of multiple simultaneously connected visualization devices, by providing a dual mode view. Consequently, the present disclosure provides the user with the ability of displaying input from two different scopes, to inspect two positions simultaneously, and allow viewing of the two inputs on the same display. Importantly, the present disclosure provides logic for determining what visualization device to display largest and what to show smallest.

Furthermore, the disclosure provides a solution for altering the displayed content, in a predictive manner and with minimum visual disturbance for the user, upon connection of an additional endoscope and/or disconnection of one of two endoscopes. Thereby, the system facilitates the user in continuing an ongoing procedure while connecting or disconnecting additional endoscopes.

The monitor device may comprise a plurality of connection ports including a first connection port and a second connection port. To establish connection to the first visualization device a first connector of the first visualization device may be received by the first connection port. To establish connection to the second visualization device a second connector of the second visualization device may be received by the second connection port.

The live representations may be overlaid with an indicator. For example, a first indicator may be overlaid on the first live representation and/or a second indicator may be overlaid on the second live representation. The first connection port may be labelled with a first port indicator resembling the first indicator. The second connection port may be labelled with a second port indicator resembling the second indicator. Thereby, the live representations may be easily mapped to the physical connection port and consequently to the connected visualization device.

In response to establishing connection to the second visualization device, the monitor device may further display a rearrange icon. The monitor device may be adapted, e.g. with the touch sensitive display, to detect a first user input corresponding to selection of the rearrange icon. In response to detection of the first user input the monitor device may replace display of the second live representation in the fourth portion and extending into the first portion of the graphical user interface, with display of the first live representation and/or the monitor device may replace display of the first live representation in the second portion and extending into the first portion of the graphical user interface, with display of the second live representation. The second live representation may be displayed in reduced size compared to the first live representation.

While the first visualization device and the second visualization device are connected to the monitor device, the monitor device, e.g. by the touch sensitive display, may be adapted to detect a second user input corresponding to selection of the image capture button of the one or more actionable items. In response to detection of the second user input, the monitor device may store a first image file corresponding to the first image data received when the second user input was detected, and store a second image file corresponding to the second image data received when second user input was detected. Thus, when the monitor device is operating in dual view mode, activation of the capture image button may cause two images to be capture, one from each connected visualization device.

Establishing connection to a visualization device may include obtaining device identifier information from a device identifier (e.g. EPROM, QR-code, NFC, RFID or similar) of the visualization device. In response to establishing connection to the first visualization device the monitor device may open a first procedure session corresponding to the first device identifier information obtained from the first device identifier of the first visualization device. In response to establishing connection to the second visualization device the monitor device may open a second procedure session corresponding to the second device identifier information obtained from the first device identifier of the first visualization device. Hence, a procedure session may be created for each connected visualization device.

In response to detection of the second user input, i.e. the user input corresponding to selection of the image capture button of the one or more actionable items, the monitor device may associate the first image file with the first procedure session; and/or associate the second image file with the second procedure session.

A procedure session may be implemented by creating a folder in the file system of the monitor device, wherein image files and video sequences obtained from a visualization device is stored in the folder corresponding to the visualization device. Hence, association of an image file to a procedure session may be implemented by storing the image file in the folder of the procedure session. Opening a procedure session may further comprise creating a log, registering the time and date for initiating the procedure, registering information about the visualization device, registering software version and/or other information.

In opening a procedure session the monitor device may determine, based on the device identifier information, whether the visualization device has been previously connected to the monitor device. For example, in accordance with determining that the visualization device has previously been connected to the monitor device, the monitor device may reopen the procedure session corresponding to the device identifier information; and/or in accordance with determining that the visualization device has not previously been connected to the monitor device, the monitor device may create the procedure session, e.g. a new procedure session, corresponding to the device identifier information.

A third user input, e.g. with the touch sensitive display, corresponding to selection of a first actionable menu item of the one or more actionable menu items, may be detected. In response to detection of the third user input the monitor device may display a primary menu, e.g. associated with the first actionable menu item. The primary menu may be displayed within the fourth portion of the graphical user interface obscuring the live representation in the fourth portion of the graphical user interface (e.g. the second live representation).

The primary menu may comprise one or more primary actionable items including a first primary actionable item. While the primary menu is displayed, the monitor device may be adapted to detect a fourth user input corresponding to selection of the first primary actionable item.

In accordance with detecting the fourth user input within a threshold amount of time, e.g. 5 seconds, after detection of the third user input, the monitor device may display a secondary menu associated with the primary actionable item in the first portion, and optionally the second portion and/or the fourth portion, of the touch sensitive display.

In accordance with not detecting the fourth user input within the threshold amount of time after detection of the first user input, the monitor device may cease display of the primary menu associated with the first actionable menu item and display the partly obscured live representation (e.g. the second live representation) in the fourth portion and extending into the first portion of the graphical user interface.

In response to the user disconnecting one of the connected visualization devices, the monitor device may display, within the first portion of the graphical user interface, the live representation of image data generated by the image sensor of the visualization device still being connected. For example, the monitor device may be adapted to detect disconnection of the first visualization device from the monitor device, and in response to detecting disconnection of the first visualization device from the monitor device, the monitor device may display, within the first portion of the graphical user interface, the second live representation of second image data generated by the second image sensor of the second visualization device. Similarly, the monitor device may be adapted to detect disconnection of the second visualization device from the monitor device, and in response to detecting disconnection of the second visualization device from the monitor device, the monitor device may display, within the first portion of the graphical user interface, the first live representation of first image data generated by the first image sensor of the first visualization device.

The monitor device may display a battery indicator, e.g. within the third portion of graphical user interface. The battery indicator may be indicative of a remaining charge, e.g. relative to full charge, of the rechargeable battery. The battery indicator may indicate an expected remaining battery time, e.g. the battery indicator may comprise a time indicator indicative of the expected remaining battery time, e.g. in hours and/or minutes.

The expected remaining battery time may be provided based on whether a visualization device is connected or not. For example, in accordance with the visualization device not being connected to the monitor device, the expected remaining battery time may be based on expected power consumption with the visualization device being connected; and in accordance with the visualization device, and optionally a second visualization device, being connected to the monitor device, the expected remaining battery time may be based on a measured power consumption. The measured power consumption may be an average of power consumption during a duration of time, e.g. 5 minutes, 10 minutes or 20 minutes. Of course if the monitor device is receiving power from the external power supply the expected remaining battery time will increase as the battery recharges while the measured power consumption, which may be measured while the monitor device is receiving or not receiving power from the external power source, will still be based on the electrical load.

The battery indicator may be displayed in one of a plurality of different states indicative of remaining charge of the rechargeable battery. In accordance with the expected remaining battery time being less than a low threshold amount of time and/or in accordance with the remaining charge being less than a low threshold charge, the battery indicator may be displayed in a low battery power state. In accordance with the expected remaining battery time being more than the low threshold amount of time and less than a high threshold amount of time and/or in accordance with the remaining charge being more than the low threshold charge and less than a high threshold charge, the battery indicator may be displayed in a medium battery power state. In accordance with the expected remaining battery time being more than the high threshold amount of time and/or in accordance with the remaining charge being more than the high threshold charge, the battery indicator may be displayed in a high battery power state. The low battery power state may comprise a red colored part of the battery indicator. The medium battery power state may comprise a yellow colored part of the battery indicator. The high battery power state comprises a green colored part of the battery indicator.

The high threshold charge may be between 30-50%, such as 40% of full charge. The high threshold charge may correspond to the high threshold amount of time. The high threshold amount of time may be between 1 hour to 1.5 hour, such as 1:12 or 1:15 (hours:minutes). The low threshold charge may be between 15-30%, such as 20% of full charge. The low threshold charge may correspond to the low threshold amount of time. The low threshold amount of time may be between 30-40 minutes, such as 36 minutes. The low threshold amount of time may be substantially equivalent to an expected time for a typical procedure using the medical visualization system. Thereby, the operator before initiating a procedure is provided with valuable information of the battery status, advising whether it is wise to continue with the current monitor device on battery power.

The monitor device may display, e.g. with the display, an enlarged rendering of the battery indicator. The enlarged rendering of the battery indicator may be displayed in the fourth portion of the graphical user interface. The enlarged rendering of the battery indicator may be displayed concurrently with the battery indicator. The enlarged rendering of the battery indicator may be displayed in the fourth portion of the graphical user interface concurrently with the battery indicator being displayed within the third portion of the graphical user interface.

The enlarged rendering may be displayed in accordance with the expected remaining battery time being less than the low threshold amount of time and/or in accordance with the remaining charge being less than the low threshold charge. For example, the monitor device, e.g. the processing unit of the monitor device, may determine that the expected remaining battery time have dropped below the low threshold amount of time and/or that the remaining charge have dropped below the low threshold charge, and in response to the expected remaining battery time having dropped below the low threshold amount of time and/or that the remaining charge have dropped below the low threshold charge, the enlarged rendering may be displayed.

Alternatively or additionally, the enlarged rendering may be displayed in response to the monitor device being turned on. This may give the operator upon turning the monitor device on a quick notification of whether the monitor device can be expected to complete an upcoming procedure. After a first duration of time after the monitor device has been turned on, display of the enlarged rendering of the battery indicator may be ceased.

In accordance with the visualization device being connected to the monitor device, the live representation of the image data may be displayed within the first portion of the graphical user interface. In accordance with the visualization device not being connected to the monitor device, a guiding animation may be shown in the first portion of the graphical user interface instead of the live representation of the image data. The guiding animation may fill the first portion of the graphical user interface.

In accordance with the visualization device not being connected to the monitor device, and in accordance with the expected remaining battery time being more than the low threshold amount of time and/or the remaining charge being more than the low threshold charge, an animation of connecting the visualization device to the monitor device may be displayed within the first portion of the graphical user interface, e.g. instead of the live representation of the image data.

In accordance with the visualization device not being connected to the monitor device, and in accordance with the expected remaining battery time being less than the low threshold amount of time and/or the remaining charge being less than the low threshold charge, an animation of connecting the external power supply to the power connection is displayed within the first portion of the graphical user interface, e.g. instead of the animation of connecting the visualization device to the monitor device. Thus, the operator is encouraged to connect the monitor device to an external power supply prior to initiating the procedure, e.g. prior to connecting the visualization device.

In accordance with the expected remaining battery time being less than the low threshold amount of time and/or in accordance with the remaining charge being less than the low threshold charge, the on/off button of the monitor device may be flashing. Thereby providing a further notification to the operator that the monitor device cannot be expected to complete a procedure without being charged and/or connected to a power supply.

The monitor device may have a first interface orientation mode and a second interface orientation mode. In the first interface orientation mode, the second portion is arranged between the fourth housing side and the first portion, e.g. along the second direction. In the second interface orientation mode, the second portion is arranged between the third housing side and the first portion, e.g. along the second direction.

Also disclosed is a method performed at a monitor device of a medical visualization system, such as the monitor device and medical visualization system as described herein.

The method may comprise receiving the image data generated by the image sensor, e.g. as the image data is being generated; displaying one or more actionable items within the second portion of the graphical user interface; and determining an interface orientation mode of the monitor device.

The method may further comprise, in accordance with the determined interface orientation mode being a first interface orientation mode, arranging the second portion between the fourth housing side and the first portion; and in accordance with the determined interface orientation mode being a second interface orientation mode, arranging the second portion between the third housing side and the first portion.

The method may further comprise displaying a live representation of the image data within the first portion of the graphical user interface.

It is an advantage of the present disclosure that a monitor device for a medical visualization system is provided, which may be oriented in a plurality of orientations and that the graphical user interface may be adapted to such orientation. For example, it may be advantageous to orientate the monitor device and/or a first housing of the monitor device according to physical features. For example, the present disclosure allows the monitor device and/or the first housing to be oriented such that, e.g. connection ports, are located on the side most convenient according to the circumstances.

The monitor device may comprise one or more connection ports for receiving a connector of the visualization device. The connection ports may be arranged on the first housing. The one or more connection ports may be provided on the third housing side. Alternatively or additionally, one or more connection ports may be provided on the fourth housing side.

The first housing may be oriented in a first orientation wherein the first direction is upwards and in a second orientation wherein the first direction is downwards. For example, the monitor device and/or the first housing may comprise a stand to support the first housing in either of the first orientation and the second orientation. In the first orientation the first housing side may be facing downwards. In the second orientation the first housing side may be facing upwards. In the first orientation the second housing side may be facing upwards. In the second orientation the second housing side may be facing downwards.

An invert interface button may be provided. For example, the invert interface button may be displayed with the touch sensitive display, e.g. by the processing unit. Alternatively, the invert interface button may be provided as a hardware button on the monitor device and/or on the first housing. The monitor device may change between operating the first interface orientation mode and operating the second interface orientation mode in response to activation of the invert interface button.

The monitor device may comprise an orientation sensor, such as a gyroscope and/or one or more accelerometers. The orientation sensor may be configured to detect the orientation of the first housing relative to gravity. The orientation sensor may be accommodated in the first housing. The orientation sensor may provide an orientation signal indicative of the orientation of the first housing, e.g. relative to gravity. The monitor device, e.g. by the processing unit, may, based on the orientation sensor and/or the orientation sensor signal, determine whether the first housing is oriented in the first orientation. Alternatively or additionally, the monitor device, e.g. by the processing unit, may, based on the orientation sensor and/or the orientation sensor signal, determine whether the first housing is oriented in the second orientation. Determining the interface orientation mode may comprise determining an orientation of the first housing by the orientation sensor, such as by the orientation sensor signal and/or by the processing unit. The monitor device may operate in the first interface orientation mode in the first orientation, e.g. based on the orientation sensor signal of the orientation sensor. The monitor device may operate in the second interface orientation mode in the second orientation, e.g. based on the orientation sensor signal of the orientation sensor. The monitor device may operate in the first interface orientation mode when a signal of the orientation sensor is indicative of the first housing being oriented in the first orientation. The monitor device may be operating in the second interface orientation mode when the signal of the orientation sensor is not indicative of the first housing being in the first orientation and/or when the signal of the orientation sensor is indicative of the first housing being in the second orientation. In the first interface orientation mode the first direction may be upwards. In the second interface orientation mode the first direction may be downwards.

The one or more actionable items, displayed within the second portion of the graphical user interface, may comprise an image capture button and/or a video capture button, as explained above. The second portion is between the first portion and the fourth housing side in the first interface orientation mode and between the first portion and the third housing side in the second interface orientation mode. The inventors have found that this provides an advantageous solution because an assistant entrusted with operating the actionable items during the procedure is usually located on the side corresponding to the third housing side in the second orientation of the first housing and corresponding to the fourth housing side in the first orientation of the first housing. For example, the assistant may be usually located to the right of the monitor device and/or the first housing. Thus, with the present disclosure, the graphical user interface may be configured to arrange the actionable items in a position which reduces the necessity for an operator to partly obstruct the visibility of live representation when performing certain operations needed during a procedure. Furthermore, it may be advantageous to be able to orient the monitor device and/or the first housing differently to arrange physical features, such as connection ports on/off button etc. to accommodate for the environment wherein the monitor device and/or the first housing is to be used.

The first image direction of the live representation of the image data and the first direction of the first housing may be the same in the first interface orientation mode. The first image direction and the first direction may be opposite in the second interface orientation mode. The second image direction and the first direction may be opposite in the first interface orientation mode. The second image direction and the first direction may be the same in the second interface orientation mode.

Effectively, a touch input in the first input direction on the control button of the visualization device may cause a movement of the distal end of the elongated flexible member corresponding to the first image direction, and/or a touch input in the second input direction on the control button of the visualization device may cause a movement of the distal end of the elongated flexible member corresponding to the second image direction. Accordingly, the operator is able to navigate the visualization device based on the live representation displayed with the touch sensitive display of the monitor device.

The monitor device may have a default view mode and in an inverted view mode. In the default view mode, the first image direction and the first direction may be the same, and in the inverted view mode, the first image direction and the first direction may be opposite. In accordance with the monitor device being in the default view mode the live representation may be displayed such that a first image direction of the live representation and the first direction are the same. In accordance with the monitor device being in the inverted view mode the live representation may be displayed such that the first image direction and the first direction are opposite.

The relationship between the image directions and the direction of the first housing may be subjective to both whether the monitor device operates the default view mode or the inverted view mode and whether the monitor device operates the first interface orientation mode or the second interface orientation mode.

In the default view mode, the first image direction and the first direction may be the same in the first interface orientation mode; and the first image direction and the first direction may be opposite in the second interface orientation mode. In the inverted view mode, the first image direction and the first direction may be opposite in the first interface orientation mode, and the first image direction and the first direction may be the same in the second interface orientation mode. In accordance with the monitor device being in the default view mode and in accordance with the determined interface orientation mode being the first interface orientation mode, the live representation may be displayed such that a first image direction of the live representation and the first direction are the same. In accordance with the monitor device being in the default view mode and in accordance with the determined interface orientation mode being the second interface orientation mode, the live representation may be displayed such that the first image direction and the first direction are opposite. In accordance with the monitor device being in the inverted view mode and in accordance with the determined interface orientation mode being the first interface orientation mode, the live representation may be displayed such that the first image direction and the first direction are opposite. In accordance with the monitor device being in the inverted view mode and in accordance with the determined interface orientation mode being the second interface orientation mode, the live representation may be displayed such that the first image direction and the first direction are the same.

Changing between the default view mode and the inverted view mode may cause the live representation to be rotated, e.g. by 180 degrees. In the inverted view mode an inverted view mode indicator may be displayed, e.g. by the monitor device with the touch sensitive display, in the first portion overlaying a portion of the live representation.

The ability to change between default view mode and inverted view mode may be advantageous in certain procedures depending on the location of the operator relative to the patient, and/or depending on how the operator is holding the handle of the visualization device.

In the inverted view mode a stored image data file, e.g. stored in response to receipt of activation of an image capture button of the one or more actionable items, may comprise information indicative of the monitor device having been operated in the inverted view mode when the image capture button was activated. The monitor device may store with the image data file being stored information indicative of the monitor device operating in the inverted view mode when the image capture button was activated. For example, metadata indicative of the inverted view mode being active may be embedded in the stored image data file. Alternatively, a visible mark, e.g. the inverted view mode indicator, may be provided on the stored image data file.

In the inverted view mode a stored video sequence of image data, e.g. stored in response to receipt of activation of a video capture button of the one or more actionable items, may comprise information indicative of the monitor device having been operated in the inverted view mode when the video capture button was activated. The monitor device may store with the video sequence being stored, information indicative of the monitor device operating in the inverted view mode when the video capture button was activated. For example, metadata indicative of the inverted view mode being active may be embedded in the stored video sequence of image data. Alternatively, a visible mark, e.g. the inverted view mode indicator, may be provided on the images of the stored video sequence.

An invert view button may be displayed with the touch sensitive display. The monitor device may display, e.g. with the touch sensitive display, the invert view button. The invert view button may be displayed within the second portion of the graphical user interface. The monitor device may change between the default view mode and the inverted view mode in response to activation of the invert view button. The user may change between the default view mode and the inverted view mode by activating the invert view button. The invert view button may be accessible from a settings menu.

In the default view mode the invert view button may be displayed in a first orientation, and in the inverted view mode the invert view button may be displayed in a second orientation. The second orientation of the invert view button may be rotated compared to the first orientation of the invert view button, e.g. by 180 degrees. The appearance of the invert view button may thereby be used to indicate the state of the monitor device, i.e. whether the monitor device operates the default view mode or the inverted view mode.

A user input corresponding to activation of the invert view button may be detected, e.g. by the touch sensitive display, and in response to detecting the user input corresponding to activation of the invert view button, in accordance with the monitor device being in the default view mode changing to the inverted view mode; and in accordance with the monitor device being in the inverted view mode changing to the default view mode.

The monitor device may comprise a settings menu. The settings menu may comprise an option for enabling the inverted view mode. In accordance with the inverted view mode being enabled in the settings menu, the invert view button may be displayed with the touch sensitive display, e.g. the monitor device may display the invert view button with the touch sensitive display, and in accordance with the inverted view mode not being enabled in the settings menu, the invert view button may not be displayed with the touch sensitive display.

A first user input corresponding to selection of a first actionable menu item of the one or more actionable menu items may be received, e.g. while displaying the live representation within the first portion and the one or more actionable menu items in the third portion. The monitor device, e.g. with the touch sensitive display, may be adapted to detect the first user input. In response to receipt of the first user input, a primary menu associated with the first actionable menu item may be displayed within the fourth portion of the graphical user interface without obscuring part of the first portion of the graphical user interface. For example, in response to detecting the first user input, the monitor device may display, e.g. with the touch sensitive display, the primary menu associated with the first actionable menu item may be displayed within the fourth portion of the graphical user interface without obscuring part of the first portion of the graphical user interface. The primary menu may comprise one or more primary actionable items including a first primary actionable item.

While displaying the primary menu associated with the first actionable menu item, a second user input corresponding to selection of the first primary actionable item may be received; and in response to receipt of the second user input, a secondary menu associated with the first primary actionable item may be displayed in the first portion, of the graphical user interface. For example, the monitor device may be adapted to detect the second user input, and in response to detecting the second user input, the monitor device may display, e.g. with the touch sensitive display, a secondary menu associated with the first primary actionable item in the first portion, of the graphical user interface. Optionally, the secondary menu may extend into the second portion and/or the fourth portion, of the graphical user interface.

It is an advantage of the present disclosure that the user needs to make two consecutive inputs to display a menu, which covers part of, or the entire live representation of the image data displayed in the first portion. Thereby, unintentional touch inputs on the screen is less likely to cause interference with the display of the live representation of the image data, which could potentially be life threatening, in case the operator is performing a critical procedure with the aid of the live representation of the image data.

The one or more actionable menu items may comprise a second actionable menu item. While the secondary menu is displayed, a third user input corresponding to selection of the second actionable menu item may be received. For example, the monitor device may be adapted to detect the third user input. In response to receipt of the third user input display of the secondary menu may be ceased and the live representation of the image data may be displayed within the first portion of the graphical user interface. For example, in response to detecting the third user input, the monitor device may cease display, e.g. with the touch sensitive display, of the secondary menu and displays the live representation of the image data within the first portion of the graphical user interface.

The one or more actionable items, e.g. displayed within the second portion of the graphical user interface, may comprise an image capture button and a video capture button. The image capture button may be a first colour and the video capture button may be a second colour. The first colour may be visually distinct from the second colour. For example, the first colour and the second colour may differ by a hue difference of at least 60 degrees, such as at least 120 degrees. The hue difference may be according to the HSL or HSV colour models, wherein hue ranges from 0-360 degrees. For example, the image capture button may be green, and the video capture button may be blue. Providing the image capture button and the video capture button in distinguishing colours allows for easy oral reference, e.g. allowing an operator to ask an assistant to take a picture by asking the assistant to push the, e.g., "green" button. Furthermore, the monitor device may support receiving spoken commands, e.g. by a microphone. In such situation it may also be advantageous that the operator can easily utter a command, which the monitor device has a high likelihood of interpreting as intended.

A fourth user input, e.g. a double tap within the first portion of the graphical user interface, may be received. For example, the monitor device may be adapted to detect a fourth user input. In response to receipt of the fourth user input, an enlarged view mode may be activated. For example, in response to detecting the fourth user input the monitor device may activate the enlarged view mode. In the enlarged view mode, a section of the live representation of the image data may be displayed in the first portion and the fourth portion of the graphical user interface. Thus, a section of the live representation of the image data may be extended to be displayed using a bigger part of the graphical user interface, and the section of the live representation of the image data may be magnified.

Furthermore, in response to detecting the fourth user input the monitor device may further display an enlarged view mode indicator. Optionally the enlarged view mode indicator is displayed in the second portion.

The live representation may comprise a first crop section and a second crop section. This may be due to the image sensor generating image data corresponding to a square image (or may be cropped to a square format), e.g. due to conventions or de-facto standards within the field of medical visualization, and therefore enlarging the image results to the image attaining a height larger than the height of the display. The section of the live representation being displayed in the enlarged view mode may be between the first crop section and the second crop section. The first crop section and the second crop section are not displayed in the enlarged view mode. The section of the live representation being displayed in the enlarged view mode may be between 30-95%, such as 40-90%, such as 50-80%, such as 60-70% of the live representation.

In the enlarged view mode the stored image data file may comprise information indicative of the monitor device having been operated in the enlarged view mode when the image capture button was activated. For example, the monitor device may store with the image data file being stored information indicative of the monitor device operating in the enlarged view mode when the image capture button was activated. For example, metadata indicative of the inverted view mode being active may be embedded in the stored image data file. Alternatively, a visible mark, e.g. the inverted view mode indicator, may be provided on the stored image data file. Thereby storing information of the view mode within the image data files.

Similarly, in the enlarged view mode the stored video sequence may comprise information indicative of the monitor device having been operated in the enlarged view mode when the video capture button was activated. The monitor device may store with the video sequence being stored, information indicative of the monitor device operating in the inverted view mode when the video capture button was activated. For example, metadata indicative of the inverted view mode being active may be embedded in the stored video sequence of image data. Alternatively, a visible mark, e.g. the inverted view mode indicator, may be provided on the images of the stored video sequence.

While in the enlarged view mode, a fifth user input corresponding to selection of the first actionable menu item of the one or more actionable menu items may be received. For example, the monitor device may be adapted to detect a fifth user input corresponding to selection of the first actionable menu item of the one or more actionable menu items. The fifth user input may correspond in location to the first user input but may be separate in time. In response to receipt of the fifth user input the primary menu associated with the first actionable menu item may be displayed within the fourth portion of the graphical user interface and may cause obscuring of a part of the section of the live representation of the image data. For example, in response to detecting the fifth user input the monitor device may display the primary menu associated with the first actionable menu item within the fourth portion of the graphical user interface, e.g. obscuring the part of the section of the live representation of the image data.

While displaying the primary menu associated with the first actionable menu item, e.g. while in the enlarged view mode, the monitor device may be adapted to detect a sixth user input corresponding to selection of a primary actionable item of the one or more primary actionable items of the primary menu. In accordance with not receiving the sixth user input within a threshold amount of time, e.g. 5 seconds, after receipt of the first user input, display of the primary menu associated with the first actionable menu item may be ceased, optionally the section of the live representation of the image data may be displayed in the first portion and the fourth portion of the graphical user interface. For example, in accordance with not receiving the sixth user input within a threshold amount of time after detecting the fifth user input, the monitor device may cease display of the primary menu associated with the first actionable menu item, optionally the monitor device may further display, e.g. with the touch sensitive display, the section of the live representation of the image data in the first portion and the fourth portion of the graphical user interface Automatically hiding the primary menu, if a second user input to an item of the primary menu is not received is particular advantageous in the enlarged view mode where the primary menu obscures a part of the live representation of the image data. However, the automatic hiding of the primary menu may also be advantageous in the normal view, wherein the live representation of the image data does not extend into the fourth portion of the graphical user interface, because automatically hiding the primary menu prevents an unintentional second input causing obscuring of the live representation of the image data.

While in the enlarged view mode, a seventh user input may be received. For example, the monitor device may be adapted to detect a seventh user input. The seventh user input may correspond to one or more of selection of the second actionable menu item, a touch input at a location of the enlarged view mode indicator, a touch input within the second portion of the graphical user interface. In response to receipt of the seventh user input the enlarged view mode may be deactivated and the live representation of the image data may be displayed within the first portion of the graphical user interface. For example, in response to detecting the seventh user input the monitor device may deactivate the enlarged view mode and display the live representation of the image data within the first portion of the graphical user interface.

The monitor device may display a second background colour within the second portion of the graphical user interface. The second background colour may be filling at least 80% of the second portion of the graphical user interface. The monitor device may display a third background colour within the third portion of the graphical user interface. The third background colour may be filling at least 80% of the third portion of the graphical user interface. The monitor device may display a fourth background colour within the fourth portion of the graphical user interface. The fourth background colour may be filling at least 80% of the fourth portion of the graphical user interface. The second background colour, the third background colour and/or the fourth background colour may have lightness values of less than 0.6, such as less than 0.4, such as less than 0.2, such as less than 0.1. The lightness value may be according to the HSL colour model, wherein lightness ranges from 0-1, 1 designating maximum light, i.e. white, and 0 designating minimum light, i.e. black.

Because visualization devices, such as endoscopes, are often used in a dark environment, emitting less light by providing the background(s) in darker colours, means less strain on the eyes of the operators during the procedure. Furthermore, a dark background also interferes less with the shown live image. Even further, a darker background may also mean, at least for some screen technologies, that the device consumes less power. Hence, battery life may be increased.

The monitor device may comprise features, which should be restricted. Therefore, the monitor device may support authentication of a user allowing access to restricted features. It is a purpose of the present disclosure to balance between enabling quick and uncomplicated use, e.g. in case the monitor device is needed in an emergency situation, while protecting access to sensitive information and functionality, which should only be done by authorized users. At the same time, it is desired to have a simple and effective method to login to obtain access to full functionality.

The first actionable menu item may be associated with a login procedure. For example, the first actionable menu item may be a log in button. The primary menu associated with the first actionable menu item displayed in response to receipt and/or detection of the first user input may comprise an indication of a pre-selected user profile and a password type field.

While displaying the primary menu associated with the first actionable menu item, a second user input corresponding to selection of the password type field may be received. For example, the monitor device may be adapted to detect the second user input corresponding to selection of the password type field. In response to receipt of the second user input, a virtual keyboard may be displayed in the first portion of the graphical user interface and optionally in the second portion of the graphical user interface. For example, in response to detecting the second user input, the monitor device may display the virtual keyboard in the first portion of the graphical user interface and optionally in the second portion of the graphical user interface The virtual keyboard may obscure at least part of the live representation of the image data within the first portion of the graphical user interface. The virtual keyboard may be configured for entering a password in the password type field. A sequence of user inputs corresponding to input of a password may be received. For example, the monitor device may be adapted to detect the sequence of user inputs corresponding to input of a password. The monitor device may determine whether the input password match a stored password for the pre-selected user profile. In accordance with the input password matching the stored password for the pre-selected user profile, the monitor device may enter an authenticated mode corresponding to the pre-selected user profile. In accordance with the typed password not matching the stored password for the pre-selected user profile, an error message may be displayed indicative of the typed password being incorrect.

The primary menu may comprise a first primary actionable item for selecting another user profile, e.g. a user profile different from the pre-selected user profile. While displaying the primary menu associated with the first actionable menu item a third user input corresponding to selection of the first primary actionable item may be received. For example, the monitor device may be adapted to detect the third user input. In response to receipt of the third user input, a list of selectable user profiles may be displayed in the first portion of the graphical user interface and optionally in the second portion of the graphical user interface. For example, in response to detecting the third user input, the monitor device may display the list of selectable user profiles in the first portion of the graphical user interface and optionally in the second portion of the graphical user interface.

While displaying the list of selectable user profiles a fourth user input corresponding to selection of a selectable user profile from the list of selectable user profiles may be received. For example, the monitor device may be adapted to detect the fourth user input. In response to receipt of the fourth user input, a virtual keyboard may be displayed in the first portion of the graphical user interface and optionally in the second portion of the graphical user interface. For example, in response to detecting the fourth user input, the monitor device may display the virtual keyboard in the first portion of the graphical user interface and optionally in the second portion of the graphical user interface. The virtual keyboard may be configured for entering a password in a password type field. A sequence of user inputs corresponding to input of a password may be received. The monitor device may determine whether the input password match a stored password for the selected user profile. In accordance with the input password matching the stored password for the selected user profile, the monitor device may enter an authenticated mode corresponding to the selected user profile. In accordance with the typed password not matching the stored password for the selected user profile, an error message may be displayed indicative of the typed password being incorrect.

While in the authenticated mode the monitor device may determine whether automatic logout criteria have been met. The automatic logout criteria may comprise that the visualization device has not been connected to the monitor device for a logout time duration, e.g. between 300-800 seconds, such as between 400-700 seconds, such as 600 seconds. The automatic logout criteria may further comprise that during the logout time duration no user input has been received via the touch sensitive display. In accordance with the automatic logout criteria being met, the monitor device may enter a non-authenticated mode.

The monitor device may, e.g. in response to establishing connection to a visualization device, such as the first visualization device, open a procedure session. Establishing connection to a visualization device may include obtaining device identifier information from a device identifier (e.g. EPROM, QR-code, NFC, RFID or similar) of the visualization device. In response to establishing connection to the first visualization device the monitor device may open a first procedure session corresponding to the first device identifier information obtained from the first device identifier of the first visualization device. In response to establishing connection to the second visualization device the monitor device may open a second procedure session corresponding to the second device identifier information obtained from the first device identifier of the first visualization device. Hence, a procedure session may be created for each individual visualization device. A procedure session may be implemented by creating a folder in the file system of the monitor device, such that image files and video sequences obtained from a visualization device can be stored in the folder corresponding to the visualization device. Hence, association of an image file to a procedure session may be implemented by storing the image file in the folder of the procedure session. Opening a procedure session may further comprise creating a log, registering the time and date for initiating the procedure, registering information about the visualization device, registering software version and/or other information.

In opening the procedure session the monitor device may determine, based on the device identifier information, whether the visualization device has been previously connected to the monitor device. For example, in accordance with determining that the visualization device has previously been connected to the monitor device, the monitor device may reopen the procedure session corresponding to the device identifier information; and/or in accordance with determining that the visualization device has not previously been connected to the monitor device, the monitor device may create the procedure session, e.g. a new procedure session, corresponding to the device identifier information.

A folder icon may be displayed, e.g. by the monitor device and/or with the touch sensitive display of the monitor device. The folder icon may be displayed within a background portion of the graphical user interface. The background portion may be a portion other than the first portion of the graphical user interface. For example, the background portion may be the second portion or the fourth portion of the graphical user interface. The folder icon may comprise a visual representation of a count of stored files stored during the procedure session.

A first user input corresponding to selection of the image capture button of the one or more actionable items may be received and/or detected on the touch sensitive display e.g. while displaying the live representation within the first portion and the one or more actionable items in the second portion. The monitor device, e.g. with the touch sensitive display, may detect the first user input. In response to detection of the first user input, the monitor device may store a first image file corresponding to the image data received when the first user input was detected. The monitor device may further, in response to the first user input, associate the first image file with the procedure session. For example, the monitor device may position the first image file in the folder of the procedure session, e.g. the procedure session corresponding to the connected visualization device.

Also in response to detection of the first user input a first representation of a still image corresponding to the stored first image file may be displayed, e.g. within the background portion of the graphical user interface, e.g. by the monitor device and/or with the touch sensitive display of the monitor device. Providing a representation of the captured still image notifies the operator that an image is stored and provides an example of the stored image allowing the operator to quickly confirm that the image shows what he/she intended to capture.

After a predetermined delay after detection of the first user input an animation of transitioning the first representation to the folder icon may be displayed, e.g. by the monitor device and/or with the touch sensitive display of the monitor device. Thereby, the operator may be visually notified that the captured image is stored and placed in the folder represented by the folder icon. Thus, the operator is made aware where he/she is able to retrieve the just captured image.

The present inventors have investigated the preferable time delay and found that optimally, the predetermined delay is between 1-8 seconds, such as between 3-7 seconds, such as between 4-6 seconds, such as 5 seconds or such as between 1.5-3 seconds, such as 1.5 seconds or such as 2 seconds. The present inventors have also investigated the preferable duration of the animation and found that optimally, the animation may have a duration between 100-1500 ms, such as between 300-1000 ms, such as between 300-800 ms, such as between 300-600 ms or between 500-700 ms. For example, the duration of the animation may be 400 ms, 500 ms or 600 ms. The duration of the animation may be a fraction of the predetermined delay, such as between 1/7 to 1/13 of the predetermined delay, such as between 1/8-1/12 of the predetermined delay, such as between 1/9-1/11 of the predetermined delay, such as 1/10 of the predetermined delay.

Also in response to detection of the first user input, alternatively after display of the animation of transitioning the first representation to the folder icon, display of the visual representation of the count of stored files of the folder icon may be updated, e.g. including increasing the count of stored files.

After detection of the first user input, a second user input corresponding to selection of the image capture button may be received and/or detected. The monitor device may be adapted to detect the second user input. In response to detection of the second user input the monitor device may store a second image file corresponding to the image data received when the second user input was detected. The monitor device may further, in response to the second user input, associate the second image file with the procedure session. For example, the monitor device may position the second image file in the folder of the procedure session, e.g. the procedure session corresponding to the connected visualization device.

Also in response to detection of the second user input a second representation of a still image corresponding to the stored second image file may be displayed, e.g. within the background portion of the graphical user interface, e.g. by the monitor device and/or with the touch sensitive display of the monitor device. After the predetermined delay after detection of the second user input an animation of transitioning the second representation to the folder icon may be displayed, e.g. by the monitor device and/or with the touch sensitive display of the monitor device.

Also in response to detection of the second user input, alternatively after display of the animation of transitioning the second representation to the folder icon, display of the visual representation of the count of stored files of the folder icon may be updated, e.g. including increasing the count of stored files.

By providing representations, animations and folder icons associated with the captured still image(s) within the background portion, e.g. within the second portion or the fourth portion of the graphical user interface, the indications related to the capturing of images may be provided simultaneously with showing the live representation of the image data, within the first portion of the graphical user interface, and without interfering with the live representation of the image data.

The monitor device may be adapted to establish connection to a second visualization device, e.g. while a first visualization device is still connected, or after connection with the first visualization device has been disconnected. In establishing connection to the second visualization device, the monitor device may obtain second device identifier information from the second device identifier of the second visualization device. In response to establishing the connection to the second visualization device, the monitor device may open a second procedure session, e.g. corresponding to the second device identifier information.

A live representation of the second image data generated by the second image sensor of the second visualization device may be displayed. The live representation of the second image data may be displayed in the first portion of the graphical user interface.

A second folder icon may be displayed, e.g. by the monitor device, such as with the touch sensitive display of the monitor device. The second folder icon may be displayed within the background portion of the graphical user interface, e.g. within the second portion or the fourth portion of the graphical user interface. The second folder icon may comprise a visual representation of a count of stored files stored during the second procedure session. Display of the second folder icon may replace display of the folder icon associated with the previously described visualization device, e.g. the first visualization device, e.g. if the connection between the monitor device and previously described visualization device has been disconnected.

While the second visualization device is connected to the monitor device and/or while displaying the live representation of the second image data within the first portion and the one or more actionable items in the second portion, a third user input corresponding to selection of the image capture button may be received and/or detected. The monitor device may be adapted to detect the third user input, e.g. with the touch sensitive display. In response to detection of the third user input, the monitor device may store a third image file corresponding to the second image data received when the third user input was detected. The monitor device may further, in response to the third user input, associate the third image file with the second procedure session. For example, the monitor device may position the third image file in the second folder of the second procedure session, e.g. the procedure session corresponding to the connected second visualization device.

Also in response to detection of the third user input a third representation of a still image corresponding to the stored third image file may be displayed, e.g. within the background portion of the graphical user interface, e.g. by the monitor device and/or with the touch sensitive display of the monitor device. After the predetermined delay after detection of the third user input an animation of transitioning the third representation to the second folder icon may be displayed, e.g. by the monitor device and/or with the touch sensitive display of the monitor device.

Also in response to detection of the third user input, alternatively after display of the animation of transitioning the third representation to the second folder icon, display of the visual representation of the count of stored files of the second folder icon may be updated, e.g. including increasing the count of stored files.

The video capture button may be displayed in a first appearance. A fourth user input corresponding to selection of the video capture button may be received and/or detected. The monitor device, e.g. with the touch sensitive display, may be adapted to detect the fourth user input. In response to detection of the fourth user input the monitor device may change the appearance of the video capture button to a second appearance. Furthermore, also in response to detection of the fourth user input, the monitor device may start collection of image data received from the image sensor (corresponding to the image sensor of the connected visualization device, e.g. the first visualization device and/or the second visualization device) and temporarily stores the data in memory.

After detection of the fourth user input, a fifth user input corresponding to selection of the video capture button may be received and/or detected. The monitor device may be adapted to detect the fifth user input, e.g. with the touch sensitive display. In response to detection of the fifth user input, the monitor device changes the appearance of the video capture button to the first appearance. Also in response to detection of the fifth user input, the monitor device stores a first video data file corresponding to the image data received between detection of the fourth user input and the fifth user input. Also in response to detection of the fifth user input, the monitor device associates the first video data file with the procedure session (corresponding to the open procedure session according to the connected visualization device, e.g. the procedure session may be the procedure session corresponding to the first visualization device and/or the second procedure session corresponding to the second visualization device).

Also in response to detection of the fifth user input a fourth representation corresponding to a frame of the stored first video data file may be displayed, e.g. within the background portion of the graphical user interface, e.g. by the monitor device and/or with the touch sensitive display of the monitor device. After the predetermined delay after detection of the fifth user input an animation of transitioning the fourth representation to the folder icon (e.g. the folder icon associated with the first visualization device or the second folder icon associated with the second first visualization device) may be displayed, e.g. by the monitor device and/or with the touch sensitive display of the monitor device.

Also in response to detection of the fifth user input, alternatively after display of the animation of transitioning the fourth representation to the folder icon, display of the visual representation of the count of stored files of the folder icon may be updated, e.g. including increasing the count of stored files.

A sixth user input corresponding to selection of the folder icon may be received and/or detected. The monitor device may be adapted to detect the sixth user input, e.g. with the touch sensitive display. In response to detection of the sixth user input, a first plurality of representations corresponding to a first plurality of stored image files stored during the procedure session may be displayed, e.g. by the monitor device and/or with the touch sensitive display of the monitor device. The first plurality of representations may be displayed within the background portion of the graphical user interface, e.g. within the fourth portion of the graphical user interface.

A seventh user input may be received and/or detected. The seventh user input may correspond to selection of a primary representation of the first plurality of representations displayed in response to detection of the sixth user input. The primary representation may correspond to a primary stored image file. The monitor device may be adapted to detect the seventh user input. In response to detection of the seventh user input an enlarged representation of the primary stored image file may be displayed, e.g. within the first portion of the graphical user interface, e.g. by the monitor device and/or with the touch sensitive display of the monitor device. Furthermore, in response to detection of the seventh user input thumbnail representations of a second plurality of the stored image files stored during the procedure session may be displayed, e.g. within the first portion of the graphical user interface, e.g. by the monitor device and/or with the touch sensitive display of the monitor device.

Further in response to detection of the sixth user input, a session overview icon may be displayed, e.g. within the background portion of the graphical user interface, e.g. by the monitor device and/or with the touch sensitive display of the monitor device. An eighth user input corresponding to selection of the session overview icon may be received and/or detected. The monitor device may be adapted to detect the eighth user input, e.g. with the touch sensitive display. In response to detection of the eighth user input a third plurality of representations corresponding to a third plurality of stored image files stored during the procedure session may be displayed, e.g. within the first portion of the graphical user interface, e.g. by the monitor device and/or with the touch sensitive display of the monitor device. The third plurality of representations may be displayed in a grid-like pattern.

Also, e.g. in response to detection of the eighth user input general information of the procedure session may be displayed, e.g. in the second portion of the graphical user interface, e.g. by the monitor device and/or with the touch sensitive display of the monitor device. Also, e.g. in response to detection of the eighth user input, a note field may be displayed, e.g. within the fourth portion of the graphical user interface, e.g. by the monitor device and/or with the touch sensitive display of the monitor device.

A ninth user input corresponding to selection of the note field may be received and/or detected. The monitor device may be adapted to detect the ninth user input. In response to detection of the ninth user input a virtual keyboard may be displayed, e.g. within the first portion of the graphical user interface and optionally extending into the second portion and/or fourth portion of the graphical user interface. The virtual keyboard may be displayed by the monitor device and/or with the touch sensitive display of the monitor device. The virtual keyboard is configured for entering text in the note field.

A sequence of keyboard user inputs corresponding to typing of a text using the displayed virtual keyboard may be displayed. The monitor device may be adapted to detect the sequence of keyboard user inputs, e.g. with the touch sensitive display. In response to detection of the sequence of keyboard user inputs, a corresponding text string may be displayed in the note field. A tenth user input indicative of accept of the text typed using the displayed virtual keyboard may be received and/or detected, e.g. the user may press an accept button. The monitor device may be adapted to detect the tenth user input, and in response to detection of the tenth user input, the monitor device may store the typed text and associate the typed text as a note for the procedure session.

The monitor device may be adapted to detect disconnection of a visualization device. In response to disconnection of the visualization device from the monitor device, e.g. in response to a detection of disconnection of the visualization device the same as in response to detection of the sixth user input as described above may be displayed, e.g. by the monitor device and/or with the touch sensitive display of the monitor device, i.e. displaying a first plurality of representations corresponding to a first plurality of stored image files stored during the procedure session, e.g. wherein the procedure session corresponds to the just removed visualization device. The first plurality of representations may be displayed within the background portion of the graphical user interface, e.g. within the fourth portion of the graphical user interface. Furthermore, also in response to disconnection of the visualization device from the monitor device the session overview icon may be displayed within the background portion of the graphical user interface.

The one or more actionable menu items, e.g. displayed in the third portion of the graphical user interface, may comprise an archive menu item. An eleventh user input corresponding to selection of the archive menu item may be received and/or detected. The monitor device may be adapted to detect the eleventh user input, e.g. with the touch sensitive display. In response to detection of the eleventh user input, a primary archive menu associated with the archive menu item may be displayed, e.g. within the fourth portion of the graphical user interface. The primary archive menu may be displayed by the monitor device and/or with the touch sensitive display of the monitor device. The primary archive menu may comprise one or more primary actionable archive items, e.g. including a first primary actionable archive item and/or a second primary actionable archive item.

While displaying the primary archive menu, a twelfth user input corresponding to selection of the first primary actionable archive item may be received and/or detected. The monitor device may be adapted to detect the twelfth user input. In response to detection of the twelfth user input a secondary archive menu associated with the first primary actionable archive item may be displayed e.g. by the monitor device and/or with the touch sensitive display of the monitor device. The secondary archive menu may be displayed in the first portion of the graphical user interface, optionally extending into the second portion and/or the fourth portion of the graphical user interface.

The monitor device may comprise features, which should be restricted. Therefore, the monitor device may support authentication of a user allowing access to restricted features. Accordingly, the monitor device may operate an authorised state and/or a non-authorised state.

In accordance with the monitor device operating in an authorised state, the secondary archive menu may comprise a list of stored procedure sessions, e.g. a complete list of all procedures stored in the memory of the monitor device. In accordance with the monitor device operating in a non-authorised state and a setting to require authorisation is activated, the secondary archive menu may comprise an empty list or a list of a subset of the stored procedure sessions. The subset may, e.g., be procedure sessions recorded on the current day or the last recorded session. In accordance with the monitor device operating in a non-authorised state and a setting to require authorisation is deactivated, the secondary archive menu may comprise the list of stored procedure sessions, e.g. the complete list of all procedures stored in the memory of the monitor device.

While displaying the secondary archive menu comprising the list of stored procedure sessions or the list of a subset of the stored procedure sessions, a thirteenth user input, corresponding to selection of a first stored procedure session of the list of stored procedure sessions or the list of a subset of the stored procedure sessions, may be received and/or detected. The monitor device may be adapted to detect the thirteenth user input, e.g. with the touch sensitive display. In response to detection of the thirteenth user input, a fourth plurality of representations corresponding to a fourth plurality of stored image files stored during the first stored procedure session may be displayed, e.g. in the first portion of the graphical user interface. The monitor device and/or the touch sensitive display of the monitor device may display the fourth plurality of representations.

Also in response to detection of the thirteenth user input, general information of the first stored procedure session may be displayed, e.g. in the fourth portion of the graphical user interface. Also in response to detection of the thirteenth user input a note field may be displayed, e.g. in the fourth portion of the graphical user interface.

The graphical user interface and/or the graphical user interface contents displayed in response to the thirteenth user input may correspond to the graphical user interface and/or the graphical user interface contents displayed in response to the eighth user input, if the procedure session is the same.

A fourteenth user input, corresponding to selection of a select representation of the fourth plurality of representations may be received and/or detected. The select representation may correspond to a select stored image file. The monitor device may be adapted to detect the fourteenth user input. In response to detection of the fourteenth user input an enlarged representation of the select stored image file may be displayed, e.g. within the first portion of the graphical user interface, e.g. by the monitor device and/or with the touch sensitive display of the monitor device. Further in response to detection of the fourteenth user input, thumbnail representations of a fifth plurality of the stored image files stored during the first stored procedure session may be displayed, e.g. within the first portion of the graphical user interface, e.g. by the monitor device and/or with the touch sensitive display of the monitor device. The thumbnail representations may comprise a thumbnail representation of the select stored image file.

Also in response to detection of the fourteenth user input image information associated with the select stored image file may be displayed, e.g. within the second portion of the graphical user interface, e.g. by the monitor device and/or with the touch sensitive display of the monitor device. The image information associated with the select stored image file may comprise information indicative of the visualization device. The information indicative of the visualization device may have been obtained from the device identifier information.

A fifteenth user input, corresponding to selection of a select thumbnail of the displayed thumbnail representations may be received and/or detected. The select thumbnail may correspond to a second select stored image file. The monitor device is further adapted to detect the fifteenth user input. In response to detection of the fifteenth user input an enlarged representation of the second select stored image file may be displayed, e.g. within the first portion of the graphical user interface, e.g. by the monitor device and/or with the touch sensitive display of the monitor device. Also in response to detection of the fifteenth user input, thumbnail representations of a sixth plurality of the stored image files stored during the first stored procedure session may be displayed, e.g. within the first portion of the graphical user interface, e.g. by the monitor device and/or with the touch sensitive display of the monitor device. The sixth plurality of the stored image files may be the same as the fifth plurality of the stored image files.

An export icon may be displayed, e.g. in response to detection of the fourteenth user input. A sixteenth user input corresponding to selection of the export icon may be received. The monitor device may be adapted to detect the sixteenth user input, e.g. with the touch sensitive display. In response to detection of the sixteenth user input the fourth plurality of representations corresponding to the fourth plurality of stored image files, may be displayed, e.g. in the first portion of the graphical user interface, e.g. by the monitor device and/or with the touch sensitive display of the monitor device. Each of the fourth plurality of representations may comprise a selection indicator, wherein the selection indicator of the select representation may be activated. Furthermore, in response to detection of the sixteenth user input, an export menu comprising an export confirm icon may be displayed, e.g. within the second portion and/or the fourth portion of the graphical user interface, e.g. by the monitor device and/or with the touch sensitive display of the monitor device.

Alternatively and/or additionally, the export icon may be displayed in response to detection of the seventh user input. In such case in response to detection of the user input corresponding to the selection of the export icon, the second plurality of representations corresponding to the second plurality of stored image files, may be displayed, e.g. in the first portion of the graphical user interface, e.g. by the monitor device and/or with the touch sensitive display of the monitor device. Each of the second plurality of representations may comprise a selection indicator, wherein the selection indicator of the primary stored image file may be activated. Similar to described above an export menu comprising an export confirm icon may be displayed.

Alternatively and/or additionally, the export icon may be displayed in response to detection of the eighth user input. In such case in response to detection of the user input corresponding to the selection of the export icon, the third plurality of representations corresponding to the third plurality of stored image files, may be displayed, e.g. in the first portion of the graphical user interface, e.g. by the monitor device and/or with the touch sensitive display of the monitor device. Each of the third plurality of representations may comprise a selection indicator, wherein none of the selection indicators are initially activated. Similar to described above an export menu comprising an export confirm icon may be displayed.

Alternatively and/or additionally, the export icon may be displayed in response to detection of the thirteenth user input. In such case in response to detection of the user input corresponding to the selection of the export icon, the fourth plurality of representations corresponding to the fourth plurality of stored image files, may be displayed, e.g. in the first portion of the graphical user interface, e.g. by the monitor device and/or with the touch sensitive display of the monitor device. Each of the fourth plurality of representations may comprise a selection indicator, wherein none of the selection indicators are initially activated. Similar to described above an export menu comprising an export confirm icon may be displayed.

After detection of the sixteenth user input, a seventeenth user input, corresponding to selection of one or more of the selection indicators, e.g. of the fourth plurality of representations, may be received and/or detected. The monitor device may be adapted to detect the seventeenth user input, e.g. with the touch sensitive display. In response to detection of the seventeenth user input, the selection indicators of the plurality of representations corresponding to the selected one or more selection indicators may be activated.

After detection of the sixteenth user input and/or after detection of the seventeenth user input, an eighteenth user input, corresponding to selection of the export confirm icon may be received and/or detected. The monitor device may be adapted to detect the eighteenth user input, e.g. with the touch sensitive display. In response to detection of the eighteenth user input stored image files corresponding to the selected one or more selection indicators may be transmitted to an auxiliary device, such as a USB-drive, or a remote server. For example, the monitor device may transmit the stored image files corresponding to the selected one or more selection indicators to the auxiliary device, e.g. via Bluetooth, USB, LAN, WiFi or any other suitable connection.

A deletion icon may be displayed, e.g. in response to detection of the fourteenth user input, the seventh user input, the eight user input, the thirteenth user input, the sixteenth user input, and/or the seventeenth user input. A nineteenth user input corresponding to selection of the deletion icon may be received and/or detected. The monitor device may be adapted to detect the nineteenth user input, e.g. with the touch sensitive display. In response to detection of the nineteenth user input, a confirmation dialogue indicative of potential deletion of one or more image files (e.g. corresponding to a displayed enlarged representation or stored image files having their selection indicators selected) may be displayed, e.g. by the monitor device and/or with the touch sensitive display of the monitor device.

A twentieth user input to the confirmation dialogue may be received. The monitor device may be adapted to detect the twentieth user input, e.g. with the touch sensitive display. In accordance with the twentieth user input being indicative of the user confirming deletion of the one or more image files, the one or more image files may be deleted, e.g. removed from memory. Furthermore, display of the enlarged representation may be replaced with an enlarged representation of a second image file. In accordance with the twentieth user input being indicative of the user cancelling deletion of the select stored image file, deletion of the one or more image file may be forgone. Furthermore, display of the enlarged representation may be maintained, e.g. within the first portion of the graphical user interface.

The deletion icon may be displayed in response to detection of the fourteenth user input. In this case, in response to detection of the nineteenth user input, a confirmation dialogue indicative of potential deletion of the select stored image file is displayed. In accordance with the twentieth user input being indicative of the user confirming deletion of the select stored image file the select stored image file is deleted. Furthermore, display of the enlarged representation of the select stored image file is replaced with an enlarged representation of a second select stored image file. In accordance with the twentieth user input being indicative of the user cancelling deletion of the select stored image file, deletion of the select stored image file is forgone. Furthermore, display of the enlarged representation of the select stored image file within the first portion of the graphical user interface is maintained.

BRIEF DESCRIPTION OF THE FIGURES

Embodiments of the disclosure will be described in more detail in the following with regard to the accompanying figures. The figures show one way of implementing the present invention and are not to be construed as being limiting to other possible embodiments falling within the scope of the attached claim set.

DETAILED DESCRIPTION

Figure 1:
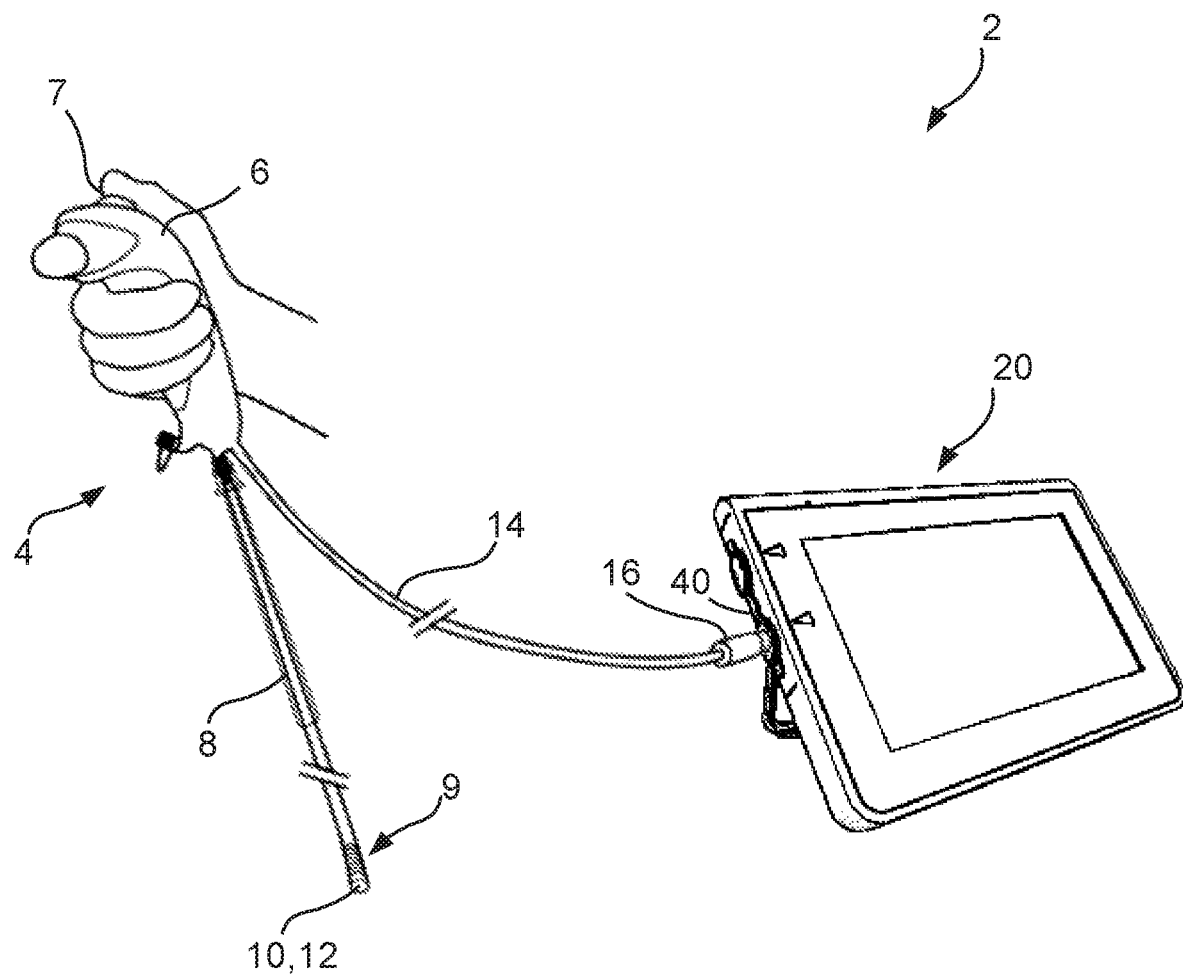
FIG. 1 schematically illustrates an exemplary medical visualization system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 schematically illustrates an exemplary medical visualization system 2 comprising a visualization device 4 and a monitor device 20. The visualization device 4 has an image sensor 12, e.g. a CCD or a CMOS, configured to generate image data indicative of a view from the visualization device 4. In the illustrated example, the visualization device 4 is an endoscope comprising a handle 6 and an elongated flexible member 8, e.g. an insertion tube, extending from the handle 6 to a distal end 10. The image sensor 12 may be configured to generate image data indicative of a view from the distal end 10 of the elongated flexible member 8.

The visualization device 4 may be connected to the monitor device 20. In the illustrated example, a device cable 14 extending from the handle 6 terminates in a device connector 16 connected to a connection port 40 of the monitor device 20. The monitor device 20 is operable to receive image data generated by the image sensor 12 of the visualization device 4. For example, the monitor device 20 may receive image data generated by the image sensor 12 via the device cable 14, the connector 16 and connection port 40. Connection ports 40 may also be designated a connection ports 40a, 4b, and 4c when relevant to the associated description of features, for example as described with reference to FIGS. 5A-5D.

The handle 6 comprises a control button 7 adapted to receive an input in a first input direction and/or in a second input direction. The touch input in the first input direction on the control button 7 causes a distal portion 9 of the elongated flexible member 8 to bend in a first bending direction, e.g. via wires extending from the handle, through the elongated flexible member 8 to the distal portion 9. The touch input in the second input direction on the control button 7 causes the distal portion 9 of the elongated flexible member 8 to bend in a second bending direction. The first input direction and the second input direction may be opposite. The first bending direction and the second bending direction may be opposite. Bending the distal portion 9 of the elongated flexible member 8 may cause a movement of the distal end 10 and the image sensor 12 in a direction relative to the image sensor 12. Thereby, seeing an image generated by the image sensor 12, a direction, e.g. up or down, in the image may correspond to a respective input on the control button 7.

Figure 2:
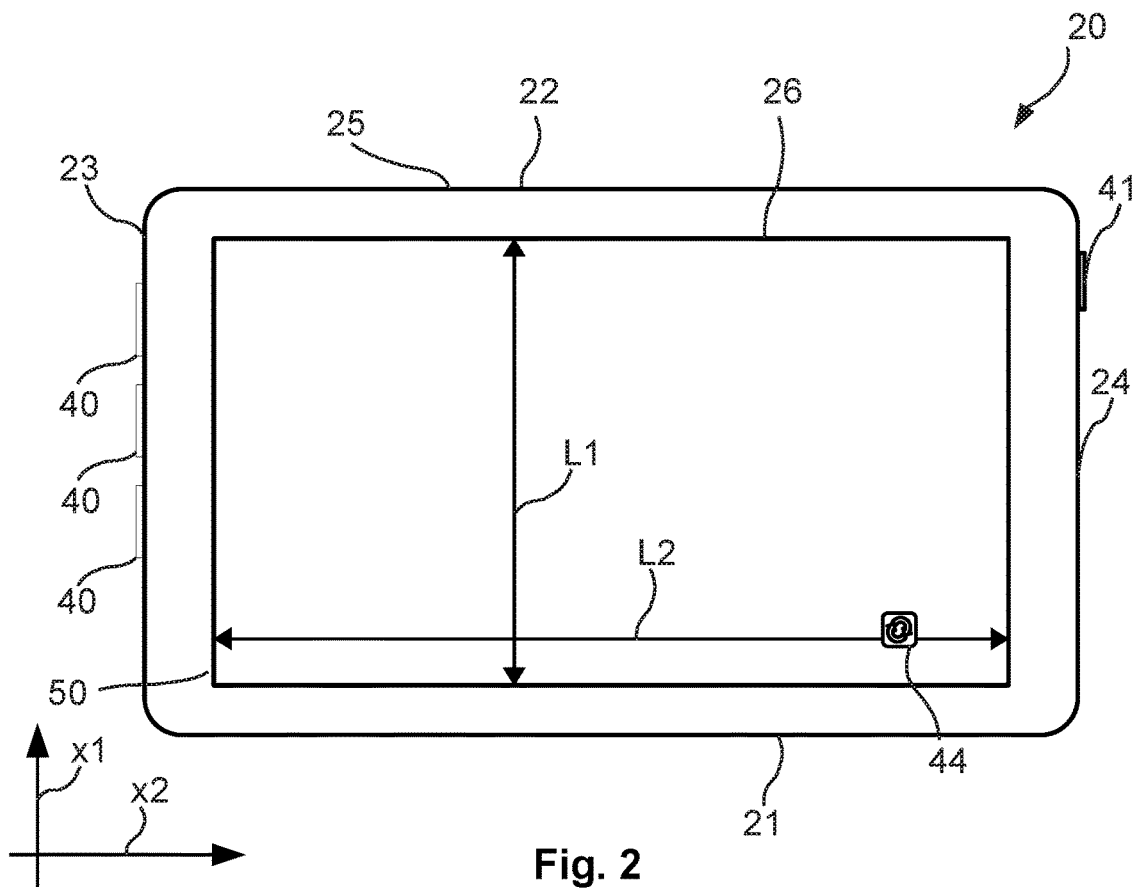
FIG. 2 schematically illustrates an exemplary monitor device.

FIG. 2 schematically illustrates an exemplary monitor device 20, such as the monitor device 20 as illustrated in FIG. 1. The monitor device 20 comprises a first housing 25. The first housing 25 extends in a first direction x1 from a first housing side 21 to a second housing side 22 and in a second direction x2 perpendicular to the first direction x1 from a third housing side 23 to a fourth housing side 24. The monitor device comprises a touch sensitive display 26 accommodated in the first housing 25. The touch sensitive display 26 has a first length L1 in the first direction x1 and a second length L2 in the second direction x2. The second length L2 may be longer than the first length L1 as illustrated.

The monitor device may comprise one or more connection port(s) 40, such as three connection ports 40, as illustrated. The connection ports 40 may allow visualization devices to be connected. The connection port(s) 40 may be arranged at the third housing side 23, as illustrated. Alternatively or additionally, connection port(s) 40 may be arranged at the fourth housing side 24.

The monitor device may comprise an on/off button 41, which may be provided on the fourth housing side 24, as illustrated.

Figure 3:
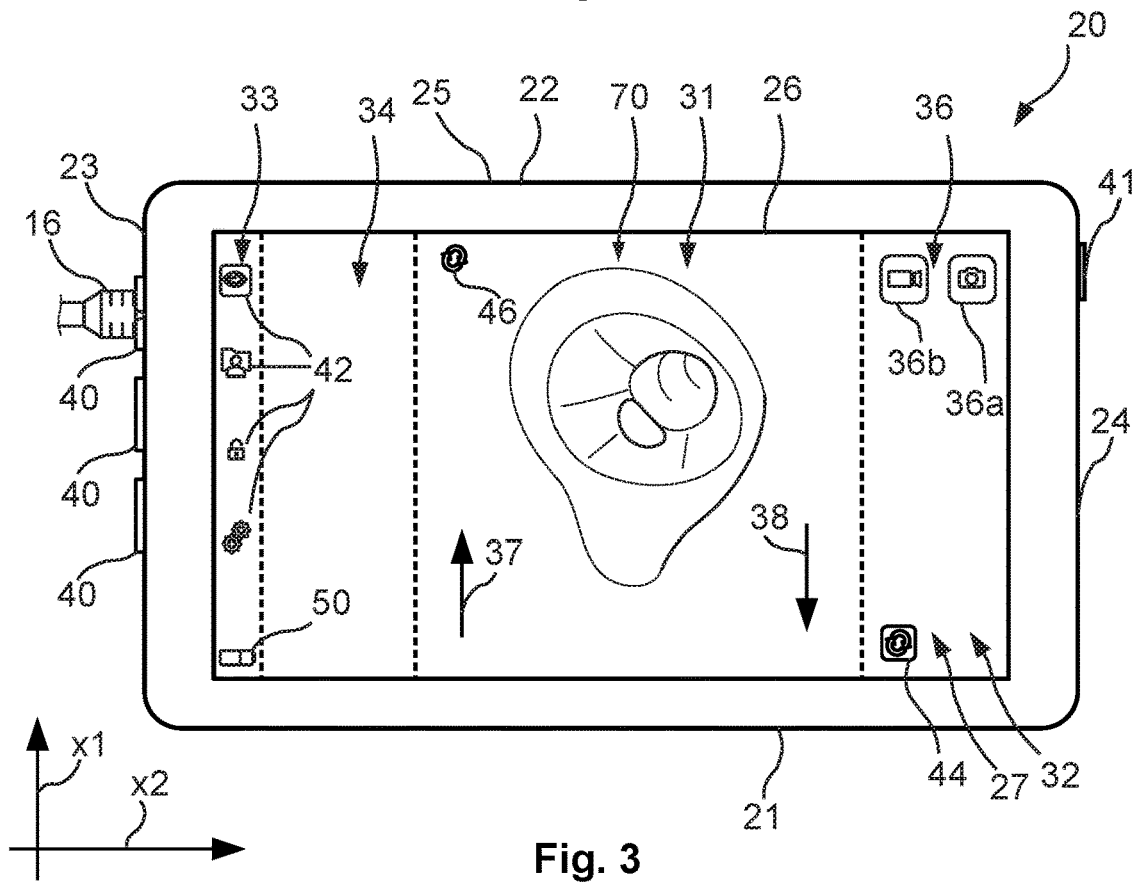
FIG. 3 schematically illustrates an exemplary monitor device.

FIG. 3 schematically illustrates an exemplary monitor device 20, such as the monitor device 20 as illustrated in FIGS. 1-2. As illustrated a device connector 16 may be connected to a connection port 40.

The monitor device 20 may be provided with a graphical user interface 27. The graphical user interface 27 may be displayed with the touch sensitive display 26, and the user may interact with the graphical user interface 27, e.g. by means of providing touch inputs on the touch sensitive display 26.

The graphical user interface 27 is displayed with the touch sensitive display 26. The graphical user interface 27 comprises a plurality of non-overlapping portions 31, 32, 33, 34. Each of the portions 31, 32, 33, 34 extends substantially throughout the first length L1 in the first direction x1. The non-overlapping portions includes a first portion 31, a second portion 32, a third portion 33 and a fourth portion 34. The first portion 31 is arranged between the fourth portion 34 and the second portion 32 along the second direction x2. The fourth portion 34 is arranged between the third portion 33 and the first portion 31 along the second direction x2. The third portion 33 is arranged between a side of the first housing, e.g. the third housing side 23, and the fourth portion 34 along the second direction x2. The second portion 32 is arranged between another side of the first housing 25, e.g. the fourth housing side 24, and the first portion 31 along the second direction x2. The first portion 31 and the fourth portion 34 are arranged between the second portion 32 and the third portion 33 along the second direction.

The monitor device 20 displays a live representation 70 of the image data within the first portion 31 of the touch sensitive display 26. The first bending direction and the second bending direction of the distal portion 9 of the elongated flexible member 8, as described with respect to FIG. 1, may corresponds to a first image direction 37 and a second image direction 38 of the live representation 70, respectively. The first image direction 37 and the second image direction 38 may be parallel to the first direction x1, as illustrated. The first image direction 37 and the second image direction 38 may be opposite, as illustrated. Thereby, a user operating the control button 7 of visualization device 2 may cause movement of the distal portion 9 of the elongated flexible member 8 to bend in a direction corresponding to the first image direction 37 or the second image direction 38 of the live representation 70.

The monitor device 20 displays with the touch sensitive display 26 one or more actionable items 36 within the second portion 32 of the graphical user interface 27. The actionable items 36 may comprise an image capture button 36a, e.g. for storing an image data file corresponding to the image data received when the image capture button 36a was activated. Alternatively or additionally, the actionable items 36 may comprise a video capture button 36b, e.g. for storing a video sequence of image data corresponding to the image data received when the video capture button 36b was activated.

The monitor device 20 displays with the touch sensitive display 26 one or more actionable menu items 42 within the third portion 33 of the graphical user interface 27. The actionable menu items 42 may, for example, comprise a login menu item for initiating a login procedure, a settings menu item for accessing a settings menu, an archive menu item for browsing an archive, and a default menu item for returning to a default view. Also a battery indicator 50 is displayed in the third portion 33. Actionable menu items 42 may also be designated as actionable menu items 40a and 4b, for example, when relevant to the associated description of features, for example as described with reference to FIGS. 25A-25H. An invert view button 44 and an inverted view mode indicator 46 may also be presented with the graphical user interface, as discussed below.

Figure 4:
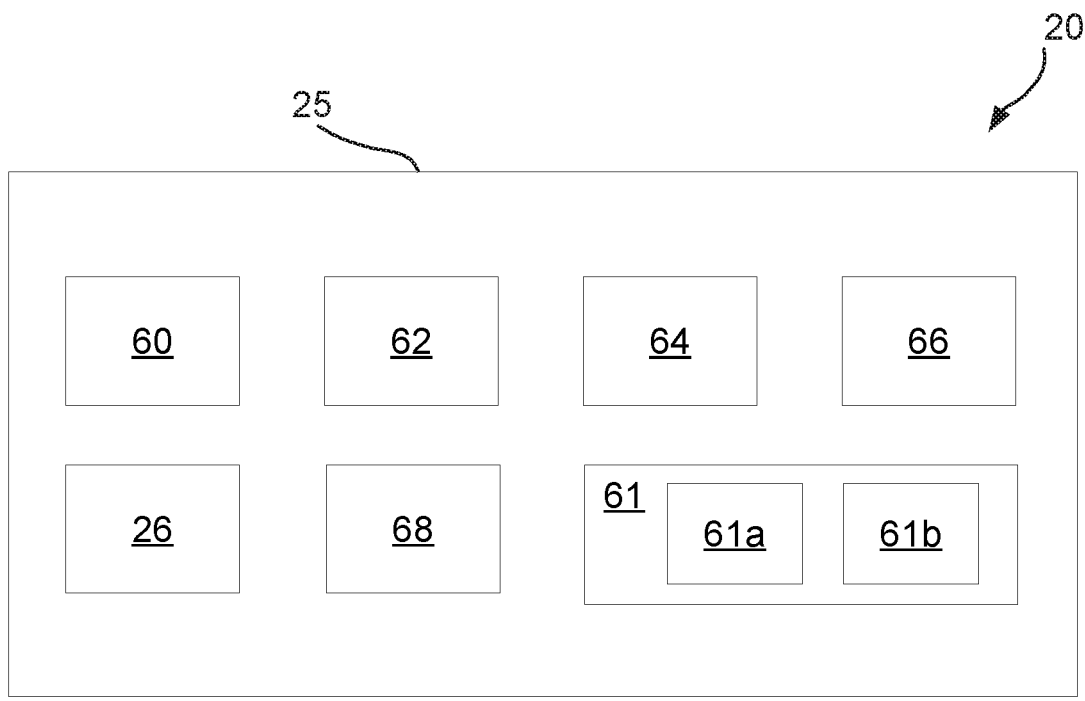
FIG. 4 is a block diagram of an exemplary monitor device.

FIG. 4 is a block diagram of an exemplary monitor device 20, such as the monitor device 20 of the previous figures. The monitor device 20 comprises a processing unit 60 and memory 62. The memory 62 may comprise both volatile and non-volatile memory. The monitor device 20 also comprise an orientation sensor 64 for determining the orientation of the first housing 25 relative to gravity. The orientation sensor 64 may comprise one or more accelerometers and/or a gyroscope. The monitor device 20 comprises input/output module 66, such as for receiving image data from the image sensor 12 via connectors of visualization device 4. The input/output module 66 may also comprise ethernet connector, WiFi transceiver, Bluetooth transceiver, video connectors, USB ports etc., and respective controllers. The monitor device 20 also comprises the touch sensitive display 26 as described earlier. The monitor device 20 may display information, graphical user interface objects, images, buttons etc, with the touch sensitive display 27. The monitor device 20 also comprises a microphone 68. The monitor device 20 comprises a power unit 61 for powering the monitor device 20. The power unit 61 may comprise a rechargeable battery 61a. The power unit 61 may comprise a power connection 61b for connecting the power unit 61 to an external power supply, such as a conventional AC power socket. The components of the monitor device 20 may be interconnected by buses or signal lines. Some or all of the components of the monitor device may be accommodated in the first housing 25 as illustrated. However, alternatively some of the components, e.g. the processing unit 60, the memory 62, input/output module 66 and/or the power unit 61 may be accommodated in a second housing of the monitor device 20.

The power unit 61 may comprise components for, e.g. indirectly measuring, capacity of the rechargeable battery 61a. For example, the power unit 61 may comprise a voltage gauge to measure the voltage of the rechargeable battery 61a. Based on the measured voltage, the remaining capacity of the rechargeable battery 61a may be estimated, e.g. by the processing unit 60. The power unit 61 may also comprise components for measuring power consumption of the monitor device 20. For example, the power unit 61 may comprise a power meter to measure the rate at which the monitor device 20 consumes power from the rechargeable battery 61a. The voltage gauge may be a low current consumption integrated circuit or a resistor coupled in parallel with the battery. A current sensor may be provided and the power may be computed as the product of the voltage and current. Additionally, an integrated circuit may be provided that includes a voltage gage and a current sensor, and which outputs a power value in digital form.

The monitor device 20 may display content with the touch sensitive display 26. For example, the monitor device 20 may display content by the processing device 60 transmitting instructions to the touch sensitive display 26 indicative of the content to be displayed. The monitor device 20 may receive user input with the touch sensitive display 26. Particularly, the monitor device 20 may detect user inputs with the touch sensitive display 26. For example, a user providing a touch input on the touch sensitive display 26 causes a change in one or more electrical parameters of the touch sensitive display 26 indicative of at least the location of the touch input. Information of the touch input is transmitted from the touch sensitive display 26 to the processing unit 60, and the processing unit 60 may determine whether the touch input corresponds to an action to perform, e.g. whether the location of the touch input corresponds to the location of a soft-button displayed at the touch sensitive display.

The user may interact with the monitor device 20 via the graphical user interface 27 by providing user inputs, e.g. by means of providing touch inputs on the touch sensitive display 26, and the monitor device 20 may detect such user inputs with the touch sensitive display 26. A touch input, e.g. a single tap, double tap, swipe or similar, and the location of the touch input on the touch sensitive display 26 is registered by the touch sensitive display 26, which transmits information of the touch input (e.g. including type of touch (double tap, single tap, swipe, etc.) and/or location of the touch) to the processing unit 60 of the monitor device 20. The processing unit 60 interprets the information received and determines whether the touch input corresponds to activation of an action, e.g. whether the touch input correspond to activation of a button displayed with the touch sensitive display 27 at the location of the touch input. In response to a determination that the touch input corresponds to activation of an action, the processing unit 60 performs the respective action.

For example, with reference to FIGS. 3 and 4, to capture an image corresponding to the presently shown live representation 70, e.g. corresponding to the image data received from the image sensor, the user may tap the image capture button 36a. The tap and the location of the tap is registered by the touch sensitive display 26, which transmits the information of the tap to the processing unit 60 of the monitor device 20. The processing unit 60 interprets the information received and determines that the user tapped the location corresponding to the image capture button 36a. In response thereto, the processing unit 60 stores, in memory 62 an image data file corresponding to the image data received.

In further reference to FIGS. 3 and 4, to capture a video sequence corresponding to the shown live representation 70 over a period of time, e.g. corresponding to the image data received from the image sensor over a period of time, the user may tap the video capture button 36b. The tap and the location of the tap is registered by the touch sensitive display 26, which transmits the information of the tap to a processing unit 60 (see FIG. 4) of the monitor device 20. The processing unit 60 interprets the information received and determines that the user tapped the location corresponding to the video capture button 36b. In response thereto, the processing unit 60 starts collection of image data received from the image sensor 12 and temporarily stores the data in memory 62. To stop the recording, the user may tap the video capture button 36b again. The processing unit 60 determines, based on the signal received from the touch sensitive display 26, that that the user tapped the video capture button 36b and stops collecting image data received from the image sensor 12. The processing unit 60 read the temporarily stored data from the memory 62 and create a complete video sequence based thereon, which the processing unit 60 stores in the memory 62.

User Interactions

FIGS. 5A-5D schematically illustrate exemplary user interactions with a graphical user interface of a monitor device 20, such as the monitor device 20 of any of the previous figures. In the illustrated examples the monitor device 20 has a first connection port 40a, a second connection port 40b, and a third connection port 40c. Each of the connection ports 40a-40c are further labelled with respective port indicators. For example, the first connection port 40a is labelled with a first port indicator 106, the second connection port 40b is labelled with a second port indicator 108, and the third connection port 40c is labelled with a third port indicator 109. The port indicators 106, 108, 109 may be printed or engraved on the monitor device 20, such as on the first housing 25 of the monitor device 20. Alternatively or additionally, the port indicators 106, 108, 109 may be displayed with the touch sensitive display 26 at the vicinity of the respective connection ports.

Figure 5A:
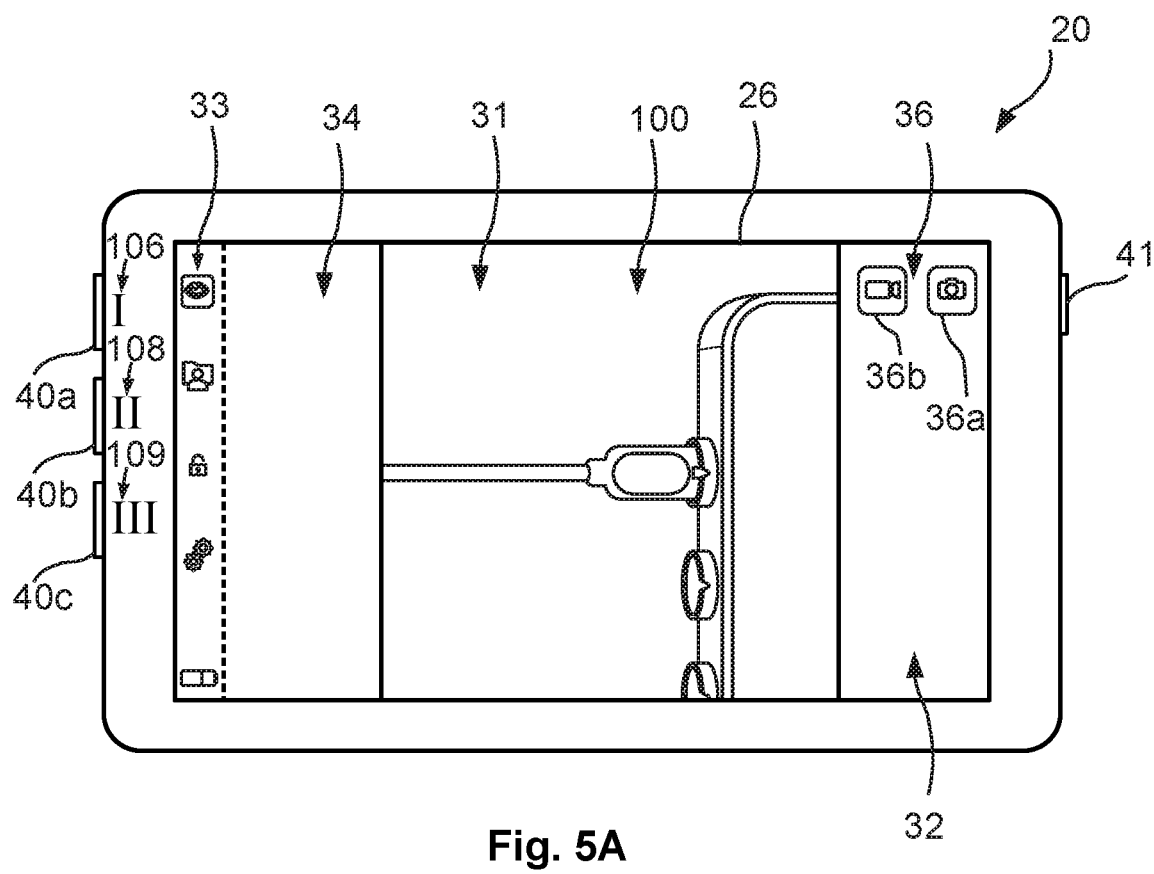
FIGS. 5A-5D schematically illustrate exemplary user interactions with an exemplary graphical user interface, FIGS. 6A-6B schematically illustrate exemplary user interactions with an exemplary graphical user interface, FIG. 7 schematically illustrates an exemplary graphical user interface, FIGS. 8A-8D schematically illustrate exemplary user interactions with an exemplary graphical user interface, FIGS. 9A-9D schematically illustrate exemplary user interactions with an exemplary graphical user interface, FIGS. 10A-10B schematically illustrate an exemplary graphical user interface of an exemplary monitor device, FIG. 11A-11C schematically illustrate exemplary battery indicators, FIGS. 12A-12B schematically illustrate an exemplary graphical user interface of an exemplary monitor device, FIGS. 13A-13D schematically illustrate an exemplary graphical user interface of an exemplary monitor device.

FIG. 5A schematically illustrates a monitor device 20 with no connected visualization devices, e.g. connection ports 40a-40c are empty. For example, this situation may correspond to a situation where a user initially powers on the device, e.g. by pressing the on/off button 41. In this situation, based on that no visualization device is connected an animation 100 of connecting the visualization device to the monitor device 20 is displayed within the first portion 31 of the graphical user interface.

Figure 5B:
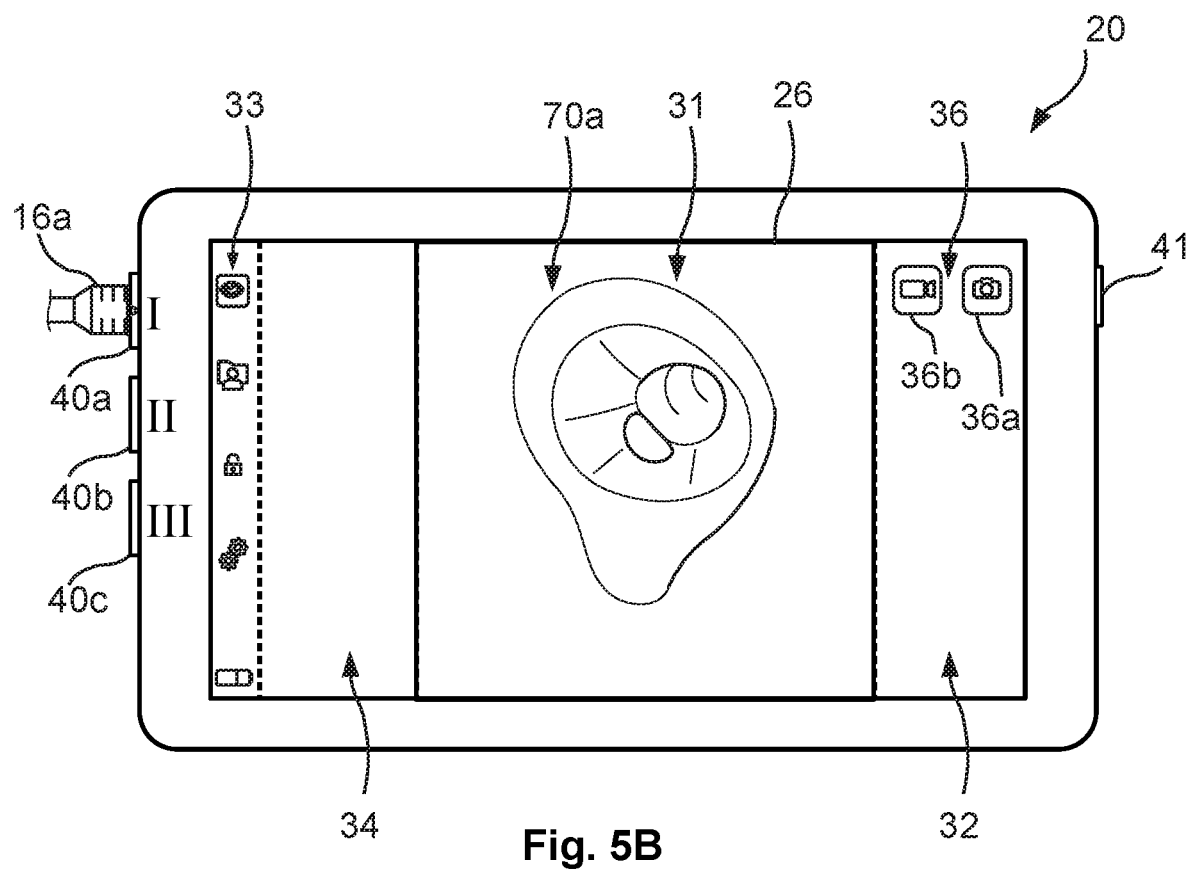

FIG. 5B schematically illustrates the monitor device 20, e.g. following the situation as shown in FIG. 5A, where, in comparison to the example of FIG. 5A, a first visualization device has been connected, by a first device connector 16a of the first visualization device being received at the first connection port 40a. In this situation, e.g. in response to establishing the connection to the first visualization device, a first live representation 70a of first image data generated by a first image sensor of the first visualization device is displayed within the first portion 31 of the graphical user interface.

Figure 5C:
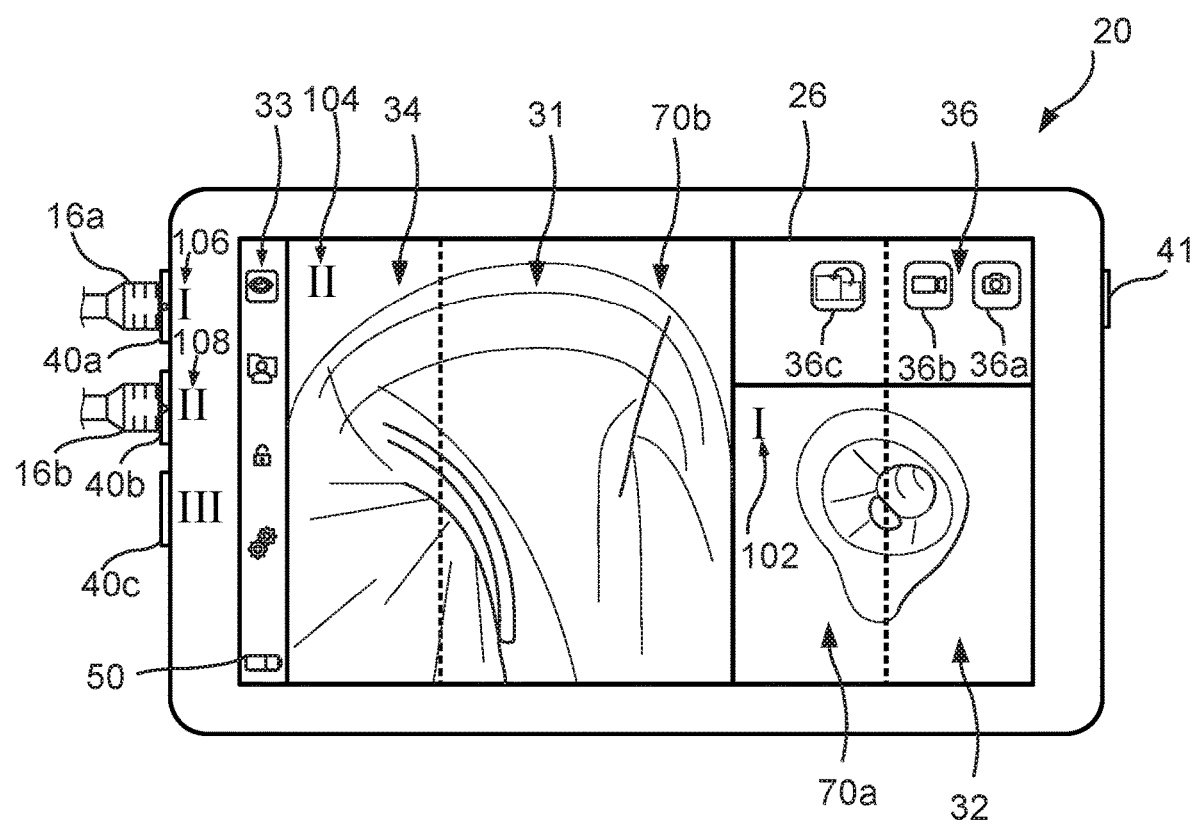

FIG. 5C schematically illustrates the monitor device 20, e.g. following the situation as shown in FIG. 5B, where, in comparison to the example of FIG. 5B, a second visualization device has been connected, by a second device connector 16b of the second visualization device being received at the second connection port 40b. The second visualization device is connected while the first visualization device is also connected to the monitor device 20.

Consequently, e.g. in response to establishing connection to the second visualization device, the monitor device 20 enters a dual view mode, wherein the monitor device concurrently displays the first live representation 70a of the first image data generated by the first image sensor and a second live representation 70b of second image data generated by a second image sensor of the second visualization device.

The second live representation 70b is displayed in the fourth portion 34 of the graphical user interface and extending into the first portion 31 of the graphical user interface. The first live representation 70a is displayed in the second portion 32 of the graphical user interface and extending into the first portion 31 of the graphical user interface.

Furthermore, as conventional display screens have a non-square aspect ratio, e.g. 16:9 or 16:10, and because the image data from the image sensor may be square (or may be cropped to a square format), e.g. due to conventions or de-facto standards within the field of medical visualization, showing the two live representations 70a, 70b side by side while utilizing the entire height of the display for a maximum size view, will result in (further) cropping, hiding or distortion of the representations or part thereof. In medical imaging, it is important that the user is aware in case he/she chooses to deviate from a standard or de-facto standard way of viewing the representation. Thus, it may be advantageous to avoid hiding or distorting part of a conventional view, unless deliberately and knowingly chosen by the operator. Thus, to maximize one image, it is necessary to reduce the other. As seen, the first live representation 70a is displayed in reduced size compared to the second live representation 70b. The newly connected visualization device, e.g. the second visualization device, is displayed in full size, while the previously connected visualization device is displayed in reduced size. It is preferred that the newly connected visualization device is shown biggest, as it has been found by the present inventors that a newly connected visualization device is connected with an intention of using that device, and that therefore it was found advantageous to show the newly connected visualization device with the biggest image. The present disclosure thereby provides a solution for optimally showing live representations from two simultaneously connected visualization devices, utilizing a conventional sized display screen. Hence, production costs may be lowered as the need for customized components is reduced.

The live representations may be overlaid with an indicator to allow mapping between the displayed representations and the physical visualization device. For example, a first indicator 102 is overlaid on the first live representation 70a, and a second indicator 104 is overlaid on the second live representation 70b. Furthermore, the first connection port 40a is labelled with a first port indicator 106 resembling the first indicator 102 and the second connection port 40b is labelled with a second port indicator 108 resembling the second indicator 104. Thereby, the operator is able to identify the visualization device corresponding to a certain live representation.

In response to establishing connection to the second visualization device, while the first visualization device remains connected, the monitor device further displays a rearrange icon 36c.

Figure 5D:
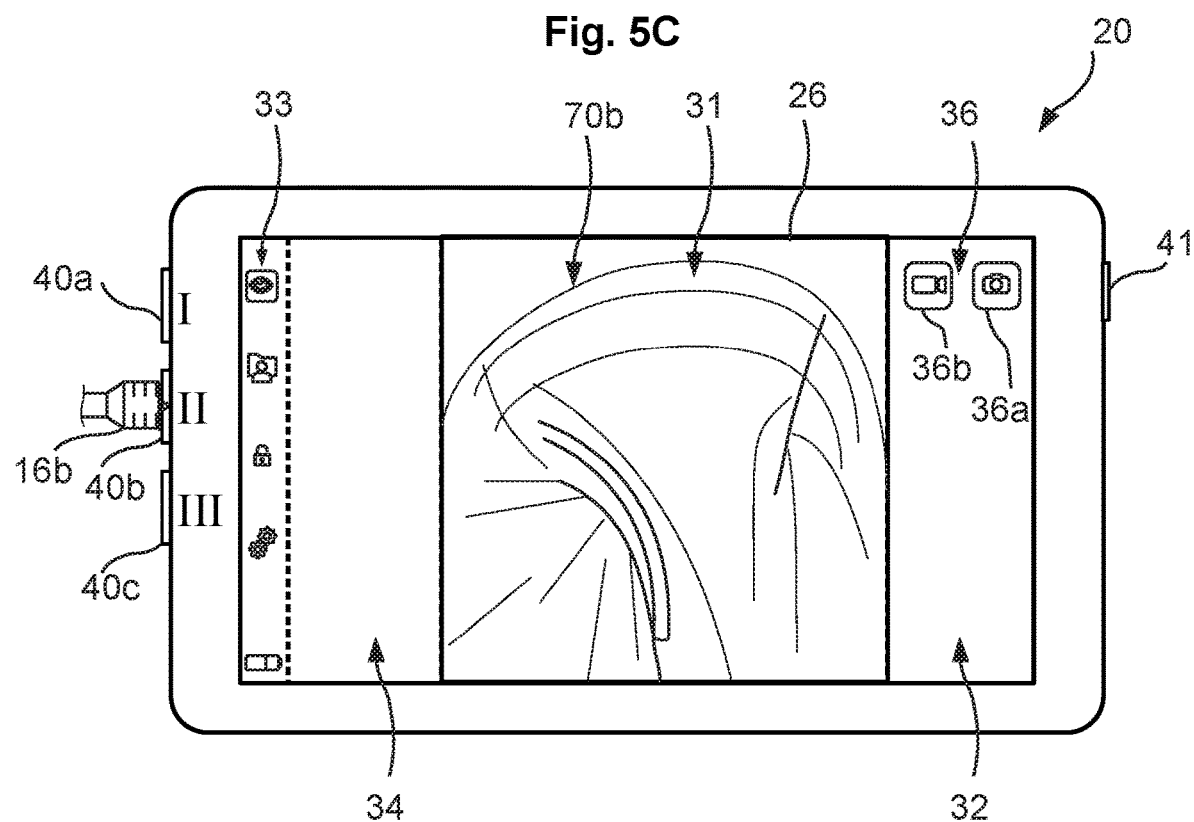

As illustrated in FIG. 5D, in the event the user disconnects the first visualization device, leaving only the connection of the second visualization device, the monitor device displays the live representation of the remaining visualization device in the first portion 31 of the graphical user interface. The monitor device 20, e.g. the processing unit of the monitor device, may be adapted to detect disconnection of a visualization device, such as of the first visualization device from the monitor device 20. In response to detecting disconnection of the first visualization device from the monitor device 20, as illustrated in FIG. 5D, the monitor device displays, within the first portion of the graphical user interface, the second live representation of second image data generated by the second image sensor of the second visualization device.

Figure 6A:
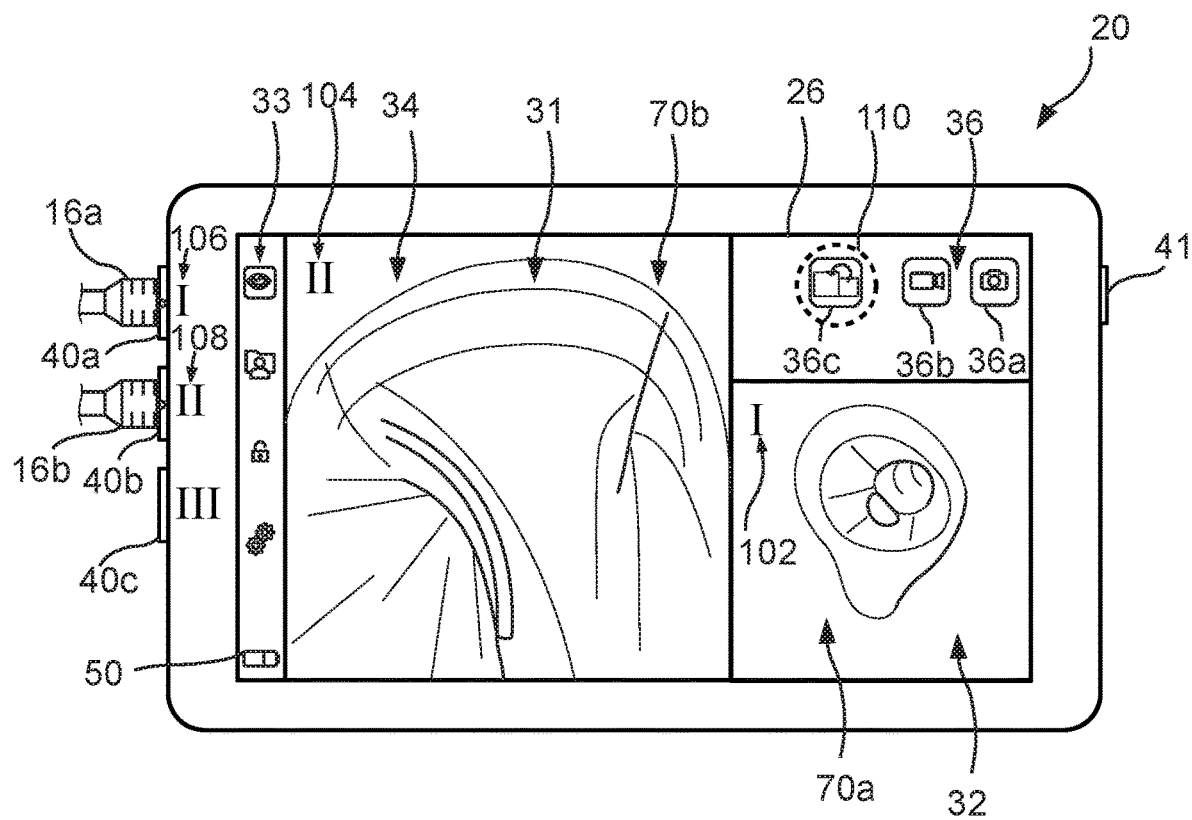
Figure 6B:
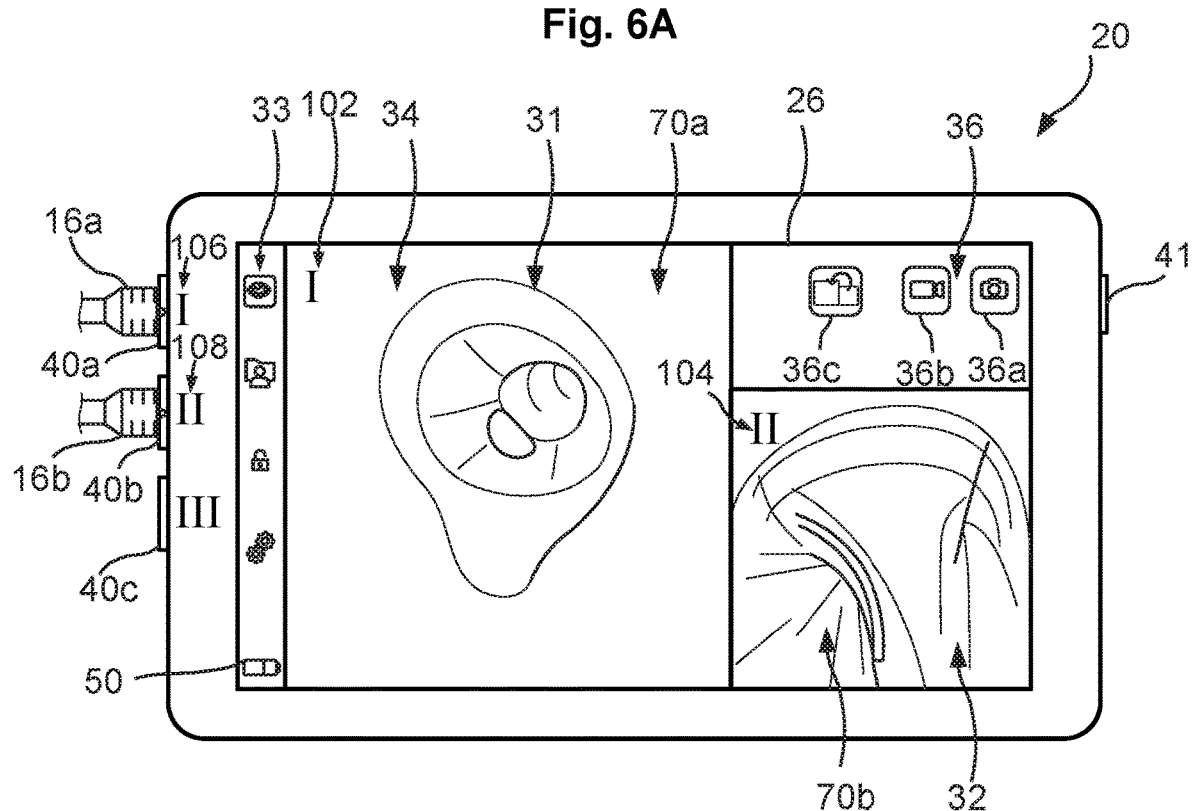

FIGS. 6A-6B schematically illustrate exemplary user interactions with a graphical user interface of a monitor device 20, such as the monitor device 20 of any of the previous figures.

FIG. 6A schematically illustrates a monitor device 20, e.g. following the situation as shown in FIG. 5C, where a first visualization device and a second visualization device are connected to the monitor device 20 at the same time. As mentioned above, the monitor device displays a rearrange icon 36c when both a first visualization device and a second visualization device are connected.

FIG. 6A particularly illustrates the situation where a user provides a first user input 110, e.g. a touch input, such as a tap, at the touch sensitive display 26 at a location corresponding to the rearrange icon 36c. Thus, the monitor device 20, such as the processing unit of the monitor device 20 may determine, based on the signal from the touch sensitive display 26, that the first user input 110 corresponds to selection of the rearrange icon 36c.

As illustrated in FIG. 6B, in response to detecting the first user input 110 the display of the second live representation 70b in the fourth portion 34 and extending into the first portion 31 of the graphical user interface is replaced with display of the first live representation 70a. Furthermore, also in response to detecting the first user input 110, the display of the of the first live representation 70a in the second portion 32 and extending into the first portion 31 of the graphical user interface is replaced with display of the second live representation 70b. Consequently, the second live representation 70b is displayed in reduced size compared to the first live representation 70a.

The first indicator 102 is repositioned to continuously be overlaid on the first live representation 70a, and the second indicator 104 is repositioned to continuously be overlaid on the second live representation 70b.

As explained with respect to FIG. 3, the monitor device 20 displays one or more actionable items 36 within the second portion 32 of the graphical user interface. The actionable items 36 may comprise an image capture button 36a, e.g. for storing an image data file corresponding to the image data received when the image capture button 36a was activated. Alternatively or additionally, the actionable items 36 may comprise a video capture button 36b, e.g. for storing a video sequence of image data corresponding to the image data received when the video capture button 36b was activated.

Figure 7:
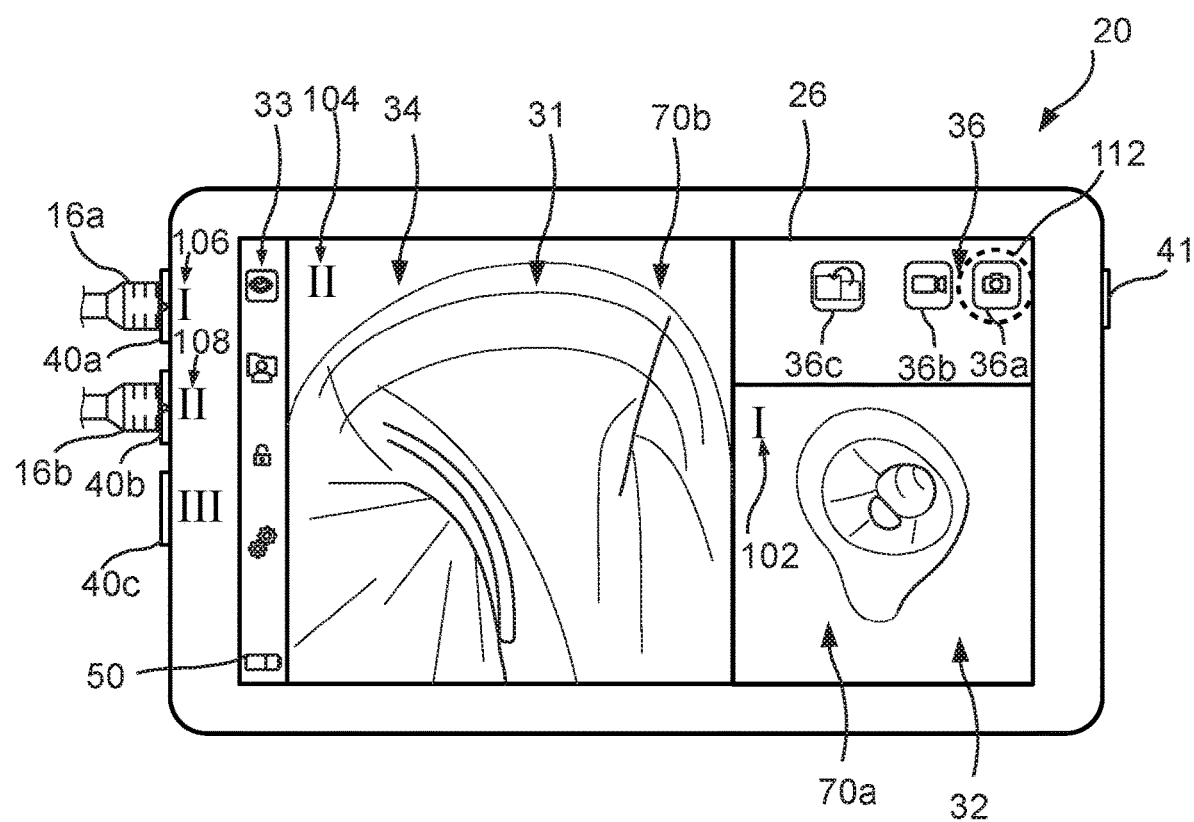

FIG. 7 schematically illustrates an exemplary user interaction with a graphical user interface of a monitor device 20, such as the monitor device 20 of any of the previous figures. Particularly, FIG. 7 illustrates that also when having a plurality of visualization devices connected (e.g. a first visualization device and a second visualization device, as illustrated), the monitor device displays the one or more actionable items 36, allowing, e.g., storing of image data as well as video sequences. The actionable items 36 are displayed within the second portion 32 of the graphical user interface.

The monitor device 20 is adapted to, e.g. via the touch sensitive display, to detect a second user input 112 corresponding to selection of the image capture button 36a. In response to detection of the second user input 112 the monitor device 20, such as the processing unit of the monitor device 20 stores a first image file corresponding to the first image data received when the second user input 112 was detected, and stores a second image file corresponding to the second image data received when second user input 112 was detected. Thus, both an image file corresponding to the first visualization device and an image file corresponding to the second visualization device may be stored. The same may be applied for video capturing. For example, in response to detection of a user input corresponding to selection of the video capture button 36b the monitor device 20, such as the processing unit of the monitor device 20 stores a first video sequence of image data corresponding to the first image data received when the user input was detected, and stores a second video sequence of image data corresponding to the second image data received when the user input was detected.

When a visualization device is connected, e.g. when the monitor device 20 and/or the processing unit of the monitor device detects connection of a visualization device, device identifier information from a device identifier of the respective visualization device may be obtained. For example, the visualization device(s) may be fitted with an EPROM (alternatively a QR code, RFID tag, NFC etc may be used), which the monitor device 20 is able to read. For example, the processing unit of the monitor device may execute a process for interrogating the device identifier, via the device connector and connection port. The EPROM may store information of the visualization device, e.g. a serial number of the visualization device, which may uniquely identify the visualization device. Also the device identifier information may be indicative of the type of visualization device, e.g. whether it is an endoscope or a laryngoscope, brand of the visualization device, production version, batch number etc.

In response to detecting connection of a visualization device, and after obtaining the device identifier information, the monitor device may open (create or reopen, depending on whether the visualization device has previously been connected) a procedure session corresponding to the device identifier information. For example, a first procedure session may be opened corresponding to the first device identifier information obtained from the first visualization device, and a second procedure session may be opened corresponding to the second device identifier information obtained from the second visualization device. The procedure sessions may be unique, and therefore reconnecting a previously connected visualization device cause the monitor device to reopen a previously created session.

Stored video sequences or image files may be associated with the procedure session for the respective visualization device. For example, the first image file stored in response to detection of the second user input 112, may be associated with the first procedure session, and the second image file stored in response to detection of the second user input 112, may be associated with the second procedure session. A procedure session may be implemented by creating a folder in the file system of the monitor device, wherein image files and video sequences obtained from a visualization device is stored in the folder corresponding to the visualization device.

FIGS. 8A-8D schematically illustrate exemplary user interactions with a graphical user interface of a monitor device 20, such as the monitor device 20 of any of the previous figures. Particularly, the examples may follow from FIG. 5B, wherein only a single visualization device is connected.

Figure 8A:
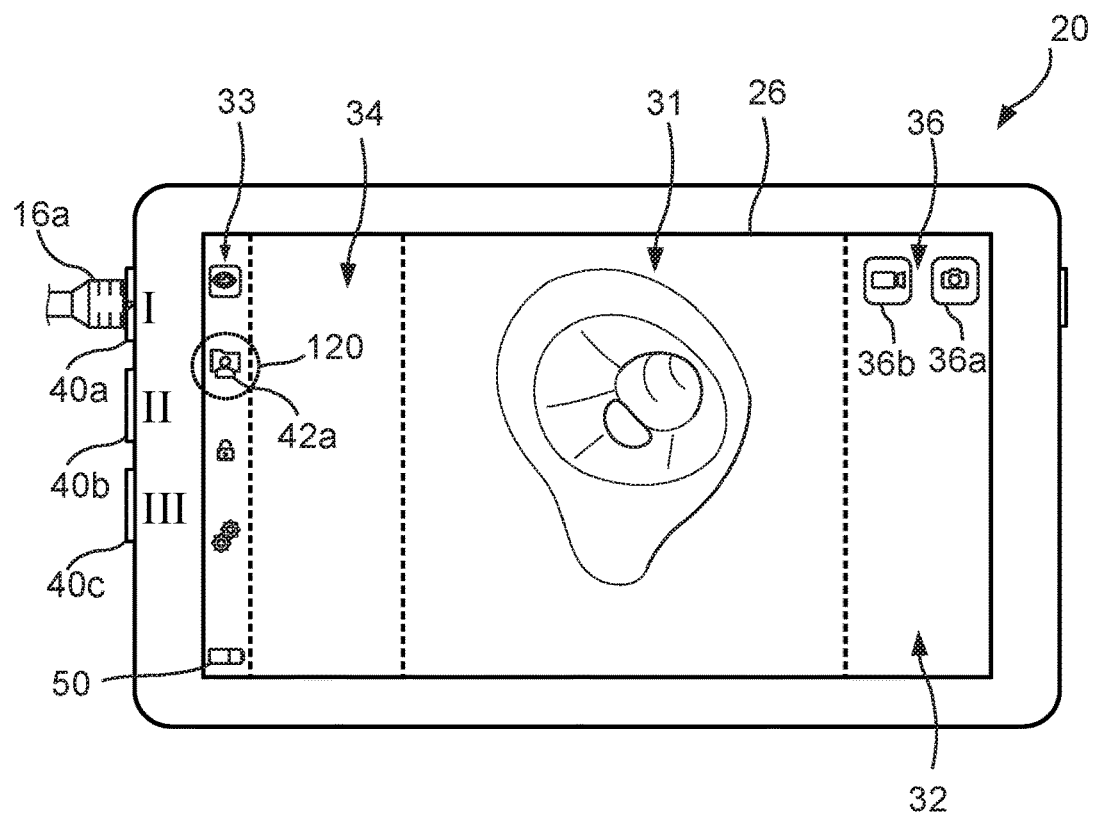

As illustrated in FIG. 8A, the monitor device 20 may receive a first primary user input 120 corresponding to selection of a first actionable menu item 42a of the one or more actionable menu items 42 (cf. FIG. 3). In the illustrated example, the first primary user input 120 is a touch input, e.g. a tap, on an icon, i.e. the first actionable menu item, indicating access to an archive.

Figure 8B:
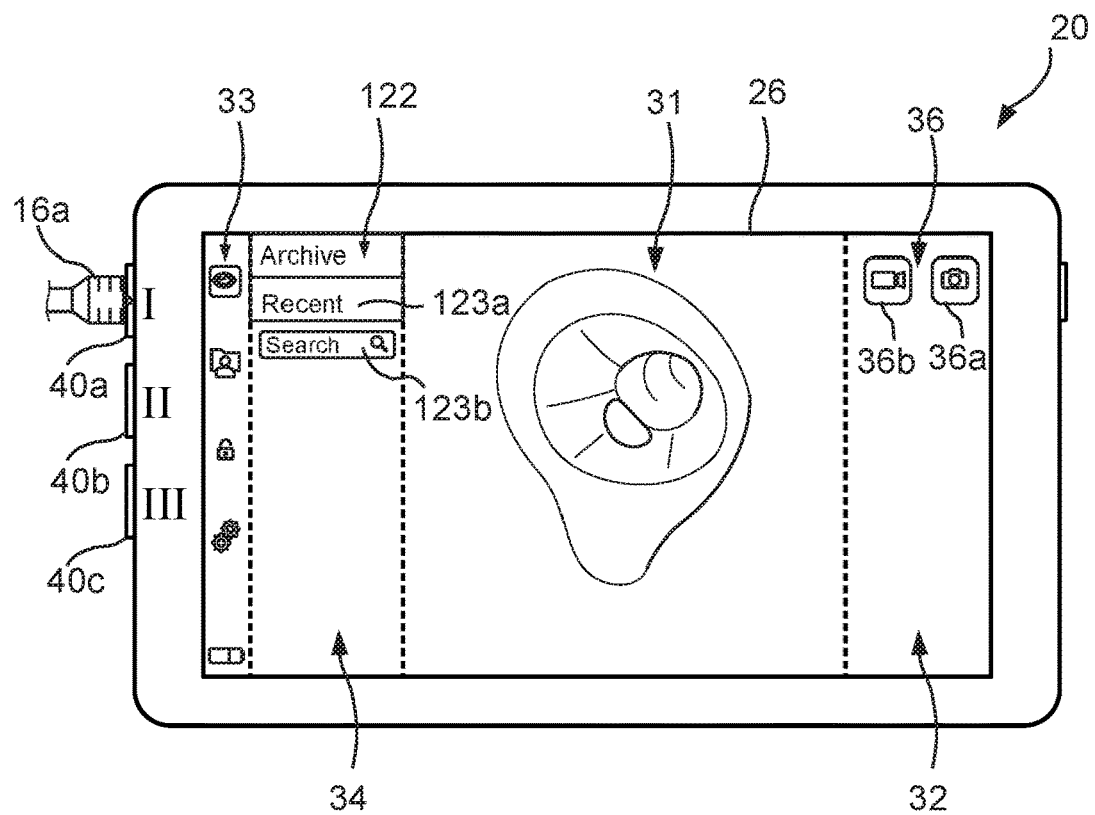

The monitor device 20 detects the primary user input 120 with the touch sensitive display 26, and in response to detecting the first primary user input 120, the monitor device 20 displays a primary menu 122, as illustrated in FIG. 8B. The primary menu 122 is associated with the first actionable menu item 42a. The primary menu 122 is displayed within the fourth portion 34 of the graphical user interface, and without obscuring part of the first portion 31 of the graphical user interface. The primary menu 122 comprises one or more primary actionable items including a first primary actionable item 123a. In the illustrated example, the primary menu 122 is an archive menu with a first primary actionable item 123a to retrieve recent (e.g. recently stored) images and videos, and a second primary actionable item 123b to search for stored images and videos.

Figure 8C:
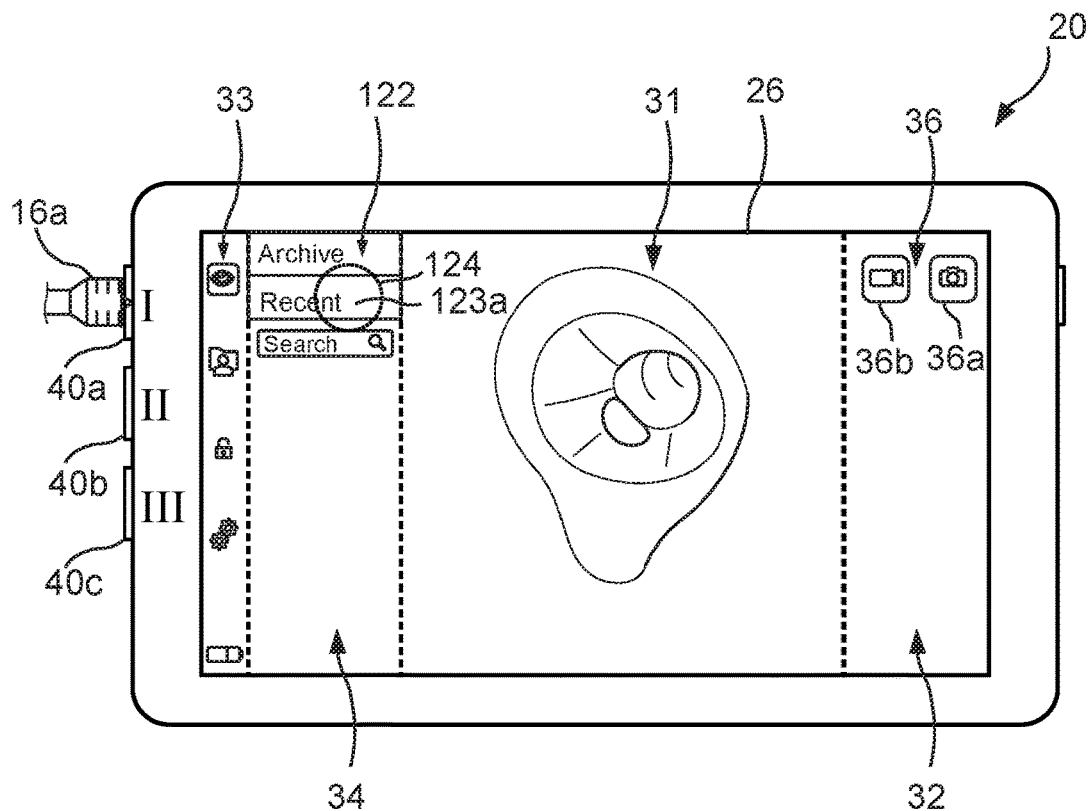
Figure 8D:
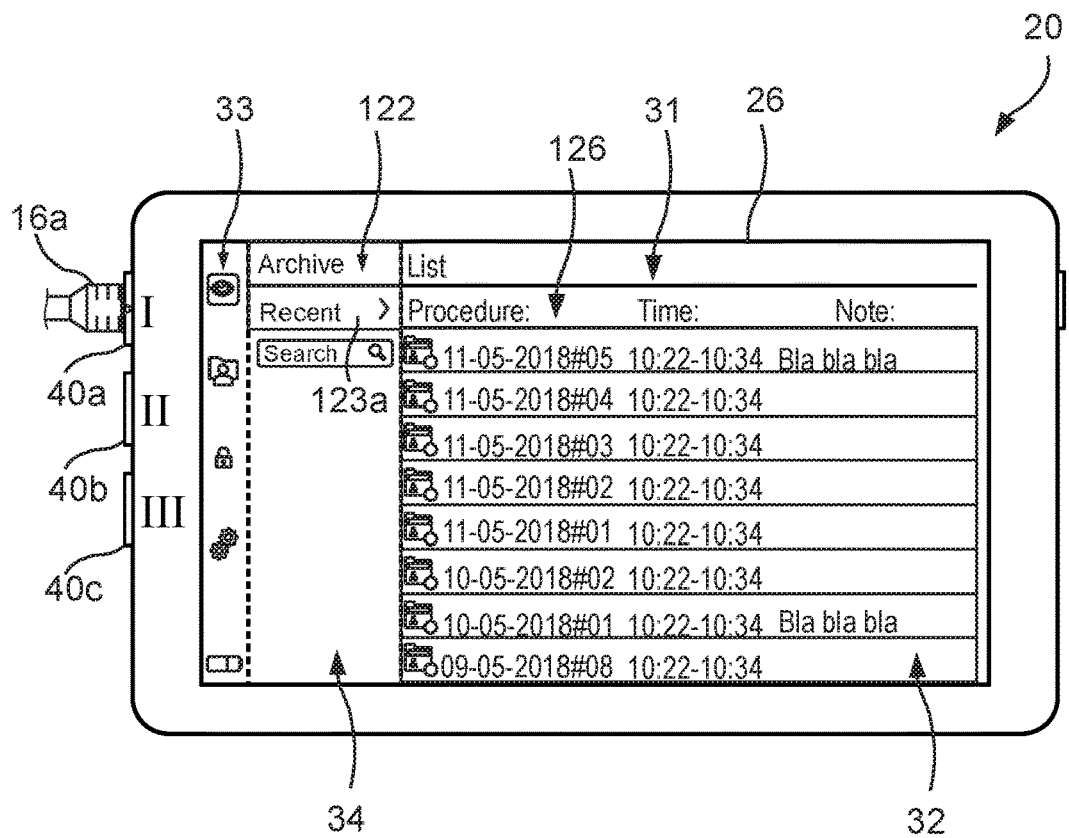

While displaying the primary menu 122, the monitor device 20 may detect with the touch sensitive display 26 a second primary user input 124 corresponding to selection of the first primary actionable item 123a, as illustrated in FIG. 8C. In response to detecting the second primary user input 124, the monitor device displays a secondary menu 126 associated with the primary actionable item 123a in the first portion 31, and optionally the second portion 32, of the graphical user interface, as illustrated in FIG. 8D. Optionally, the secondary menu 126 extends into also the fourth portion 34 of the graphical user interface.

In the illustrated example, the user provides touch input 124 on the first primary actionable item 123a being a button for retrieving recent images and videos (FIG. 8C). In response to detecting the touch input 124 with the touch sensitive display, the monitor device 20 displays the secondary menu 126, in the illustrated example being a list of the recently stored procedures (FIG. 8D), wherefrom the user may navigate to retrieve images and videos stored therein. The list of stored procedures 126 are named according to the date for performing them, and the list 126 shows the timeframe of each procedure and any notes that the user may have added to the procedure.

As seen in FIGS. 8A-8D, the user needs to make two consecutive inputs to display a menu, which covers part of, or the entire live representation of the image data displayed in the first portion 31 of the graphical user interface. Thereby, unintentional touch inputs on the screen is less likely to cause interference with the display of the live representation of the image data, which could potentially be life threatening, in case the operator is performing a critical procedure with the aid of the live representation of the image data. In some examples, the primary menu (e.g. 122 as illustrated in FIG. 8B) being displayed in response to the first primary user input (e.g. 120 as illustrated in FIG. 8A), is ceased to be displayed if a second primary user input (e.g. the second primary user input 124 in FIG. 8C) is not received within a predetermined time from receiving/detecting the first primary user input and/or from displaying the primary menu. Thereby, the likelihood of receiving two unintentional inputs causing the live representation of the image data to be obstructed may be decreased.

Figure 9A:
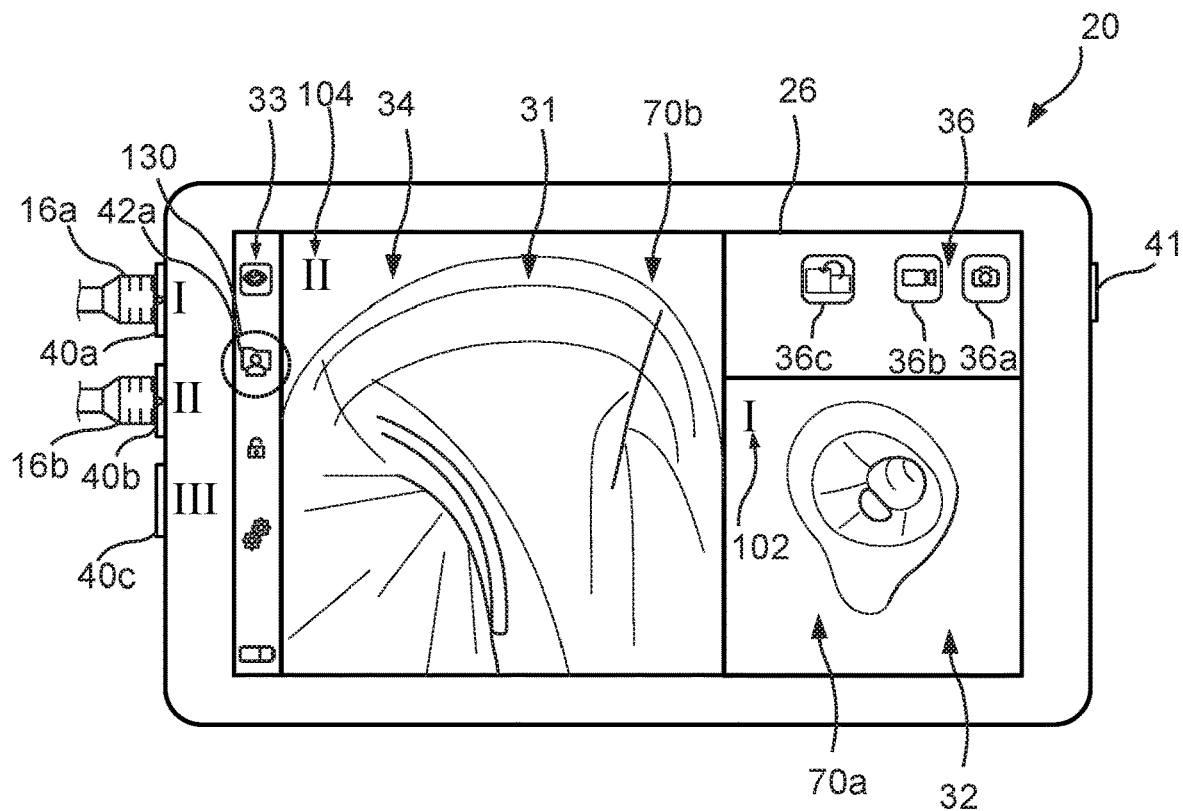
Figure 9B:
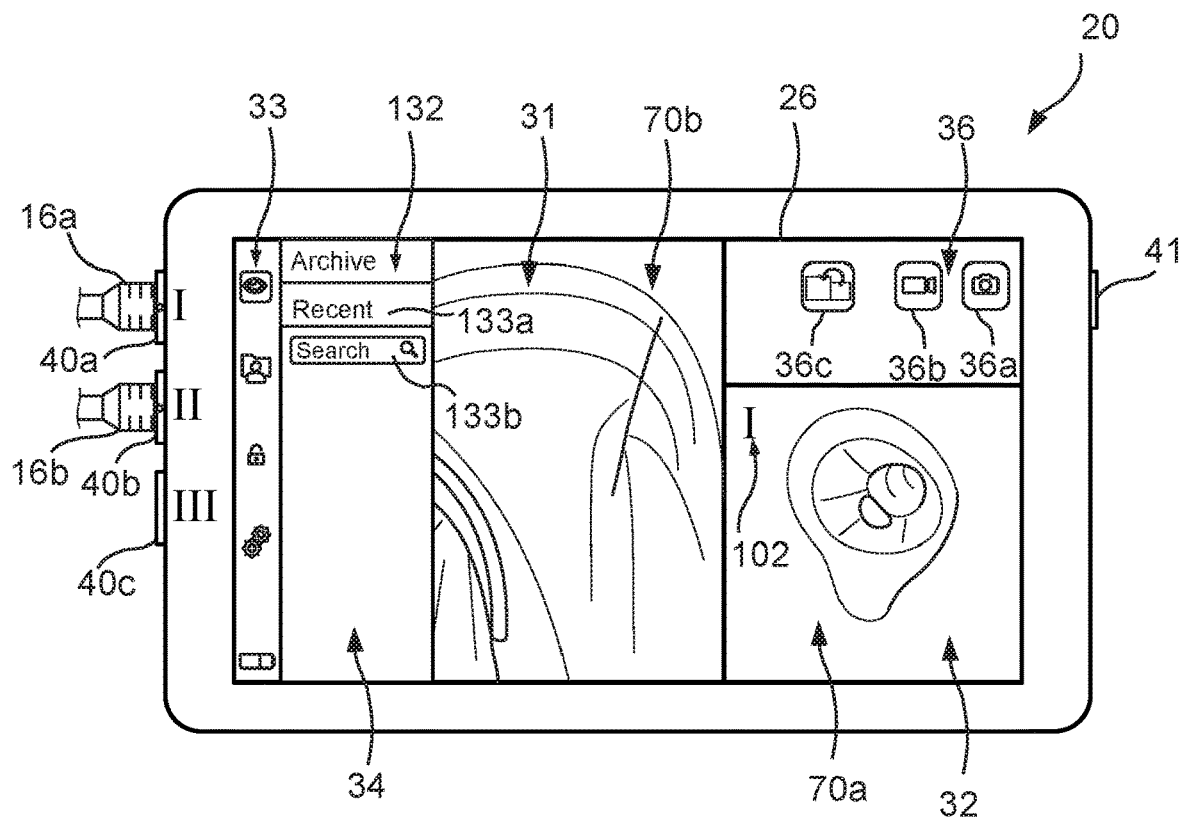

FIGS. 9A-9D schematically illustrate exemplary user interactions with a graphical user interface of a monitor device 20, such as the monitor device 20 of any of the previous figures. FIG. 9A illustrates a situation, which may continue from the situation illustrated in, e.g., FIG. 5C.

FIG. 9A illustrates the monitor device 20 and the graphical user interface in a situation where two visualization devices are connected, and that one live representation, e.g. the second live representation 70b is displayed in the fourth portion 34 of the graphical user interface and extending into the first portion 31, and the first live representation 70a is displayed in the second portion 32 of the graphical user interface and extending into the first portion 31.

As illustrated, the monitor device receives a third user input 130, e.g. corresponding to the first primary user input 120 of FIG. 8A, to an actionable menu item, such as to the first actionable menu item 42a. The monitor device 20 detects the third user input 130 with the touch sensitive display 26, and in response to detecting the third user input 130, the monitor device 20 displays, within the fourth portion 34 of the graphical user interface, the primary menu 132 associated with the actionable menu item receiving the third user input 130. In the present example, the monitor device displays the first primary menu 132 within the fourth portion 34 of the graphical user interface. Because the monitor device 20 is operating in the dual view mode, where live representations of two connected visualization devices are displayed, including displaying a live representation 70b in the fourth portion 34, display of the first primary menu 132 within the fourth portion 34 of the graphical user interface causes a part of the live representation 70b of the image data to be obscured.

The primary menu 132 is associated with the first actionable menu item 42a. The primary menu 132 comprises one or more primary actionable items including a first primary actionable item 133a. In the illustrated example, the primary menu 132 is an archive menu (similar to the primary menu 122 of FIGS. 8B and 8C) with a first primary actionable item 133a to retrieve recent (e.g. recently stored) images and videos, and a second primary actionable item 133b to search for stored images and videos.

Figure 9C:
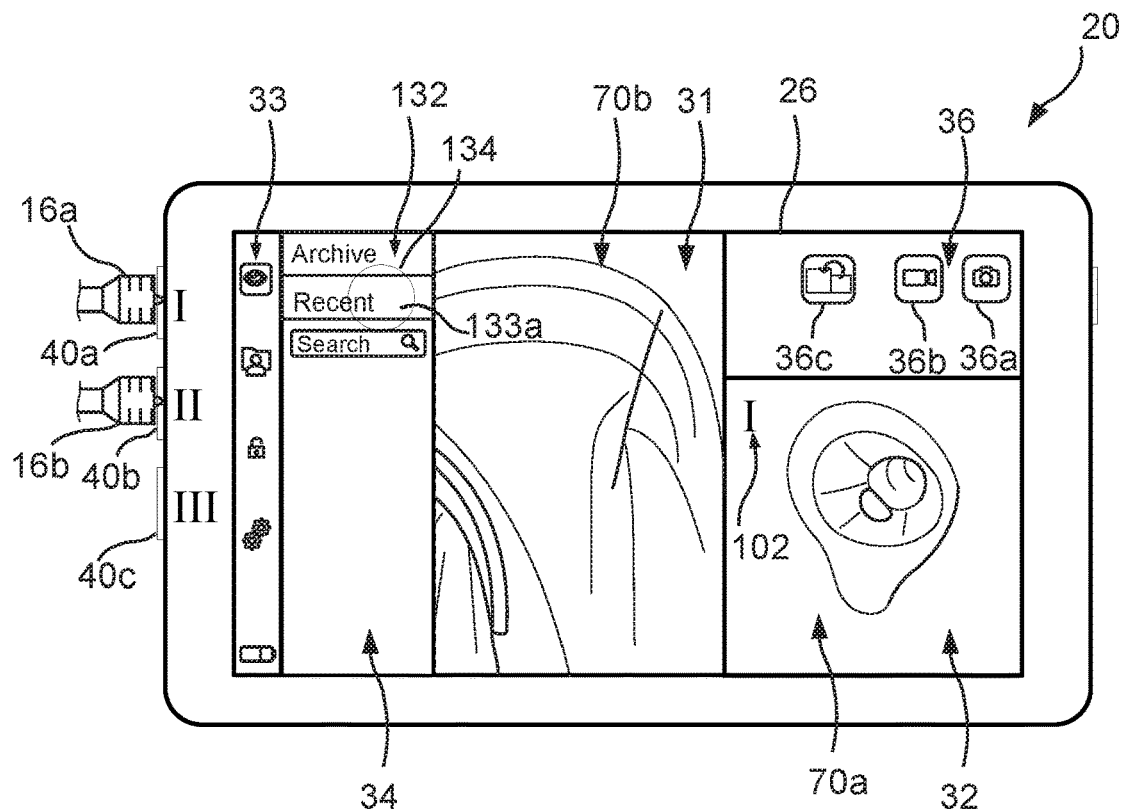
Figure 9D:
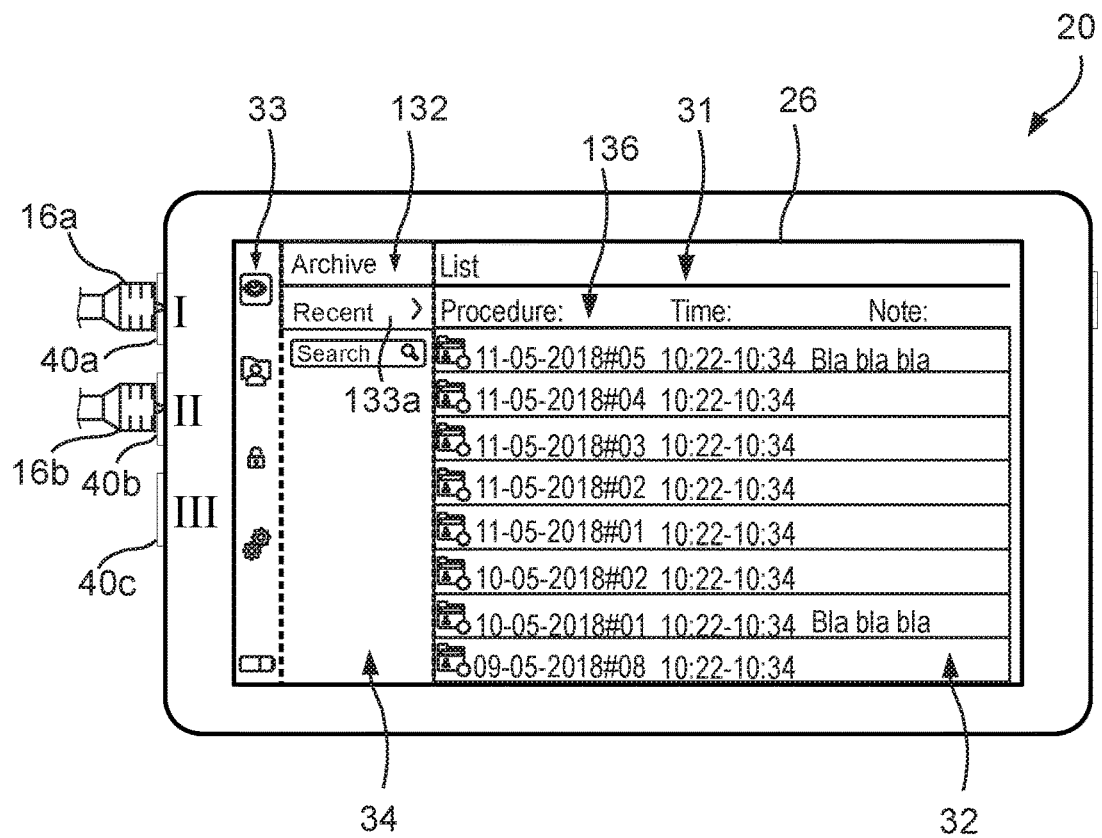

While displaying the primary menu 132, the monitor device 20 may detect with the touch sensitive display 26 a fourth user input 134 corresponding to selection of the first primary actionable item 133a, as illustrated in FIG. 9C, e.g. corresponding to the second primary user input 124 of FIG. 8C. In response to detecting the fourth user input 134, the monitor device displays a secondary menu 136 associated with the primary actionable item 133a in the first portion 31, and optionally the second portion 32, of the graphical user interface, as illustrated in FIG. 9D. Optionally, the secondary menu 136 extends into also the fourth portion 34 of the graphical user interface.

In accordance with not receiving and/or detecting the fourth user input 134, within a threshold amount of time, e.g. 5 seconds, after receipt/detection of the third user input 130, the monitor device may cease display of the primary menu 132 and display the entire live representation 70b of the image data in the fourth portion 34 and extending into the first portion 31 of the graphical user interface. Thus, obscuring part of the live representation 70b of the image data in the dual view mode, may be limited by a timeout. Furthermore, the likelihood of receiving two unintentional inputs causing the live representations 70a 70b to be completely obstructed may be decreased.

Similar to when operating in the normal view mode (FIGS. 8A-8D), the monitor device 20, in the dual view mode (FIGS. 9A-9D), needs to receive two consecutive inputs, e.g. within a time frame, to display a menu, which covers the entire live representation of the image data displayed in the first portion 31 of the graphical user interface.

Additional exemplary embodiments of the foregoing aspect of the present disclosure are set out in the following items:

1. A monitor device of a medical visualization system comprising a plurality of visualization devices each having an image sensor configured to generate image data indicative of a view from the visualization device, the monitor device being operable to receive the image data as the image data is being generated by the image sensors of the plurality of visualization devices,
   the monitor device comprising a first housing extending in a first direction from a first housing side to a second housing side and in a second direction perpendicular to the first direction from a third housing side to a fourth housing side, the monitor device comprising a touch sensitive display accommodated in the first housing and having a first length in the first direction and a second length in the second direction, and the monitor device comprising a graphical user interface comprising a plurality of non-overlapping portions including a first portion, a second portion, a third portion and a fourth portion, wherein the first portion and the fourth portion are arranged between the second portion and the third portion along the second direction, and wherein the fourth portion is arranged between the first portion and the third portion along the second direction, the monitor device displays the graphical user interface with the touch sensitive display,
   wherein the monitor device is adapted to establish connection to a first visualization device of the plurality of visualization devices; and in response to establishing the connection to the first visualization device, the monitor device displays, within the first portion of the graphical user interface, a first live representation of first image data generated by a first image sensor of the first visualization device; and
   wherein the monitor device, while the first visualization device is connected to the monitor device, is further adapted to establish connection to a second visualization device of the plurality of visualization devices, and in response to establishing the connection to the second visualization device the monitor device concurrently displays:
   in the fourth portion and extending into the first portion of the graphical user interface, a second live representation of second image data generated by a second image sensor of the second visualization device; and
   in the second portion and extending into the first portion of the graphical user interface, the first live representation of first image data generated by the first image sensor of the first visualization device, wherein the first live representation is displayed in reduced size compared to the second live representation.

2. Monitor device according to item 1, wherein the monitor device comprises a plurality of connection ports for receiving connectors of the visualization devices, the plurality of connection ports including a first connection port and a second connection port, and wherein to establish connection to the first visualization device a first connector of the first visualization device is received by the first connection port, and to establish connection to the second visualization device a second connector of the second visualization device is received by the second connection port.

3. Monitor device according to any of the preceding items, wherein a first indicator is overlaid on the first live representation, and a second indicator is overlaid on the second live representation.

4. Monitor device according to item 3 as dependent on item 2 wherein the first connection port is labelled with a first port indicator resembling the first indicator and the second connection port is labelled with a second port indicator resembling the second indicator.

5. Monitor device according to any of the preceding items, wherein in response to establishing connection to the second visualization device, the monitor device further displays a rearrange icon and is adapted to detect a first user input corresponding to selection of the rearrange icon, and in response to detection of the first user input the monitor device:
   replaces display of the second live representation in the fourth portion and extending into the first portion of the graphical user interface, with display of the first live representation; and
   replaces display of the first live representation in the second portion and extending into the first portion of the graphical user interface, with display of the second live representation, wherein the second live representation is displayed in reduced size compared to the first live representation.

6. Monitor device according to any of the preceding items, wherein the monitor device displays one or more actionable items within the second portion of the graphical user interface, and wherein the one or more actionable items comprise an image capture button, and wherein the monitor device is adapted to, while the first visualization device and the second visualization device are connected to the monitor device, detect a second user input corresponding to selection of the image capture button, and in response to detection of the second user input the monitor device:

stores a first image file corresponding to the first image data received when the second user input was detected; and stores a second image file corresponding to the second image data received when second user input was detected.

7. Monitor device according to any of the preceding items, wherein establishing connection to the first visualization device includes obtaining first device identifier information from a first device identifier of the first visualization device, and in response to establishing connection to the first visualization device the monitor device opens a first procedure session corresponding to the first device identifier information, and establishing connection to the second visualization device includes obtaining second device identifier information from a second device identifier of the second visualization device, and in response to establishing connection to the second visualization device the monitor device opens a second procedure session corresponding to the second device identifier information.

8. Monitor device according to item 7 as dependent on item 6, wherein in response to detection of the second user input the monitor device:

associates the first image file with the first procedure session; and associates the second image file with the second procedure session.

9. Monitor device according to any of the preceding items, wherein the monitor device displays one or more actionable menu items within the third portion of the graphical user interface, and wherein the monitor device is further adapted to detect a third user input corresponding to selection of a first actionable menu item of the one or more actionable menu items, and in response to detection of the third user input the monitor device displays a primary menu associated with the first actionable menu item within the fourth portion of the graphical user interface obscuring the second live representation in the fourth portion of the graphical user interface, wherein the primary menu comprises one or more primary actionable items including a first primary actionable item, while the primary menu is displayed, the monitor device is adapted to detect a fourth user input corresponding to selection of the first primary actionable item, and in accordance with detecting the fourth user input within a threshold amount of time after detection of the third user input, the monitor device displays a secondary menu associated with the primary actionable item in the first portion, and optionally the second portion and/or the fourth portion, of the touch sensitive display, in accordance with not detecting the fourth user input within the threshold amount of time after detection of the first user input, the monitor device ceases display of the primary menu associated with the first actionable menu item and displays the second live representation in the fourth portion and extending into the first portion of the graphical user interface.

10. Monitor device according to any of the preceding items, wherein the monitor device is adapted to detect disconnection of the first visualization device from the monitor device, and in response to detecting disconnection of the first visualization device from the monitor device, the monitor device displays, within the first portion of the graphical user interface, the second live representation of second image data generated by the second image sensor of the second visualization device.

Battery Monitoring

Figure 10A:
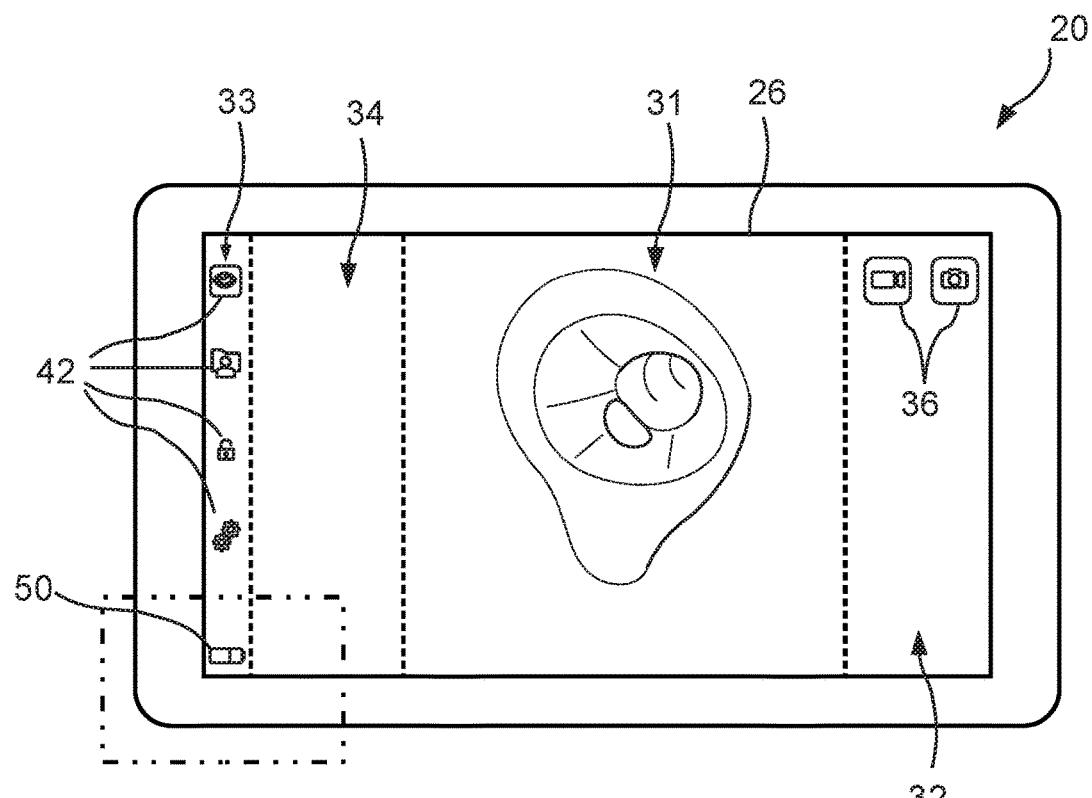
Figure 10B:
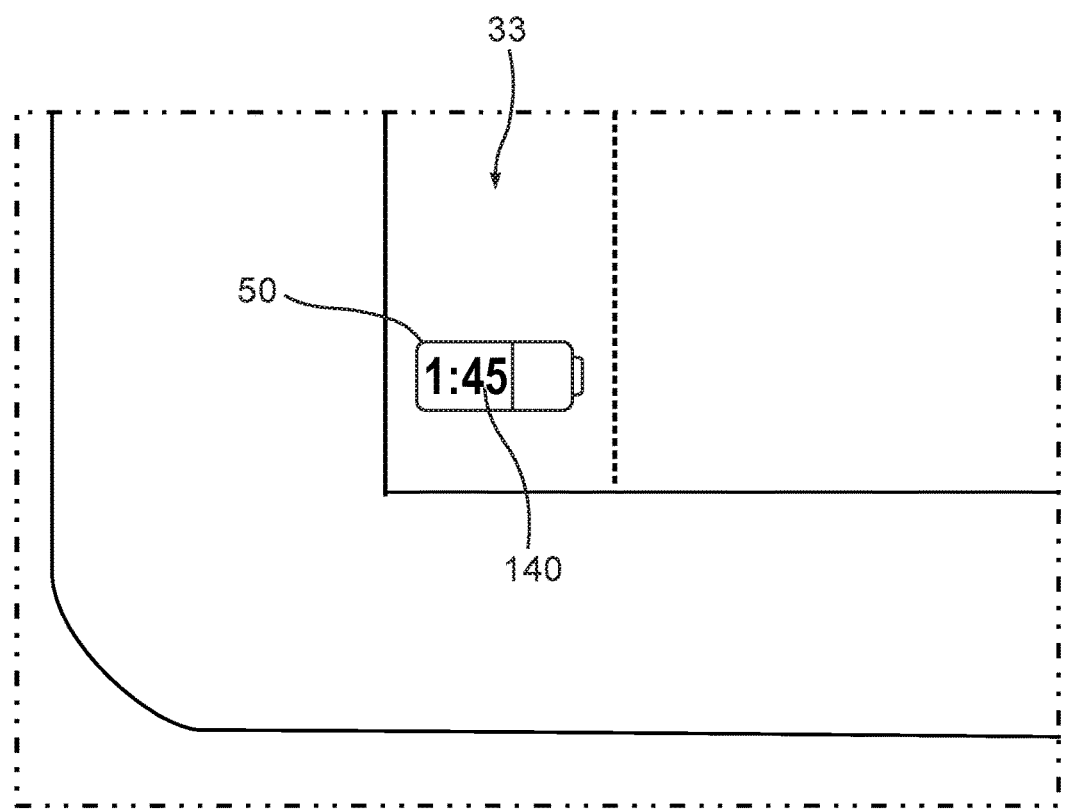

FIG. 10A illustrates an exemplary graphical user interface of a monitor device 20, such as the monitor device 20 of any of the previous figures. FIG. 10B is an enlarged view of a part of the monitor device 20 of FIG. 10A, as illustrated by the dashed rectangle. As illustrated, the monitor device displays a battery indicator 50, e.g. in the third portion 33 of the touch sensitive display 26. The battery indicator 50 may be indicative of a remaining charge of the rechargeable battery 61a of the monitor device 20. For example, the battery indicator 50 comprises a time indicator 100 indicating an expected remaining battery time.

Figure 11A:
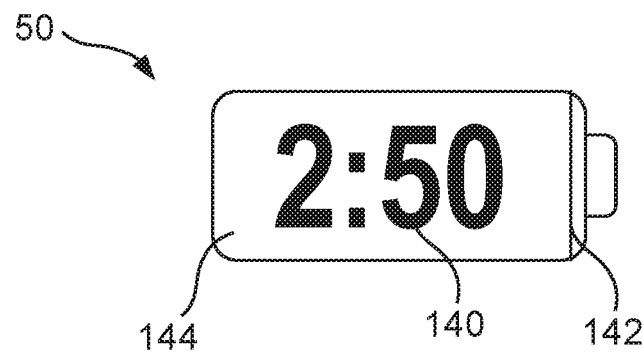
Figure 11B:
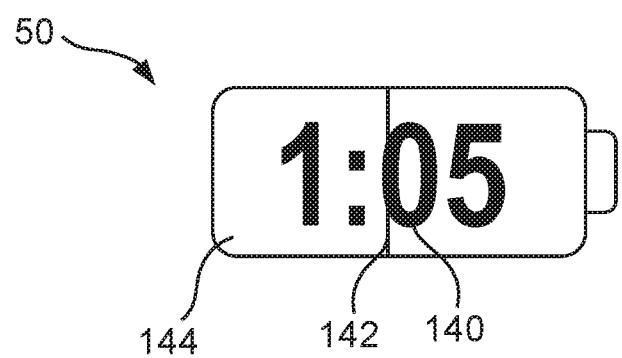
Figure 11C:
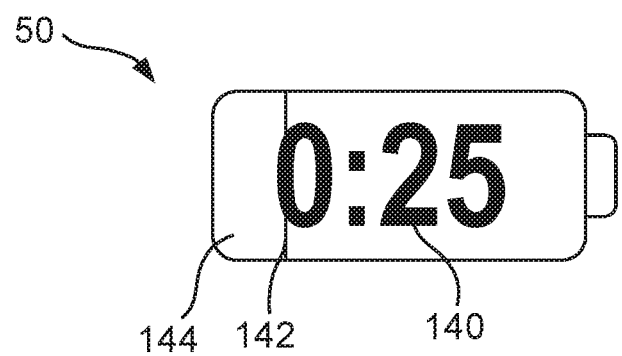

FIGS. 11A-11C schematically illustrate exemplary battery indicators 50. The battery indicator 50 may be displayed in one of a plurality of different states indicative of remaining charge of the rechargeable battery 61a of the monitor device 20. For example, the battery indicator 50 may be displayed in a high power state as exemplified in FIG. 11A, a medium power state as exemplified in FIG. 11B, and a low power state as exemplified in FIG. 11C. The battery indicator 50 comprises a time indicator 100 indicative of expected remaining battery time.

Remaining charge of the rechargeable battery may be estimated based on measuring of the battery voltage. As battery voltage drops capacity decreases. Knowing the characteristics of the rechargeable battery being provided in the monitor device 20, a certain voltage measurement may be used to estimate a certain remaining capacity of the rechargeable battery (e.g. measured in mAh, Ah, Wh or J), although factors, such as temperature, may influence the relationship between measured voltage and remaining capacity.

The expected remaining battery time may be estimated based on a consumption of power (e.g. measured in A or W). Dividing the remaining capacity (e.g. J) with the consumption of power (e.g. \N) yields the expected remaining battery time.

The consumption of power used to calculate the expected remaining battery time, may be a measured consumption of power. For example, a component, e.g. of the power unit 61, may measure the present power consumption of the monitor device 20. The power unit 61 and/or the processing unit 60 may average the power consumption over a certain time frame, e.g. the previous 10 minutes. Alternatively or additionally, the consumption of power used to calculate the expected remaining battery time, may be a set value, or at least include a set value. For example, the consumption of power may be set to the power consumption the monitor device 20 is known to have in certain conditions. Such values may be found empirically. For example, the consumption of power used to calculate the expected remaining battery time may be set to an expected power consumption, e.g. corresponding to a consumption, e.g. empirically established, of the monitor device 20 with a single visualization device being connected.

The expected remaining battery time, indicated by the battery indicator 50, may be calculated based on whether or not the visualization device 4 is connected to the monitor device 10. For example, in accordance with the visualization device not being connected to the monitor device, the expected remaining battery time may be based on expected power consumption with the visualization device being connected, and in accordance with the visualization device being connected to the monitor device, the expected remaining battery time may be based on a measured power consumption.

The high power state (FIG. 11A) may be displayed when the battery capacity is more than 40% and/or if the expected remaining battery time is more than a high threshold amount of time, e.g. between 1:00 (hours:mins) and 1:20, such as 1:12. The medium power state (FIG. 11B) may be displayed when the battery capacity is between 20-40% and/or if the expected remaining battery time is more than a low threshold amount of time and less than the high threshold amount of time. The low threshold amount of time may, e.g., be between 30 and 40 minutes, such as 36 minutes. The low power state (FIG. 11C) may be displayed when the battery capacity is less than 20% and/or less than the low threshold amount of time. The low threshold amount of time may be substantially equivalent to an expected time for a typical procedure using the medical visualization system. Such expected time for a typical procedure may be empirically established. The inventors have found this to be about 36 minutes.

As illustrated in FIGS. 11A-11C, when the expected remaining battery time decreases a battery level indicator 102 is moved to visually indicate the relative remaining battery capacity. Furthermore, the battery indicator 50, such as a part 104 of the battery indicator may change colour depending on the state of battery indicator. For example, in the high power state as exemplified in FIG. 11A, the battery indicator 50 and/or the part 104 of the battery indicator 50 may be displayed in green. In the medium power state as exemplified in FIG. 11B, the battery indicator 50 and/or the part 104 of the battery indicator 50 may be displayed in yellow. In the low power state as exemplified in FIG. 11C, the battery indicator 50 and/or the part 104 of the battery indicator 50 may be displayed in red.

Figure 12A:
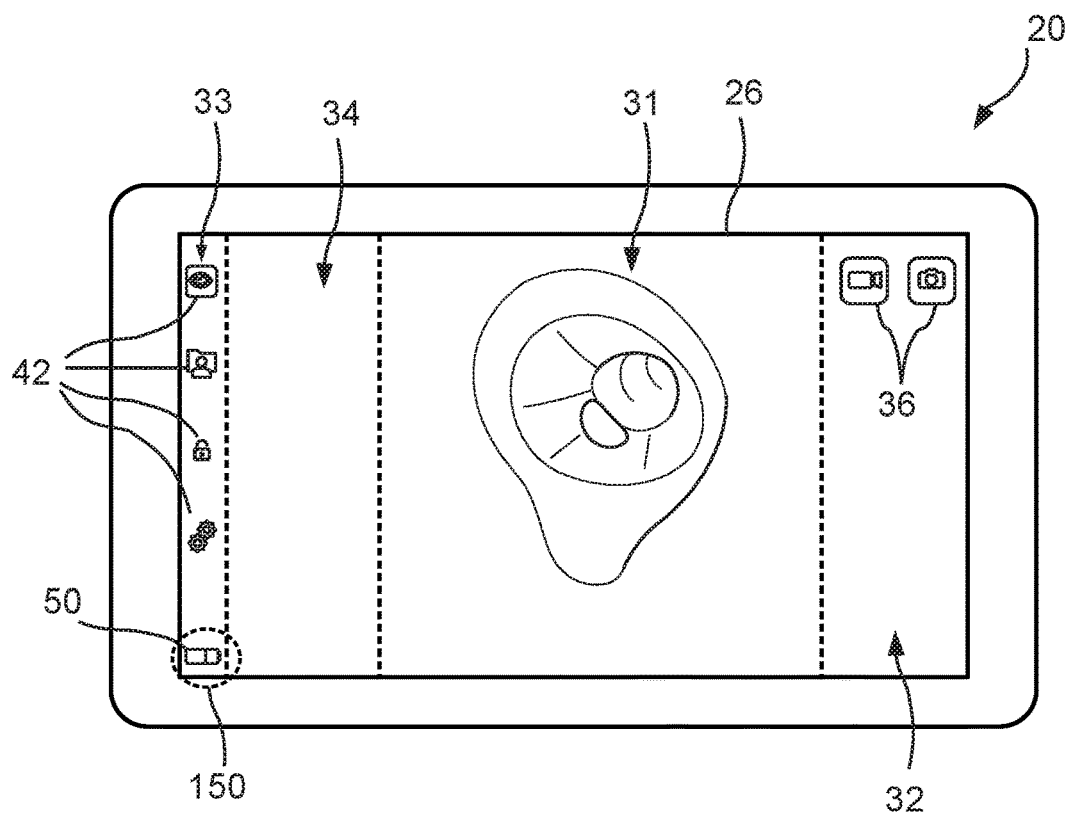
Figure 12B:
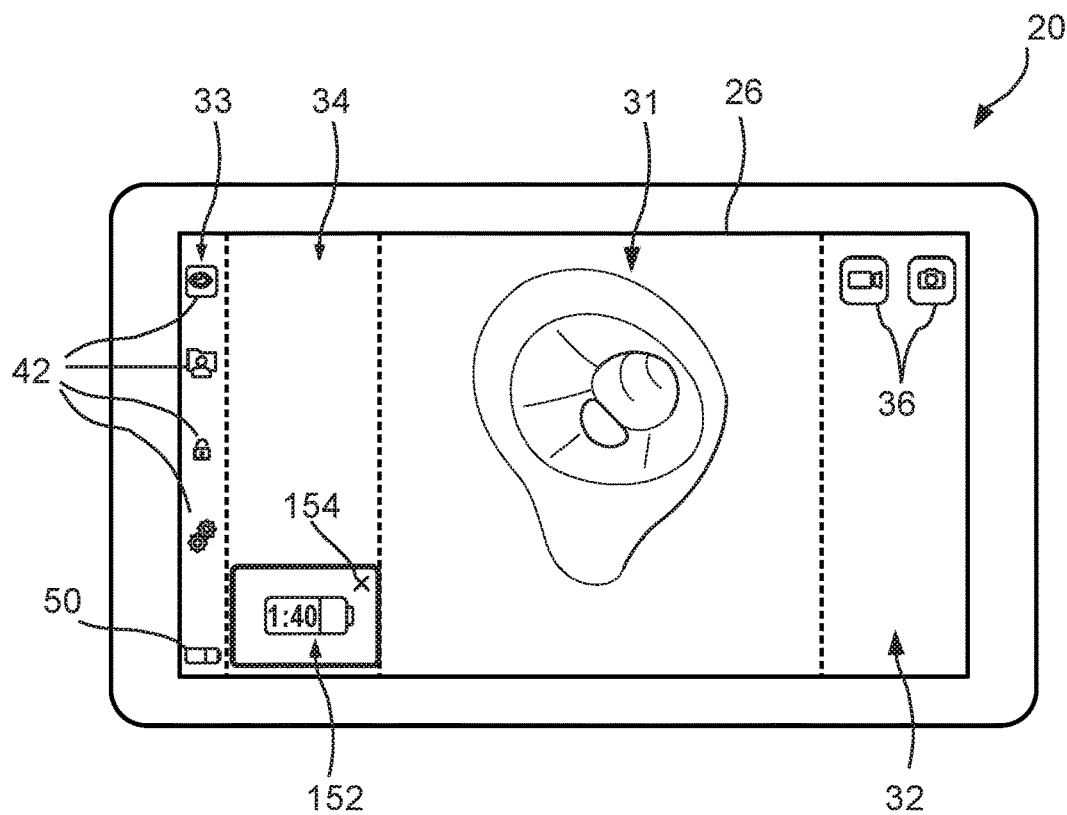

FIGS. 12A-12B illustrate an exemplary graphical user interface of the monitor device 20, such as the same graphical user interface as described with respect to FIG. 10A. In FIG. 12A a user provides an input 150 to the battery indicator 50, e.g. the user provides a touch input 150 on the touch sensitive display 26 at the location corresponding to the battery indicator 50. The monitor device 20 detects the user input 150 with the touch sensitive display 26, and in response, as illustrated in FIG. 12B, an enlarged rendering 152 of the battery indicator 50 is displayed in the fourth portion 34 of the graphical user interface. Display of the enlarged rendering 152 may be ceased after a duration of time, e.g. 5 seconds after the monitor device detected the touch input 150. Alternatively, the user may manually close the enlarged rendering 152 by providing a touch input at the location of the cross 154 of the window containing the enlarged rendering 152.

The enlarged rendering 152 of the battery indicator 50 may also be displayed in accordance with the expected remaining battery time being less than the low threshold amount of time. For example, in response to the expected remaining battery time dropping below the low threshold amount of time, the enlarged rendering 152 of the battery indicator 50 may be displayed. The processing unit 60 may comprise instructions for updating the expected remaining battery time, and in response to a determination that the remaining battery time drops below the low threshold amount of time, the processing unit 60 may cause display of the enlarged rendering 152 of the battery indicator 50 on the touch sensitive display, e.g. within the fourth portion of the graphical user interface.

Figure 13A:
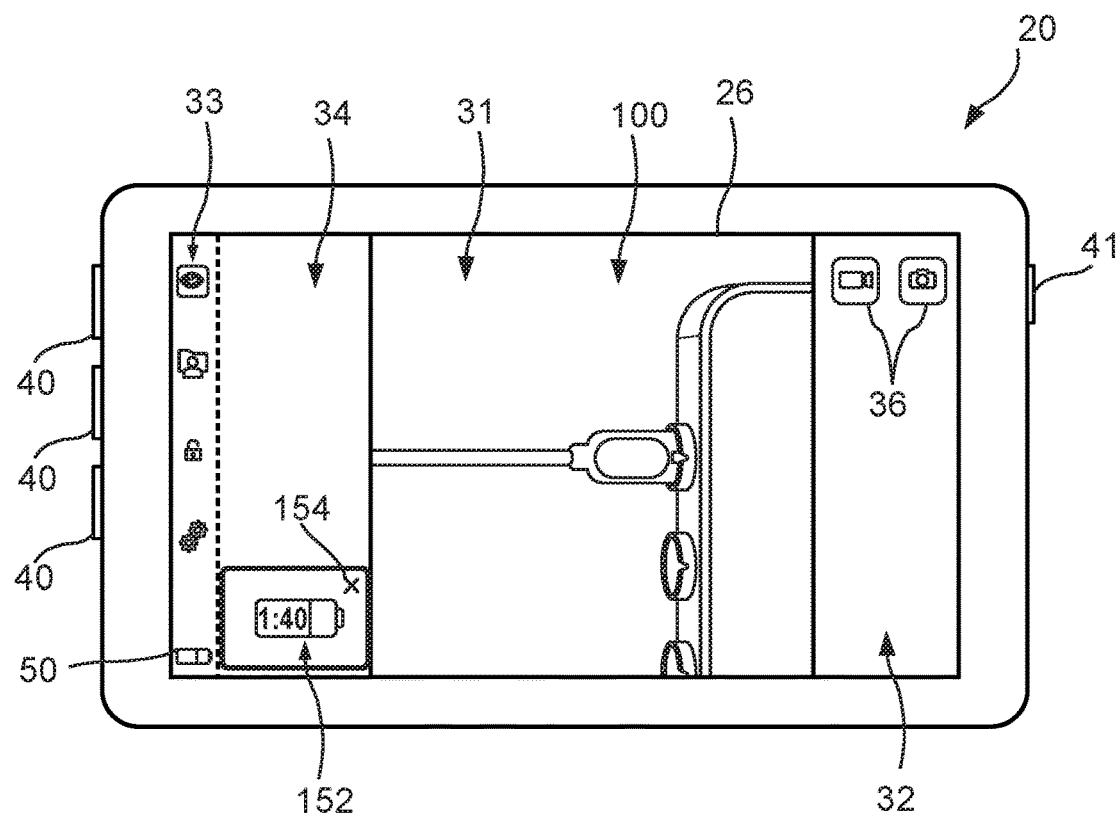

FIGS. 13A-8D schematically illustrate an exemplary graphical user interface of a monitor device 20, such as the monitor device 20 of any of the previous figures. Particularly, FIGS. 13A-13D illustrate that different content is displayed within the first portion 31 of the graphical user interface in accordance with whether a visualization device is connected and depending on the expected remaining battery time.

FIG. 13A schematically illustrates an exemplary graphical user interface of a monitor device 20, wherein a visualization device is not connected to the monitor device 20, and wherein the expected remaining battery time is more than the low threshold amount of time. For example, this situation may correspond to a situation where a user initially powers on the device, e.g. by pressing the on/off button 41. In this situation, based on that no visualization device is connected and that the expected remaining battery time is more than the low threshold amount of time, the animation 100 of connecting the visualization device to the monitor device 20 is displayed within the first portion 31 of the graphical user interface.

As also illustrated in FIG. 13A, an enlarged rendering 152 of the battery indicator 50 is displayed in the fourth portion 34 of the graphical user interface. The enlarged rendering 152 of the battery indicator 50 may be displayed in response to the monitor device 20 being turned on, notifying the user of the measured battery capacity, e.g. to let the user decide whether he/she wants to proceed with using the monitor device for the upcoming procedure. Display of the enlarged rendering 152 may be ceased after a duration of time, e.g. 5 seconds after the monitor device has been turned on. Alternatively, the user may manually close the enlarged rendering 152 by providing a touch input at the location of the cross 154 of the window containing the enlarged rendering 152.

Figure 13B:
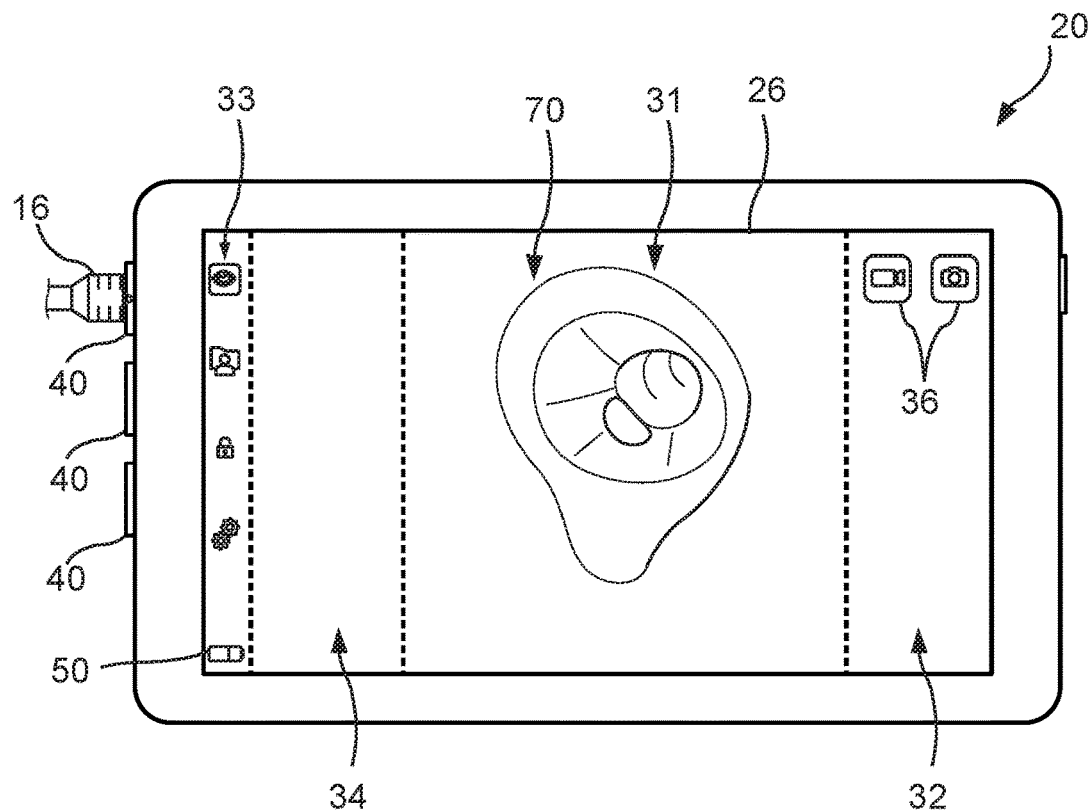

FIG. 13B schematically illustrates an exemplary graphical user interface, e.g. following the graphical user interface as shown in FIG. 13A. In FIG. 13B, a visualization device has been connected to the monitor device 20 by connecting the device connector 16 of the visualization device to a connection port 40 of the monitor device 20. In this situation, because a visualization device is connected, the live representation 70 of the image data is displayed within the first portion 31 of the graphical user interface.

Figure 13C:
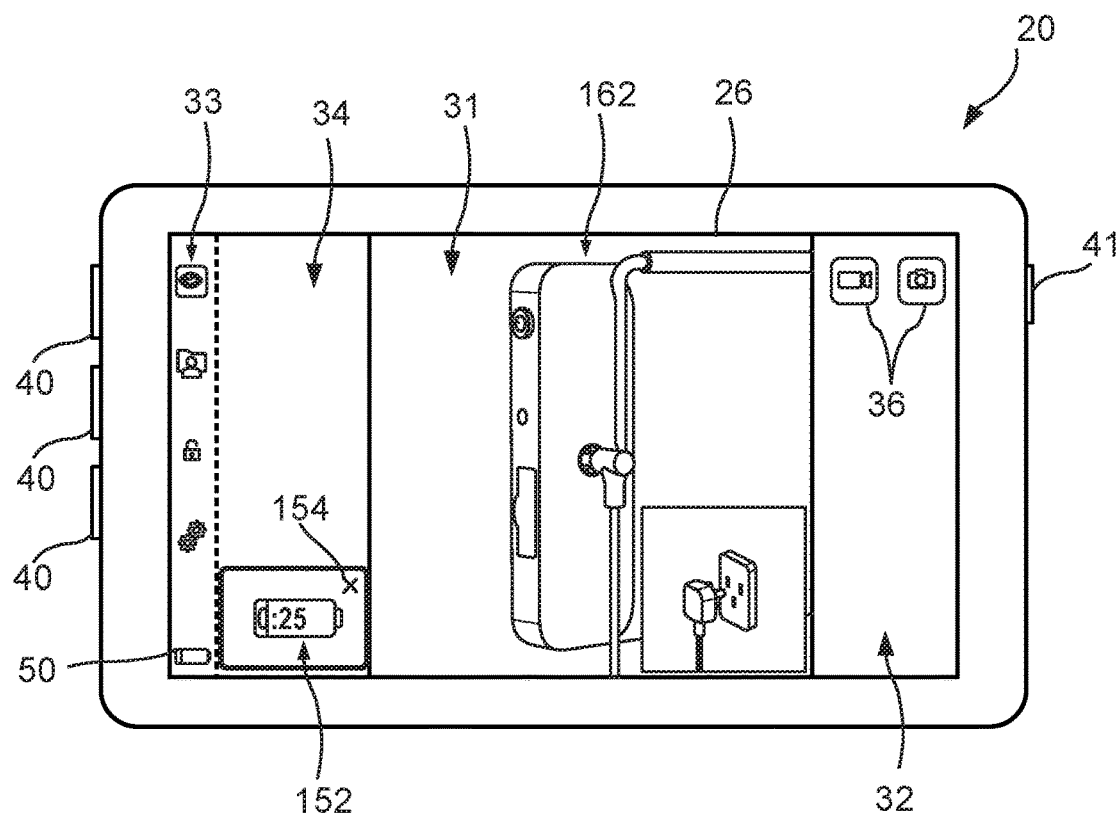

FIG. 13C schematically illustrates another example, similar to the example described with respect to FIG. 13A, wherein no visualization device is connected to the monitor device 20. However, in FIG. 13C, the expected remaining battery time is less than the low threshold amount of time. In this situation, instead of displaying the animation 100 of connecting the visualization device to the monitor device within the first portion 31 of the graphical user interface, as illustrated in FIG. 13A, an animation 162 of connecting the external power supply to the power connection is displayed within the first portion of the graphical user interface. Furthermore, in accordance with the expected remaining battery time being less than the low threshold amount of time, the on/off button 41 of the monitor device 20 may be flashing.

Figure 13D:
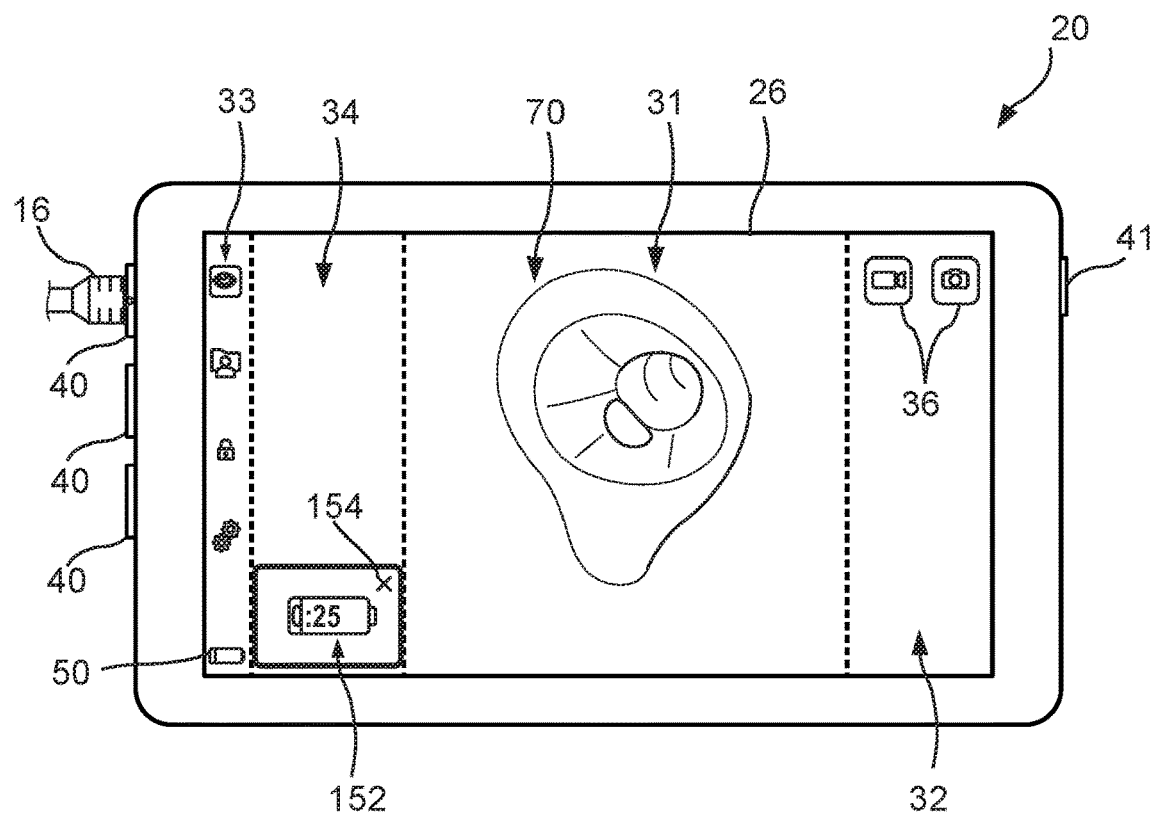

FIG. 13D schematically illustrates an exemplary graphical user interface, e.g. following the graphical user interface as shown in FIG. 13C. In FIG. 13D, a visualization device has been connected to the monitor device 20 by connecting the device connector 16 of the visualization device to the connection port 40 of the monitor device 20. In this situation, because a visualization device is connected, the live representation 70 of the image data is displayed within the first portion 31 of the graphical user interface, even though the expected remaining battery time is less than the low threshold amount of time. In this situation, the on/off button 41 may continue flashing. Optionally, the enlarged rendering 152 of the battery indicator 50 may be displayed until the user actively closes it by providing a touch input at the location of the cross 154 of the window containing the enlarged rendering 152.

Additional exemplary embodiments of the foregoing aspect of the present disclosure are set out in the following items:

1. A monitor device for a medical visualization system comprising a visualization device having an image sensor configured to generate image data indicative of a view from the visualization device,
   the monitor device being operable to receive the image data as the image data is being generated by the image sensor, the monitor device comprising a display, a graphical user interface and a power unit for powering the monitor device, the power unit comprising a rechargeable battery and a power connection for being connected to an external power supply, the monitor device displays the graphical user interface with the display,
   wherein the monitor device displays with the display a live representation of the image data within a first portion of the graphical user interface with the display, and the monitor device displays a battery indicator indicative of a remaining charge of the rechargeable battery, wherein the battery indicator indicates an expected remaining battery time, wherein:
   in accordance with the visualization device not being connected to the monitor device, the expected remaining battery time is based on expected power consumption with the visualization device being connected, and
   in accordance with the visualization device being connected to the monitor device, the expected remaining battery time is based on a measured power consumption.
2. Monitor device according to item 1, wherein the battery indicator is displayed in one of a plurality of different states indicative of remaining charge of the rechargeable battery, and wherein, in accordance with the expected remaining battery time being less than a low threshold amount of time, the battery indicator is displayed in a low battery power state, wherein the low threshold amount of time is substantially equivalent to an expected time for a typical procedure using the medical visualization system.
3. Monitor device according to item 2, wherein, in accordance with the expected remaining battery time being less than the low threshold amount of time, the monitor device displays an enlarged rendering of the battery indicator.
4. Monitor device according to any of items 2-3, wherein:
   in accordance with the visualization device being connected to the monitor device the live representation of the image data is displayed within the first portion of the graphical user interface; and
   in accordance with the visualization device not being connected to the monitor device:
   in accordance with the expected remaining battery time being more than the low threshold amount of time, an animation of connecting the visualization device to the monitor device is displayed within the first portion of the graphical user interface; and
   in accordance with the expected remaining battery time being less than the low threshold amount of time, an animation of connecting the external power supply to the power connection is displayed within the first portion of the graphical user interface.
5. Monitor device according to any of items 2-4, wherein, in accordance with the expected remaining battery time being less than the low threshold amount of time, flashing an on/off button of the monitor device.
6. Monitor device according to any of items 2-5, wherein the low battery power state comprises a red colored part of the battery indicator.
7. Monitor device according to item 2-6, wherein, in accordance with the expected remaining battery time being more than the low threshold amount of time and less than a high threshold amount of time, the battery indicator is displayed in a medium battery power state.
8. Monitor device according to item 7, wherein the medium battery power state comprises a yellow colored part of the battery indicator.
9. Monitor device according to item 2-8, wherein, in accordance with the expected remaining battery time being more than the high threshold amount of time, the battery indicator is displayed in a high battery power state.
10. Monitor device according to item 9, wherein the high battery power state comprises a green colored part of the battery indicator.
11. Monitor device according to any of the preceding items, wherein in accordance with the visualization device being connected to the monitor device and a second visualization device being connected to the monitor device, the expected remaining battery time is based on the measured power consumption.
12. Monitor device according to any of the preceding items, wherein the battery indicator is displayed within a third portion of the graphical user interface, the third portion and the first portion being non-overlapping.
13. Monitor device according to item 12, wherein one or more actionable menu items is displayed within the third portion of the graphical user interface.
14. Monitor device according to any of the preceding items, wherein, in response to the monitor device being turned on, an enlarged rendering of the battery indicator is displayed, and, after a first duration of time after the monitor device has been turned on, display of the enlarged rendering of the battery indicator is ceased.
15. A medical visualization system comprising a visualization device having an image sensor configured to generate image data indicative of a view from the visualization device, and a monitor device according to any of the preceding items.

Rotational User Interface

Figure 14:
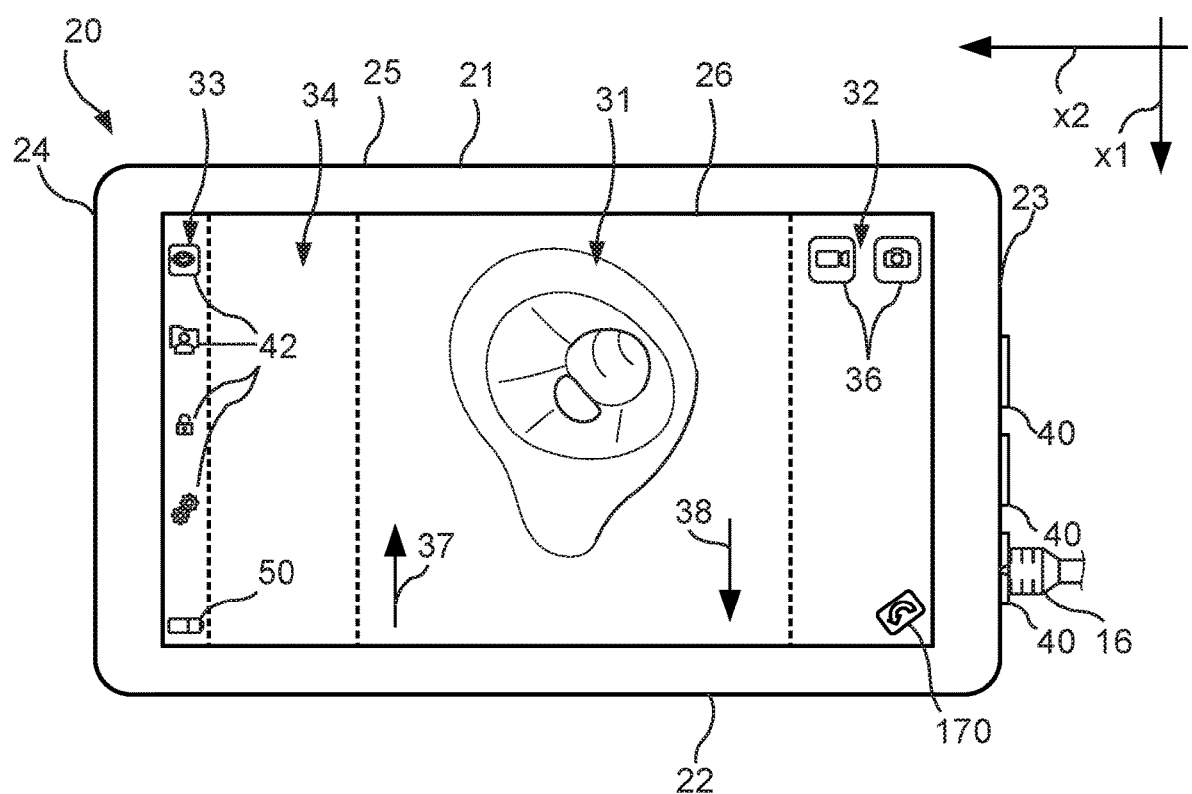
FIG. 14 illustrates an exemplary monitor device, FIGS. 15A and 15B schematically illustrate a monitor device.

FIG. 14 illustrates an exemplary monitor device 20, such as the monitor device 20 of the previous figures, wherein the monitor device 20, such as the first housing 25 of the monitor device 20, has been rotated 180 degrees relative to the monitor device 20 of FIGS. 2-3, such that the second housing side 22 is now downwards and the first housing side 21 is upwards. By rotating the monitor device 20 and/or the first housing 25 180 degrees the second direction x2 of the first housing 25 is in FIG. 14 from right to left whereas in the FIGS. 2-3, the second direction x2 was from left to right. Similarly, by rotating the first housing 25 the first direction x1 of the first housing 25 is in FIG. 14 downwards whereas in the FIGS. 2-3, the first direction x1 was upwards.

To enhance operability of the monitor device 20, the monitor device 20 may operate a first interface orientation mode, as illustrated in FIG. 3, and a second interface orientation mode, as illustrated in FIG. 14. As illustrated in FIG. 3, in the first interface orientation mode, the second portion 32 is between the fourth housing side 24 and the first portion 31, and the third portion 33 is between the third housing side 23 and the first portion 31. As illustrated in FIG. 14, in the second interface orientation mode, the second portion 32 is between the third housing side 23 and the first portion 31, and the third portion 33 is between the fourth housing side 24 and the first portion 31.

The monitor device 20 may change between the first interface orientation mode and the second interface orientation mode based on a value of a manual setting. For example, the user may press an invert interface button 170, e.g. displayed with the touch sensitive display 26, e.g. in a settings menu, or being a hardware button. The monitor device 20 may change between the first interface orientation mode and the second interface orientation mode upon activation of the invert interface button 170. The processing unit 60 of the monitor device 20 may determine that the user has tapped the touch sensitive display 26 at the position corresponding to the invert interface button 170 and in response change between the first interface orientation mode and the second interface orientation mode.

Alternatively or additionally, the monitor device 20 may comprise an orientation sensor 64 (see FIG. 4), e.g. accommodated in the first housing 25, and the monitor device 20 may change between the first interface orientation mode and the second interface orientation mode based on input from the orientation sensor 64. For example, the first housing 25 may be oriented in a first orientation, e.g. as illustrated in FIG. 3, wherein the first direction is upwards. The monitor device 20 may operate in the first interface orientation mode, as illustrated in FIG. 3, when being oriented in the first orientation, e.g. based on an orientation signal received from the orientation sensor. For example, the processing unit 60, based on the orientation signal received from the orientation signal, may determine the orientation of the first housing 25 and change between the first interface orientation mode and the second interface orientation mode, accordingly. Similarly, the first housing 25 may be oriented in a second orientation, e.g. as illustrated in FIG. 14, wherein the first direction is downwards. The monitor device 20 may operate in the second interface orientation mode, as illustrated in FIG. 14, when being oriented in the second orientation. In the first orientation, the connection ports 40 may be on the left side of first housing 25. In the second orientation, the connection ports 40 may be on the right side of the first housing 25. Alternatively, in the first orientation, the connection ports 40 may be on the right side of first housing 25. In the second orientation, the connection ports 40 may be on the left side of the first housing 25.

As explained above (see FIG. 1), the visualization device 2 may comprise a control button 7 configured to cause a movement of the image sensor 12 corresponding to a first image direction 37 and/or a second image direction 38 of the live representation. The first image direction 37 and the first direction x1 may be the same in the first interface orientation mode (cf. FIG. 3). The first image direction 37 and the first direction x1 may be opposite in the second interface orientation mode (cf. FIG. 14).

Figure 15A:
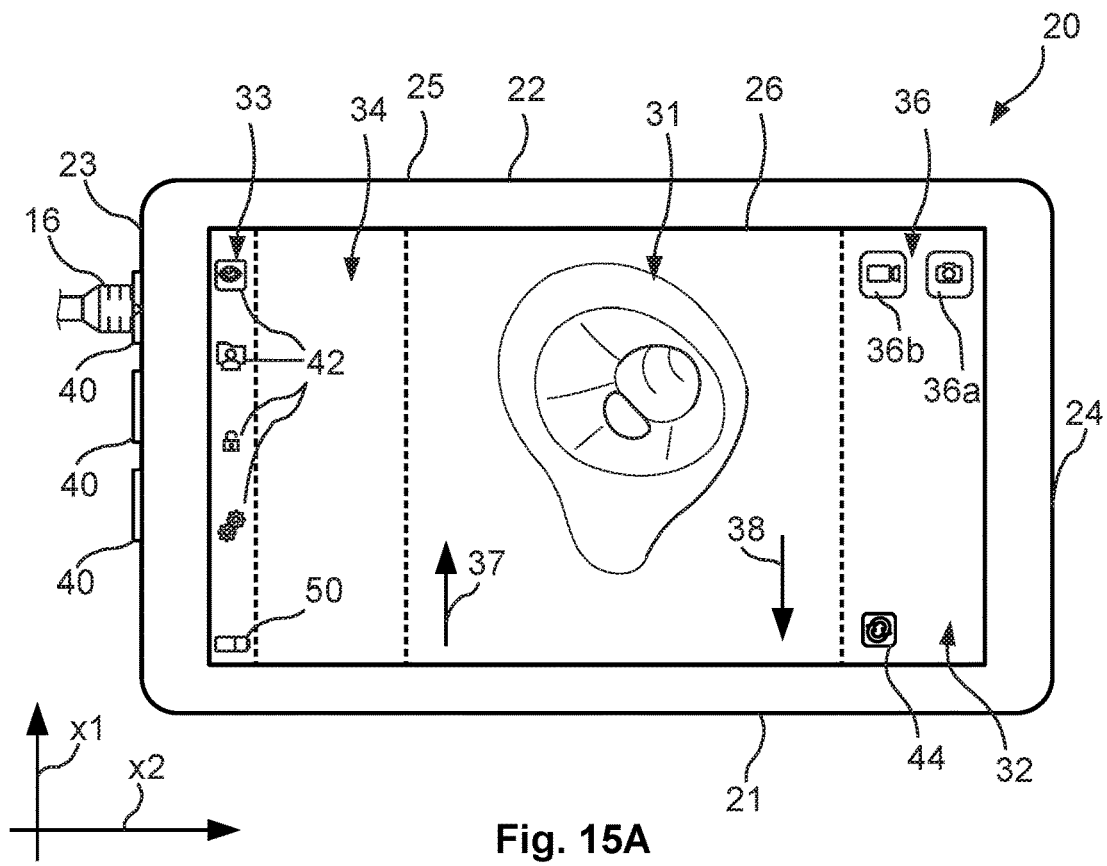
Figure 15B:
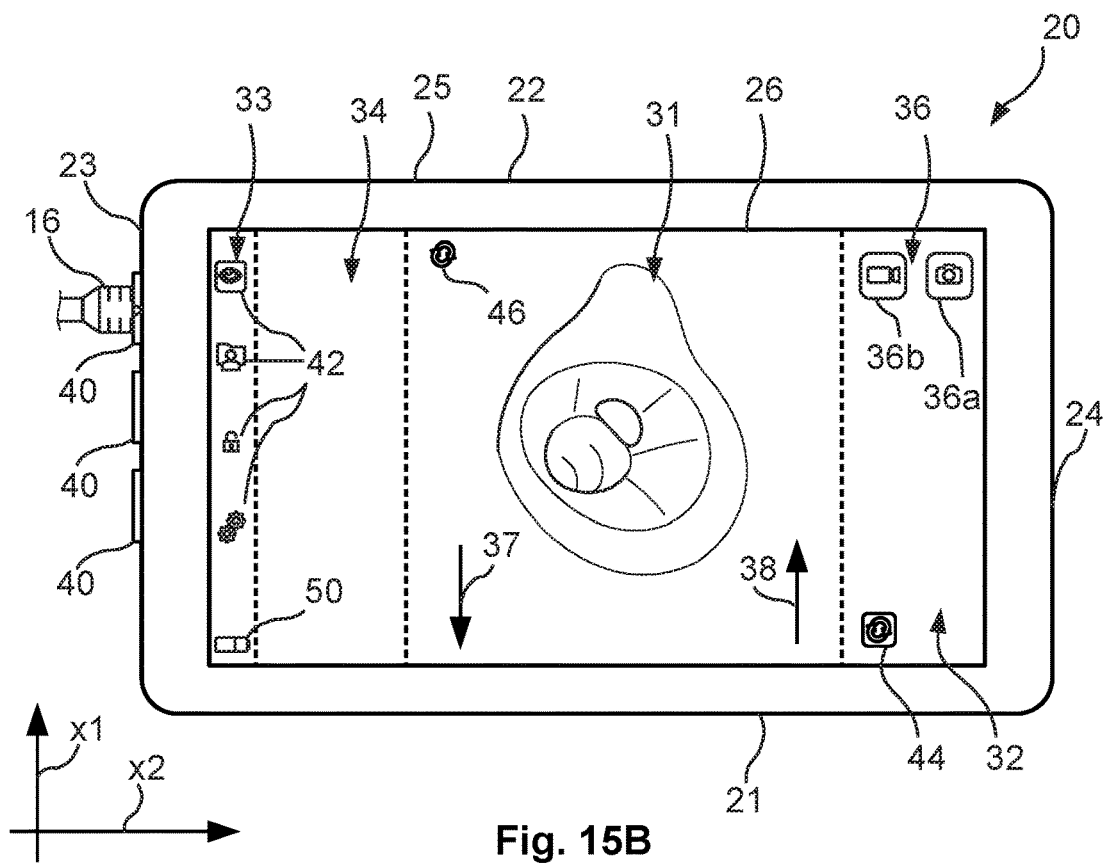

FIGS. 15A and 15B schematically illustrate a monitor device 20, such as the monitor device 20 of any of the previous figures. The first housing 25 of the monitor device 20 is in FIGS. 15A and 15B shown in the first orientation, as described above.

The monitor device 20 may operate a default view mode, e.g. as illustrated in FIG. 15A, and an inverted view mode, e.g. as illustrated in FIG. 15B. The orientation of the live representation within the first portion 31 is rotated 180 degrees when changing between the default view mode and the inverted view mode. In the default view mode (FIG. 15A) the first image direction 37 and the first direction x1 are the same, e.g. when the monitor device 20 operates the first interface orientation mode, e.g. when the first housing 25 is in the first orientation; as illustrated. In the inverted view mode (FIG. 15B) the first image direction 37 and the first direction x1 are opposite, e.g. when the monitor device 20 operates the first interface orientation mode, e.g. when the first housing 25 is in the first orientation; as illustrated.

If the monitor device 20, in contrast to the examples of FIGS. 15A and 15B, operates the second interface orientation mode, e.g. as illustrated in FIG. 14, the first image direction 37 and the first direction x1 are the same, in the inverted view mode; and the first image direction 37 and the first direction x1 are opposite, in the default view mode.

In the inverted view mode (FIG. 15B) an inverted view mode indicator 46 may be displayed in the first portion 31, e.g. overlaying a portion of the live representation. The inverted view mode indicator 46 may be partly transparent to reduce obstruction of the live representation.

In the inverted view mode (FIG. 15B) a stored image data file, e.g. stored in response to the user activating the image capture button 36a of the actionable items 36, and/or a stored video sequence of image data, e.g. stored in response to the user activating the video capture button 36b of the actionable items 36, may be saved with information, e.g. metadata or a watermark, indicative of the monitor device 20 having operated in the inverted view mode when the respective actionable item 36, image capture button or video capture button, was activated.

The user may change between the default view mode and the inverted view mode by activating the invert view button 44. In some exemplary monitor devices, the invert view button 44 may be accessible from a settings menu. The monitor device 20 may display, with the touch sensitive display 26, the invert view button 44, e.g. in the second portion of the graphical user interface, as illustrated. The monitor device 20 may change between the default view mode (FIG. 15A) and the inverted view mode (FIG. 15B) in response to activation of the invert view button 44. In the default view mode (FIG. 15A) the invert view button 44 may be displayed in a first orientation, and in the inverted view mode (FIG. 15B) the invert view button 44 may be displayed in a second orientation, e.g. rotated compared to the first orientation, e.g. by 180 degrees.

Figure 16:
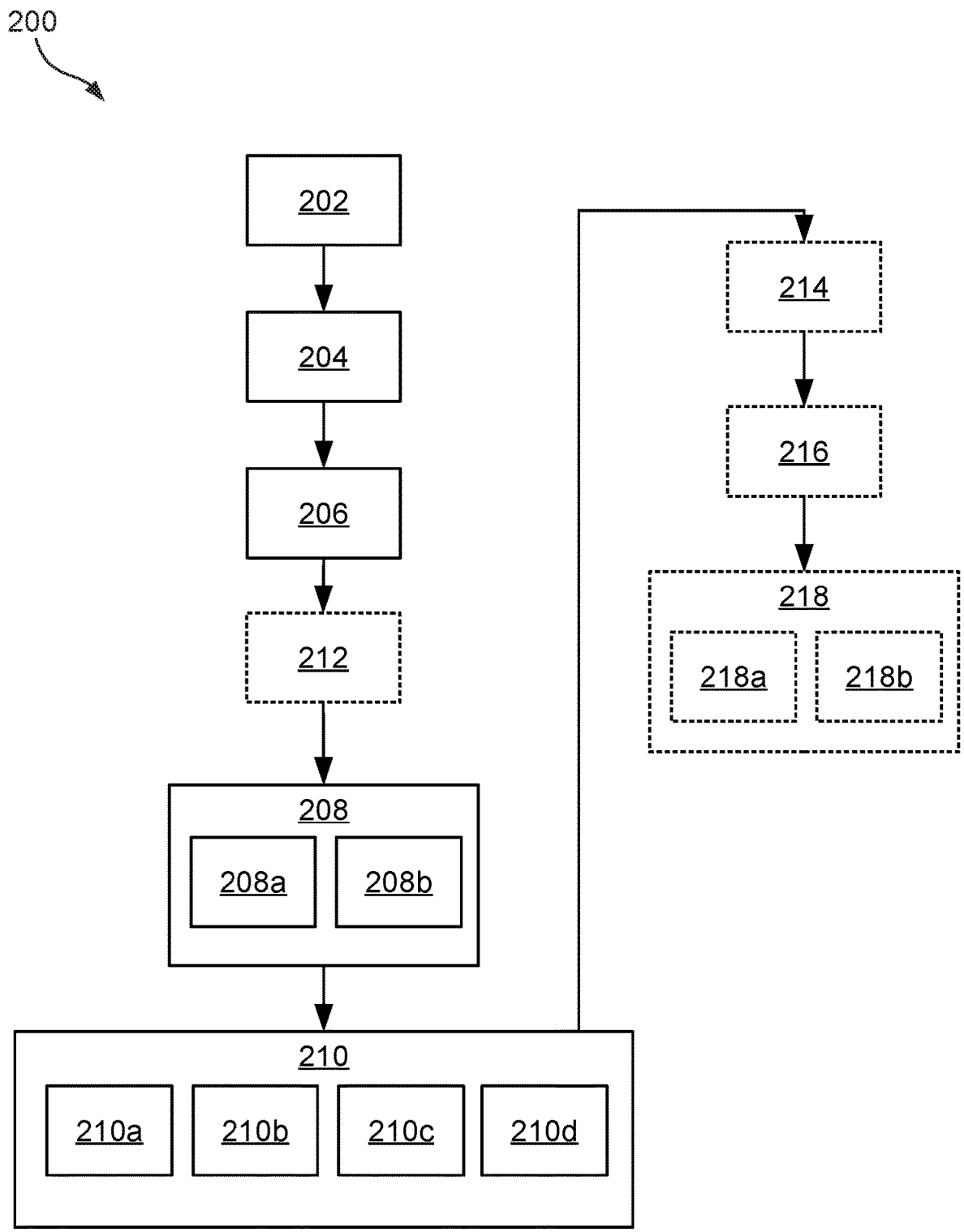
FIG. 16 is a block diagram of an exemplary method.

FIG. 16 is a block diagram of an exemplary method 200 performed at a monitor device, such as a monitor device as disclosed in relation to previous figures, such as a monitor device of a medical visualization system comprising a visualization device having an image sensor configured to generate image data indicative of a view from the visualization device. As explained above, the monitor device may comprise a first housing extending in a first direction from a first housing side to a second housing side and in a second direction perpendicular to the first direction from a third housing side to a fourth housing side. The monitor device may comprise a touch sensitive display, e.g. being accommodated in the first housing. The touch sensitive display may have a first length in the first direction and a second length in the second direction, and a graphical user interface comprising a plurality of non-overlapping portions including a first portion and a second portion, and optionally a third portion and/or a fourth portion.

The method 200 comprises receiving 202 the image data generated, as the image data is being generated by the image sensor; displaying 204 one or more actionable items within the second portion of the graphical user interface; determining 206 an interface orientation mode of the monitor device; and displaying 210 a live representation of the image data within the first portion of the graphical user interface. The monitor device may comprise an orientation sensor and determining 206 the interface orientation mode may comprise determining an orientation of the first housing by the orientation sensor. The interface orientation mode may be determined 206 to be the first interface orientation mode when the first housing is oriented in a first orientation wherein the first direction is upwards. The interface orientation mode may be determined 206 to be the second interface orientation mode when the first housing is not oriented in the first orientation. Alternatively, the interface orientation mode may be determined 206 to be the second interface orientation mode when the first housing is oriented in the second orientation.

The method 200 further comprises arranging 208 the second portion. The method 200 comprise, in accordance with the determined interface orientation mode being a first interface orientation mode, arranging 208a the second portion between the fourth housing side and the first portion; and in accordance with the determined interface orientation mode being a second interface orientation mode, arranging 208b the second portion between the third housing side and the first portion.

Displaying 210 the live representation may comprise in accordance with the monitor device being in a default view mode and in accordance with the determined 206 interface orientation mode being the first interface orientation mode, the live representation may be displayed 210a such that a first image direction of the live representation and the first direction are the same.

Displaying 210 the live representation may comprise in accordance with the monitor device being in an inverted view mode and in accordance with the determined 206 interface orientation mode being the first interface orientation mode, the live representation may be displayed 210b such that the first image direction of the live representation and the first direction are opposite.

Displaying 210 the live representation may comprise in accordance with the monitor device being in the default view mode and in accordance with the determined 206 interface orientation mode being the second interface orientation mode, the live representation may be displayed 210c such that the first image direction of the live representation and the first direction are opposite.

Displaying 210 the live representation may comprise in accordance with the monitor device being in an inverted view mode and in accordance with the determined 206 interface orientation mode being the second interface orientation mode, the live representation may be displayed 210d such that the first image direction of the live representation and the first direction are the same.

The method 200 may comprise, e.g. in accordance with the monitor device being in the inverted view mode, displaying 214 an inverted view mode indicator in the first portion, e.g. overlaying a portion of the live representation.

The method 200 may comprise displaying 212 an invert view button with the touch sensitive display. The method 200 may further comprise receiving 216 a user input corresponding to activation of the invert view button. In response to receiving 216 the user input corresponding to activation of the invert view button, the method 200 may comprise changing 218 the view mode. For example, the method 200 may comprise in response to receiving 216 the user input corresponding to activation of the invert view button, in accordance with the monitor device being in the default view mode, changing 218a to the inverted view mode; and in accordance with the monitor device being in the inverted view mode changing 218b to the default view mode.

Figure 17:
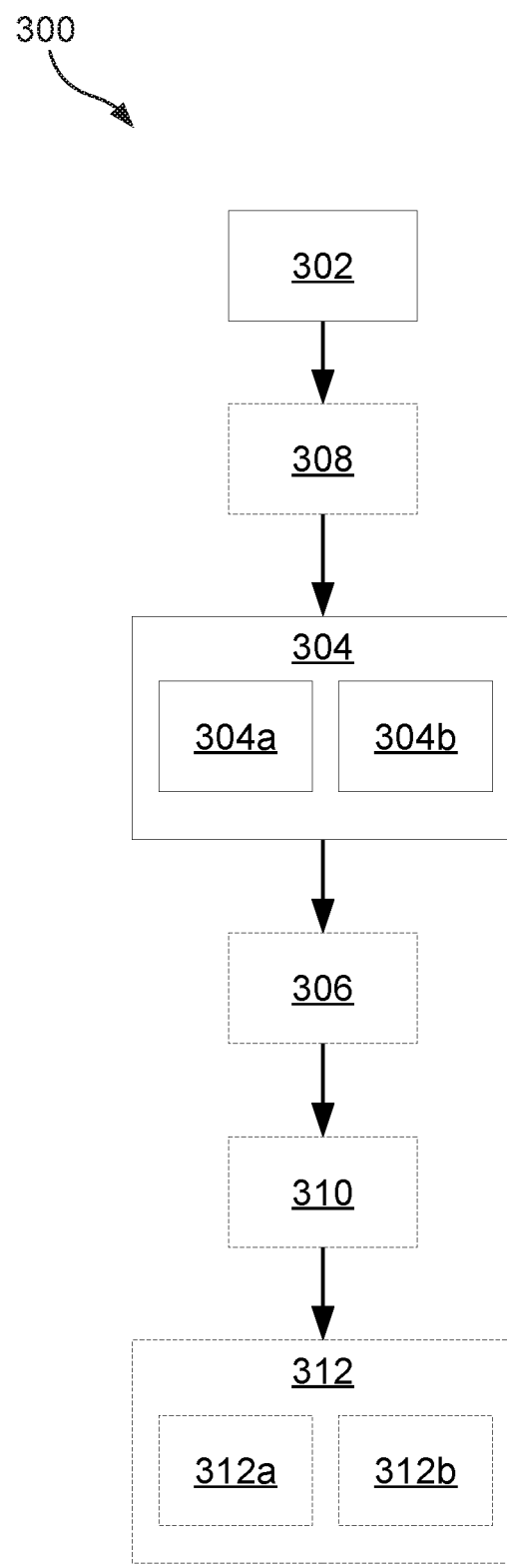
FIG. 17 is a block diagram of an exemplary method, FIGS. 18A-18F schematically illustrate exemplary user interactions with a graphical user interface of an exemplary monitor device, FIGS. 19A-19I schematically illustrate exemplary user interactions with a graphical user interface of an exemplary monitor device, FIGS. 20A-20I schematically illustrate exemplary user interactions with a graphical user interface of an exemplary monitor device.

FIG. 17 is a block diagram of an exemplary method 300 performed at a monitor device, such as a monitor device as disclosed in relation to previous figures, such as a monitor device of a medical visualization system comprising a visualization device having an image sensor configured to generate image data indicative of a view from the visualization device. The monitor device may comprise a first housing extending in a first direction from a first housing side to a second housing side and in a second direction perpendicular to the first direction from a third housing side to a fourth housing side. The monitor device comprising a touch sensitive display. The touch sensitive display may be accommodated in the first housing.

The method 300 comprising receiving 302 the image data generated by the image sensor; and displaying 304 a live representation of the image data within a first portion of the graphical user interface, including in accordance with the monitor device being in a default view mode, displaying 304a the live representation such that a first image direction of the live representation and the first direction are the same; and in accordance with the monitor device being in an inverted view mode, displaying 304b the live representation such that the first image direction and the first direction are opposite.

The method 300 may comprise, e.g. in accordance with the monitor device being in the inverted view mode, displaying 306 an inverted view mode indicator, e.g. in the first portion overlaying a portion of the live representation.

The method 300 may comprise displaying 308 an invert view button with the touch sensitive display. The method 300 may further comprise receiving 310 a user input corresponding to activation of the invert view button. In response to receiving 310 the user input corresponding to activation of the invert view button, the method 300 may comprise changing 312 the view mode. For example, the method 300 may comprise in response to receiving 310 the user input corresponding to activation of the invert view button, in accordance with the monitor device being in the default view mode, changing 312a to the inverted view mode; and in accordance with the monitor device being in the inverted view mode changing 312b to the default view mode.

Additional exemplary embodiments of the foregoing aspect of the present disclosure are set out in the following exemplary items:

1. Medical visualization system comprising a visualization device having an image sensor configured to generate image data indicative of a view from the visualization device, the medical visualization system further comprising a monitor device operable to receive the image data as the image data is being generated by the image sensor, the monitor device comprising a first housing extending in a first direction from a first housing side to a second housing side and in a second direction perpendicular to the first direction from a third housing side to a fourth housing side, the monitor device comprising a touch sensitive display accommodated in the first housing and having a first length in the first direction and a second length in the second direction, and the monitor device comprising a graphical user interface comprising a plurality of non-overlapping portions including a first portion and a second portion, the monitor device displays the graphical user interface with the touch sensitive display, wherein the monitor device displays with the touch sensitive display one or more actionable items within the second portion of the graphical user interface and displays a live representation of the image data within the first portion of the graphical user interface, the monitor device having a first interface orientation mode and a second interface orientation mode, wherein in the first interface orientation mode, the second portion is arranged between the fourth housing side and the first portion, and wherein in the second interface orientation mode, the second portion is arranged between the third housing side and the first portion.

2. Medical visualization system according to item 1, wherein the monitor device comprises an orientation sensor, and wherein the monitor device operates the first interface orientation mode when a signal of the orientation sensor is indicative of the first housing being oriented in a first orientation wherein the first direction is upwards, and wherein the monitor device operates the second interface orientation mode when the signal of the orientation sensor is not indicative of the first housing being in the first orientation.

3. Medical visualization system according to any of the preceding items wherein the monitor device displays with the touch sensitive display an invert interface button, and wherein the monitor device changes between operating the first interface orientation mode and operating the second interface orientation mode in response to activation of the invert interface button.

4. Medical visualization system according to any of the preceding items, wherein the monitor device comprises one or more connection ports configured to receive a connector of the visualization device, and wherein the one or more connection ports are provided on the third housing side.

5. Medical visualization system according to any of the preceding items, wherein the one or more actionable items comprise an image capture button, and wherein the monitor device stores an image data file corresponding to the image data received when the image capture button is activated.

6. Medical visualization system according to any of the preceding items, wherein the one or more actionable items comprises a video capture button, and wherein the monitor device stores a video sequence of image data corresponding to the image data received when the video capture button is activated.

7. Medical visualization system according to any of the preceding items, wherein the plurality of non-overlapping portions includes a third portion, and wherein the monitor device displays with the touch sensitive display one or more actionable menu items within the third portion, and wherein the third portion is arranged between the third housing side and the first portion in the first interface orientation mode, and the third portion is arranged between the fourth housing side and the first portion in the second interface orientation mode.

8. Medical visualization system according to item 7, wherein the plurality of non-overlapping portions includes a fourth portion, and wherein the fourth portion is arranged between the third portion and the first portion.

9. Medical visualization system according to any of the preceding items, wherein each of the plurality of non-overlapping portions extends substantially throughout the first length in the first direction.

10. Medical visualization system according to any of the preceding items, wherein the visualization device comprises a handle and an elongated flexible member extending from the handle to a distal end, the image data being indicative of a view from the distal end of the elongated flexible member, the handle comprises a control button adapted to receive an input in a first input direction, and wherein the touch input in the first input direction causes a distal portion of the elongated flexible member to bend in a first bending direction, and wherein the first bending direction corresponds to a first image direction of the live representation, and wherein the first image direction is parallel to the first direction.

11. Medical visualization system according to item 10, wherein the first image direction and the first direction are the same in the first interface orientation mode, and wherein the first image direction and the first direction are opposite in the second interface orientation mode.

12. Medical visualization system according to any of items 10-11, wherein the monitor device has a default view mode and an inverted view mode, wherein in the default view mode: the first image direction and the first direction are the same in the first interface orientation mode; and the first image direction and the first direction are opposite in the second interface orientation mode, and wherein in the inverted view mode: the first image direction and the first direction are opposite in the first interface orientation mode; and the first image direction and the first direction are the same in the second interface orientation mode.

13. Medical visualization system according to item 12, wherein in the inverted view mode the monitor device displays with the touch sensitive display an inverted view mode indicator in the first portion overlaying a portion of the live representation.

14. Medical visualization system according to any of items 12-13 as dependent on item 5, wherein in the inverted view mode the monitor device stores with the image data file being stored information indicative of the monitor device operating in the inverted view mode when the image capture button was activated.

15. Medical visualization system according to any of items 12-14 as dependent on item 6, wherein in the inverted view mode the monitor device stores with the video sequence of image data being stored information indicative of the monitor device operating in the inverted view mode when the video capture button was activated.

16. Medical visualization system according to any of items 12-15, wherein the monitor device displays with the touch sensitive display an invert view button, and wherein the monitor device changes between the default view mode and the inverted view mode in response to activation of the invert view button.

17. Medical visualization system according to item 16, wherein in the default view mode the invert view button is displayed in a first orientation, and in the inverted view mode the invert view button is displayed in a second orientation, wherein the second orientation of the invert view button is rotated compared to the first orientation of the invert view button, e.g. by 180 degrees.

18. Medical visualization system according to any of items 16-17, wherein the monitor device comprises a settings menu comprising an option for enabling the inverted view mode, and wherein in accordance with the inverted view mode being enabled in the settings menu, the monitor device displays with the touch sensitive display the invert view button, and in accordance with the inverted view mode not being enabled in the settings menu, the monitor device does not display the invert view button.

19. A method performed at a monitor device of a medical visualization system comprising a visualization device having an image sensor configured to generate image data indicative of a view from the visualization device, the monitor device comprising a first housing extending in a first direction from a first housing side to a second housing side and in a second direction perpendicular to the first direction from a third housing side to a fourth housing side, the monitor device comprising a touch sensitive display accommodated in the first housing and having a first length in the first direction and a second length in the second direction, and the monitor device comprising a graphical user interface comprising a plurality of non-overlapping portions including a first portion and a second portion, the method comprising:

receiving the image data generated as the image data is being generated by the image sensor;
displaying one or more actionable items within the second portion of the graphical user interface;
determining an interface orientation mode of the monitor device;
in accordance with the determined interface orientation mode being a first interface orientation mode, arranging the second portion between the fourth housing side and the first portion;
in accordance with the determined interface orientation mode being a second interface orientation mode, arranging the second portion between the third housing side and the first portion;
displaying a live representation of the image data within the first portion of the graphical user interface.

20. Method according to item 19, wherein the monitor device comprises an orientation sensor, and wherein determining the interface orientation mode comprise determining an orientation of the first housing by the orientation sensor, wherein the interface orientation mode is determined to be the first interface orientation mode when the first housing is oriented in a first orientation wherein the first direction is upwards, and wherein the interface orientation mode is determined to be the second interface orientation mode when the first housing is not oriented in the first orientation.

21. Method according to any of items 19-20 wherein displaying the live representation comprises:
in accordance with the monitor device being in a default view mode:
  in accordance with the determined interface orientation mode being the first interface orientation mode displaying the live representation such that a first image direction of the live representation and the first direction are the same; and
  in accordance with the determined interface orientation mode being the second interface orientation mode displaying the live representation such that the first image direction and the first direction are opposite,
in accordance with the monitor device being in an inverted view mode:
  in accordance with the determined interface orientation mode being the first interface orientation mode displaying the live representation such that the first image direction and the first direction are opposite; and
  in accordance with the determined interface orientation mode being the second interface orientation mode displaying the live representation such that the first image direction and the first direction are the same.

22. Method according to item 21, wherein in accordance with the monitor device being in the inverted view mode, displaying an inverted view mode indicator in the first portion overlaying a portion of the live representation.

23. Method according to any of items 21-22 comprising displaying an invert view button with the touch sensitive display, receiving a user input corresponding to activation of the invert view button, and in response to receiving the user input corresponding to activation of the invert view button:
in accordance with the monitor device being in the default view mode changing to the inverted view mode; and
in accordance with the monitor device being in the inverted view mode changing to the default view mode.

24. A medical visualization system comprising a visualization device having an image sensor configured to generate image data indicative of a view from the visualization device,
the visualization device comprising a handle and an elongated flexible member extending from the handle to a distal end, the image data being indicative of a view from the distal end of the elongated flexible member, the handle comprises a control button adapted to receive an input in a first input direction, and wherein the touch input in the first input direction causes a distal portion of the elongated flexible member to bend in a first bending direction,
the medical visualization system further comprising a monitor device operable to receive the image data as the image data is being generated by the image sensor, the monitor device comprising a first housing extending in a first direction from a first housing side to a second housing side and in a second direction perpendicular to the first direction from a third housing side to a fourth housing side, the monitor device comprising a touch sensitive display accommodated in the first housing and having a first length in the first direction and a second length in the second direction, and the monitor device comprising a graphical user interface comprising a first portion,
wherein the monitor device displays with the touch sensitive display a live representation of the image data within a first portion of the graphical user interface, and wherein the first bending direction of the distal portion of the elongated flexible member corresponds to a first image direction of the live representation, the first image direction being parallel to the first direction,
the monitor device having a default view mode and an inverted view mode, wherein in the default view mode, the first image direction and the first direction are the same, and in the inverted view mode, the first image direction and the first direction are opposite.

25. Medical visualization system according to item 24, wherein in the inverted view mode the monitor device displays with the touch sensitive display an inverted view mode indicator in the first portion overlaying a portion of the live representation.

26. Medical visualization system according to item any of items 24-25, wherein the monitor device displays with the touch sensitive display an image capture button, and wherein the monitor device stores an image data file corresponding to the image data received when the image capture button is activated, and wherein in the inverted view mode the monitor device stores with the image data file being stored information indicative of the monitor device operating in the inverted view mode when the image capture button was activated.

27. Medical visualization system according to any of items 24-26, wherein the monitor device displays with the touch sensitive display a video capture button, and wherein the monitor device stores a video sequence of image data corresponding to the image data received when the video capture button is activated, and wherein in the inverted view mode the monitor device stores with the video sequence of image data being stored information indicative of the monitor device operating in the inverted view mode when the video capture button was activated.

28. Medical visualization system according to any of items 24-27, wherein the monitor device displays with the touch sensitive display an invert view button, and wherein the monitor device changes between the default view mode and the inverted view mode in response to activation of the invert view button.

29. Medical visualization system according to item 28, wherein in the default view mode the invert view button is displayed in a first orientation, and in the inverted view mode the invert view button is displayed in a second orientation, wherein the second orientation of the invert view button is rotated compared to the first orientation of the invert view button, e.g. by 180 degrees.

30. Medical visualization system according to any of items 28-29, wherein the monitor device comprises a settings menu comprising an option for enabling the inverted view mode, and wherein in accordance with the inverted view mode being enabled in the settings menu, the monitor device displays with the touch sensitive display the invert view button, and in accordance with the inverted view mode not being enabled in the settings menu, the monitor device does not display the invert view button.

31. A method performed at a monitor device of a medical visualization system comprising a visualization device having an image sensor configured to generate image data indicative of a view from the visualization device, the monitor device comprising a first housing extending in a first direction from a first housing side to a second housing side and in a second direction perpendicular to the first direction from a third housing side to a fourth housing side, the monitor device comprising a touch sensitive display accommodated in the first housing, and a graphical user interface, the method comprising:
receiving the image data generated by the image sensor as the image data is being generated by the image sensor;
displaying a live representation of the image data within a first portion of the graphical user interface, including:

in accordance with the monitor device being in a default view mode, displaying the live representation such that a first image direction of the live representation and the first direction are the same; and
in accordance with the monitor device being in an inverted view mode: displaying the live representation such that the first image direction and the first direction are opposite.

32. Method according to item 31 comprising, in accordance with the monitor device being in the inverted view mode, displaying an inverted view mode indicator in the first portion overlaying a portion of the live representation.

33. Method according to any of items 31-32 comprising displaying an invert view button with the touch sensitive display, receiving a user input corresponding to activation of the invert view button, and in response to receiving the user input corresponding to activation of the invert view button:
in accordance with the monitor device being in the default view mode changing to the inverted view mode; and
in accordance with the monitor device being in the inverted view mode changing to the default view mode.

Additional User Interactions

FIGS. 18A-18F schematically illustrate exemplary user interactions with a graphical user interface of a monitor device 20, such as the monitor device 20 of any of the previous figures.

Figure 18A:
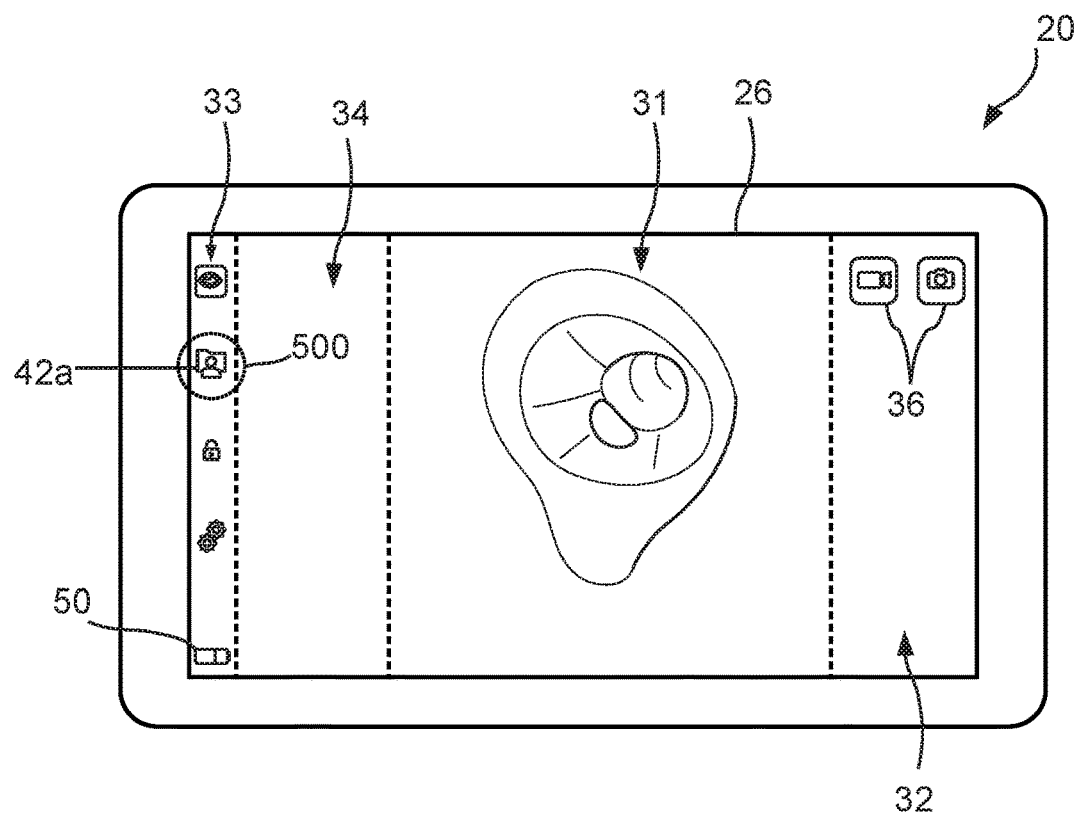

As illustrated in FIG. 18A, the monitor device 20 may receive a first user input 500 corresponding to selection of a first actionable menu item 42a of the one or more actionable menu items 42 (cf. FIG. 3). In the illustrated example, the first user input 500 is a touch input, e.g. a tap, on an icon, i.e. the first actionable menu item, indicating access to an archive.

Figure 18B:
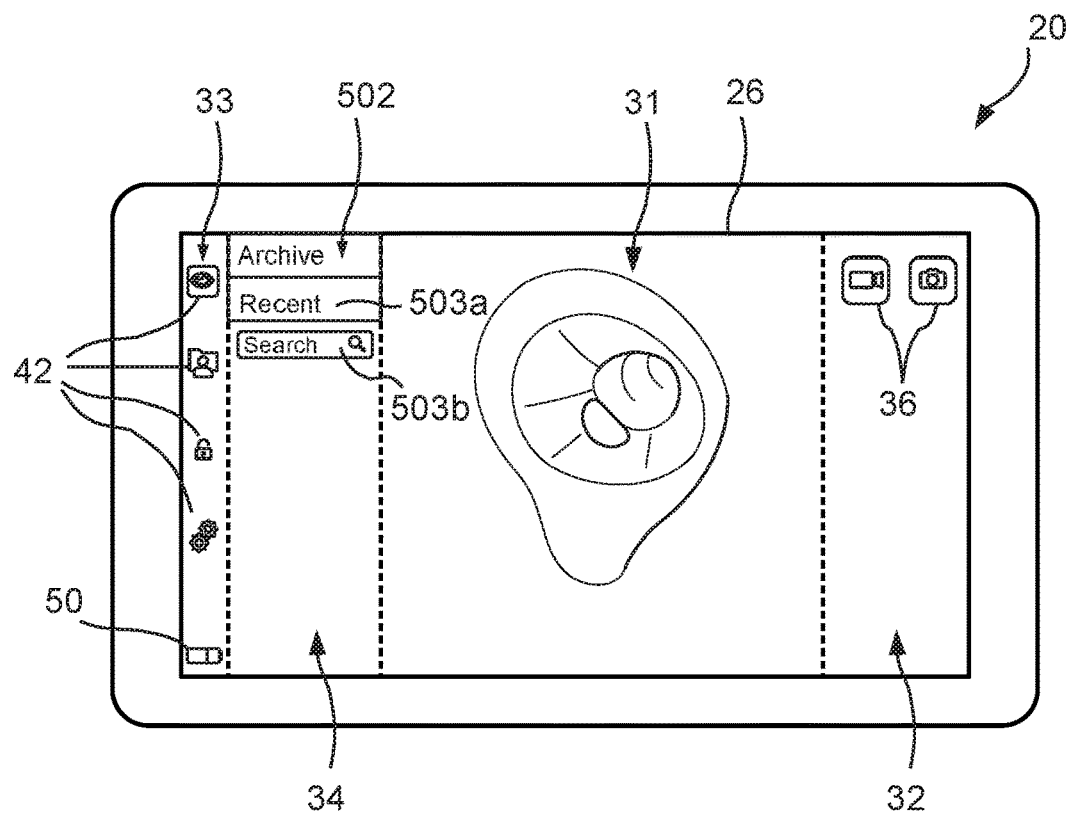

The monitor device 20 detects the user input 500 with the touch sensitive display 26, and in response to detecting the first user input 500, the monitor device 20 displays a primary menu 502, as illustrated in FIG. 18B. The primary menu 502 being associated with the first actionable menu item 42a. The primary menu 502 is displayed within the fourth portion 34 of the graphical user interface, and without obscuring part of the first portion 31 of the graphical user interface. The primary menu 502 comprises one or more primary actionable items including a first primary actionable item 503a. In the illustrated example, the primary menu 502 is an archive menu with a first primary actionable item 503a to retrieve recent (e.g. recently stored) images and videos, and a second primary actionable item 503b to search for stored images and videos.

Figure 18C:
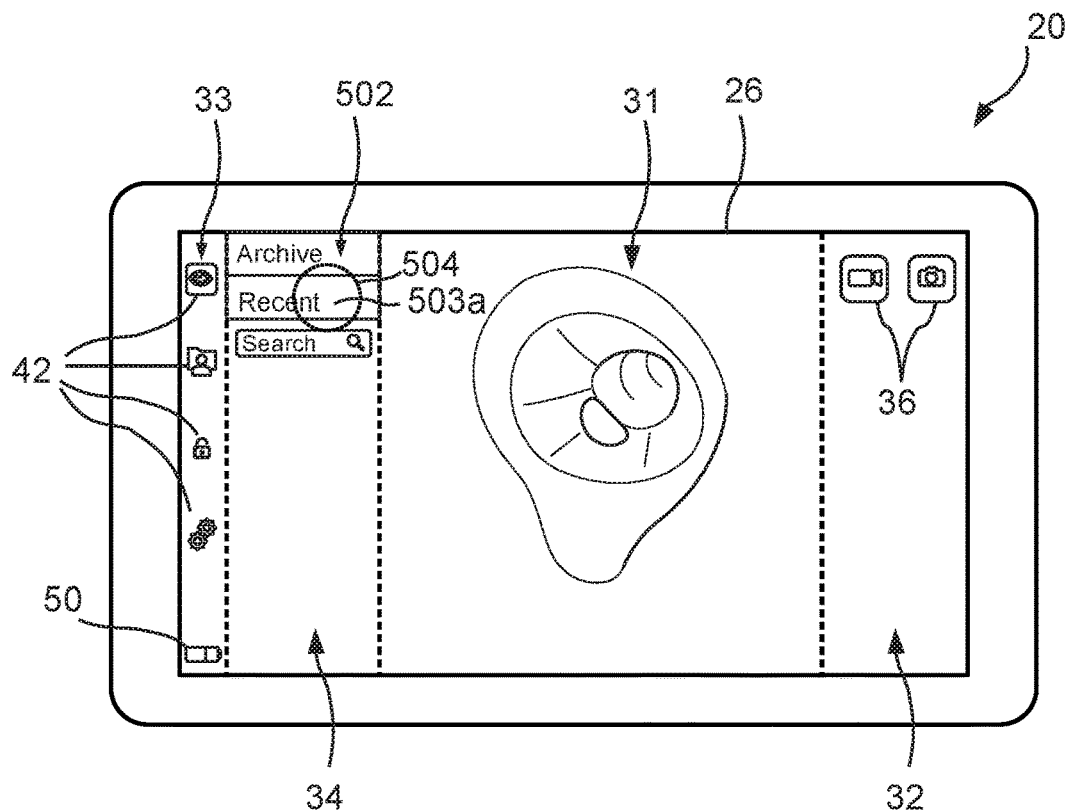
Figure 18D:
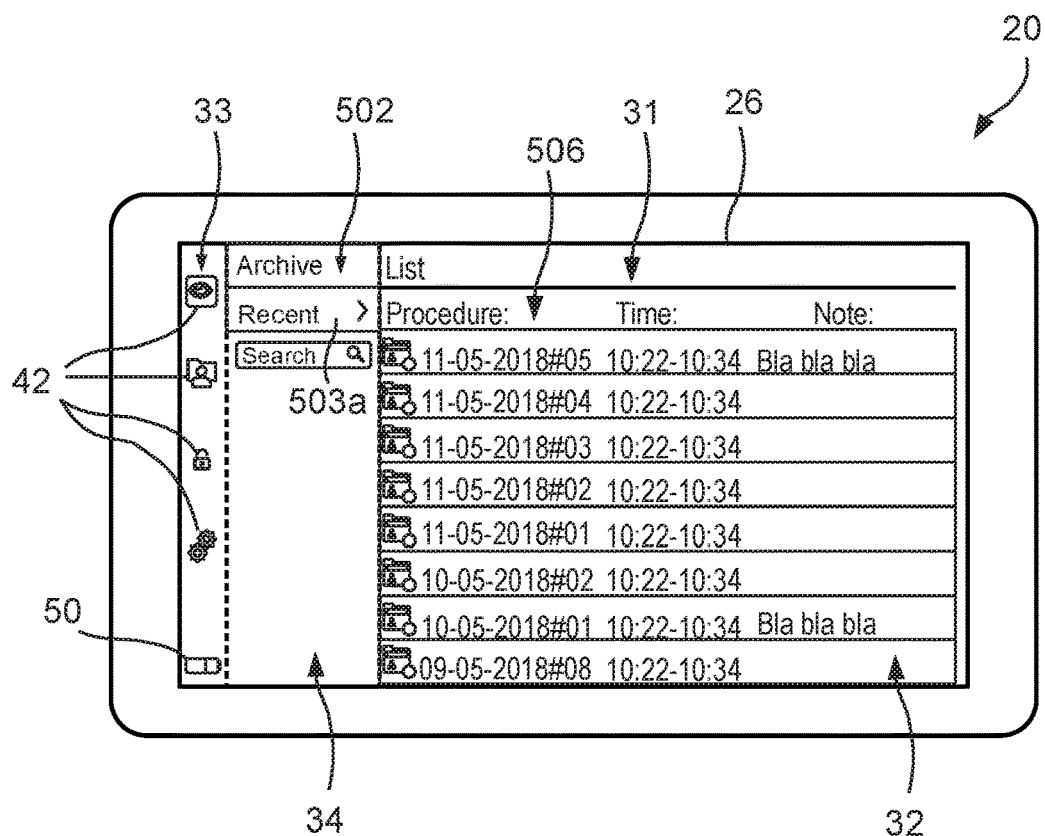

While displaying the primary menu 502, the monitor device 20 may detect with the touch sensitive display 26 a second user input 504 corresponding to selection of the first primary actionable item 503a, as illustrated in FIG. 18C. In response to detecting the second user input 504, the monitor device displays a secondary menu 506 associated with the primary actionable item 503a in the first portion 31, and optionally the second portion 32, of the graphical user interface, as illustrated in FIG. 18D. Optionally, the secondary menu 506 extends into also the fourth portion 34 of the graphical user interface.

In the illustrated example, the user provides touch input 504 on the first primary actionable item 503a being a button for retrieving recent images and videos (FIG. 18C). In response to detecting the touch input 504 with the touch sensitive display, the monitor device 20 displays the secondary menu 506, in the illustrated example being a list of the recently stored procedures (FIG. 18D), wherefrom the user may navigate to retrieve images and videos stored therein. The list of stored procedures 506 are named according to the date for performing them, and the list 506 shows the timeframe of each procedure and any notes that the user may have added to the procedure.

As seen in FIGS. 18A-18D, the user needs to make two consecutive inputs to display a menu, which covers part of, or the entire live representation of the image data displayed in the first portion 31 of the graphical user interface. Thereby, unintentional touch inputs on the screen is less likely to cause interference with the display of the live representation of the image data, which could potentially be life threatening, in case the operator is performing a critical procedure with the aid of the live representation of the image data. In some examples, the primary menu (e.g. 502 as illustrated in FIG. 18B) being displayed in response to the first user input (e.g. 500 as illustrated in FIG. 18A), is ceased to be displayed if a second user input (e.g. the second user input 504 in FIG. 18C) is not received within a predetermined time from receiving/detecting the first user input and/or from displaying the primary menu. Thereby, the likelihood of receiving two unintentional inputs causing the live representation of the image data to be obstructed may be decreased.

Figure 18E:
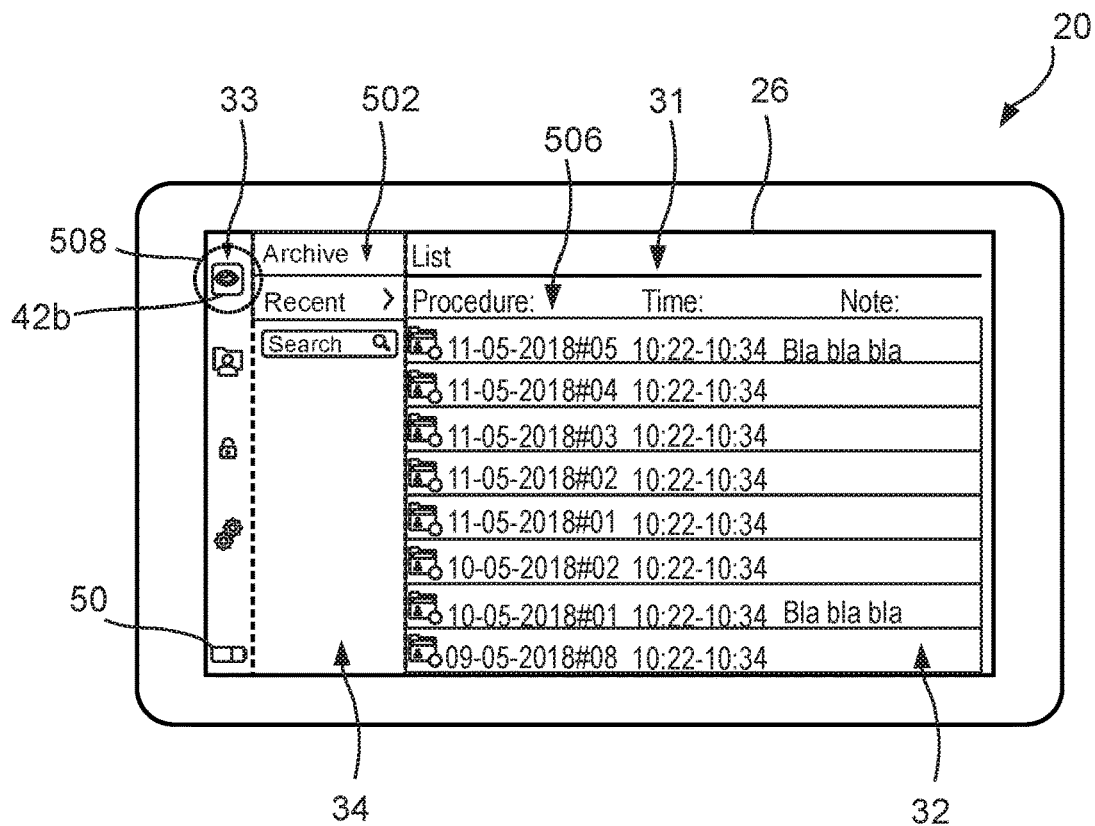
Figure 18F:
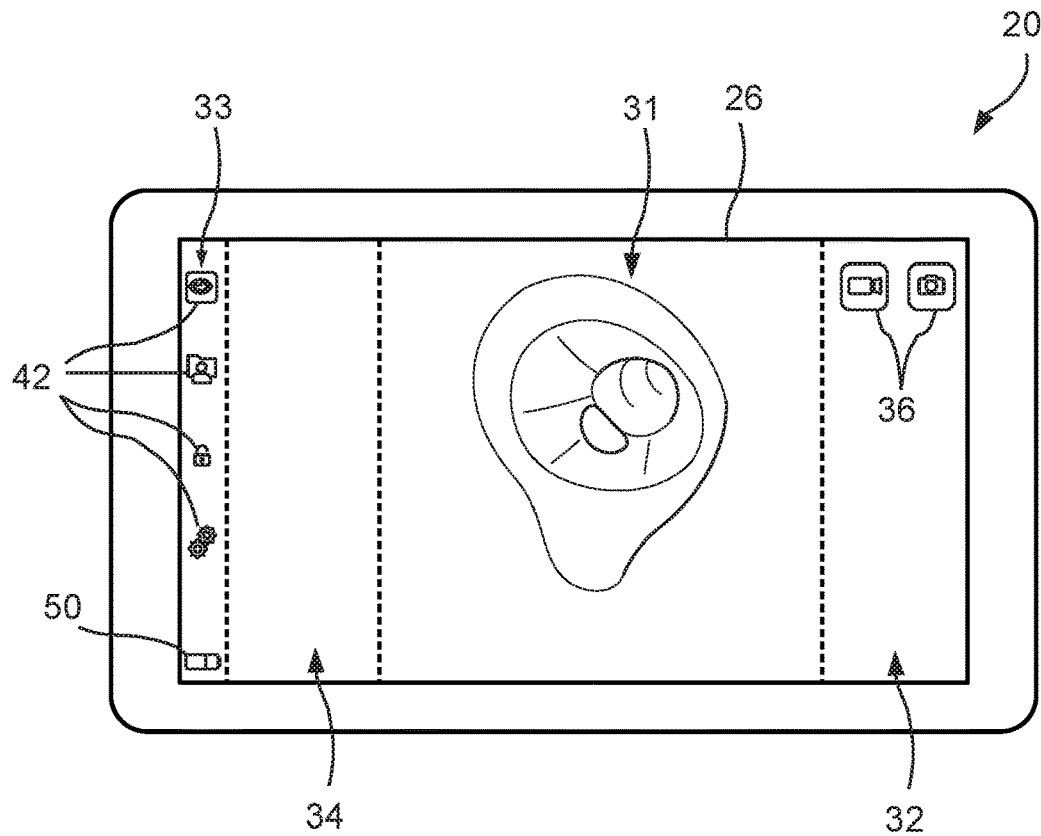

The one or more actionable menu items 42 may comprise a second actionable menu item 42b (see FIG. 18E). The second actionable menu item 42b may be indicative of a live view. As illustrated in FIG. 18E, the monitor device may, e.g. while the primary menu 502 and/or the secondary menu 506 is displayed, detect with the touch sensitive display a third user input 508 corresponding to selection of the second actionable menu item 42b. In response to detecting the third user input 508, the monitor device may cease display of the primary menu 502 and/or the secondary menu 506, and display the live representation of the image data within the first portion 31 of the graphical user interface, as illustrated in FIG. 18F. Thus, the second actionable menu item 42b may cause the monitor device 20 to return to the initial view, as illustrated in FIG. 18A. In case of, e.g. unintentional, obstruction of the live representation of the image data, the user may fast and easily remove any such obstruction and return to displaying the live representation of the image data.

Figure 19A:
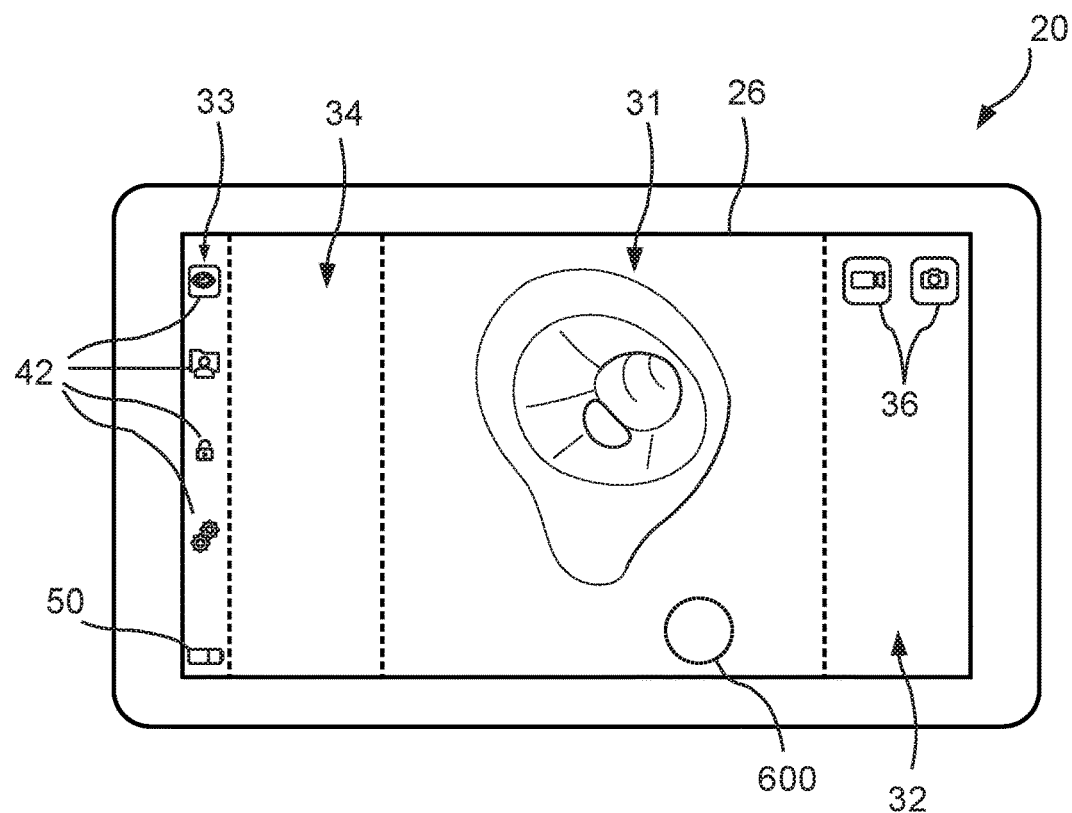

Referring now to FIGS. 19A-19I schematically illustrating exemplary user interactions with a graphical user interface of a monitor device 20, such as the monitor device 20 of any of the previous figures. FIG. 19A illustrates a situation, which may continue from the situation illustrated in, e.g., FIG. 18F or be prior to receiving the first touch input 500 in FIG. 18A.

As illustrated in FIG. 19A, the monitor device 20 receives a fourth user input 600, e.g. a double tap, on the touch sensitive display 26, e.g. within the first portion 31 of the graphical user interface. The monitor device 20 detects the fourth user input 600 with the touch sensitive display 26, and in response to detecting the fourth user input 600, the monitor device 20 may activate an enlarged view mode, as illustrated in FIG. 19B, wherein a section 602 of the live representation of the image data is displayed in the first portion 31 and the fourth portion 34 of the graphical user interface.

Figure 19B:
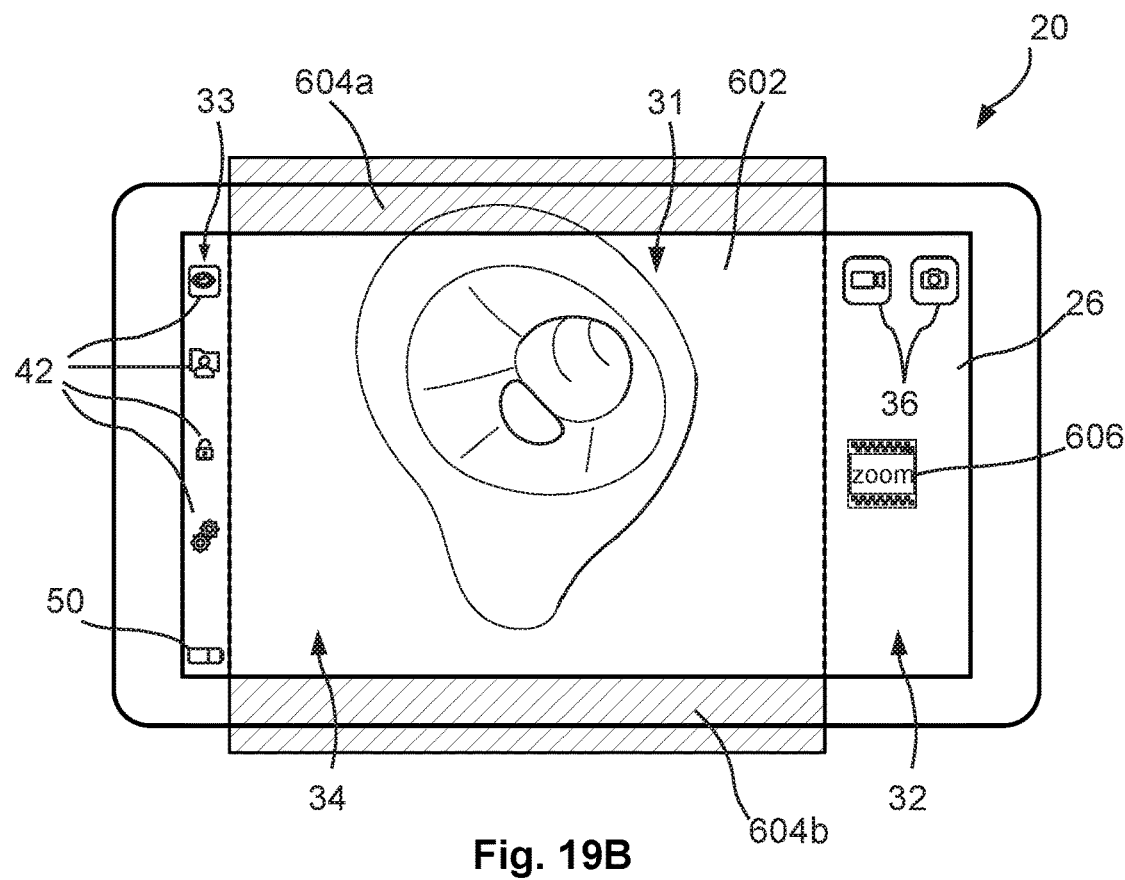

As illustrated in FIG. 19B, a first crop section 604a and a second crop section 604b of the live representation may be omitted from being displayed in the enlarged view mode. In FIG. 19B, the first crop section 604a and the second crop section 604b are merely shown for illustrative purposes. As illustrated, the section 602 of the live representation being displayed in the enlarged view mode may be between the first crop section 604a and the second crop section 604b.

Furthermore, in the enlarged view mode, an enlarged view mode indicator 606 may be displayed, e.g. in the second portion 32, as illustrated. The enlarged view mode indicator 606 indicates to the user that the monitor device 20 is operating in the enlarged view mode and notifies the user that part of the image data (the first crop section 604a and the second crop section 604b) is not being displayed.

Figure 19C:
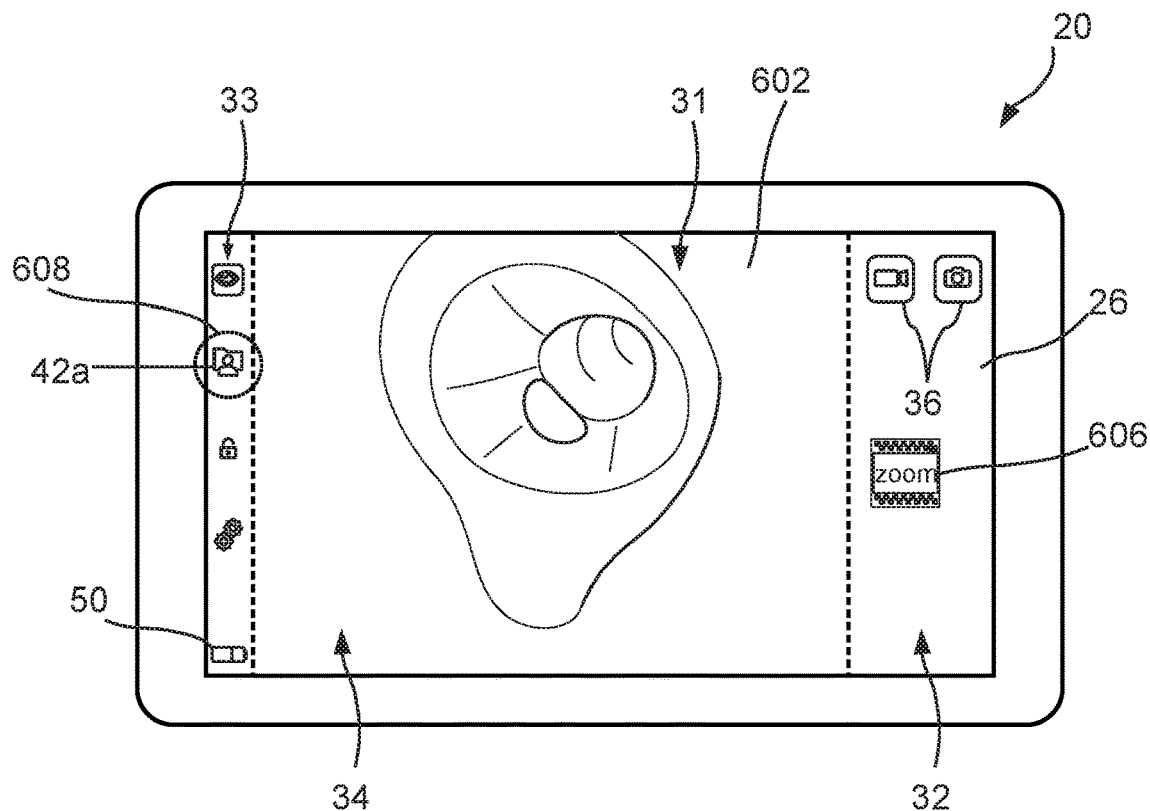
Figure 19D:
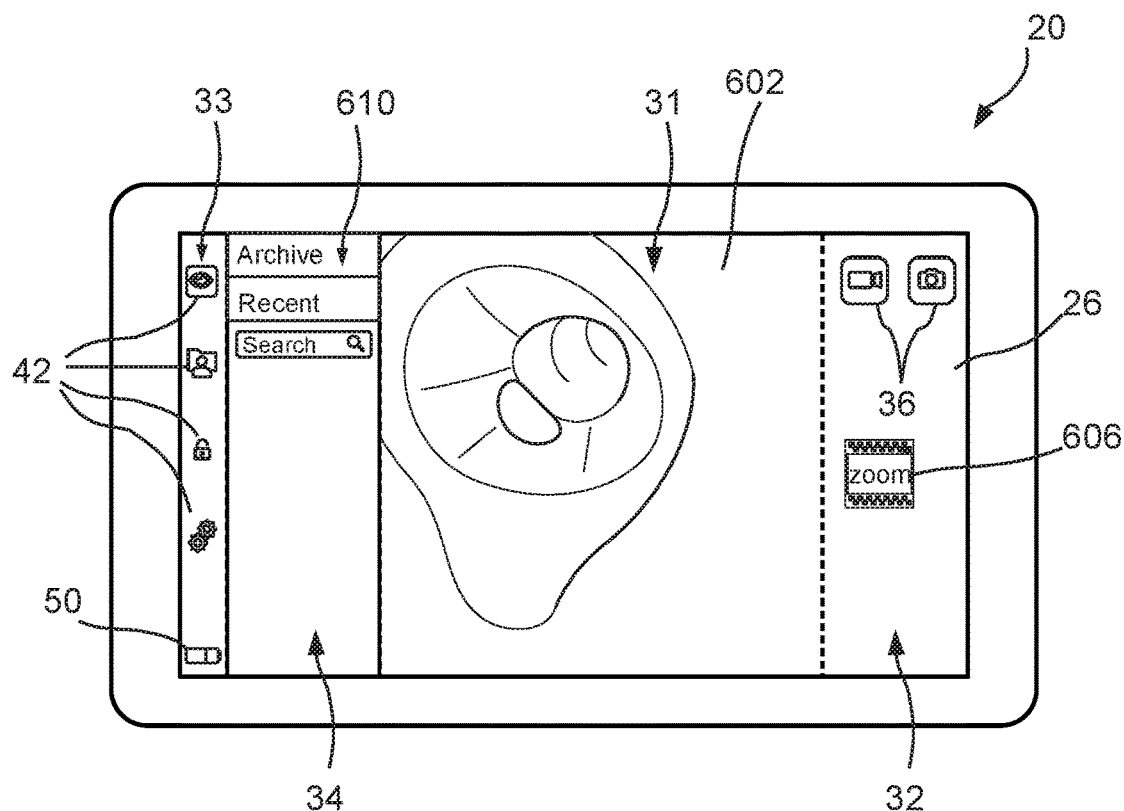

Referring now to FIG. 19C, wherein the monitor device is operating in the enlarged view mode, the monitor device receives a fifth user input 608, e.g. corresponding to the first user input of FIG. 18A, to a actionable menu item, such as to the first actionable menu item 42a. The monitor device 20 detects the user input 608 with the touch sensitive display, and in response to detecting the user input 608, the monitor device 20 displays, within the fourth portion 34 of the graphical user interface, the primary menu 610 associated with the actionable menu item receiving the user input 608. In the present example, the monitor device displays the first primary menu 610 within the fourth portion 34 of the graphical user interface. Because the monitor device is operating in the enlarged view mode, display of the first primary menu 610 within the fourth portion 34 of the graphical user interface causes a part of the section 602 of the live representation of the image data to be obscured.

Figure 19E:
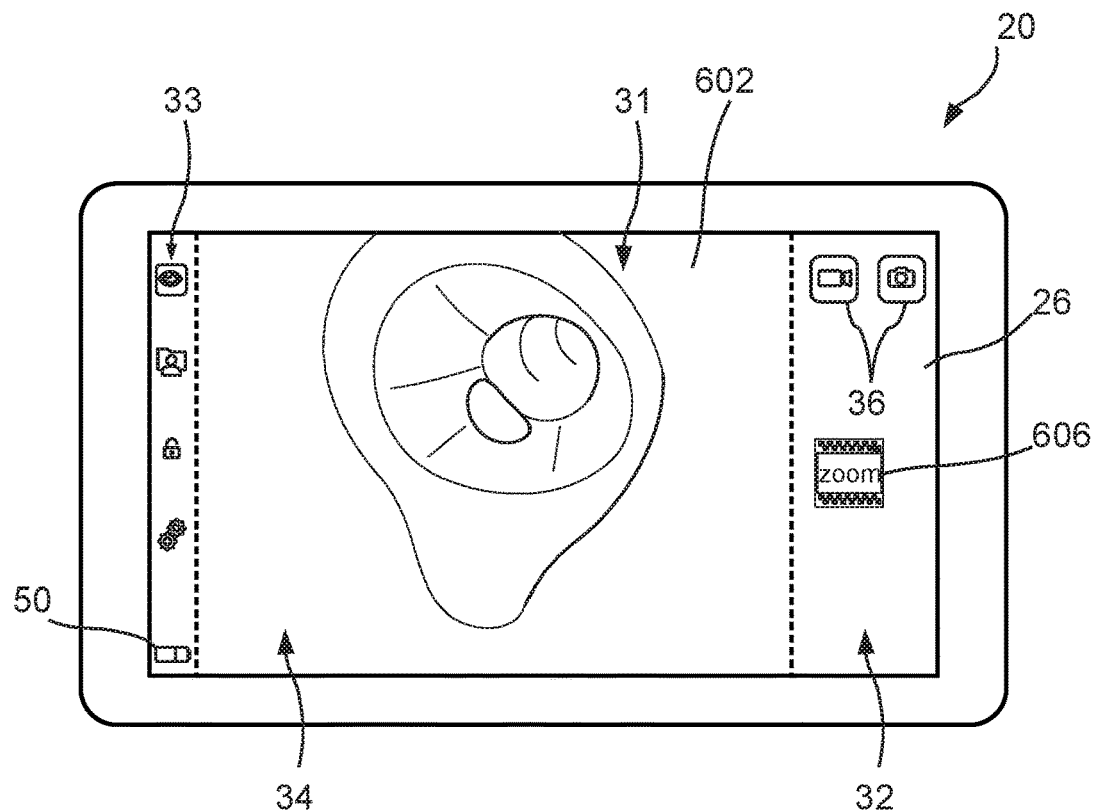
Figure 19F:
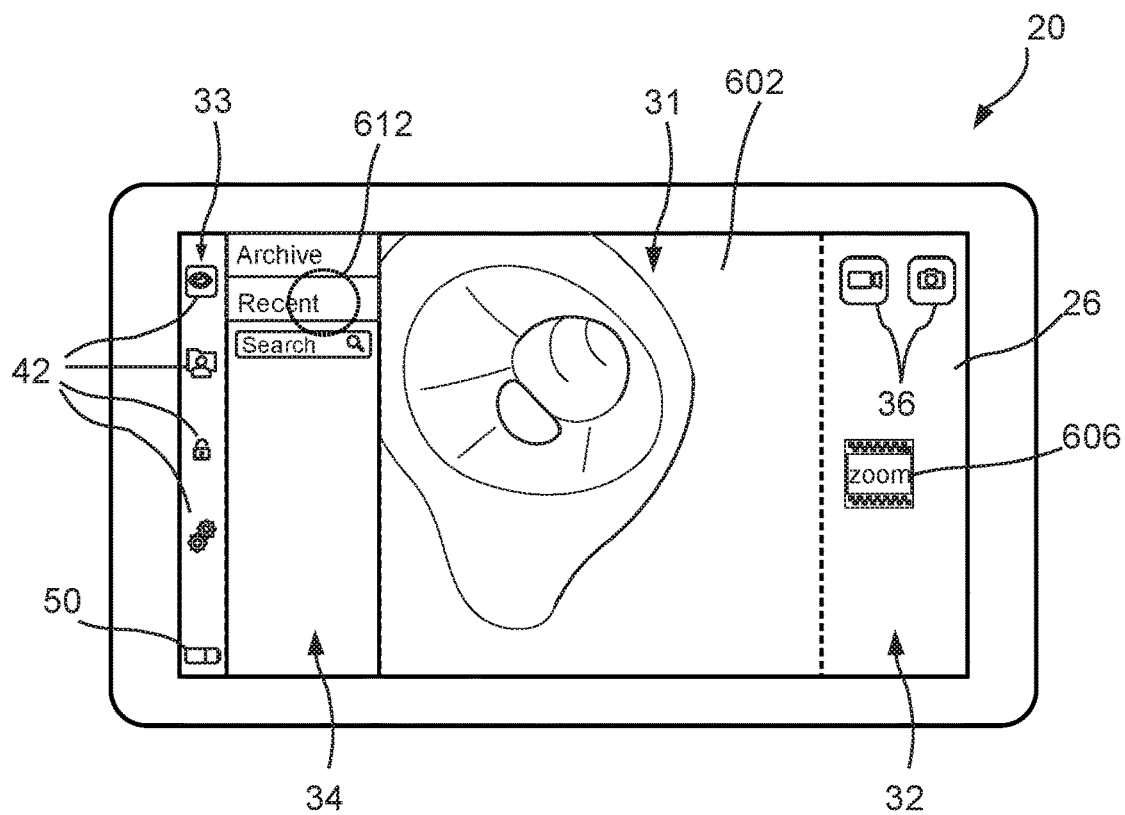

In accordance with not receiving and/or detecting a sixth user input 612, e.g. corresponding to the second user input 504 of FIG. 5C, within a threshold amount of time, e.g. 5 seconds, after receipt/detection of the fifth user input 608, the monitor device may, as illustrated in FIG. 19E, cease display of the primary menu 610 and display the section 602 of the live representation of the image data in the first portion 31 and the fourth portion 34 of the graphical user interface. Thus, obscuring part of the section 602 of the live representation of the image data in the enlarged view mode, may be limited by a timeout. Furthermore, the likelihood of receiving two unintentional inputs causing the live representation of the image data to be completely obstructed may be decreased.

Figure 19G:
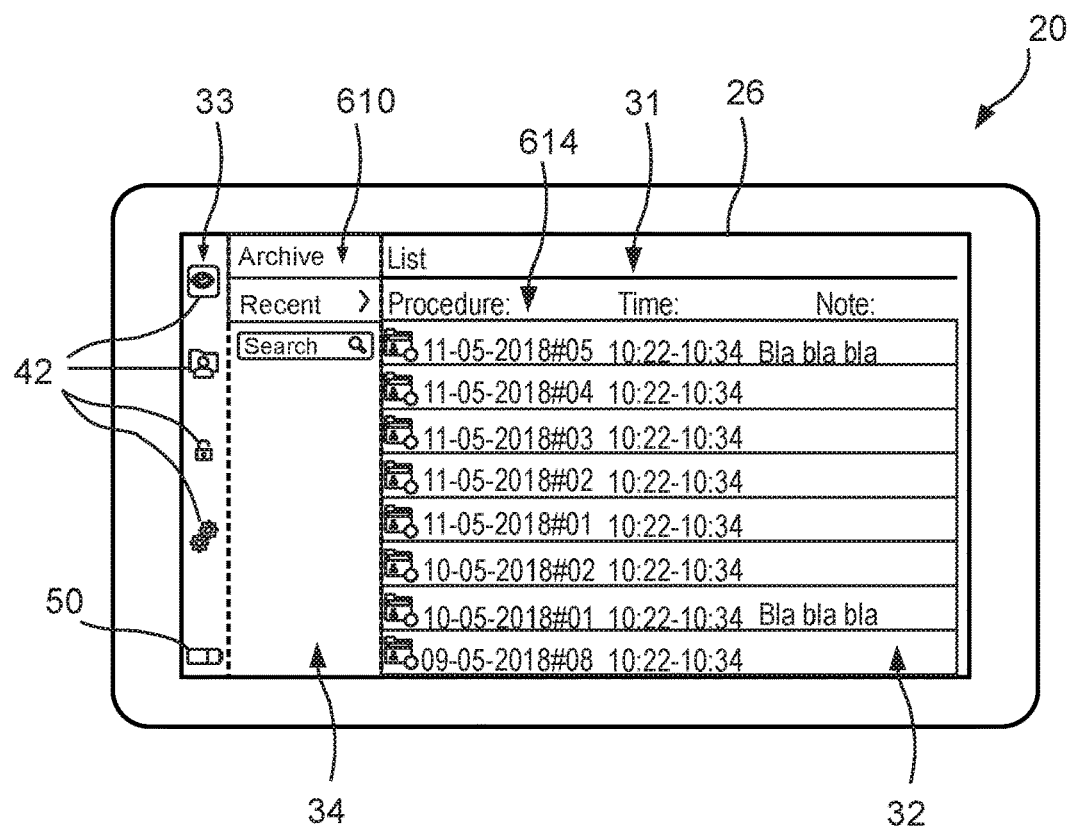

In accordance with receiving and/or detecting the sixth user input 612, e.g. corresponding to the second user input 504 of FIG. 18C, e.g. the user provides the sixth user input 612 on the first primary actionable item being a button for retrieving recent images and videos. In response, the monitor device 20 displays the secondary menu 614, in the illustrated example being a list of the recently stored procedures (FIG. 19G).

Similar to when operating in the normal view mode (FIGS. 18A-5D), the monitor device 20, in the enlarged view mode (FIGS. 19A-19G), needs to receive two consecutive inputs, e.g. within a time frame, to display a menu, which covers the entire live representation of the image data displayed in the first portion 31 of the graphical user interface.

Figure 19H:
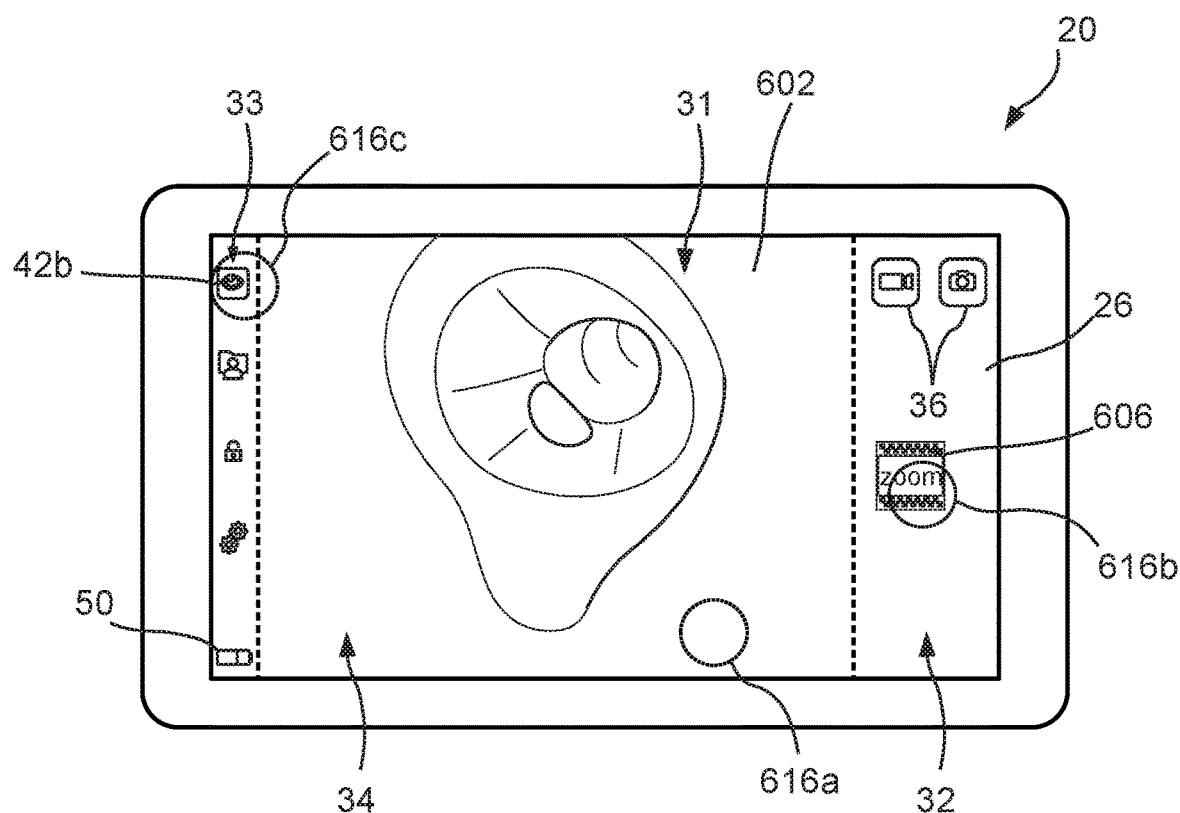

Referring now to FIG. 19H, the monitor device 20, while in the enlarged view mode, may receive a seventh user input 616a; 616b; 616c. As illustrated, the seventh user input may be a user input 616a, e.g. a double tap, at a location of the touch sensitive display corresponding to the first portion 31 of the graphical user interface. Alternatively or additionally, the seventh user input may be a user input 616b, e.g. a single tap or a double tap, at a location of the touch sensitive display corresponding to the enlarged view mode indicator 606. Alternatively or additionally, the seventh user input may be a user input 616c, e.g. a single tap or a double tap, at a location of the touch sensitive display corresponding to the second actionable menu item 42*b*, e.g. for causing the monitor device to cease display of any menus and display the live representation of the image data within the first portion 31 of the graphical user interface, such as described in more detail with respect to FIGS. 18E-18F.

Figure 19I:
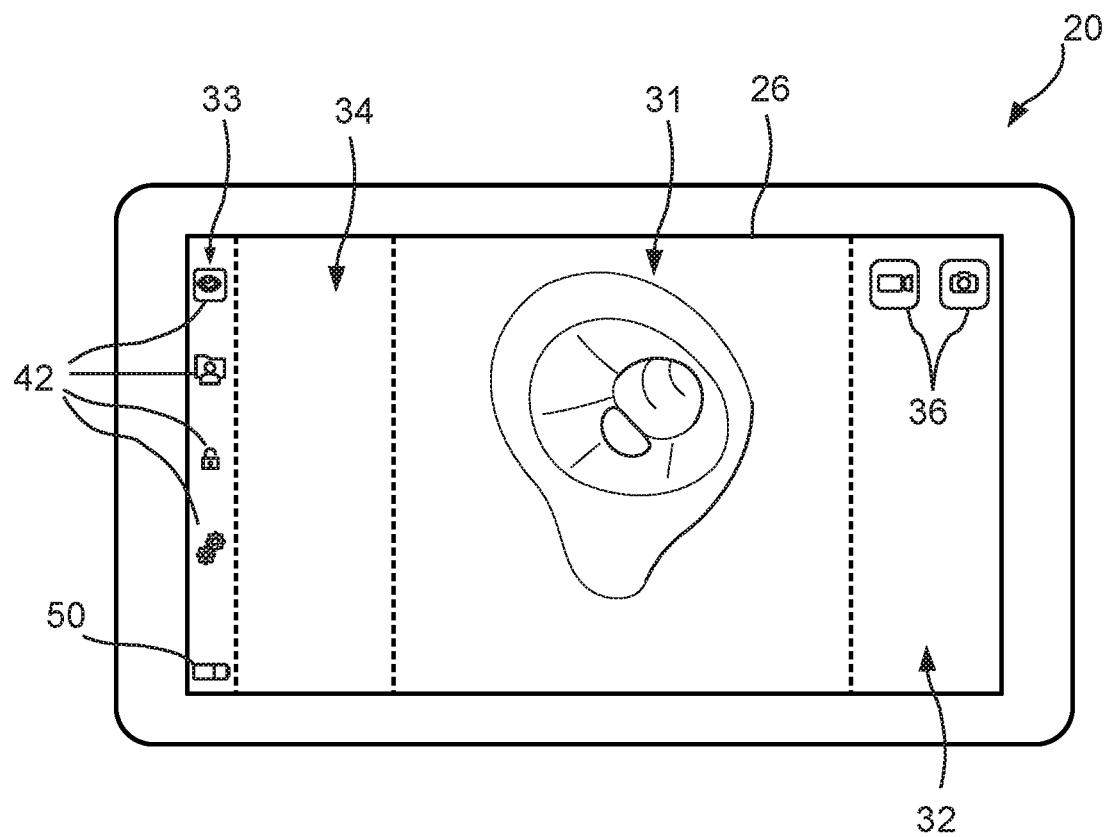

In response to receipt of the seventh user input 616*a*; 616*b*; 616*c*, the monitor device deactivates the enlarged view mode and display the live representation of the image data, e.g. only, within the first portion 31 of the graphical user interface, as illustrated in FIG. 19I, e.g. such that the live representation of the image data does not extend into the second portion and/or the fourth portion of the graphical user interface.

Figure 20A:
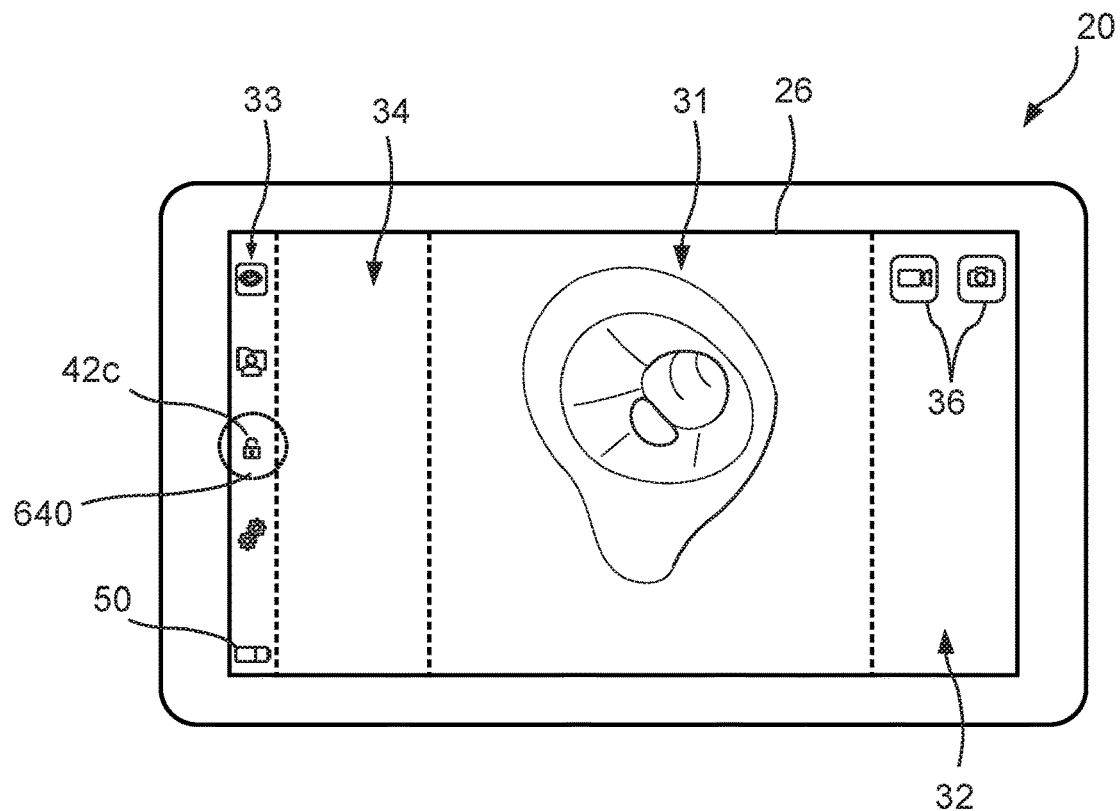

Referring now to FIGS. 20A-20I schematically illustrating exemplary user interactions with a graphical user interface of a monitor device 20, such as the monitor device 20 of any of the previous figures. FIG. 20A illustrates a situation, which could originate from any of FIGS. 18A-19I.

As illustrated in FIG. 20A, the monitor device 20 may receive a first user input 640 corresponding to selection of an actionable menu item 42*c* of the one or more actionable menu items 42, wherein the actionable menu item 42*c* corresponds to a login procedure. In the present example, the actionable menu item 42*c* illustrates a padlock.

The monitor device 20 detects the first user input 640 with the touch sensitive display, and in response to detection of the first user input 640, the monitor device 20 displays a primary menu 642 associated with the actionable menu item within the fourth portion 31 of the graphical user interface, e.g. without obscuring part of the first portion 31 of the graphical user interface, such as to avoid obstruction of the live representation, as explained in more detail above. The primary menu 642 may comprise an indication of a pre-selected user profile and a password type field, as illustrated. The pre-selected user profile may, e.g. be the last used user profile. By having a user profile pre-selected, the login procedure is made faster and more convenient, especially in common situations where the same user profile is used in most use cases of a monitor device.

The primary menu 642 may comprise at least two primary actionable items for receiving a user input, namely a first primary actionable item 642*a* for selecting another user profile, and a second primary actionable item 642*b* being a password type field configured to receive inputs corresponding to a password for authenticating as the selected user.

While displaying the primary menu 642, the monitor device may receive a second user input 644 corresponding to selection of the password type field 642*b*. The monitor device 20 detects the second user input 644 with the touch sensitive display, and in response to receipt of the second user input 644, the monitor device, with reference to FIG. 20C, displays a virtual keyboard 646 for entering a password in the password type field. The virtual keyboard 646 may be displayed in the first portion 31 of the graphical user interface and optionally in the second portion 32 of the graphical user interface. The virtual keyboard may obscure part of the live representation of the image data within the first portion 31 of the graphical user interface. The monitor device 20 is adapted to receive a sequence of user inputs, e.g. via the virtual keyboard, corresponding to input of a password. Thus, the user may type the password associated with the selected user, and the typed password will be written in the password type field 642*b*, and optionally in a designated area of the virtual keyboard 646, as illustrated. The typed password may be obscured by exchanging the characters with asterisks as the password is typed, thereby avoiding others to see the password, while still allowing the operator to identify having typed in a number of characters.

The monitor device 20 may determine whether the typed password matches a stored password for the pre-selected user, and in accordance with the typed password matching the stored password for the pre-selected user profile, the monitor device 20 may display a login message (e.g. 656 of FIG. 20G) indicative of the login attempt being successful. Following successful authentication, the monitor device 20 may further enter an authenticated mode corresponding to the selected user profile. The authenticated mode may be based on the user type (e.g. Admin, Advanced user, Regular user, Service provider, etc.) of the selected user profile. In accordance with the typed password not matching the stored password for the pre-selected user profile, the monitor device 20 may display an error message (e.g. 658 of FIG. 20H) indicative of the typed password being incorrect.

Figure 20B:
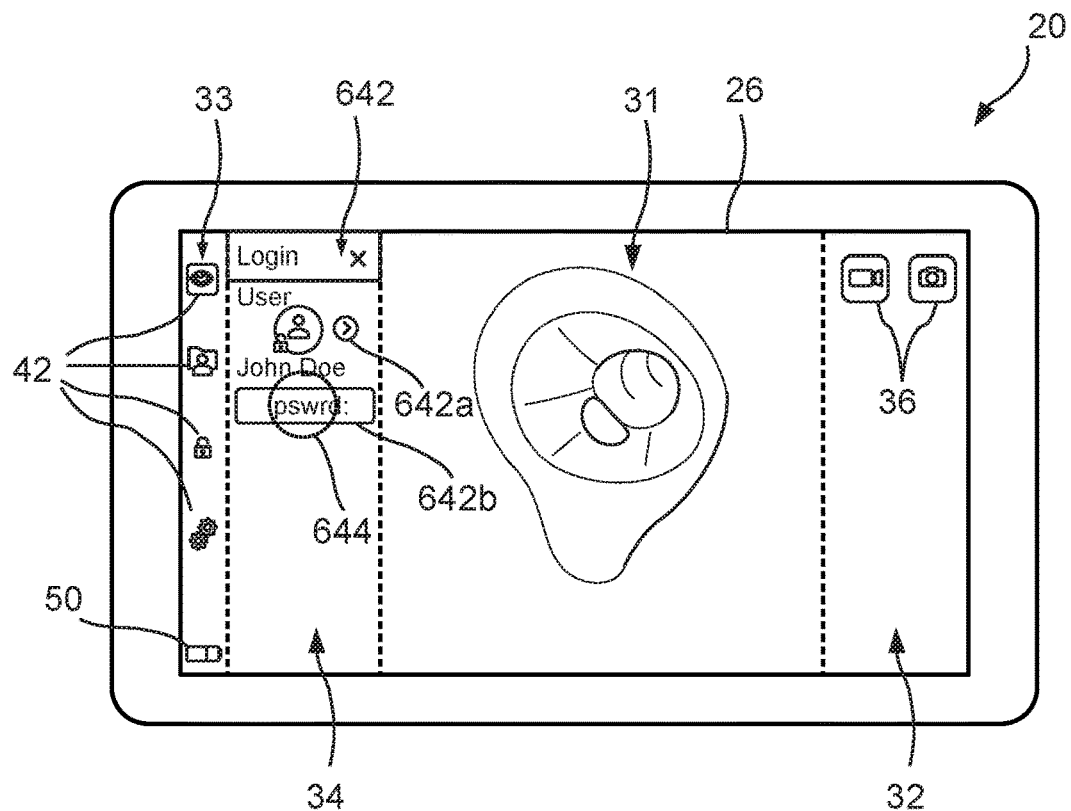
Figure 20C:
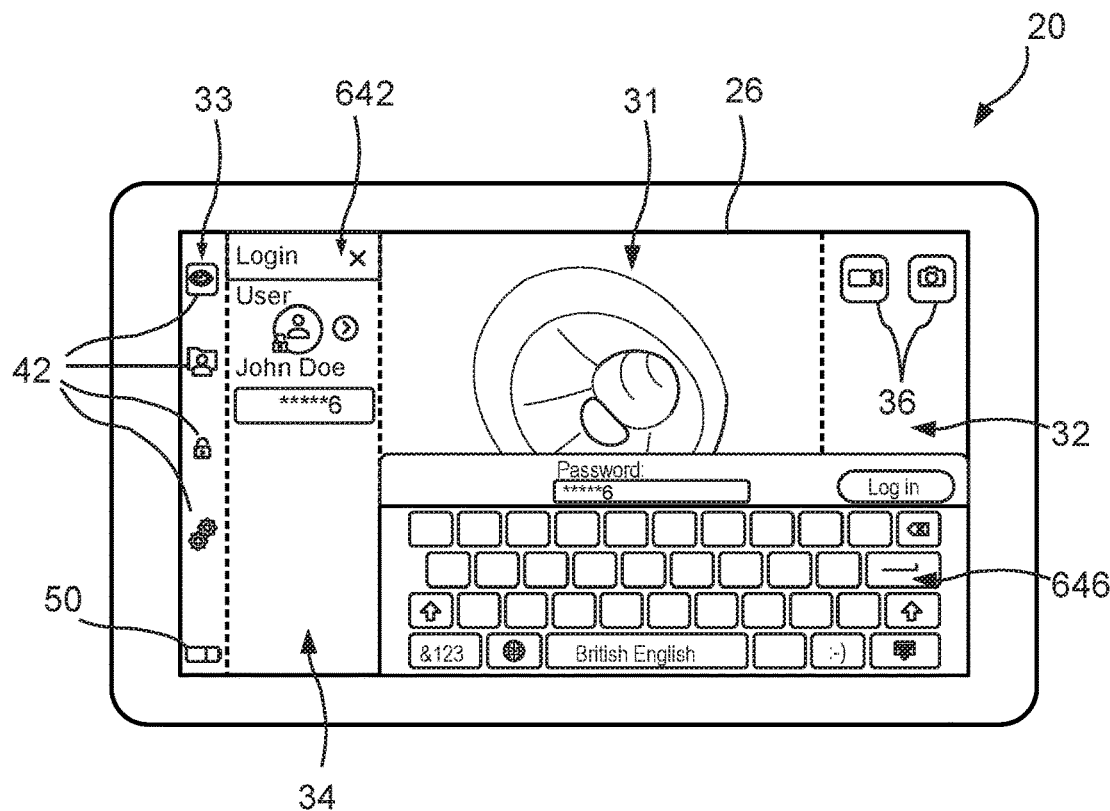
Figure 20D:
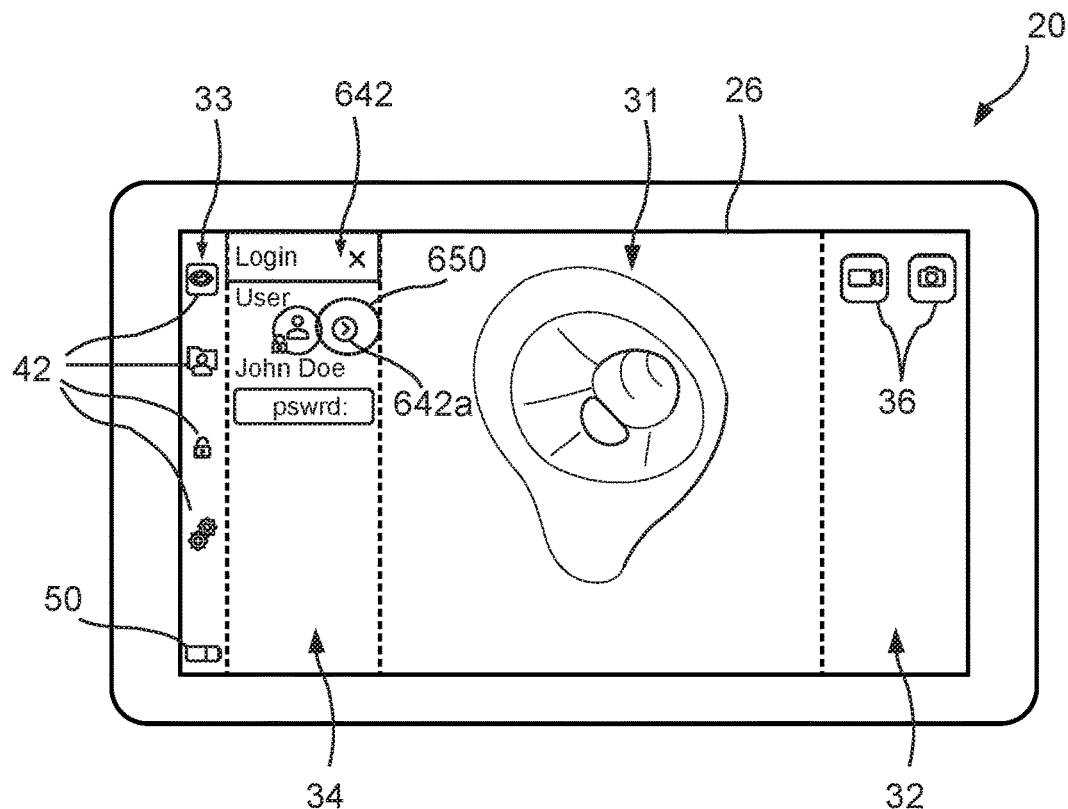
Figure 20E:
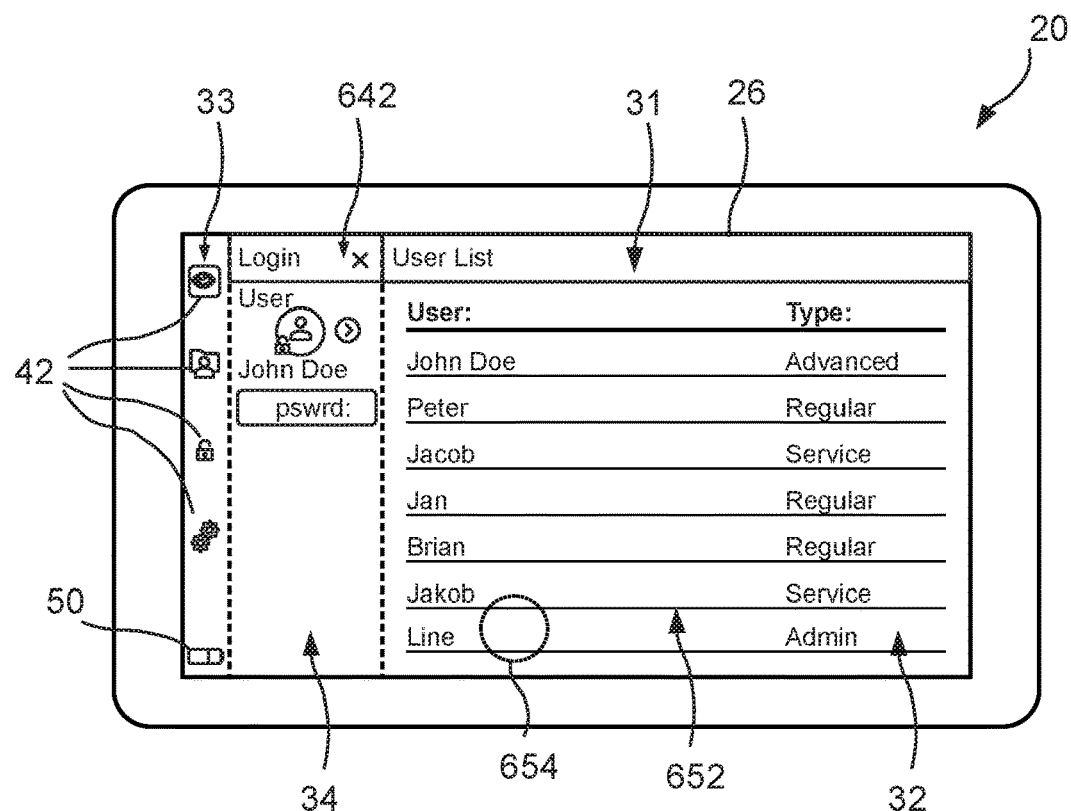
Figure 20F:
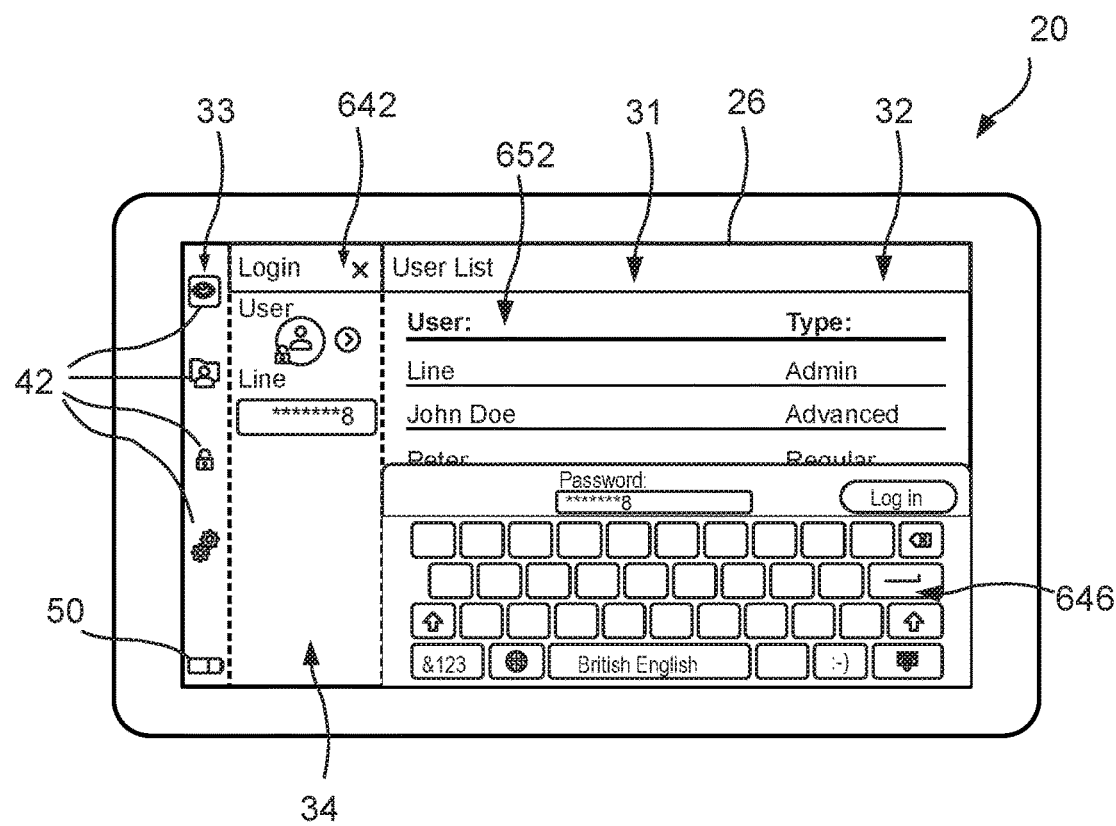

Instead of providing the second user input 644 to the password type field 642*b*, as illustrated in FIG. 20B, the user may want to select another user profile. To do this, while the monitor device displays the primary menu 642, the user may provide a third user input 650 corresponding to selection of the first primary actionable item 642*b* for selecting another user profile, see FIG. 20D. The monitor device 20 detects the third user input 650 with the touch sensitive display, and in response to detection of the third user input 650 the monitor device displays a list of selectable user profiles 652 in the first portion 31 of the graphical user interface and optionally in the second portion 32 of the graphical user interface, as illustrated in FIG. 20E. While displaying the list of selectable user profiles 652, the monitor device may receive a fourth user input 654 corresponding to selection of a selectable user profile. The monitor device 20 detects the fourth user input 654 with the touch sensitive display In response to detection of the fourth user input 654, i.e. in response to selection of a selectable user profile, the monitor device displays the virtual keyboard 646 for entering a password in the password type field. The virtual keyboard 646 may be displayed in the first portion 31 of the graphical user interface and optionally in the second portion 32 of the graphical user interface. The monitor device 20 is adapted to receive a sequence of user inputs, e.g. via the virtual keyboard 646, corresponding to input of a password. The user may type the password associated with the selected user, and the typed password will be written in a password type field. The typed password may be obscured by exchanging the characters with asterisks as the password is typed.

Figure 20G:
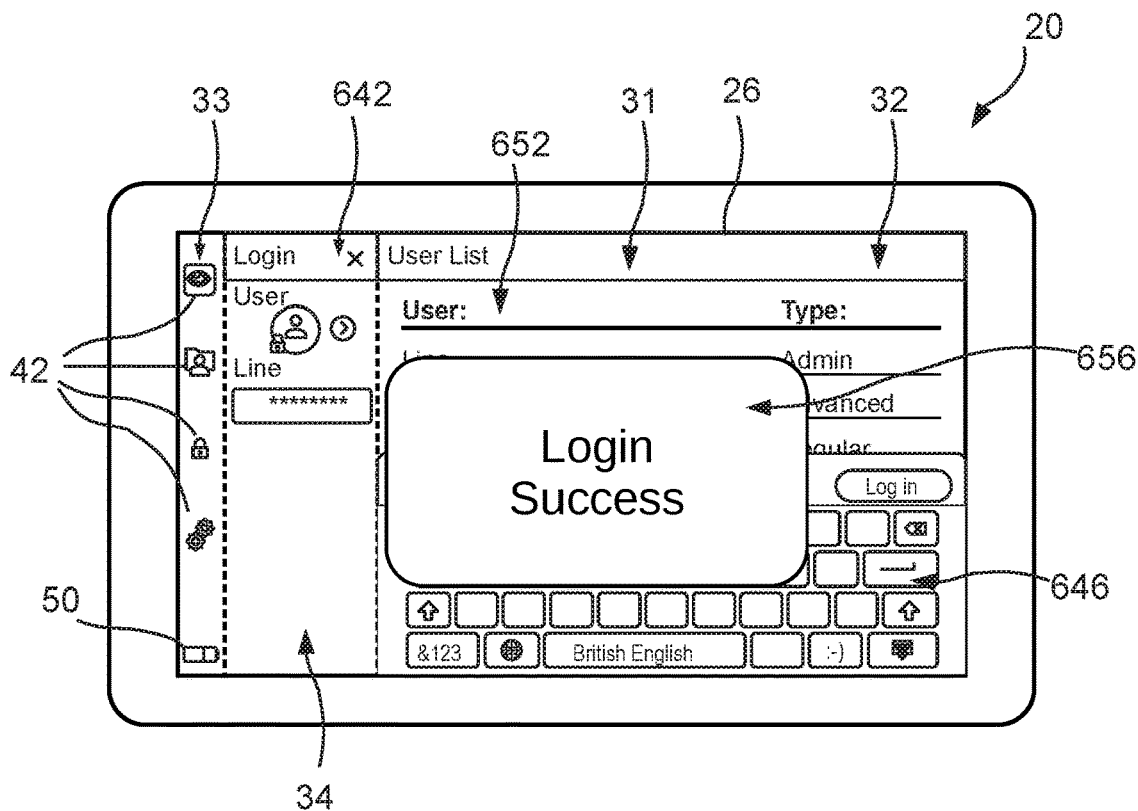

The monitor device 20 may determine whether the typed password matches a stored password for the selected user profile, and in accordance with the typed password matching the stored password for the selected user profile, the monitor device 20 may display a login message 656 indicative of the login attempt being successful, see FIG. 20G. Following successful authentication, the monitor device 20 further enter an authenticated mode corresponding to the selected user profile. The authenticated mode may be based on the user type (e.g. Admin, Advanced user, Regular user, Service provider, etc.) of the selected user profile.

Figure 20H:
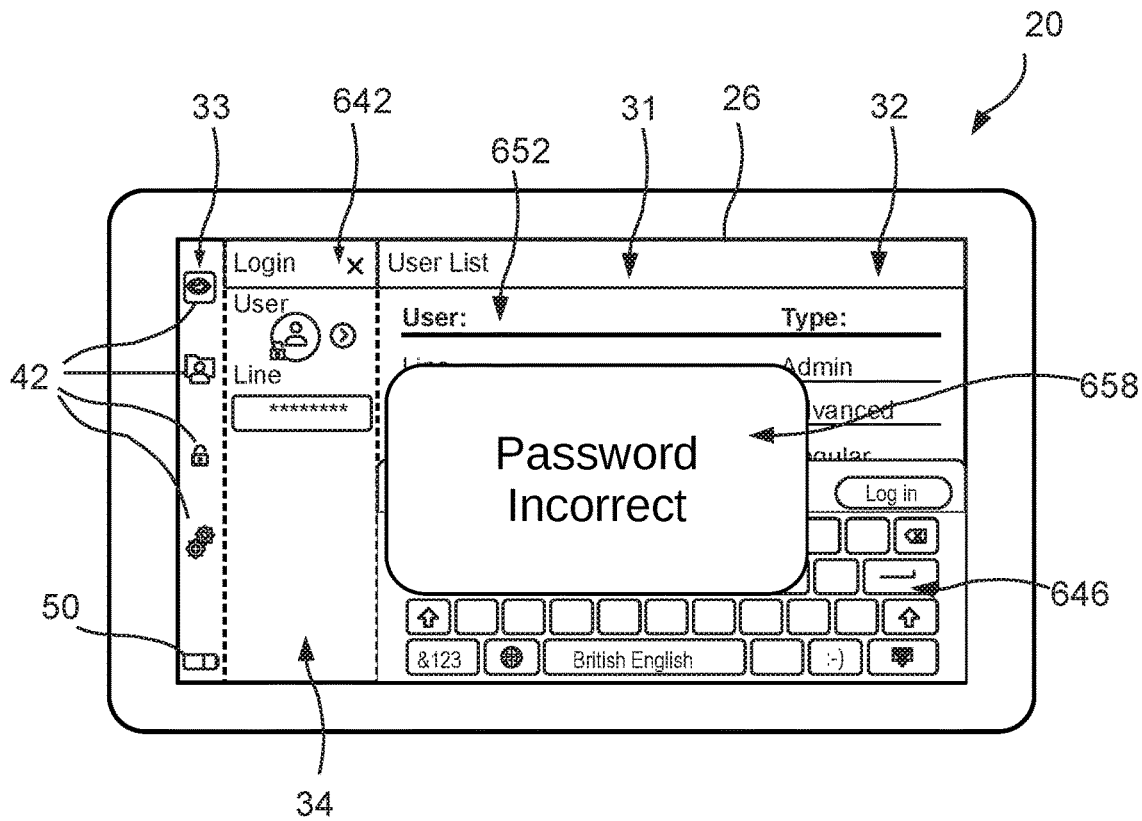

In accordance with the typed password not matching the stored password for the selected user profile, the monitor device 20 may display an error message 658 indicative of the typed password being incorrect, see FIG. 20H.

Figure 20I:
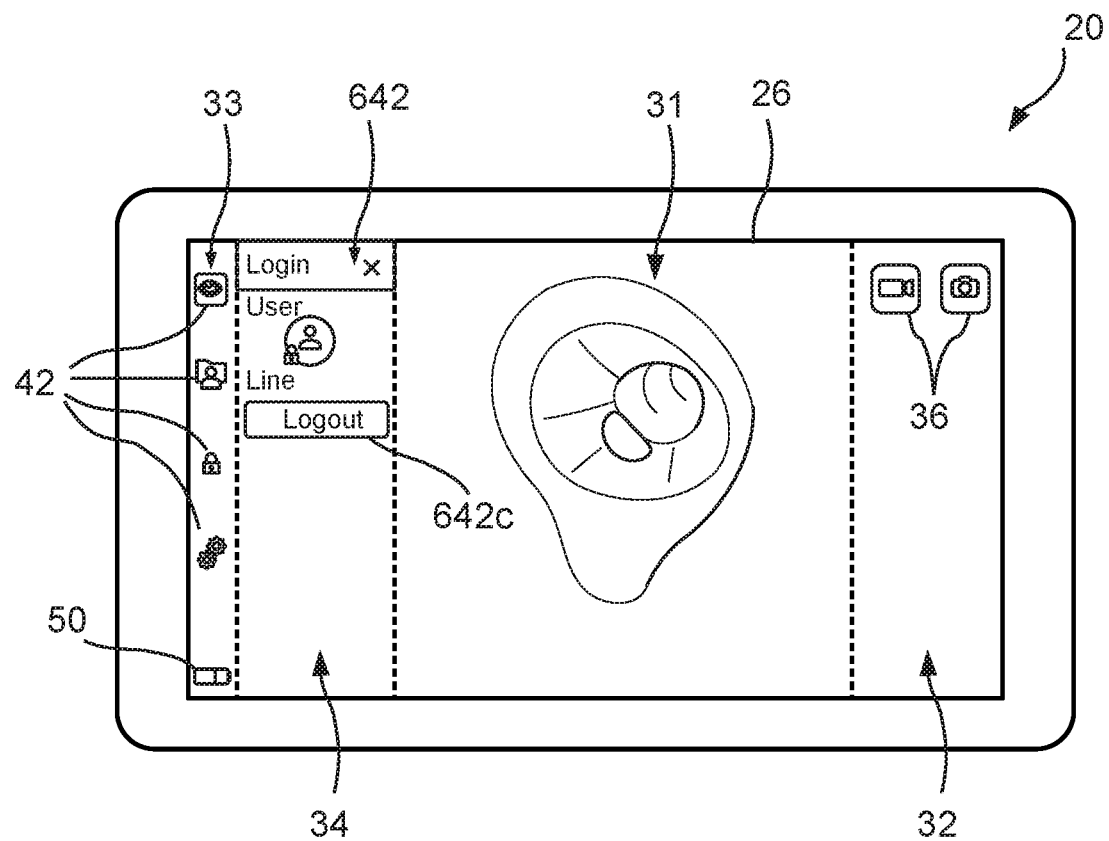

After authenticating a user profile, receiving and/or detecting the first user input 640, as illustrated in FIG. 20A, corresponding to selection of the actionable menu item 42*c* associated with the login procedure, the monitor device 20 may display a modified version of the primary menu 642, see FIG. 20I. The modified version of the primary menu 642 comprises a third primary actionable item 642c for logging out. Upon receipt of an input to the logout item 642c, the monitor device 20 may detect the input and in response to detecting the input enter a non-authenticated mode.

The monitor device 20 may further automatically enter the non-authenticated mode, e.g. if automatic logout criteria have been met. For example, the monitor device 20 may determine whether automatic logout criteria have been met. The automatic logout criteria may comprise that a visualization device has not been connected to the monitor device for a logout time duration. Furthermore, the automatic logout criteria may comprise that during the logout time duration no user input has been received via the touch sensitive display 26.

Additional exemplary embodiments of the foregoing aspects of the present disclosure are set out in the following exemplary items:

1. A medical visualization system comprising a visualization device having an image sensor configured to generate image data indicative of a view from the visualization device,
the medical visualization system further comprising a monitor device operable to receive the image data as the image data is being generated by the image sensor, the monitor device comprising a first housing extending in a first direction from a first housing side to a second housing side and in a second direction perpendicular to the first direction from a third housing side to a fourth housing side, the monitor device comprising a touch sensitive display accommodated in the first housing and having a first length in the first direction and a second length in the second direction,
wherein the monitor device displays with the touch sensitive display a graphical user interface comprising a plurality of non-overlapping portions including a first portion, a second portion, a third portion and a fourth portion, wherein the first portion and the fourth portion are arranged between the second portion and the third portion along the second direction, and wherein the fourth portion is arranged between the first portion and the third portion along the second direction,
wherein the monitor device displays a live representation of the image data within the first portion of the graphical user interface; and displays one or more actionable menu items within the third portion of the graphical user interface,
and wherein the monitor device is adapted to detect a first user input with the touch sensitive display corresponding to selection of a first actionable menu item of the one or more actionable menu items, and in response to detecting the first user input the monitor device displays a primary menu associated with the first actionable menu item within the fourth portion of the graphical user interface without obscuring part of the first portion of the graphical user interface, wherein the primary menu comprises one or more primary actionable items including a first primary actionable item,
and wherein while displaying the primary menu associated with the first actionable menu item, the monitor device is adapted to detect a second user input corresponding to selection of the first primary actionable item, and in response to detecting the second user input, the monitor device displays a secondary menu associated with the first primary actionable item in the first portion, and optionally the second portion and/or the fourth portion, of the graphical user interface.

2. Medical visualization system according to item 1, wherein the one or more actionable menu items comprises a second actionable menu item, and wherein, while the secondary menu is displayed, the monitor device is adapted to detect a third user input corresponding to selection of the second actionable menu item, and in response to detecting the third user input, the monitor device ceases display of the secondary menu and displays the live representation of the image data within the first portion of the graphical user interface.

3. Medical visualization system according to any of the preceding items, wherein the monitor device displays one or more actionable items within the second portion of the graphical user interface.

4. Medical visualization system according to item 3, wherein the one or more actionable items comprise an image capture button, and wherein the monitor device stores an image data file corresponding to the image data received when the image capture button is activated.

5. Medical visualization system according to any of items 3-4, wherein the one or more actionable items comprises a video capture button, and wherein the monitor device stores a video sequence of image data corresponding to the image data received when the video capture button is activated.

6. Medical visualization system according to item 5 as dependent on item 4, wherein the image capture button is a first colour and the video capture button is a second colour, and wherein the first colour is visually distinct from the second colour.

7. Medical visualization system according to item 6, wherein the first colour and the second colour differ by a hue difference of at least 60 degrees, such as at least 120 degrees.

8. Medical visualization system according to any of the preceding items, wherein the monitor device is adapted to detect a fourth user input, and in response to detecting the fourth user input the monitor device activates an enlarged view mode wherein a section of the live representation of the image data is displayed in the first portion and the fourth portion of the graphical user interface.

9. Medical visualization system according to item 8, wherein the fourth user input corresponds to a double tap on the touch sensitive display inside the first portion.

10. Medical visualization system according to any of items 8-9, wherein the live representation comprises a first crop section and a second crop section, the section of the live representation being displayed in the enlarged view mode being between the first crop section and the second crop section, wherein the first crop section and the second crop section are not displayed in the enlarged view mode.

11. Medical visualization system according to any of items 8-10, wherein in response to detecting the fourth user input the monitor device further displays an enlarged view mode indicator, optionally the enlarged view mode indicator is displayed in the second portion.

12. Medical visualization system according to any of items 8-11 as dependent on item 4, wherein in the enlarged view mode the monitor device stores with the image data file being stored information indicative of the monitor device operating in the enlarged view mode when the image capture button was activated.

13. Medical visualization system according to any of items 8-12 as dependent on item 5, wherein in the enlarged view mode the monitor device stores with the video sequence being stored information indicative of the monitor device operating in the enlarged view mode when the video capture button was activated.

14. Medical visualization system according to any of items 8-13, wherein, while in the enlarged view mode, the monitor device is adapted to detect a fifth user input corresponding to selection of the first actionable menu item of the one or more actionable menu items, and in response to detecting the fifth user input the monitor device displays the primary menu associated with the first actionable menu item within the fourth portion of the graphical user interface obscuring a part of the section of the live representation of the image data.

15. Medical visualization system according to any of items 8-14, wherein, while in the enlarged view mode, while displaying the primary menu associated with the first actionable menu item, the monitor device is adapted to detect a sixth user input corresponding to selection of a primary actionable item of the one or more primary actionable items of the primary menu, and in accordance with not receiving the sixth user input within a threshold amount of time after detecting the fifth user input, the monitor device ceases display of the primary menu associated with the first actionable menu item and displays the section of the live representation of the image data in the first portion and the fourth portion of the graphical user interface.

16. Medical visualization system according to any of items 8-15, wherein, while in the enlarged view mode, the monitor device is adapted to detect a seventh user input, and in response to detecting the seventh user input the monitor device deactivates the enlarged view mode and displays the live representation of the image data within the first portion of the graphical user interface.

17. Medical visualization system according to item 16, wherein the seventh user input corresponds to one or more of selection of the second actionable menu item, a touch input at a location of the enlarged view mode indicator, a touch input within the second portion of the graphical user interface.

18. Medical visualization system according to any of the preceding items, wherein the monitor device comprises one or more connection ports configured to receive a connector of the visualization device, and wherein the one or more connection ports are provided on the third housing side.

19. Medical visualization system according to any of the preceding items, wherein the first portion of the graphical user interface is square.

20. Medical visualization system according to any of the preceding items, wherein the first portion of the graphical user interface occupies the center of the graphical user interface.

21. Medical visualization system according to any of the preceding items, wherein a battery indicator and/or a time indicator is displayed within the third portion of the graphical user interface.

22. Medical visualization system according to any of the preceding items, wherein the monitor device displays a second background colour within the second portion of the graphical user interface, the second background colour filling at least 80% of the second portion of the graphical user interface, and wherein the second background colour has a lightness value of less than 0.6, such as less than 0.4, such as less than 0.2, such as less than 0.1.

23. Medical visualization system according to any of the preceding items, wherein the monitor device displays a fourth background colour within the fourth portion of the graphical user interface, the fourth background colour filling at least 80% of the fourth portion of the graphical user interface, and wherein the fourth background colour has a lightness value of less than 0.6, such as less than 0.4, such as less than 0.2, such as less than 0.1.

24. A medical visualization system comprising a visualization device having an image sensor configured to generate image data indicative of a view from the visualization device,
the medical visualization system further comprising a monitor device operable to receive the image data as the image data is being generated by the image sensor, the monitor device comprising a first housing extending in a first direction from a first housing side to a second housing side and in a second direction perpendicular to the first direction from a third housing side to a fourth housing side, the monitor device comprising a touch sensitive display accommodated in the first housing and having a first length in the first direction and a second length in the second direction,
wherein the monitor device displays with the touch sensitive display a graphical user interface, the graphical user interface comprising a plurality of non-overlapping portions including a first portion, a second portion, a third portion and a fourth portion, wherein the first portion and the fourth portion are arranged between the second portion and the third portion along the second direction, and wherein the second portion is arranged between the first portion and the fourth portion along the second direction, wherein the monitor device:
displays a live representation of the image data within the first portion of the graphical user interface;
displays a second background colour within the second portion of the graphical user interface, the second background colour filling at least 80% of the second portion of the graphical user interface, and wherein the second background colour has a lightness value of less than 0.6, such as less than 0.4, such as less than 0.2, such as less than 0.1;
displays one or more actionable menu items within the third portion of the graphical user interface; and
displays a fourth background colour within the fourth portion of the graphical user interface, the fourth background colour filling at least 80% of the fourth portion of the graphical user interface, and wherein the fourth background colour has a lightness value of less than 0.6, such as less than 0.4, such as less than 0.2, such as less than 0.1.

25. Medical visualization system comprising a visualization device having an image sensor configured to generate image data indicative of a view from the visualization device,
the medical visualization system further comprising a monitor device operable to receive the image data as the image data is being generated by the image sensor, the monitor device comprising a first housing extending in a first direction from a first housing side to a second housing side and in a second direction perpendicular to the first direction from a third housing side to a fourth housing side, the monitor device comprising a touch sensitive display accommodated in the first housing and having a first length in the first direction and a second length in the second direction, wherein the monitor device displays with the touch sensitive display a graphical user interface comprising a plurality of non-overlapping portions including a first portion, a second portion, a third portion and a fourth portion, wherein the first portion and the fourth portion are arranged between the second portion and the third portion along the second direction, and wherein the second portion is arranged between the first portion and the fourth portion along the second direction, wherein the monitor device:

displays a live representation of the image data within the first portion of the graphical user interface; and displays one or more actionable menu items within the third portion of the graphical user interface, the one or more actionable menu items including a first actionable menu item, wherein the first actionable menu item is associated with a login procedure, and wherein the monitor device is adapted to detect a first user input corresponding to selection of the first actionable menu item, and in response to detecting the first user input the monitor device displays a primary menu associated with the first actionable menu item within the fourth portion of the graphical user interface without obscuring part of the first portion of the graphical user interface, wherein the primary menu comprises an indication of a pre-selected user profile and a password type field;

while displaying the primary menu associated with the first actionable menu item the monitor device is adapted to detect a second user input corresponding to selection of the password type field, and in response to detecting the second user input, the monitor device displays a virtual keyboard in the first portion of the graphical user interface and optionally in the second portion of the graphical user interface, wherein the virtual keyboard obscures at least part of the live representation of the image data within the first portion of the graphical user interface, the virtual keyboard being configured for entering a password in the password type field.

26. Medical visualization system according to item 25, wherein the primary menu comprises a first primary actionable item for selecting another user profile, and wherein, while displaying the primary menu associated with the first actionable menu item, the monitor device is adapted to detect a third user input corresponding to selection of the first primary actionable item, and in response to detecting the third user input, the monitor device displays a list of selectable user profiles in the first portion of the graphical user interface and optionally in the second portion of the graphical user interface.

27. Medical visualization system according to item 26, wherein while displaying the list of selectable user profiles, the monitor device is adapted to detect a fourth user input corresponding to selection of a selectable user profile from the list of selectable user profiles, and in response to detecting the fourth user input, the monitor device displays a virtual keyboard in the first portion of the graphical user interface and optionally in the second portion of the graphical user interface, wherein the virtual keyboard is configured for entering a password in a password type field.

28. A medical visualization system comprising a visualization device having an image sensor configured to generate image data indicative of a view from the visualization device, the medical visualization system further comprising a monitor device operable to receive the image data as the image data is being generated by the image sensor, the monitor device comprising a touch sensitive display, and wherein the monitor device displays a primary menu comprising an indication of a selected user profile, and is adapted to detect a sequence of user inputs corresponding to input of a password, and determine whether the input password match a stored password for the selected user profile, in accordance with the input password matching the stored password for the selected user profile, the monitor device enters an authenticated mode corresponding to the selected user profile;

while the monitor device is in the authenticated mode, the monitor device determines whether automatic logout criteria have been met, wherein the automatic logout criteria comprise that the visualization device has not been connected to the monitor device for a logout time duration, and in accordance with the automatic logout criteria being met, the monitor device enters a non-authenticated mode.

29. Medical visualization system according to item 28, wherein the automatic logout criteria comprise that during the logout time duration no user input has been detected via the touch sensitive display.

30. Medical visualization system according to any of items 28-29, wherein, in accordance with the typed password not matching the stored password for the selected user profile, the monitor device displays an error message indicative of the typed password being incorrect.

31. Medical visualization system according to any of the preceding items, wherein each of the plurality of portions extend substantially throughout the first length in the first direction.

32. Medical visualization system according to any of the preceding items, wherein the first portion is square.

33. Medical visualization system according to any of the preceding items, wherein the first portion of the graphical user interface occupy the center of the touch sensitive display.

34. Medical visualization system according to any of the preceding items, wherein the first portion of the graphical user interface extends throughout more than 40% of the second length in the second direction.

Capturing and Browsing Images

FIGS. 21A-21H schematically illustrate exemplary user interactions with a graphical user interface of a monitor device 20, such as the monitor device 20 of any of the previous figures.

Figure 21A:
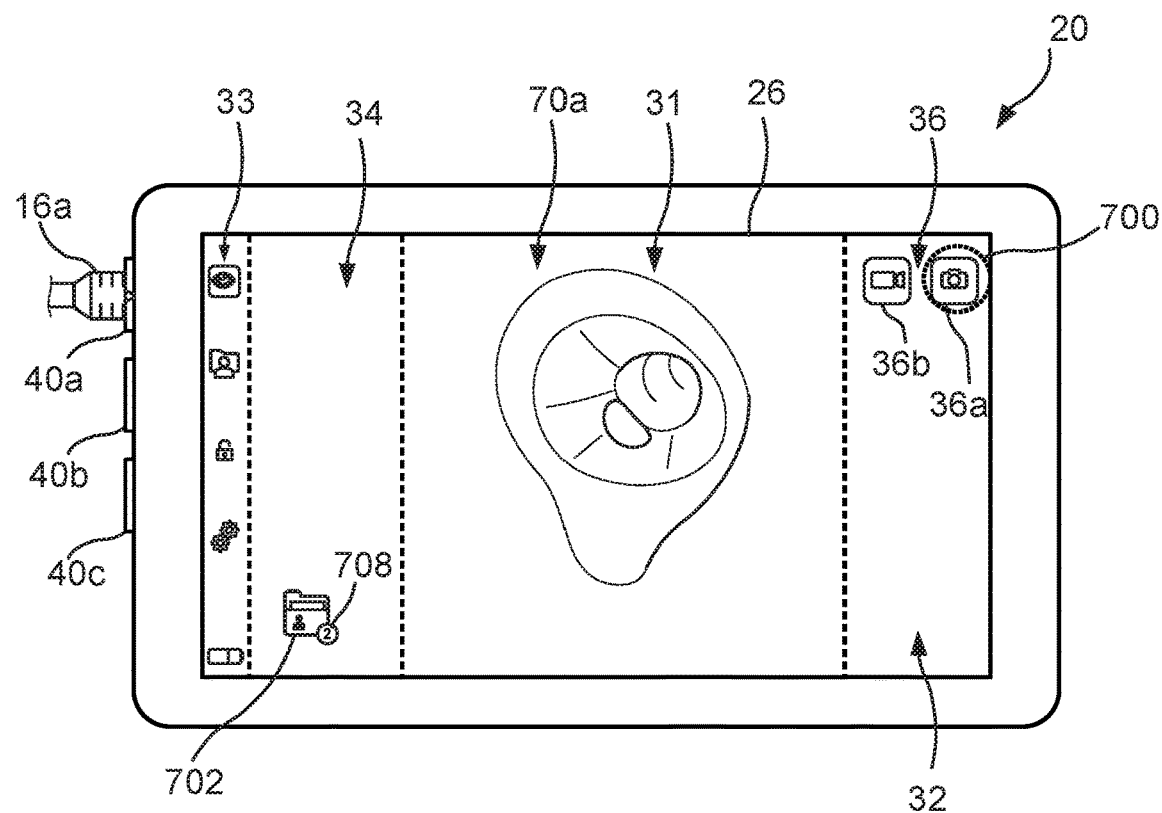
FIGS. 21A-21H schematically illustrate exemplary user interactions with an exemplary graphical user interface, FIGS. 22A-22D schematically illustrate exemplary user interactions with an exemplary graphical user interface, FIGS. 23A-23F schematically illustrate exemplary user interactions with an exemplary graphical user interface, FIGS. 24A-24H schematically illustrate exemplary user interactions with an exemplary graphical user interface, FIGS. 25A-25J schematically illustrate exemplary user interactions with an exemplary graphical user interface, FIGS. 26A-26D schematically illustrate exemplary user interactions with an exemplary graphical user interface, and FIGS. 27A-27E schematically illustrate exemplary user interactions with an exemplary graphical user interface.

In FIG. 21A, as illustrated that a first visualization device has been connected to the monitor device 20, by a first device connector 16a of the first visualization device being received at the first connection port 40a. A first live representation 70a of first image data generated by a first image sensor of the first visualization device is displayed within the first portion 31 of the graphical user interface.

When a visualization device is connected, e.g. when the monitor device 20 and/or the processing unit of the monitor device detects connection of a visualization device, device identifier information from a device identifier of the respective visualization device may be obtained. For example, the visualization device may be fitted with an EPROM (alternatively a QR code, RFID tag, NFC etc may be used), which the monitor device 20 is able to read. For example, the processing unit of the monitor device may execute a process for interrogating the device identifier, via the device connector and connection port. The EPROM may store information of the visualization device, e.g. a serial number of the visualization device, which may uniquely identify the visualization device. Also the device identifier information may be indicative of the type of visualization device, e.g. whether it is an endoscope or a laryngoscope, brand of the visualization device, production version, batch number etc.

In response to detecting connection of the visualization device, and after obtaining the device identifier information, the monitor device may open (create or reopen, depending on whether the visualization device has previously been connected) a procedure session corresponding to the device identifier information. For example, a first procedure session may be opened corresponding to the first device identifier information obtained from the first visualization device, and a second procedure session may be opened corresponding to a second device identifier information obtained from a second visualization device, if connected. The procedure sessions may be unique, and therefore reconnecting a previously connected visualization device may cause the monitor device 20 to reopen a previously created session. A procedure session may be implemented by creating a folder in the file system of the monitor device 20, e.g. within the memory of the monitor device 20. Image files and video sequences obtained with a particular visualization device may be stored in the folder corresponding to the visualization device.

Thus, the monitor device 20 in opening the procedure session may determine, e.g. based on the device identifier information, whether the visualization device has been previously connected to the monitor device. Accordingly, if determined that the visualization device has previously been connected to the monitor device 20, the monitor device 20 reopens the procedure session corresponding to the device identifier information, and if determined that the visualization device has not previously been connected to the monitor device 20, the monitor device 20 creates a new procedure session corresponding to the device identifier information.

The session, and the folder of images/videos, may be based on the device identifier information of the attached visualization device. Hence, when attaching a new endoscope a new folder is created, and if reattaching a scope that was previously attached the previously created folder is reopened, and additionally captured still images or videos are saved to this existing folder. Hence, if an endoscope is pulled out by accident and inserted again, captured images/videos are not saved into a new folder, but organised in the same folder.

A folder icon 702 is displayed within a background portion (e.g. second portion 32 and/or fourth portion 34) of the graphical user interface. In the present example, the folder icon 702 is displayed within the fourth portion. Alternatively, the folder icon 702 may be shown in the second portion 32. The folder icon 702 comprises a visual representation 708 of a count of stored files, e.g. stored during the procedure session.

As illustrated in FIG. 21A, a user may provide a first user input 700 corresponding to selection of the image capture button 36a. The monitor device 20, e.g. with the touch sensitive display 26, is adapted to detect the first user input 700. In response to detection of the first user input 700, the monitor device stores a first image file corresponding to the image data received when the first user input 700 was detected, e.g. corresponding to the live representation 70a being displayed in the first portion 31. The monitor device 20 associates the first image file with the procedure session. For example, the monitor device 20 may store the first image file in the folder corresponding to the procedure session.

Figure 21B:
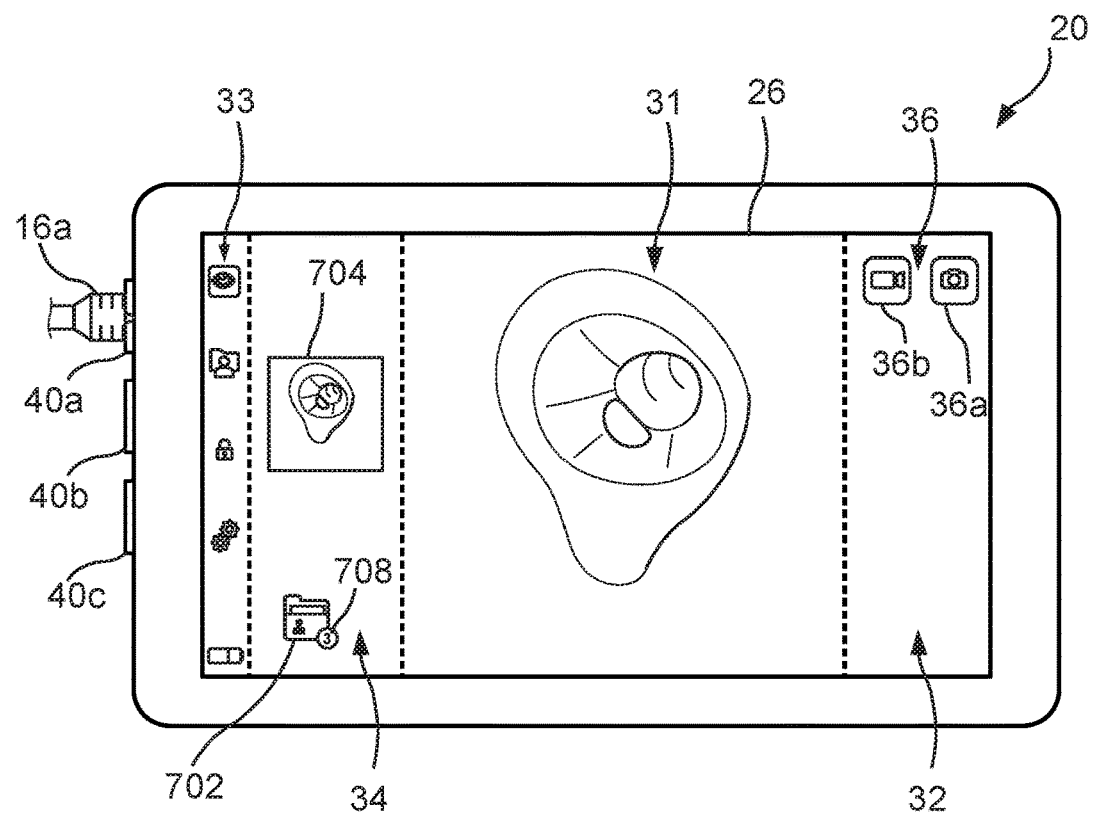

Furthermore, as illustrated in FIG. 21B, the monitor device, in response to detection of the first user input 700 and storing of the first image file displays within the background portion of the graphical user interface, e.g. the fourth portion 34 as illustrated, a first representation 704 of a still image corresponding to the stored first image file. Thereby, the operator is notified that the monitor device 20 has stored an image, and the operator is further provided with an example of the stored image, e.g. to allow the operator to quickly confirm that the image does show what he/she intended it to show.

Figure 21C:
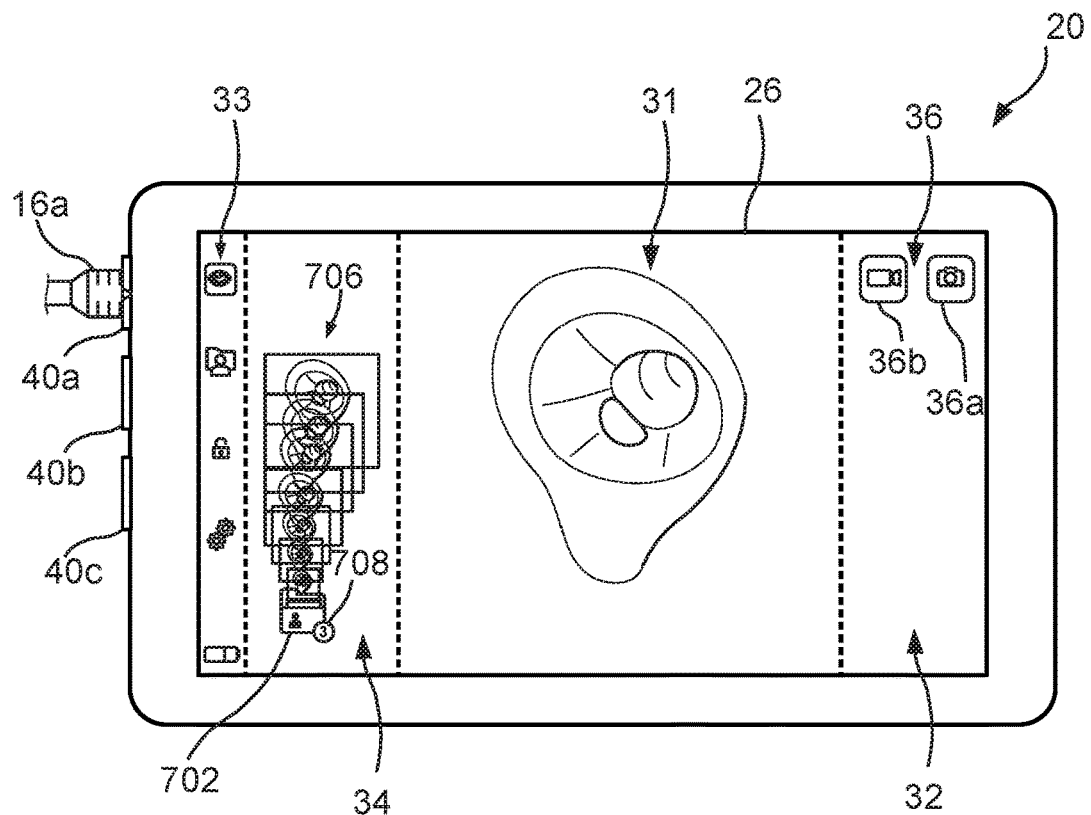
Figure 21D:
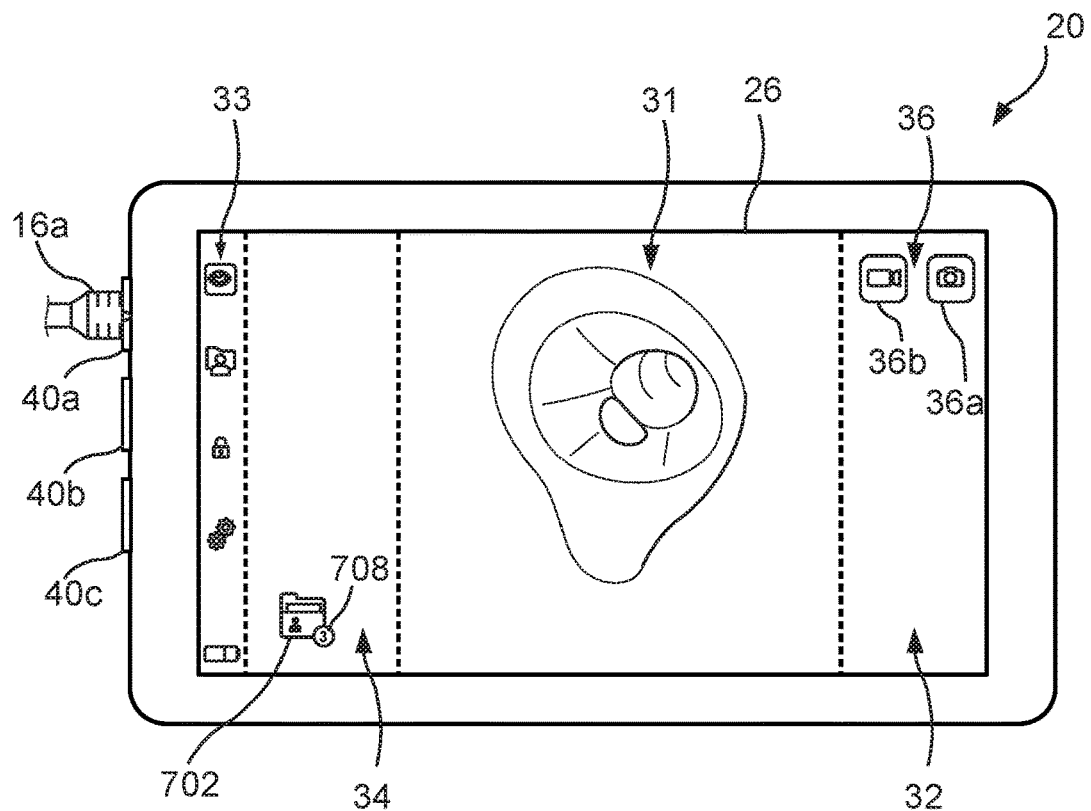

As shown in FIG. 21C, after a predetermined delay after detection of the first user input, the monitor device displays an animation 706 of transitioning the first representation 704 to the folder icon 702. The predetermined delay may be between 1-5 seconds, such as between 1.5-3 seconds, such as 1.5 seconds or such as 2 seconds. Thus, the operator is visually notified that the captured image is stored and is placed in the folder represented by the folder icon 702. The animation 706 may have a duration between 100-1500 ms, such as between 300-1000 ms, such as between 300-600 ms, such as 400 ms or 500 ms.

Furthermore, also in response to detection of the first user input 700 and storing of the first image file (cf. FIG. 21B), the display of the visual representation 708 of the count of stored files stored during the procedure session is updated by increasing the count of stored files. Alternatively, the display of the visual representation 708 of the count of stored files stored during the procedure session may be updated by increasing the count of stored files after display of the animation 706, e.g. in the transition between FIG. 21C and FIG. 21D.

FIGS. 21E-21H, shows capturing of a second image file after having stored the first image file as explained with reference to FIGS. 21A-5D.

Figure 21E:
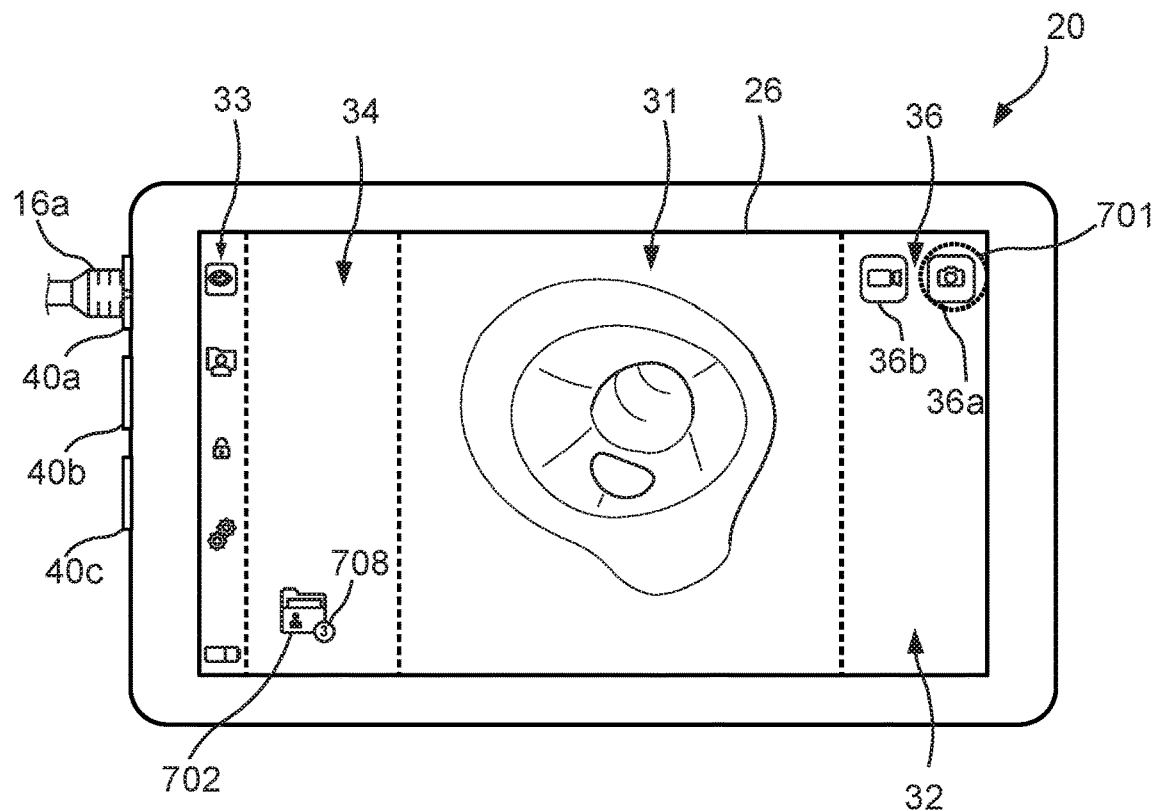

As illustrated in FIG. 21E, a user may provide a second user input 701 corresponding to selection of the image capture button 36a. In response to detection of the second user input 701, the monitor device stores a second image file corresponding to the image data received when the second user input 701 was detected, e.g. corresponding to the live representation 70a being displayed in the first portion 31. The monitor device 20 associates the second image file with the procedure session, e.g., the monitor device 20 may store the second image file in the folder corresponding to the procedure session, i.e. in the same folder as the first image file.

Figure 21F:
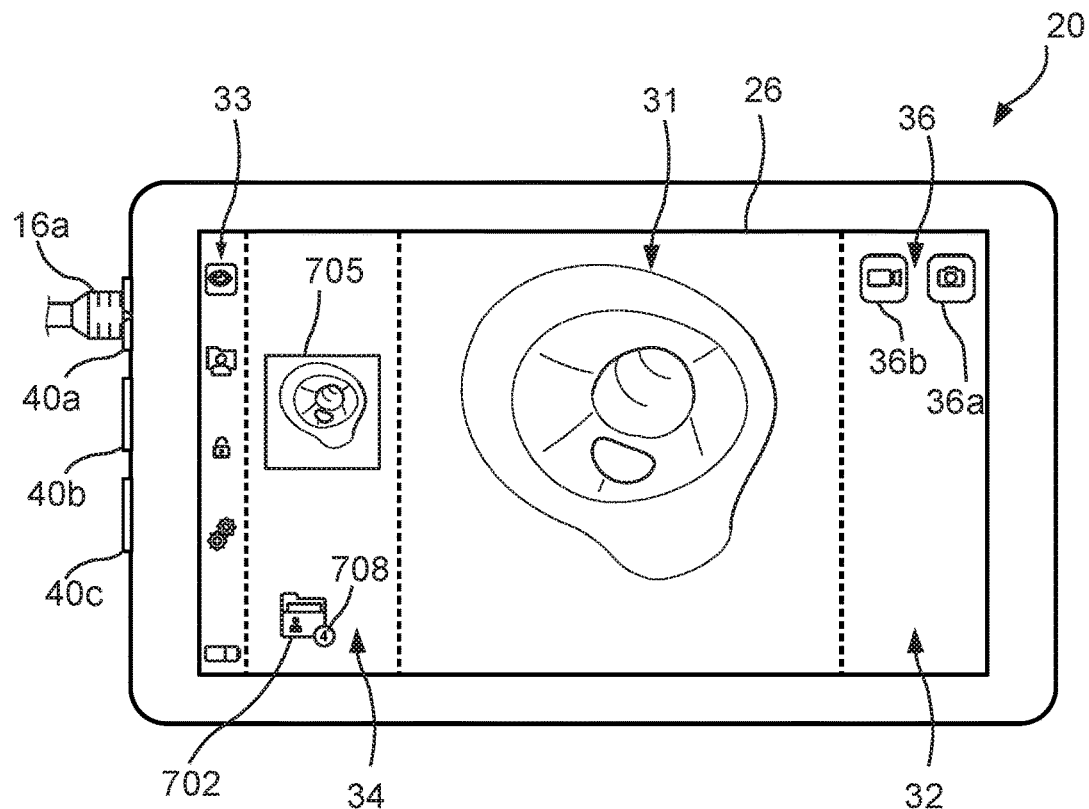

As illustrated in FIG. 21F, the monitor device, in response to detection of the second user input 701 and storing of the second image file displays within the background portion of the graphical user interface, e.g. the fourth portion 34 as illustrated, a second representation 705 of a still image corresponding to the stored second image file.

Figure 21G:
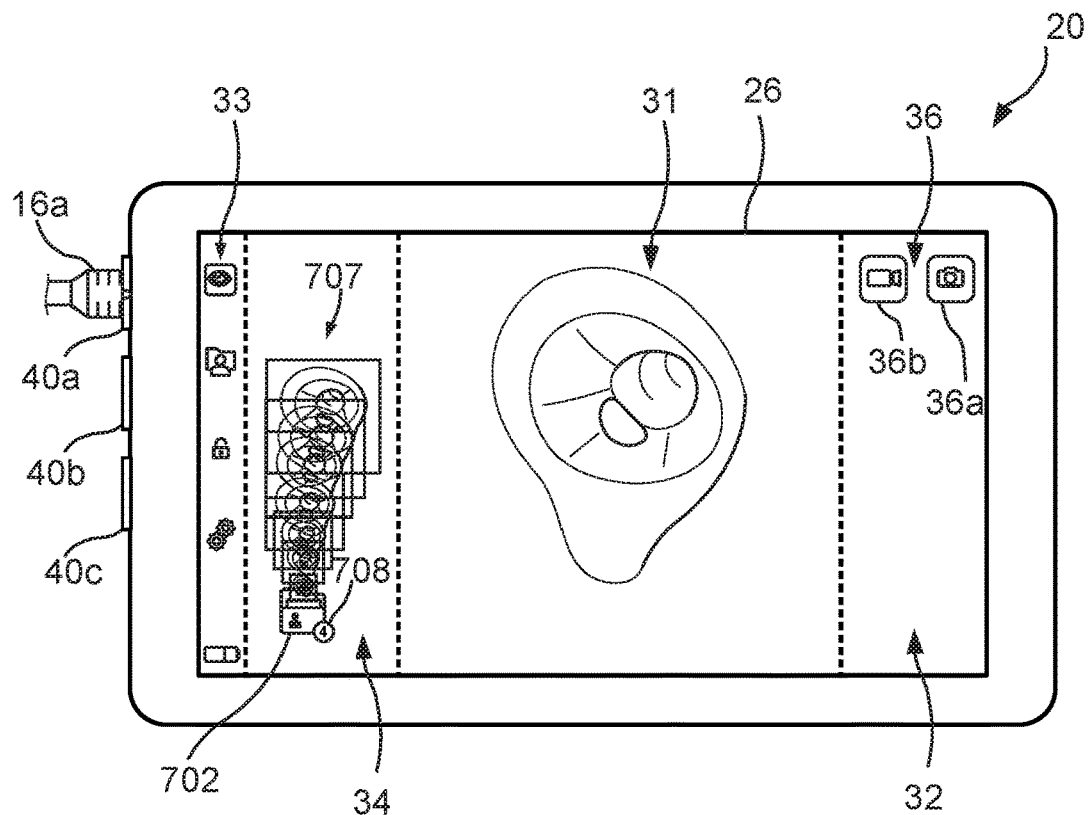
Figure 21H:
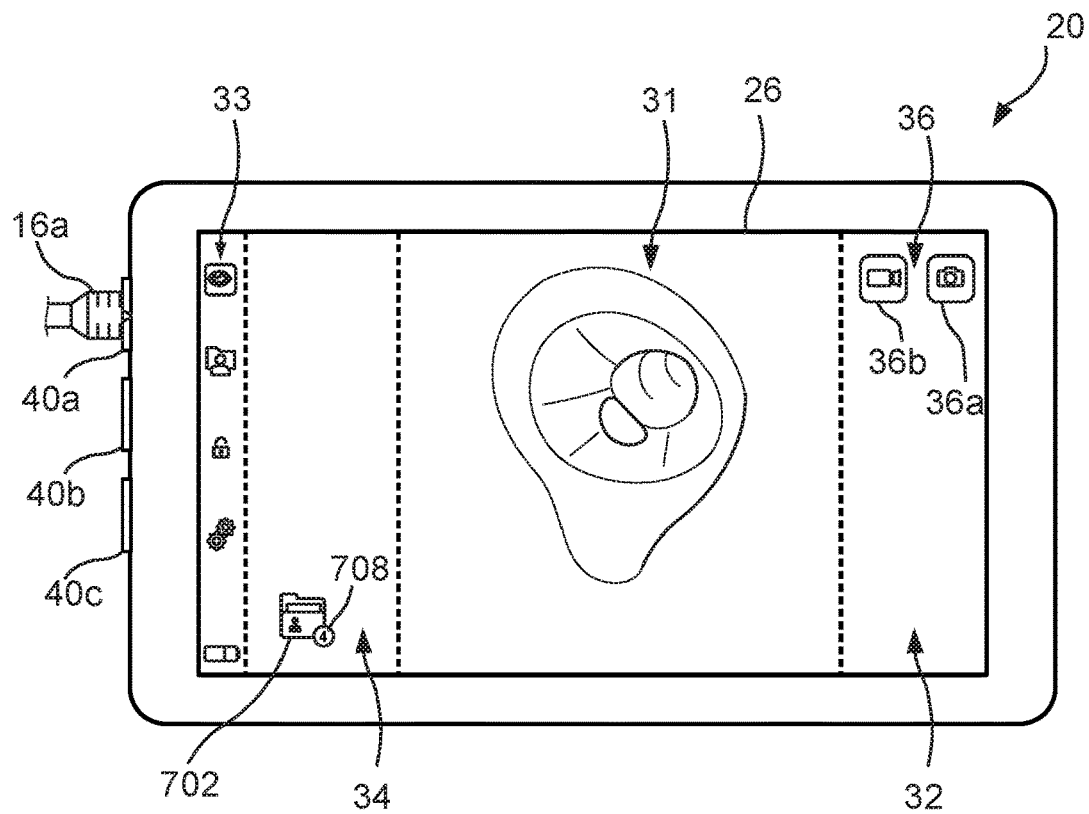

As shown in FIG. 21G after the predetermined delay after detection of the second user input 701, the monitor device displays an animation 707 of transitioning the second representation 705 to the folder icon 702. The animation 707 may have a duration between 100-1500 ms, such as between 300-1000 ms, such as between 300-600 ms, such as 400 ms or 500 ms.

FIGS. 22A-22D schematically illustrate exemplary user interactions with a graphical user interface of a monitor device 20, such as the monitor device 20 of any of the previous figures.

Figure 22A:
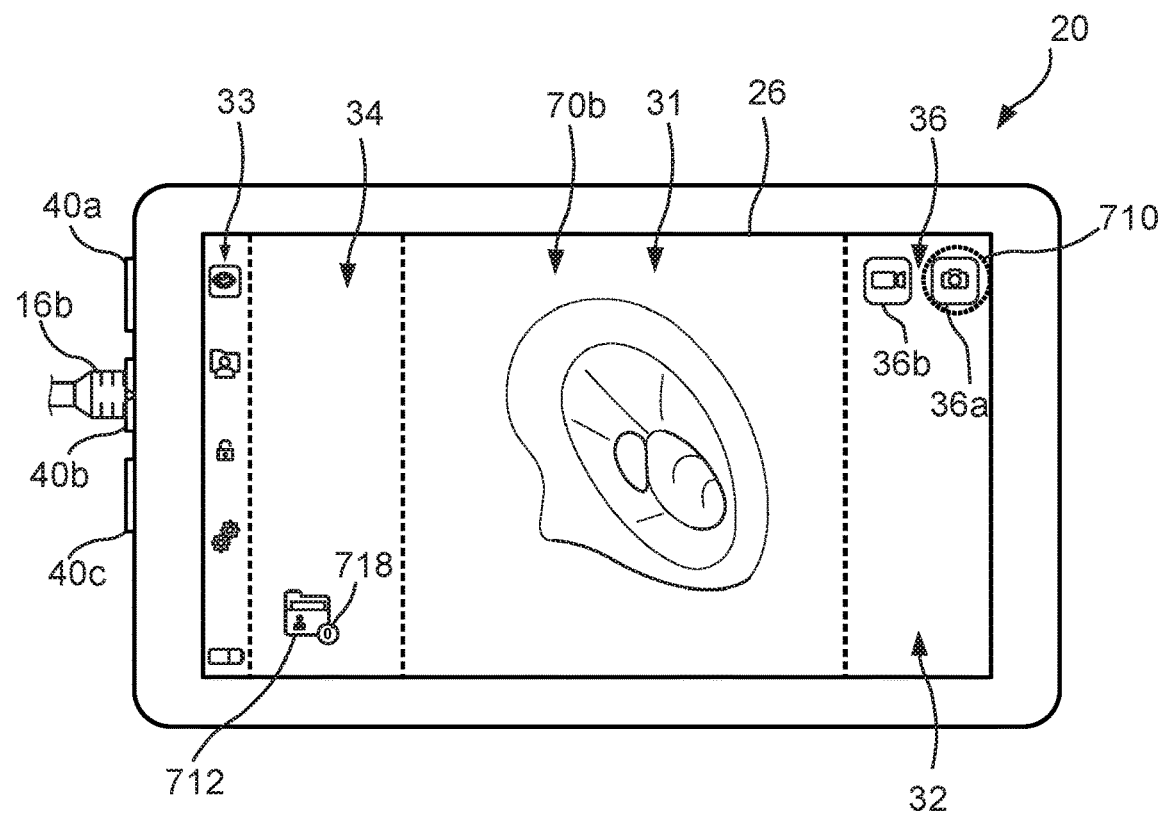

As seen in FIG. 22A, the first visualization device, which was connected to the monitor device in FIGS. 21A-21H, as illustrated by device connector 16a has been disconnected. Instead a second visualization device having device connector 16b has been connected to the monitor device 20 via the second connection port 40b. The second visualization device could have been equally connected to the first connection port 40a.

As explained above, when a visualization device is connected, device identifier information from a device identifier of the respective visualization device may be obtained, and the monitor device 20 may open a procedure session based on the device identifier information. Thus, in establishing connection to the second visualization device, including obtaining second device identifier information from a second device identifier of the second visualization device, the monitor device 20 may open a second procedure session corresponding to the second device identifier information, e.g. different from the procedure session as described with respect to FIGS. 21A-21H.

Accordingly, the monitor device 20, as illustrated in FIG. 22A, displays a live representation 70b of second image data generated by a second image sensor of the second visualization device, and a folder icon 712 is displayed within a background portion (e.g. second portion 32 and/or fourth portion 34) of the graphical user interface. In the present example, the folder icon 712 is displayed within the fourth portion. Alternatively, the folder icon 712 may be shown in the second portion 32. The folder icon 712 comprises a visual representation 718 of a count of stored files, e.g. stored during the second procedure session. As the second procedure session is different from the procedure session of FIGS. 21A-21H, because the visualization device is different, the visual representation 718 may have a different count than the visual representation 708 of FIGS. 21A-21H.

As illustrated in FIG. 22A, a user may provide a third user input 710 corresponding to selection of the image capture button 36a. The monitor device 20, e.g. with the touch sensitive display 26, is adapted to detect the third user input 710. In response to detection of the third user input 710, the monitor device stores a third image file corresponding to the second image data received when the third user input 710 was detected, e.g. corresponding to the live representation 70b being displayed in the first portion 31. The monitor device 20 associates the third image file with the second procedure session. For example, the monitor device 20 stores the third image file in the folder corresponding to the second procedure session.

Figure 22B:
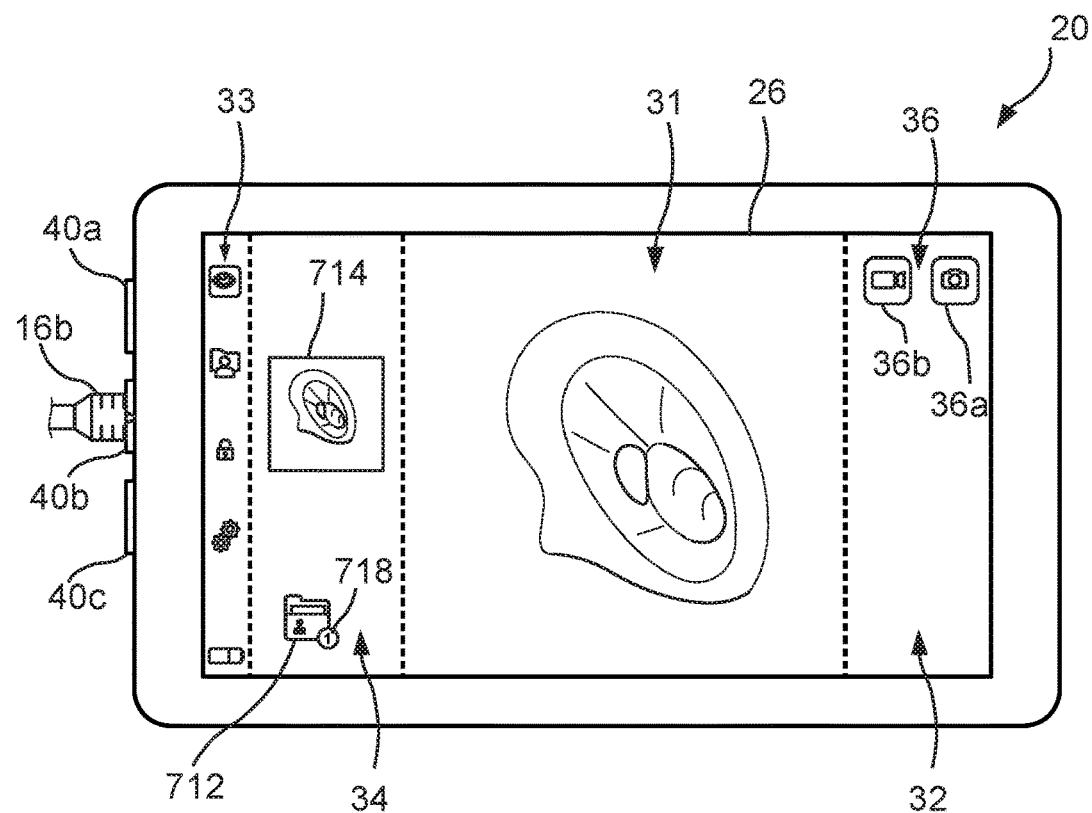

As illustrated in FIG. 22B, the monitor device 20, in response to detection of the third user input 710 and storing of the third image file displays within the background portion of the graphical user interface, e.g. the fourth portion 34 as illustrated, a third representation 714 of a still image corresponding to the stored third image file.

Figure 22C:
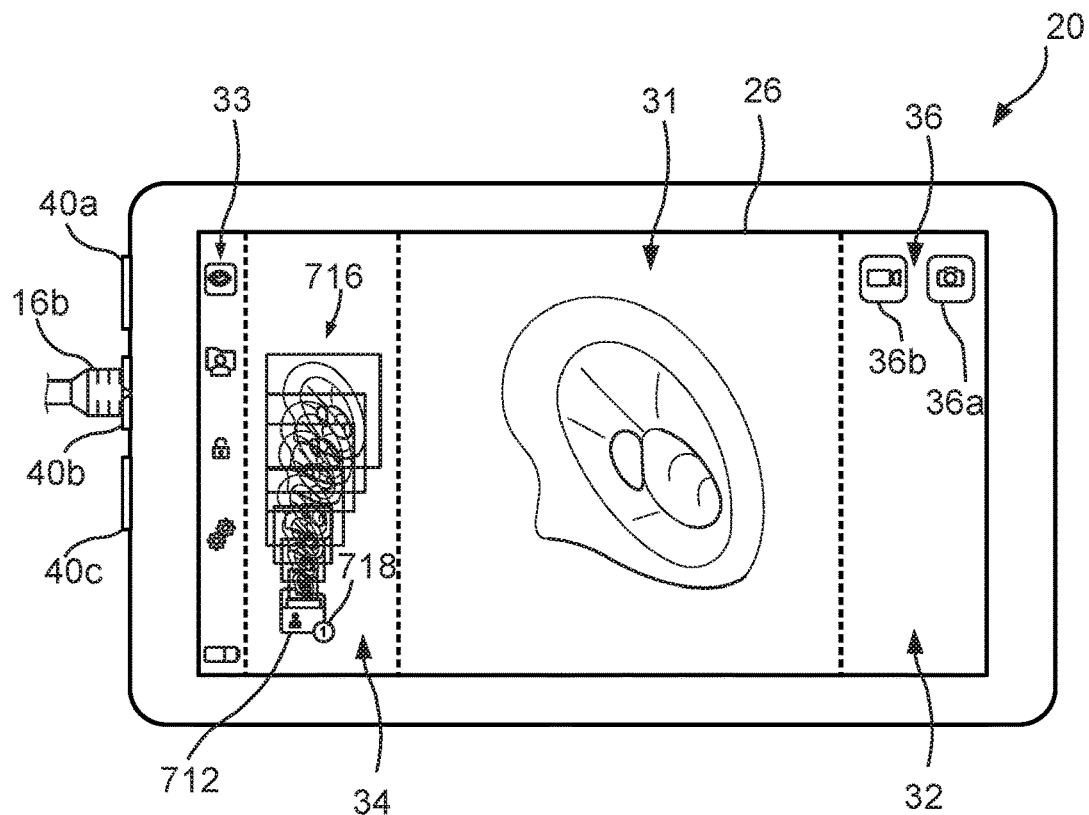
Figure 22D:
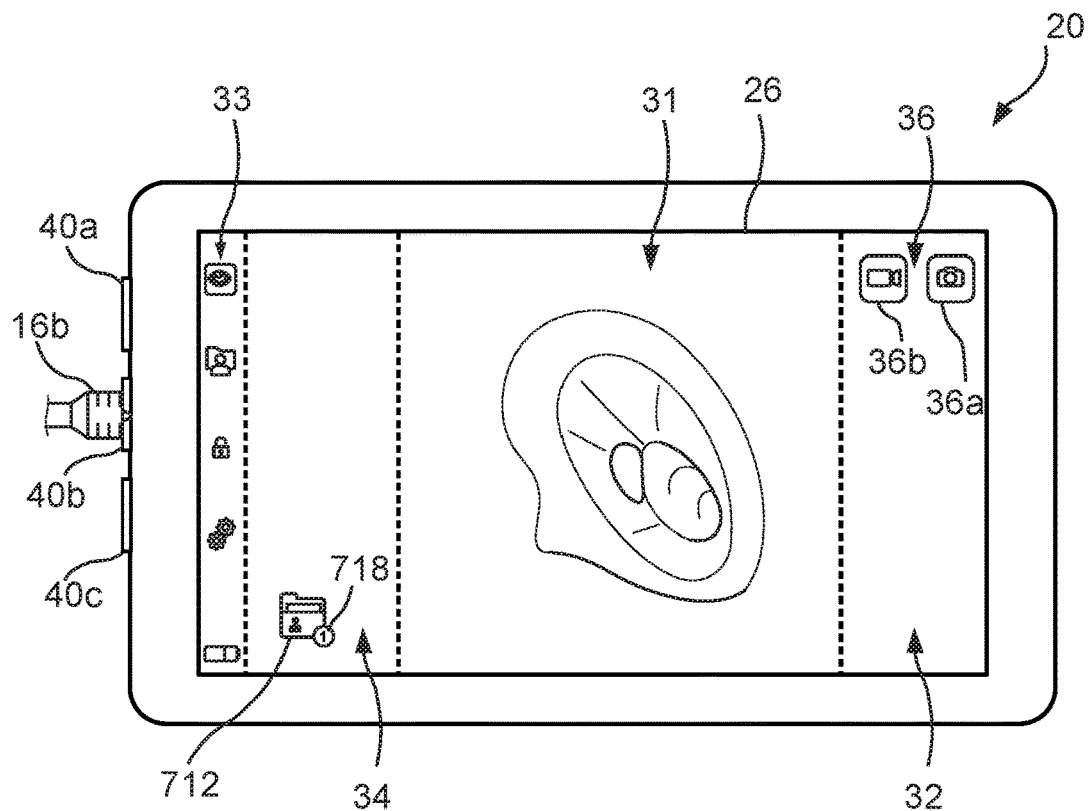

As shown in FIG. 22C, after a predetermined delay after detection of the third user input, the monitor device displays an animation 716 of transitioning the third representation 714 to the folder icon 712. The predetermined delay may be the same delay as explained with respect to FIG. 21C. The animation 716 may have a duration like the duration of the animation 706 as explained with respect to FIG. 21C.

Furthermore, also in response to detection of the third user input 710 and storing of the third image file (cf. FIG. 22B), the display of the visual representation 718 of the count of stored files stored during the second procedure session is updated by increasing the count of stored files.

FIGS. 23A-23F schematically illustrate exemplary user interactions with a graphical user interface of a monitor device 20, such as the monitor device 20 of any of the previous figures. The exemplary graphical user interface of FIG. 23A may follow, e.g., after the exemplary graphical user interface of FIG. 21H. Thus, the folder icon 722 illustrated in FIGS. 23A-23F may correspond to the folder icon 702 of FIGS. 21A-21H, and the procedure session as referred to with respect to FIGS. 23A-23F may be the same procedure session as explained in relation to FIGS. 21A-21H.

Figure 23A:
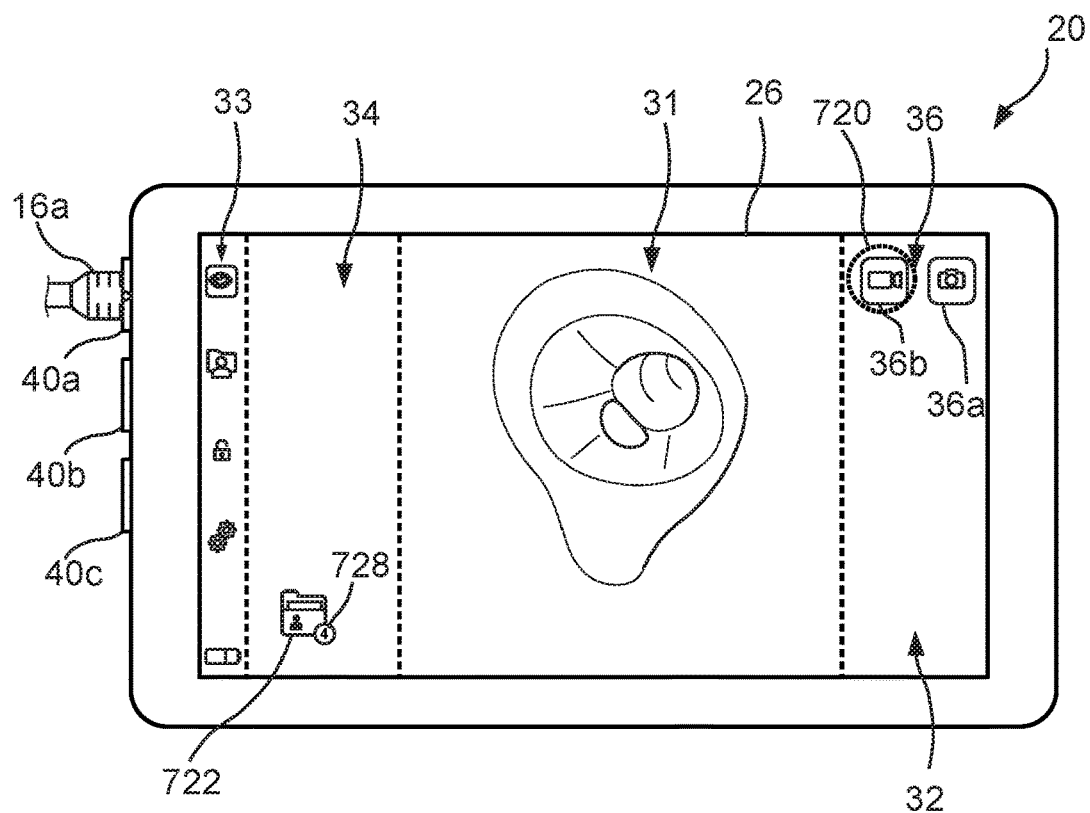
Figure 23B:
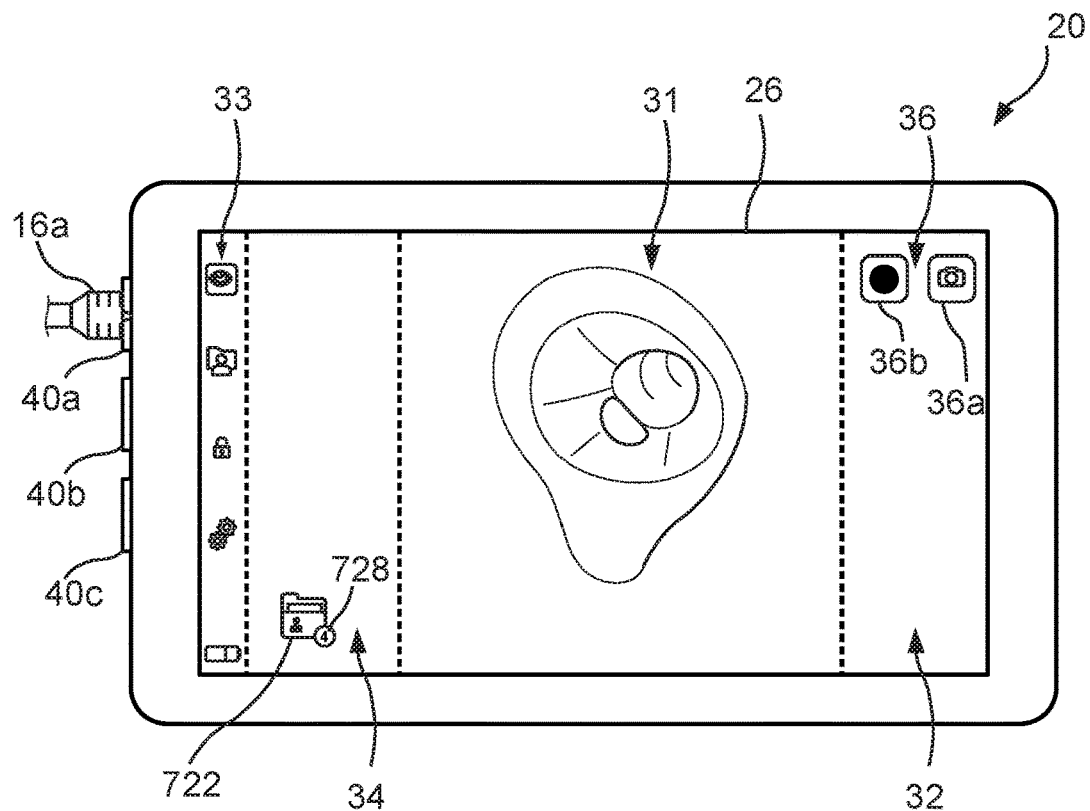
Figure 23C:
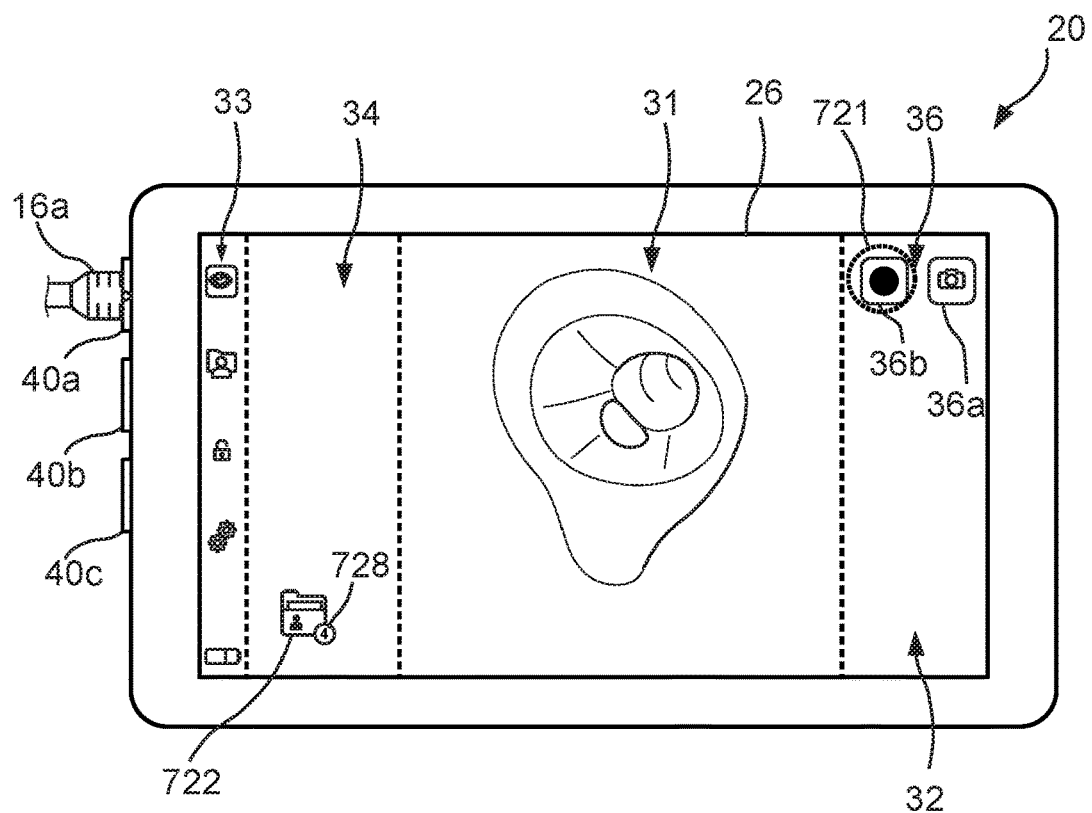

As illustrated in FIG. 23A, a user may provide a fourth user input 720 corresponding to selection of the video capture button 36b. The video capture button 36b may initially be displayed in a first appearance, as illustrated in FIG. 23A. The monitor device 20, e.g. with the touch sensitive display 26, is adapted to detect the fourth user input 720. In response to detection of the fourth user input 720, the monitor device changes the appearance of the video capture button 36b to a second appearance, as illustrated in FIG. 23B. Furthermore, also in response to detection of the fourth user input 720, the monitor device starts collection of image data received from the image sensor and temporarily stores the data in memory.

After detection of the fourth user input 720, the monitor device is adapted to detect a fifth user input 721 (as provided in FIG. 23C) corresponding to selection of the video capture button 36b.

In response to detection of the fifth user input 721, the monitor device stops the recording. More specifically, the monitor device stores a first video data file corresponding to the image data received between detection of the fourth user input 720 (FIG. 23A) and detection of the fifth user input 721. The monitor device 20, e.g. the processing unit of the monitor device 20, may read the temporarily stored data from the memory and create the first video data file based thereon. The monitor device 20 further associates the first video data file with the procedure session. For example, the monitor device 20 may store the first video data file in the folder corresponding to the procedure session.

Figure 23D:
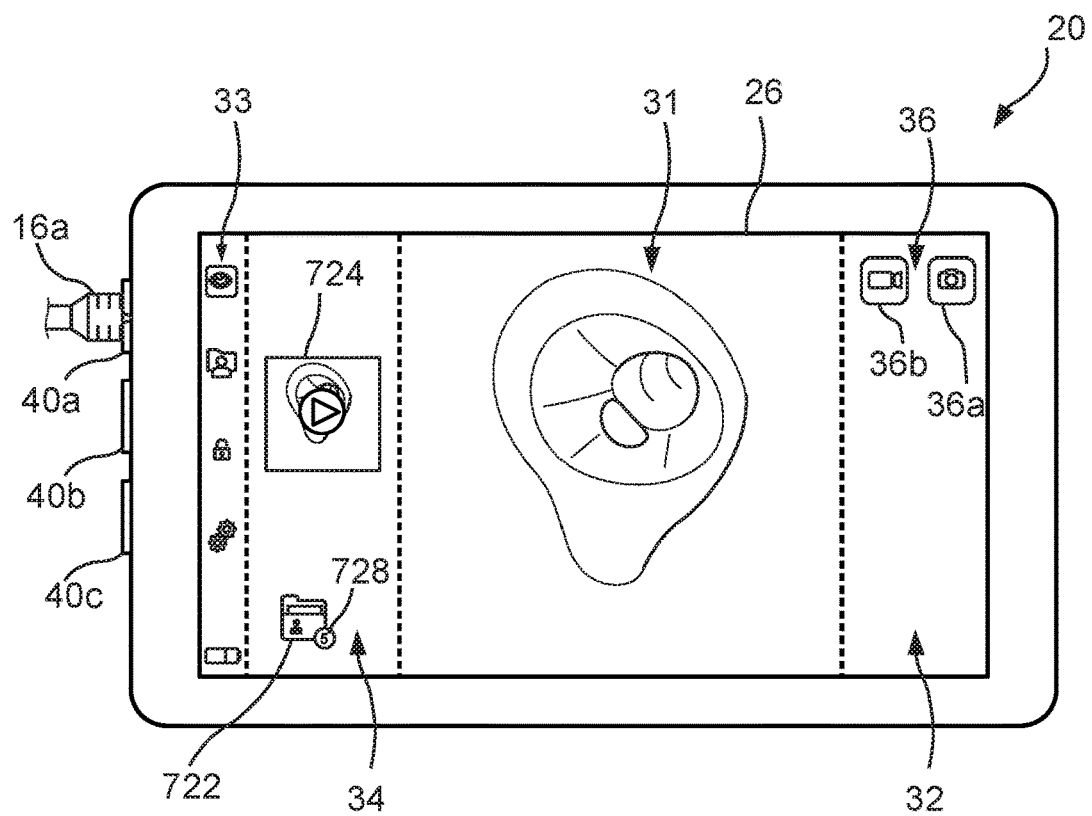

Furthermore, as illustrated in FIG. 23D, the monitor device, in response to detection of the fifth user input 721 and storing of the first video data file displays within the background portion of the graphical user interface, e.g. the fourth portion 34 as illustrated, a fourth representation 724 corresponding to a frame of the stored first video data file.

Furthermore, as also illustrated in FIG. 23D, the monitor device, in response to detection of the fifth user input 721 changes the appearance of the video capture button 36b to the first appearance.

Furthermore, also in response to detection of the fifth user input 720 and storing of the first video data file, the display of the visual representation 728 of the count of stored files stored during the procedure session is updated by increasing the count of stored files.

Figure 23E:
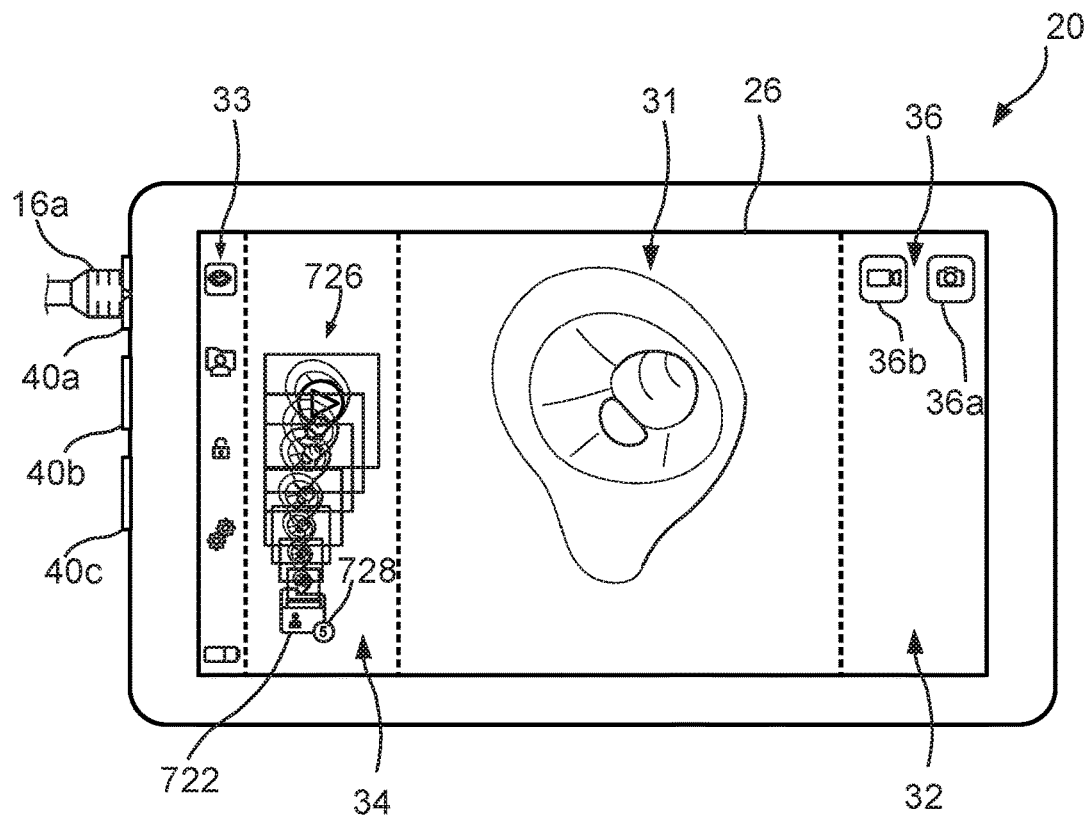
Figure 23F:
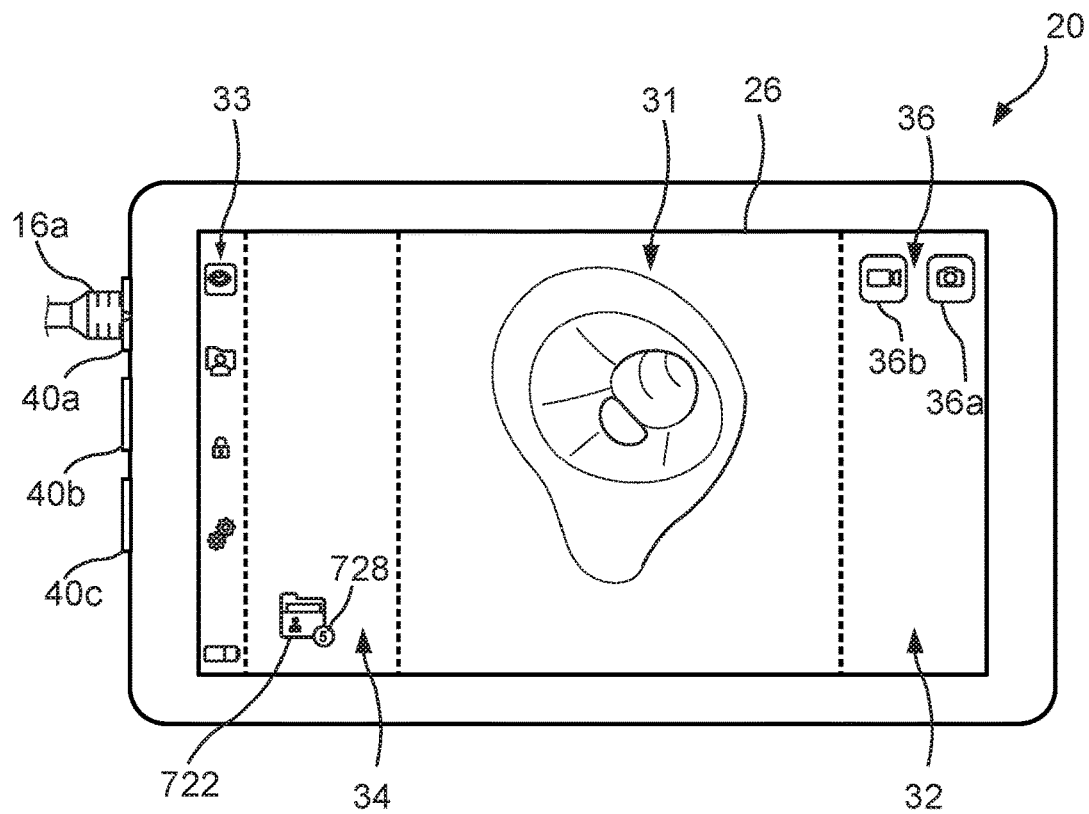

As shown in FIG. 23E, after a predetermined delay after detection of the fifth user input 721, the monitor device displays an animation 726 of transitioning the fourth representation 724 to the folder icon 722. The predetermined delay may be the same delay as explained with respect to FIG. 21C. The animation 166 may have a duration like the duration of the animation 706 as explained with respect to FIG. 21C.

FIGS. 24A-24H schematically illustrate exemplary user interactions with a graphical user interface of a monitor device 20, such as the monitor device 20 of any of the previous figures. The exemplary graphical user interface of FIG. 24A may follow, e.g., after the exemplary graphical user interface of FIG. 23F. Thus, the folder icon 802 illustrated in FIGS. 24A-24F may correspond to the folder icon 722 of FIGS. 23A-23F, and the procedure session as referred to with respect to FIGS. 24A-24F may be the same procedure session as explained in relation to FIGS. 23A-23F.

Figure 24A:
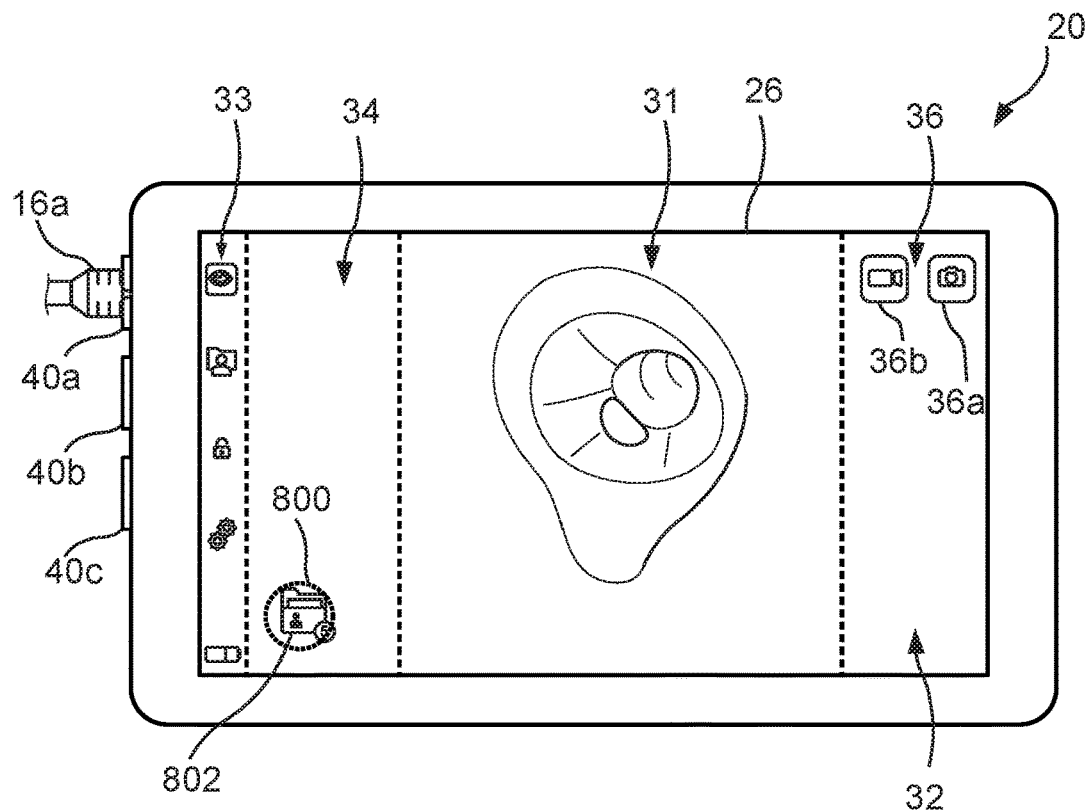
Figure 24B:
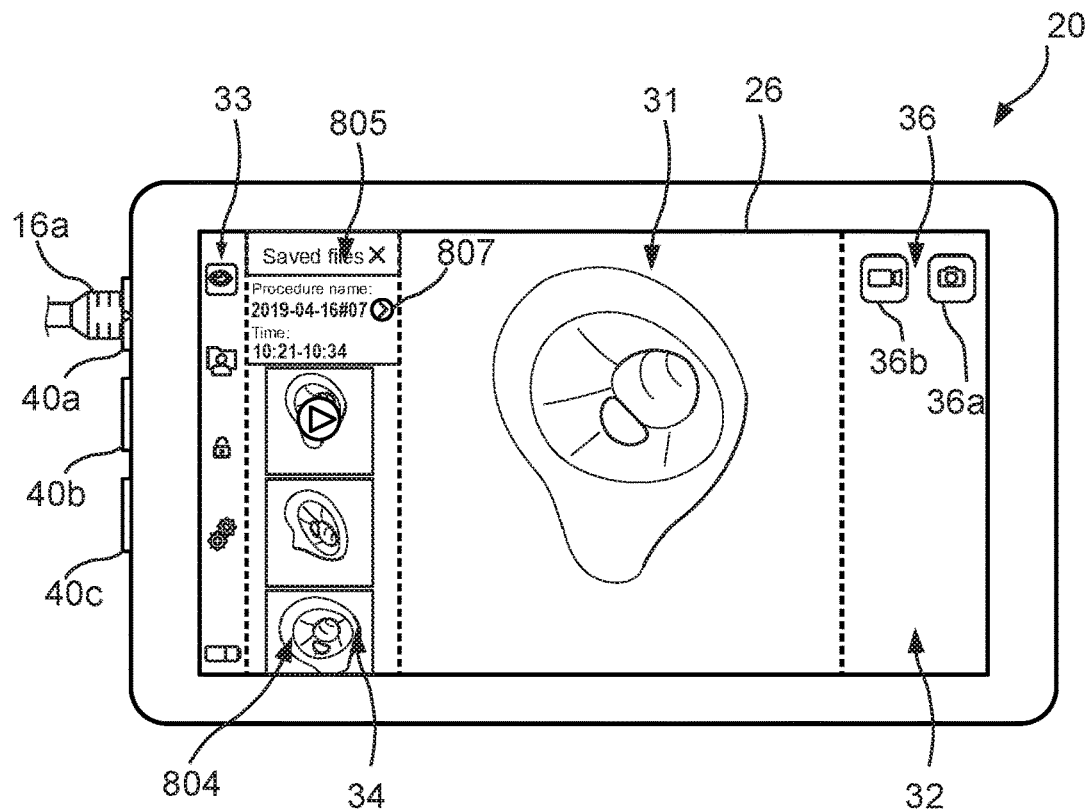

As illustrated in FIG. 24A, a user may provide a sixth user input 800 corresponding to selection of the folder icon 802. The monitor device 20 is adapted to detect the sixth user input 800, and in response to detection of the sixth user input 800, as illustrated in FIG. 24B, the monitor device 20 displays, within the background portion (e.g. second portion or fourth portion 34) of the graphical user interface, a first plurality of representations 804 corresponding to a first plurality of stored image files stored during the procedure session. In the present example, first plurality of representations 804 is displayed within the fourth portion 34 of the graphical user interface. Alternatively, the first plurality of representations 804 may be displayed in the second portion 32 of the graphical user interface. Advantageously, the first plurality of representations 804 is displayed in the same portion as the folder icon 802.

Also, in response to detection of the sixth user input 800, a session info box 805 and a session overview icon 807 is displayed within the background portion of the graphical user interface, such as within the fourth portion 34 of the graphical user interface.

The exemplary graphical user interface of FIG. 24B may alternatively be reached by disconnecting the visualization device from the monitor device 20. For example, in response to disconnection of the visualization device from the monitor device 20, the monitor device 20 may display the graphical user interface as illustrated in FIG. 24B, e.g. comprising the first plurality of representations 804 corresponding to a first plurality of stored image files stored during the procedure session, and the session info box 805 and the session overview icon 807.

Figure 24C:
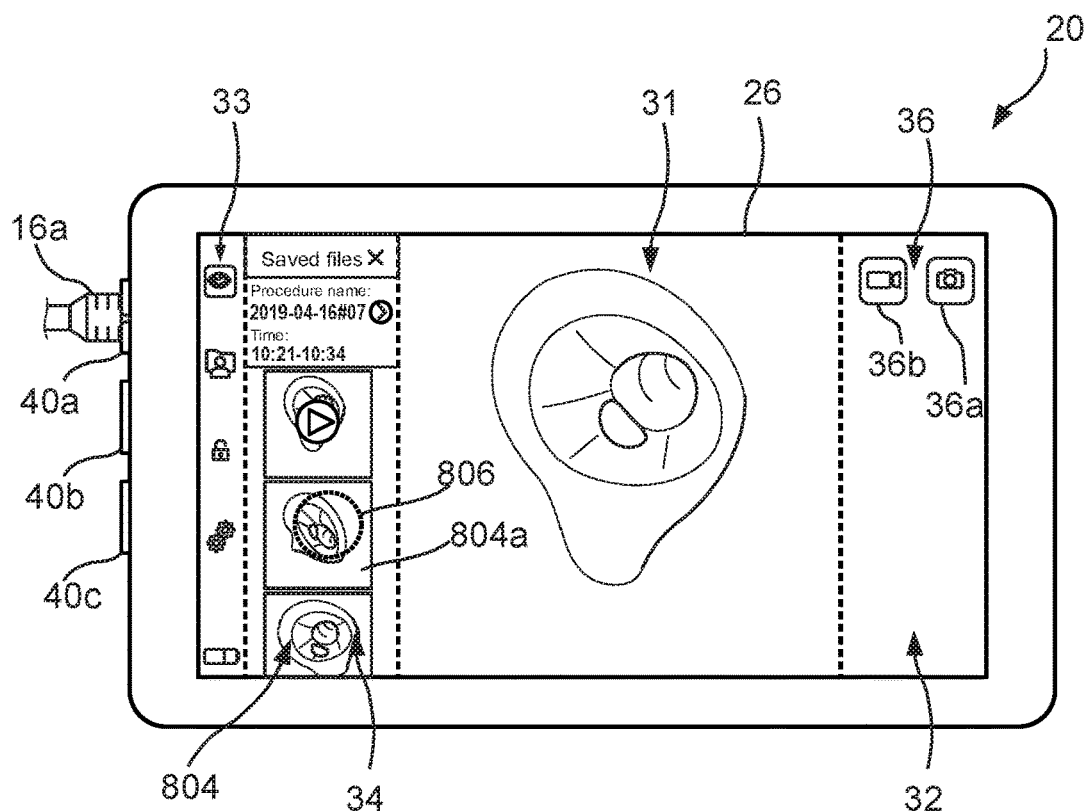
Figure 24D:
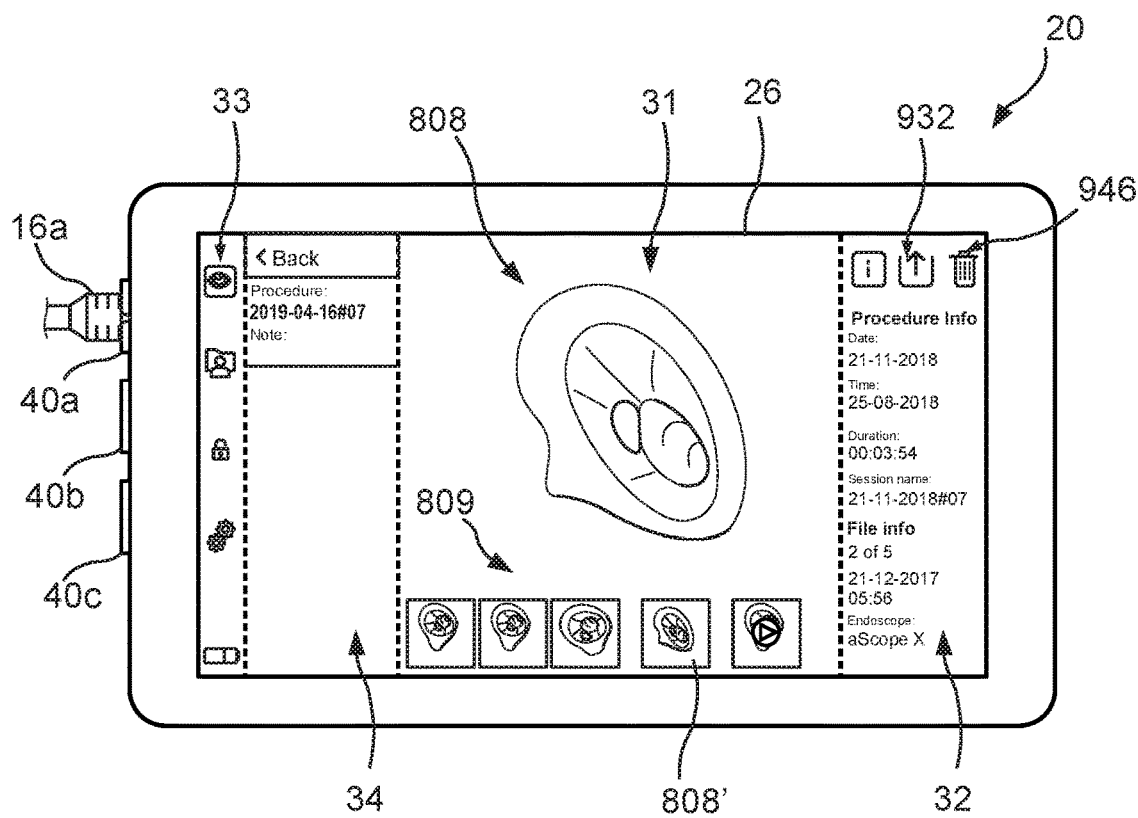

As illustrated in FIG. 24C, a user may provide a seventh user input 806 corresponding to selection of a primary representation 804a of the first plurality of representations 804. The primary representation 804a corresponds to a primary stored image file. The monitor device 20 is adapted to detect the seventh user input 806, and in response to detection of the seventh user input 806, as illustrated in FIG. 24D, the monitor device 20 displays an enlarged representation 808 of the primary stored image file within the first portion 31 of the graphical user interface. Furthermore, the monitor device 20 also displays thumbnail representations 809 of a second plurality of the stored image files stored during the procedure session. Displaying the thumbnail representations 809 differentiates the view from a live view, e.g. FIG. 3, thereby notifying the user that monitor device 20 is not currently showing a live representation of image data received from the visualization device, but instead the monitor device 20 is displaying stored images.

Figure 24E:
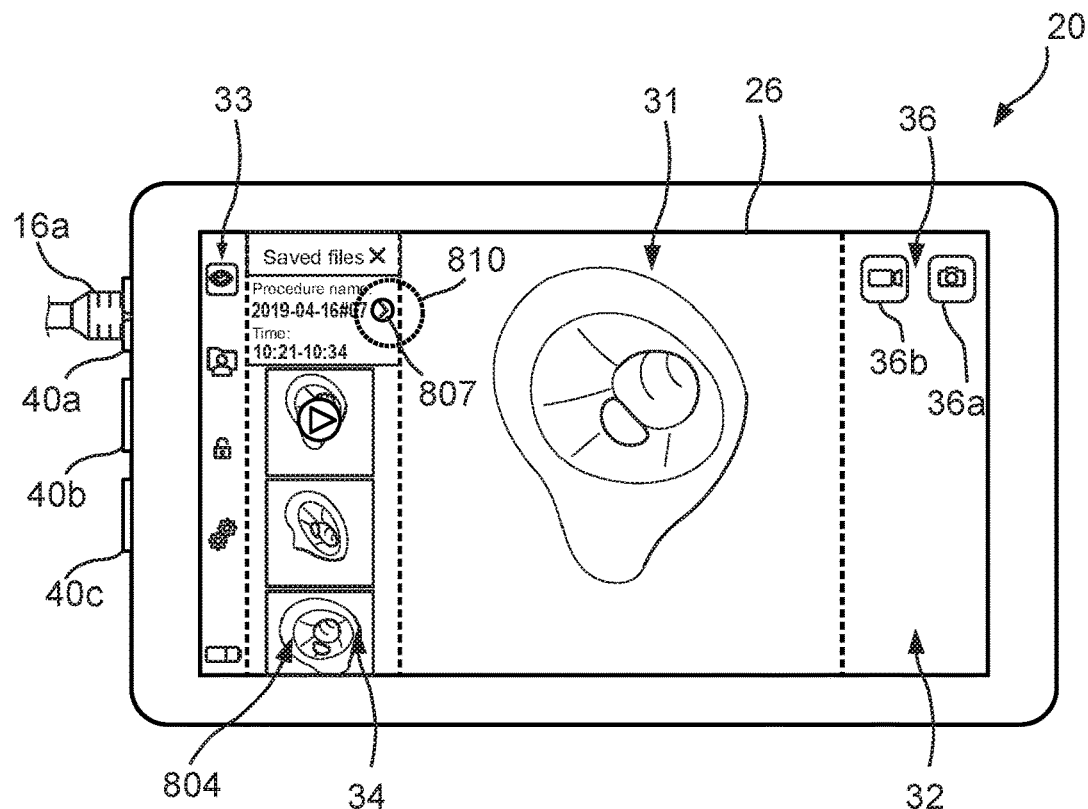
Figure 24F:
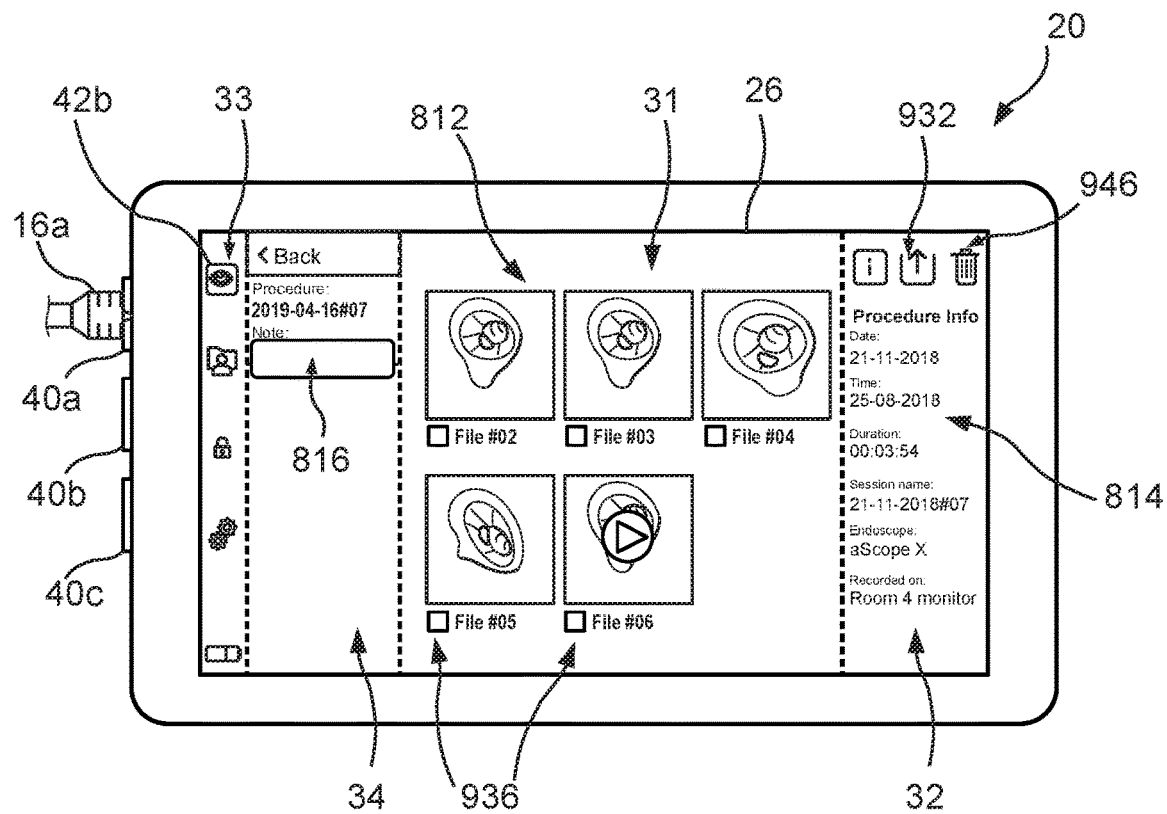

As illustrated in FIG. 24E, originating from the situation as described with respect to FIG. 24B, a user may provide an eighth user input 810 corresponding to selection of the session overview icon 807. The monitor device 20 is adapted to detect the eighth user input 810, and in response to detection of the eighth user input 810, as illustrated in FIG. 24F, the monitor device 20 displays in the first portion of the graphical user interface a third plurality of representations 812 corresponding to a third plurality of stored image files stored during the procedure session. Furthermore, also in response to detection of the eighth user input 810, the monitor device displays general information 814 of the procedure session, e.g. in the second portion 32 of the graphical user interface, and a note field 816 in the fourth portion 34 of the graphical user interface.

The monitor device also displays an export icon 932 and a deletion icon 946, in the second portion of the graphical user interface. These will be described in more detail later.

Figure 24G:
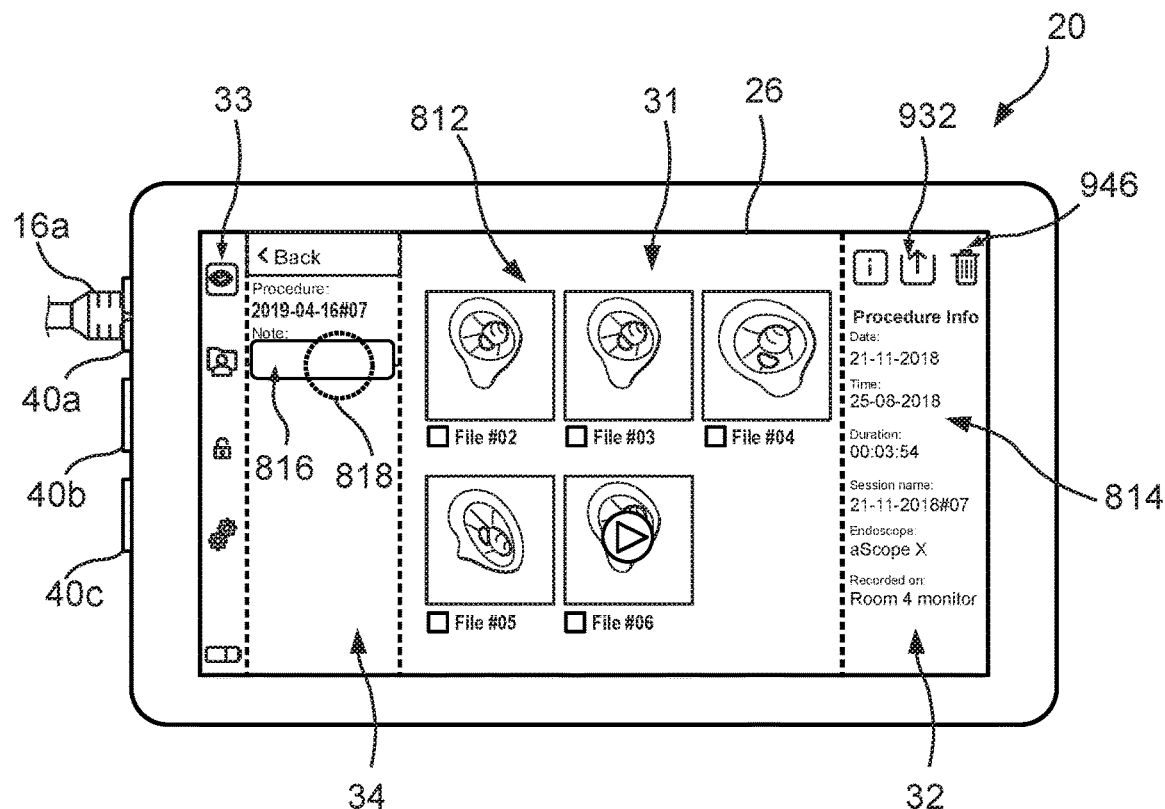
Figure 24H:
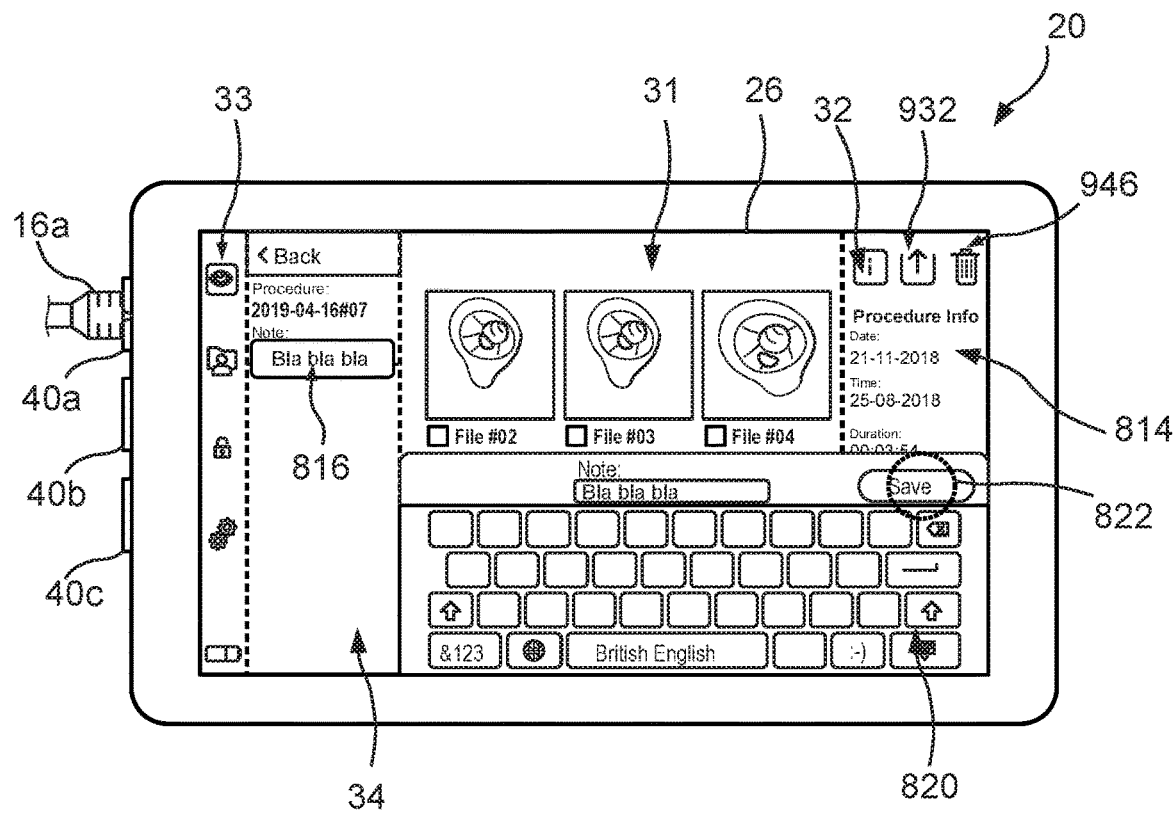

As illustrated in FIG. 24G a user may provide a ninth user input 818 corresponding to selection of the note field 816. The monitor device 20 is adapted to detect the ninth user input 818, and in response to detection of the ninth user input 818, as illustrated in FIG. 24H the monitor device 20 displays a virtual keyboard 820 in the first portion 31 of the graphical user interface and optionally extending into the second portion 32 of the graphical user interface. The virtual keyboard is configured for entering text in the note field 816. Thus, the monitor device 20 is further adapted to, e.g. with the touch sensitive display 26, detect a sequence of keyboard user inputs corresponding to typing of a text using the displayed virtual keyboard, and detect a tenth user input 822 indicative of acceptance of the text typed using the displayed virtual keyboard 820. For example, the tenth user input 822 may be corresponding to selection of a "save" button, as illustrated. In response to detection of the tenth user input 822, the monitor device 20 stores and associates the typed text as a note for the procedure session.

FIGS. 25A-25J schematically illustrate exemplary user interactions with a graphical user interface of a monitor device 20, such as the monitor device 20 of any of the previous figures. The monitor device 20 may have a visualization device connected, or it may not have a visualization device connected.

Figure 25A:
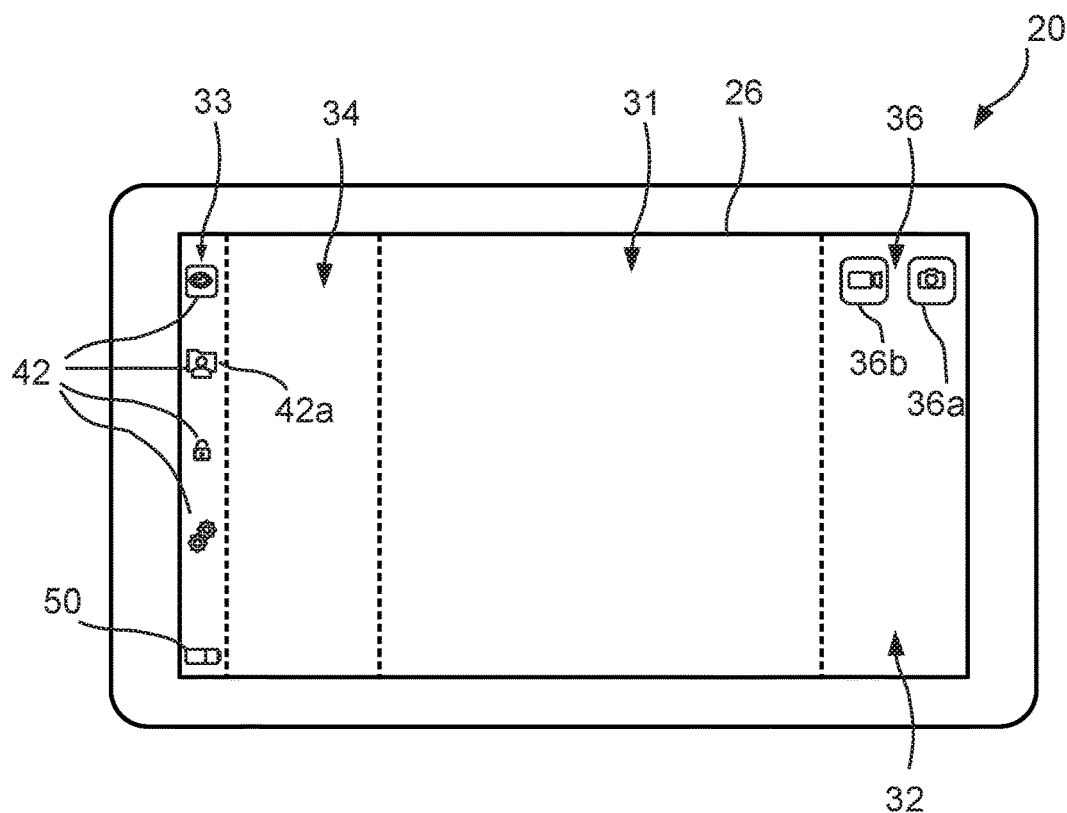

With reference to FIG. 25A, the one or more actionable menu items 42 displayed in the third portion 33 of the graphical user interface comprises a first actionable menu item being an archive menu item 42a.

Figure 25B:
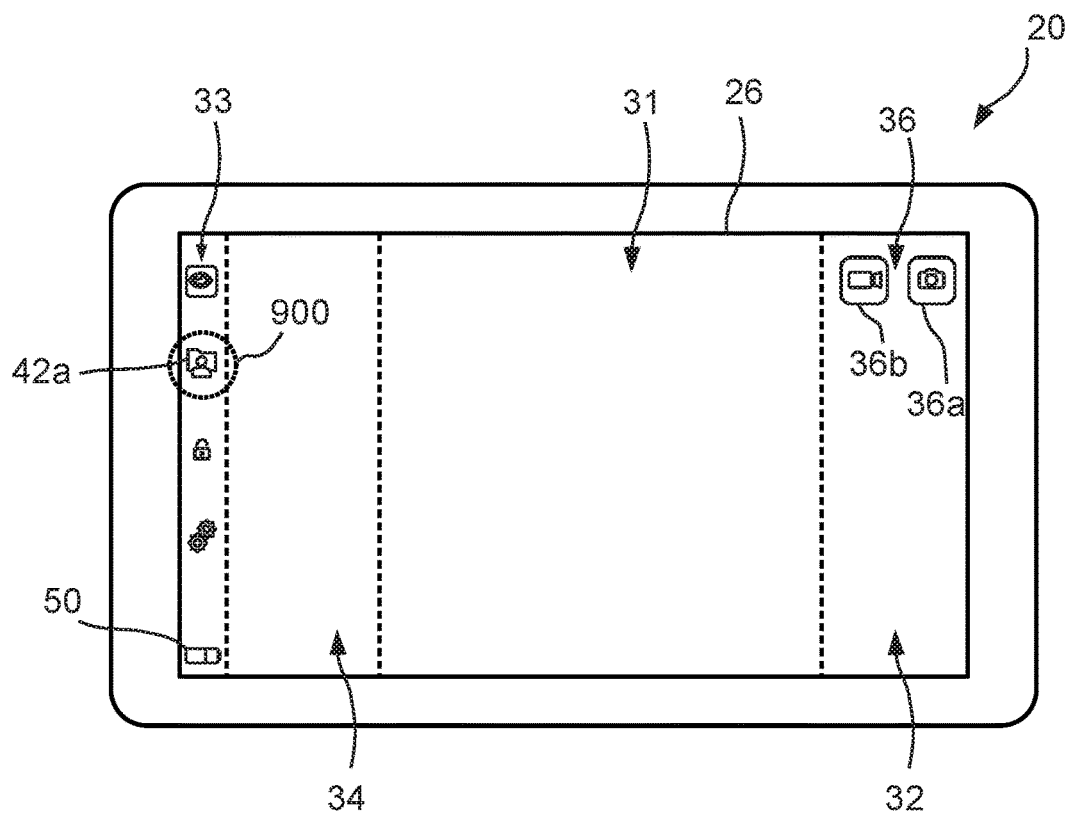
Figure 25C:
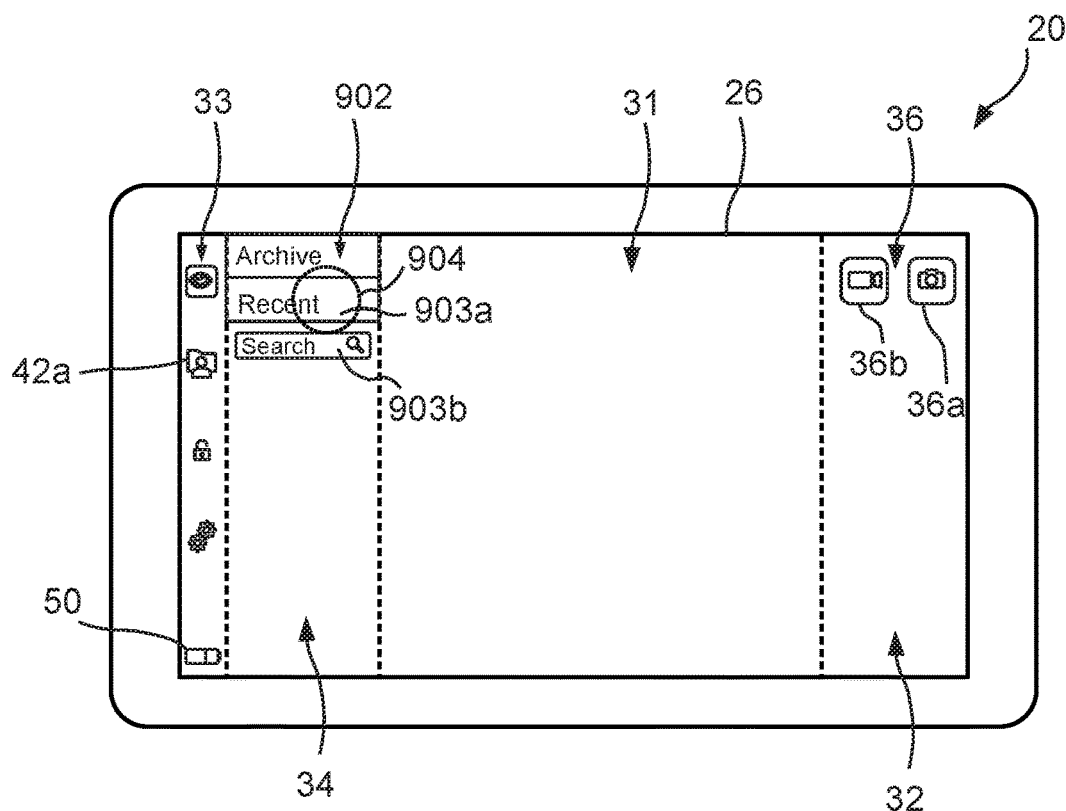

As illustrated in FIG. 25B, an eleventh user input 900 corresponding to selection of the archive menu item 42a may be received. The monitor device 20 is adapted to detect the eleventh user input 900, and in response to detection of the eleventh user input 900, as illustrated in FIG. 25C, the monitor device 20 displays a primary archive menu 902 associated with the archive menu item 42a within the fourth portion of the graphical user interface. The primary archive menu 902 comprises one or more primary actionable archive items including a first primary actionable archive item 903a. In the illustrated example, the one or more primary actionable archive items includes a first primary actionable item 903a to retrieve recent (e.g. recently stored) images and videos, and a second primary actionable item 903b to search for stored images and videos.

As illustrated in FIG. 25C, while displaying the primary archive menu 902, a twelfth user input 904 corresponding to selection of the first primary actionable archive item 903a may be received. The monitor device is adapted to detect the twelfth user input 904, and in response to detection of the twelfth user input 904, as illustrated in FIG. 25D, the monitor device 20 displays in the first portion of the graphical user interface, optionally extending into the second portion 32 and/or the fourth portion 34 of the graphical user interface, a secondary archive menu 906a associated with the first primary actionable archive item.

The content of the secondary archive menu may be subject to authorisation. For example, subject to whether a user is logged (e.g. having authenticated by typing in user name and password) in to the monitor device and whether the user being logged in has certain privileges. For example, in accordance with the monitor device operating in an authorised state, the secondary archive menu may comprise a list of stored, such as all stored, procedure sessions, e.g. such as the secondary archive menu 906a as illustrated in FIG. 25D. In accordance with the monitor device 20 operating in a non-authorised state and a setting to require authorisation is activated, the secondary archive menu may comprise an empty list, e.g. such as the secondary archive menu 906c as illustrated in FIG. 25F, or a list of a subset, e.g. such as the secondary archive menu 906b as illustrated in FIG. 25E, of the stored procedure sessions. In accordance with the monitor device 20 operating in a non-authorised state and a setting to require authorisation is deactivated, the secondary archive menu may comprise the list of stored procedure sessions, e.g. such as the secondary archive menu 906a as illustrated in FIG. 25D.

Figure 25D:
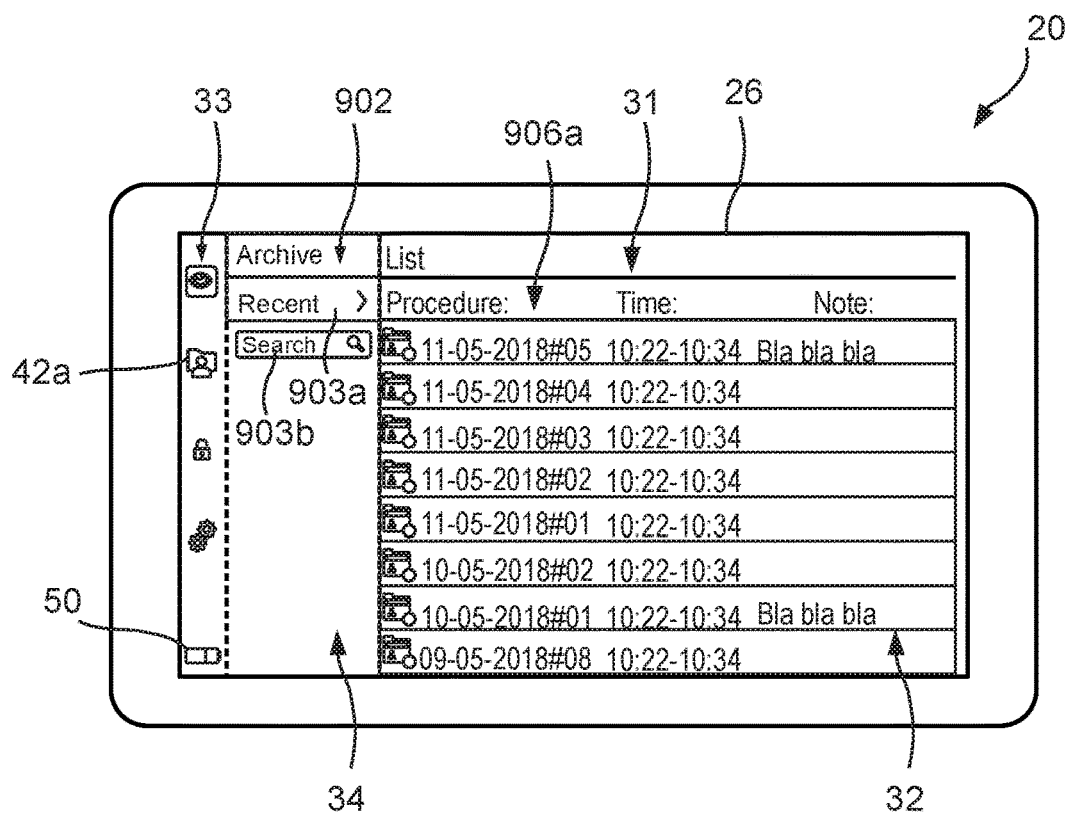
Figure 25E:
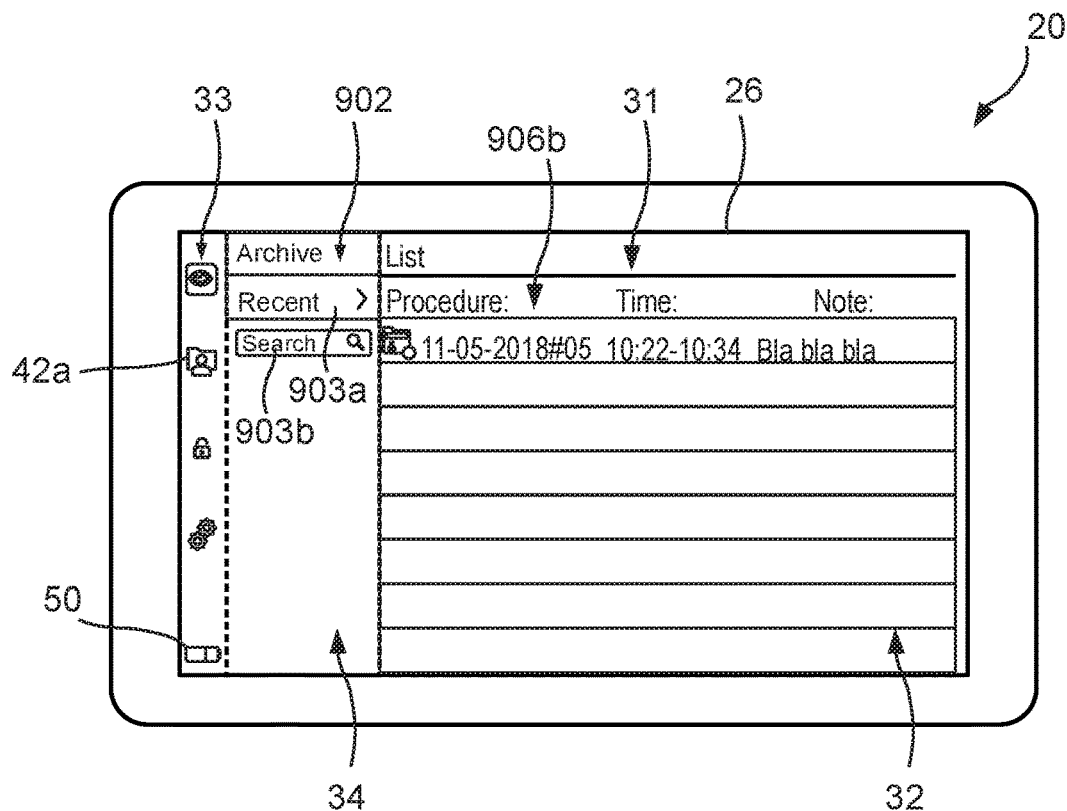
Figure 25F:
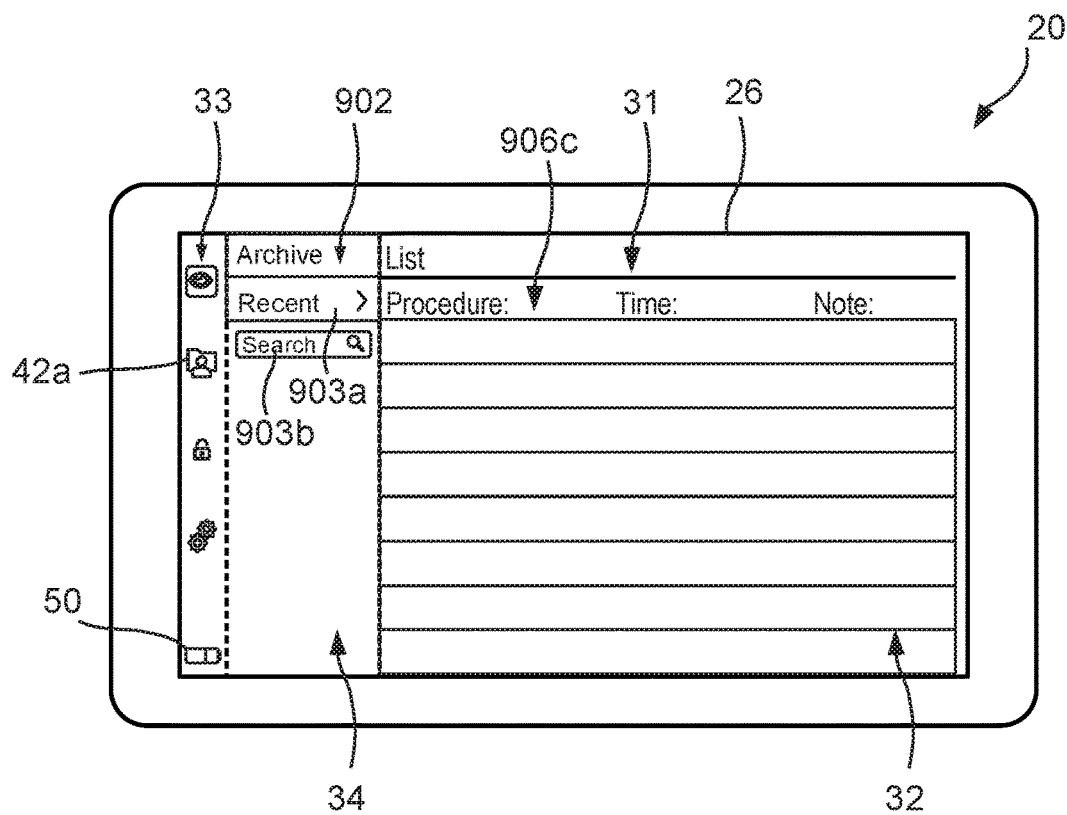
Figure 25G:
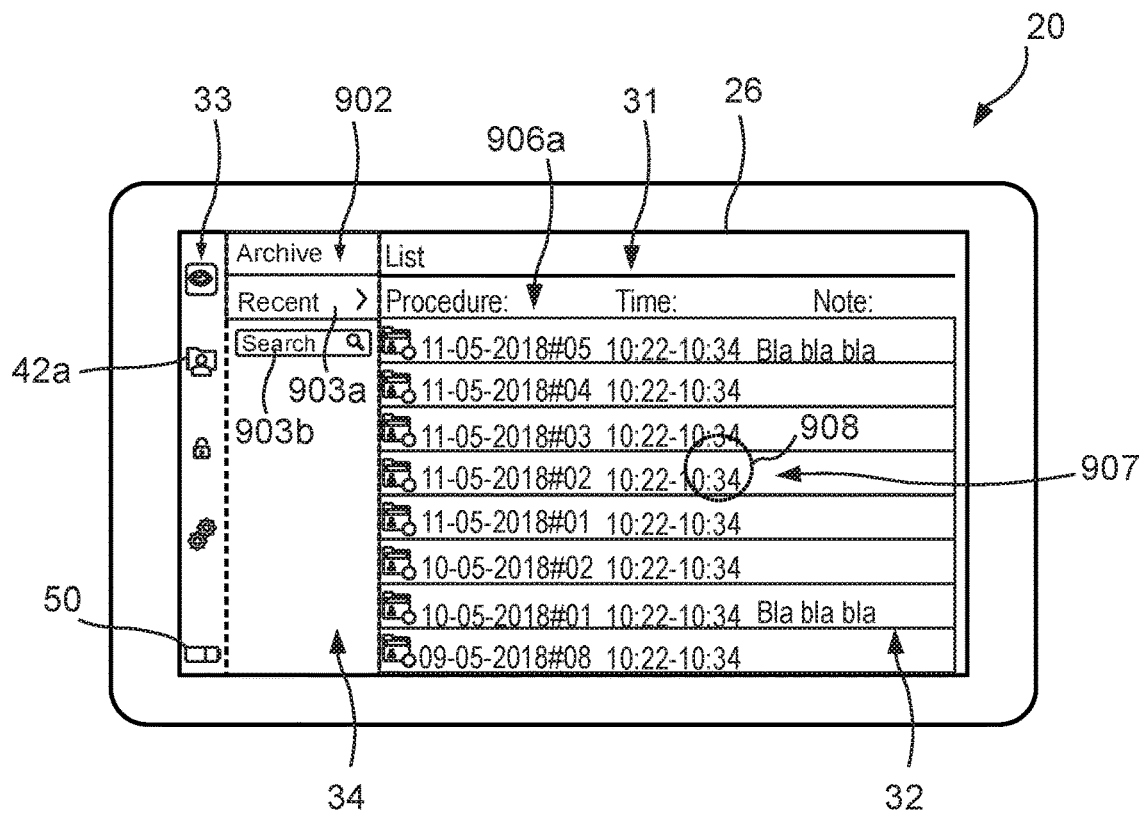
Figure 25H:
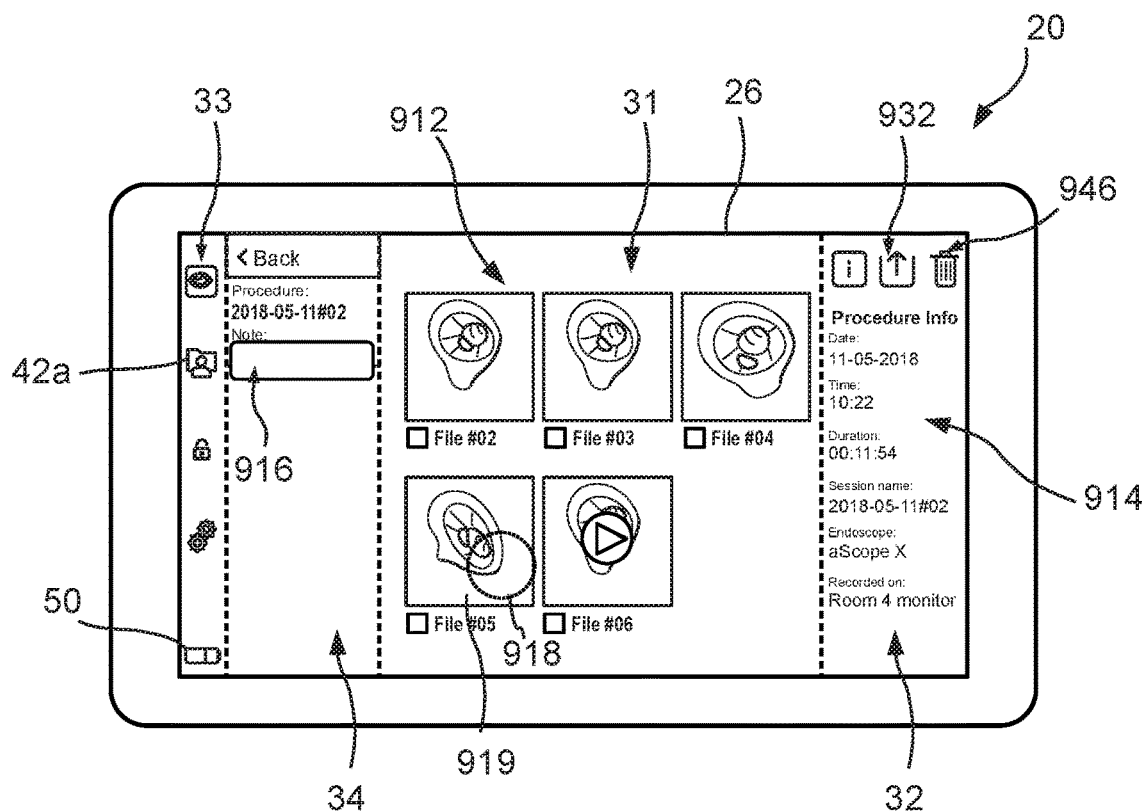

As illustrated in FIG. 25G, while displaying the secondary archive menu 906a (the illustrated example shows the secondary archive menu 906a in accordance with FIG. 25D. However, the same would apply for a secondary archive menu 906b in accordance with FIG. 25E), a thirteenth user input 908 corresponding to selection of a first stored procedure session 907. The monitor device is adapted to detect the thirteenth user input 908, and in response to detection of the thirteenth user input 908, as illustrated in FIG. 25H the monitor device displays in the first portion 31 of the graphical user interface a fourth plurality of representations 912 corresponding to a fourth plurality of stored image files stored during the first stored procedure session 907. Furthermore, also in response to detection of the thirteenth user input 908, the monitor device 20 displays general information 914 of the first stored procedure session 907, e.g. in the second portion 32 of the graphical user interface. Furthermore, also in response to detection of the thirteenth user input 908, the monitor device 20 displays a note field 916, e.g. in the fourth portion 34 of the graphical user interface.

In the event that the first stored procedure session 907 selected by the thirteenth user input 908 was the same as the procedure session of FIGS. 24A-24H, the graphical user interface as provided in response to detection of the thirteenth user input 908, and as illustrated in FIG. 25H, would be the same graphical user interface as provided in response to detection of the eighth user input 810, and as illustrated in FIG. 24F. Thus, the disclosure with respect to selection of the notes field 816 by the ninth user input 818 as described with respect to FIG. 24F applies, mutatis mutandis, to the situation of FIG. 25H. Similarly, the following disclosure with respect to FIG. 25H applies, mutatis mutandis to the situation of FIG. 24F.

Figure 25I:
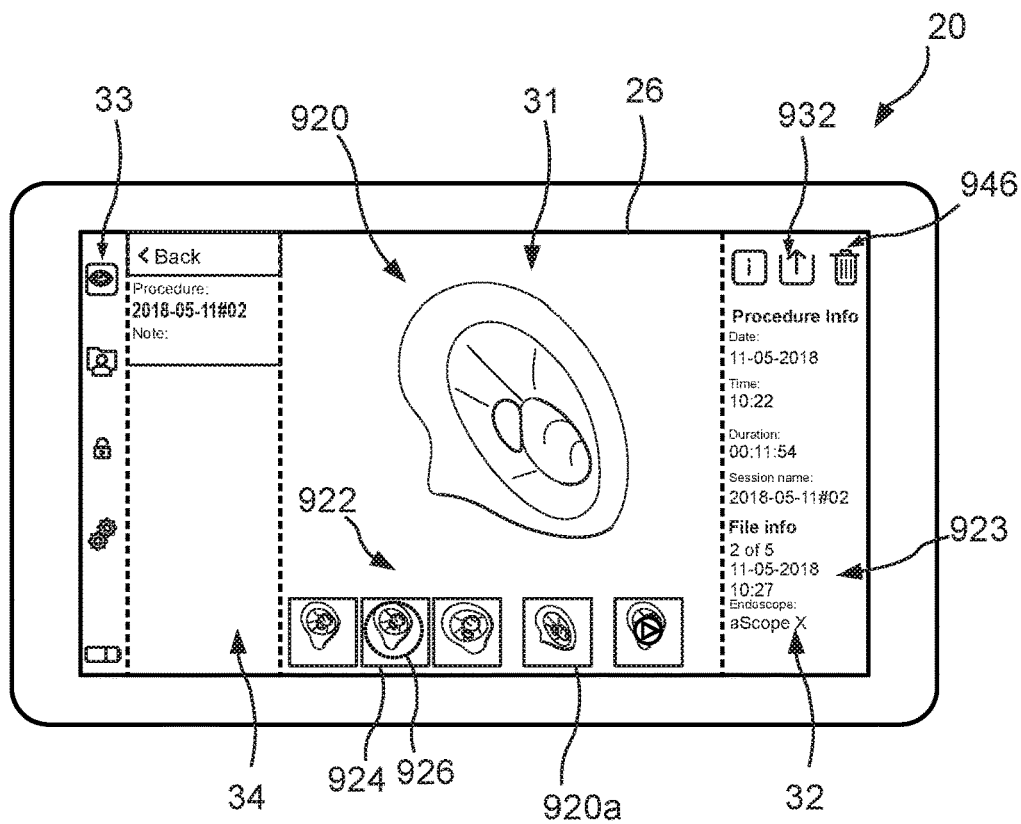

As illustrated in FIG. 25H, a fourteenth user input 918 corresponding to selection of a select representation 919 of the fourth plurality of representations 912 may be received. The select representation 919 corresponds to a select stored image file. The monitor device is adapted to detect the fourteenth user input 918, and in response to detection of the fourteenth user input 918, as illustrated in FIG. 25I, the monitor device displays an enlarged representation 920 of the select stored image file within the first portion 31 of the graphical user interface. Furthermore, also in response to the fourteenth user input 918, the monitor device 20, displays thumbnail representations 922 of a fifth plurality of the stored image files stored during the first stored procedure session 917. The thumbnail representations 922 comprises a thumbnail representation 920a of the select stored image file. The thumbnail representations 922 further comprises a further thumbnail 924 corresponding to a further stored image file.

Furthermore, also in response to detection of the fourteenth user input 918, the monitor device 20 displays, within the second portion 32 of the graphical user interface, image information 923 associated with the select stored image file. The image information 923 associated with the select stored image file comprise information indicative of the visualization device. This information is saved based on the device identifier information obtained in response to detection of the visualization device.

Figure 25J:
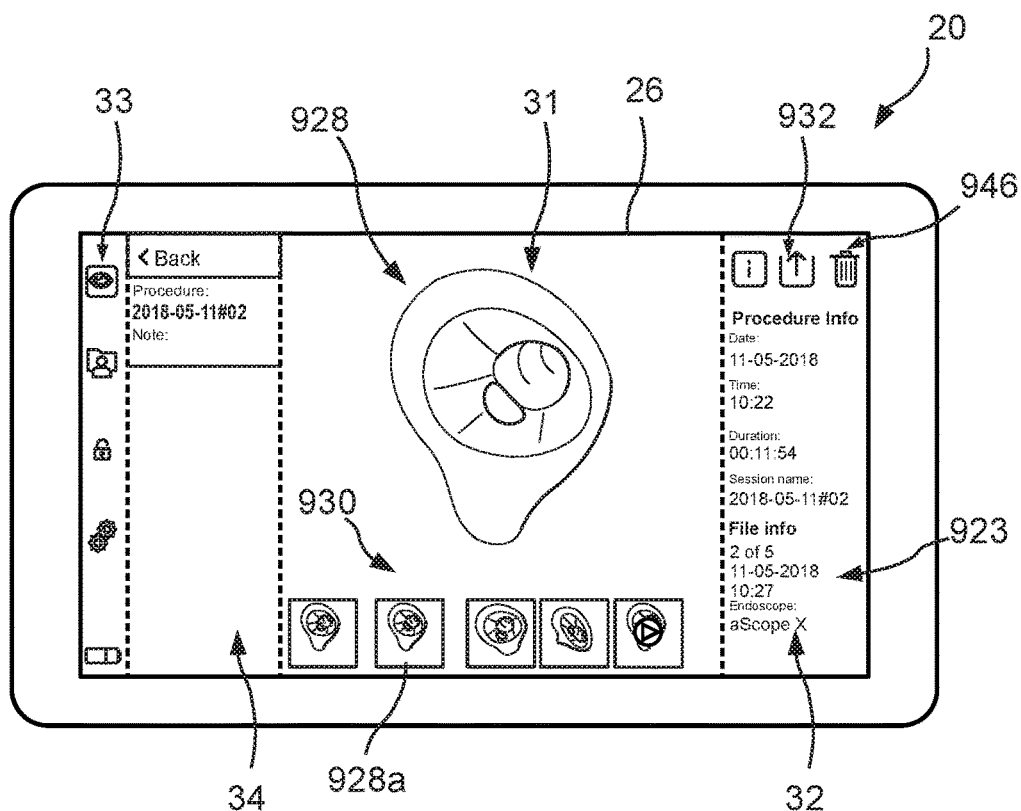

As illustrated in FIG. 25I, a fifteenth user input 926 corresponding to selection of a select thumbnail 924 of the displayed thumbnail representations 922 may be received. The select thumbnail corresponds to a second select stored image file. The monitor device is adapted to detect the fifteenth user input 926, and in response to detection of the fifteenth user input 926, as illustrated in FIG. 25J, the monitor device displays an enlarged representation 928 of the second select stored image file within the first portion 31 of the graphical user interface. The thumbnail representations 922 are updated to display representations 930 of a sixth plurality of the stored image files stored during the first stored procedure session. In the illustrated example, the thumbnail representations 922 of the fifth plurality of the stored image files, as seen in FIG. 25I, and the thumbnail representations 930 of the sixth plurality of the stored image files, as seen in FIG. 25J, are the same plurality of stored image files. However, in some examples, e.g. where the number of images are large, so that all images are unable to fit concurrently on the screen, the thumbnail representations may differ.

FIGS. 26A-26D schematically illustrate exemplary user interactions with a graphical user interface of a monitor device 20, such as the monitor device 20 of any of the previous figures. The monitor device 20 may have a visualization device connected, or it may not have a visualization device connected. The exemplary graphical user interface of FIG. 26A may follow, e.g., after the exemplary graphical user interfaces of FIGS. 25I, 25J or FIG. 24D. In the illustrated example, the monitor device 20 displays an enlarged representation 1001 of a stored image file. The enlarged representation 1001 may correspond to the enlarged representation 920 of the select stored image file of FIG. 25I, the enlarged representation 928 of the second select stored image file of FIG. 25J, or the enlarged representation 808 of the primary stored image file of FIG. 24D.

Figure 26A:
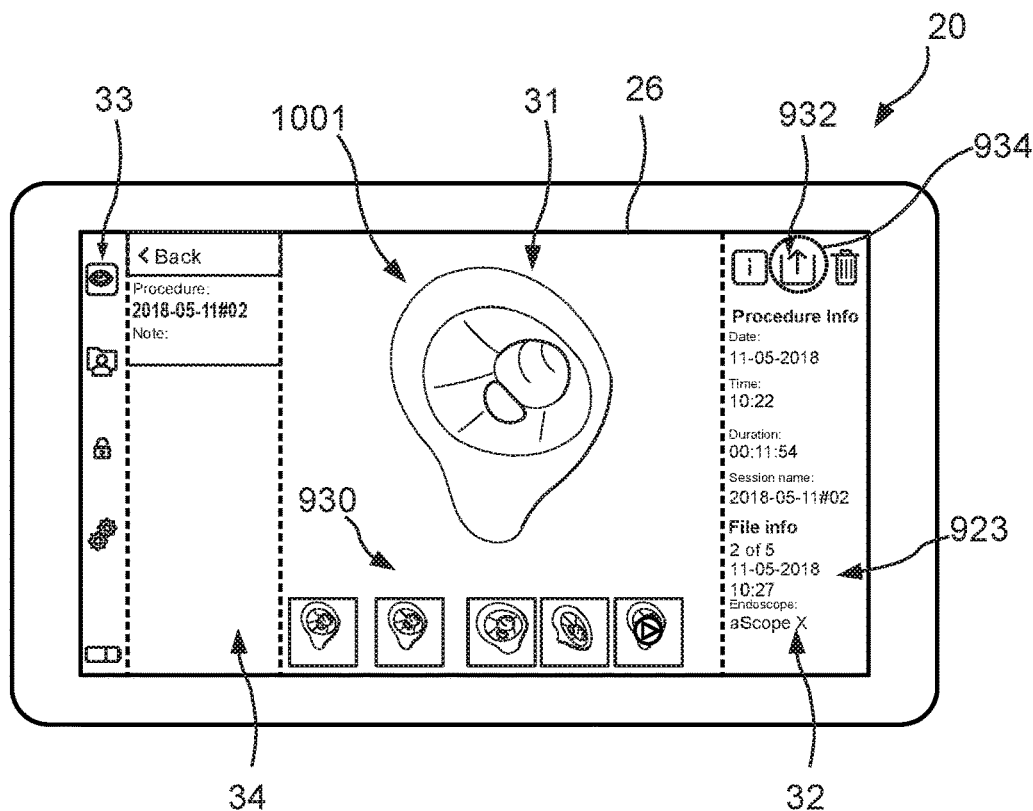
Figure 26B:
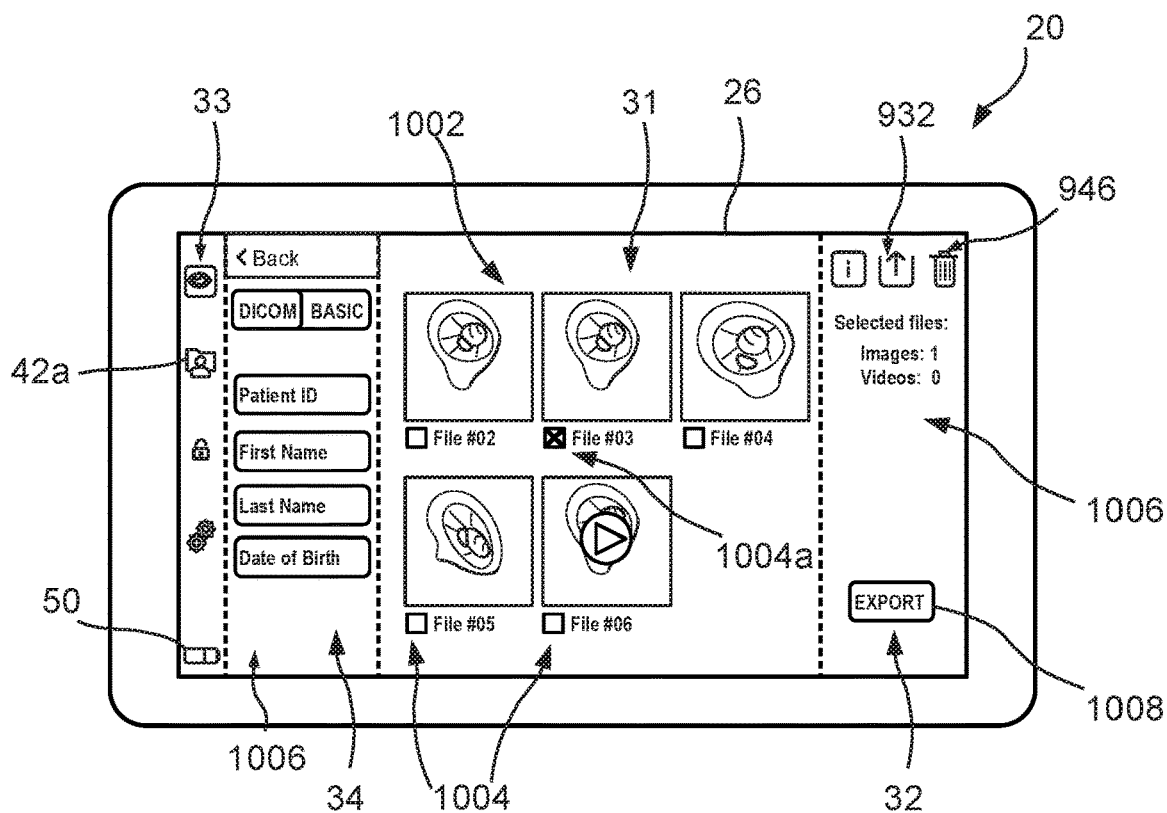

With reference to FIG. 26A, an export icon 932 is displayed, e.g. in the second portion of the graphical user interface. As illustrated, a sixteenth user input 934 corresponding to selection of the export icon 932 may be received. The monitor device 20 is adapted to detect the sixteenth user input 934, and in response to detection of the sixteenth user input 934, as illustrated in FIG. 26B, the monitor device displays in the first portion 31 of the graphical user interface a plurality of representations 1002 corresponding to a plurality of stored image files, e.g. the plurality of representations 1002 may be the fourth plurality of representations 912 corresponding to the fourth plurality of stored image files, as illustrated in relation to FIG. 25H. Each of the plurality of representations 1002 comprises a selection indicator 1004, wherein the selection indicator 1004a of the representation of the stored image file (of which the enlarged representation 1001 was displayed when the sixteenth user input 934 was detected) is activated.

Furthermore, also in response to detection of the sixteenth user input 934, the monitor device displays an export menu 1006 in the second portion 32 and fourth portion 34 of the graphical user interface. The export menu 1006 may be separated into two parts as illustrated. The export menu 1006 comprises an export confirm icon 1008.

Figure 26C:
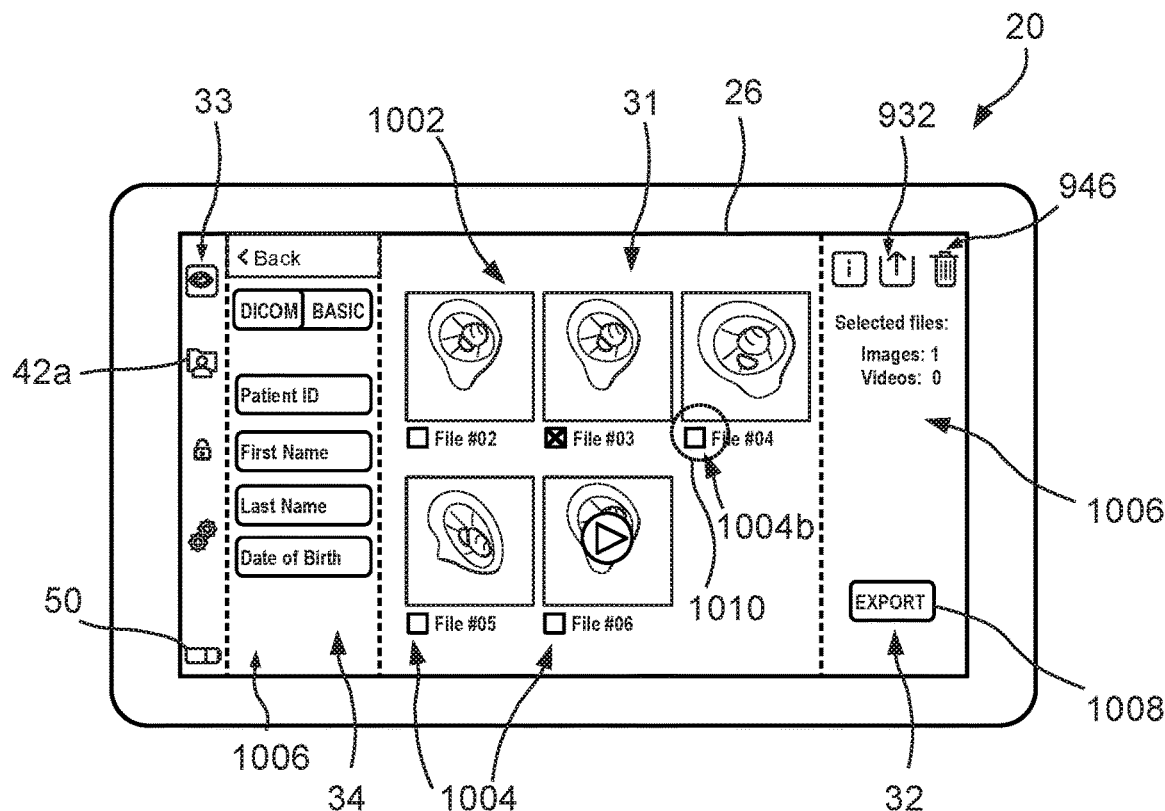
Figure 26D:
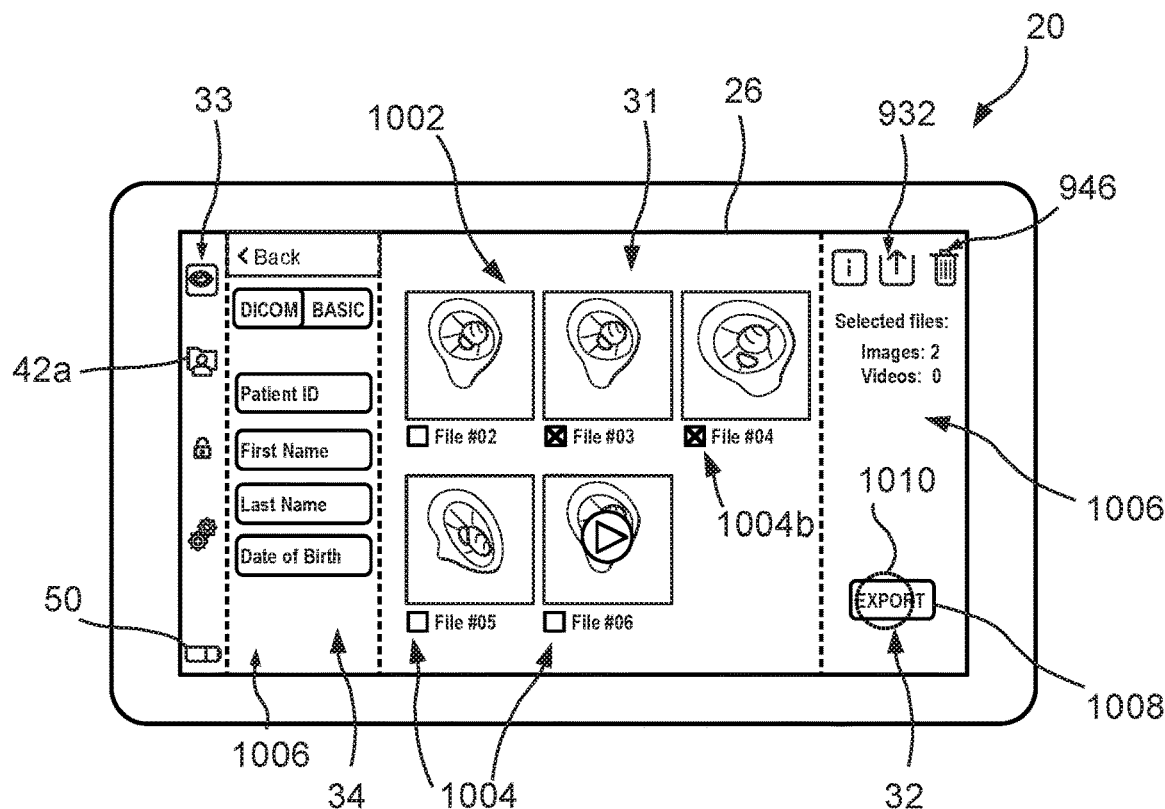

After detection of the sixteenth user input 934, and as illustrated in FIG. 26C, a seventeenth user input 1010, corresponding to selection of one or more of the selection indicators 1004 of the plurality of representations 1002, may be received. In the illustrated example, the seventeenth user input 1010 correspond to selection of a second selection indicator 1004b of the selection indicators 1004. The monitor device 20 is adapted to detect the seventeenth user input 1010, and in response to detection of the seventeenth user input 1010, the monitor device 20 activates the selection indicators corresponding to the selected one or more selection indicators. Hence, in the illustrated example, as illustrated in FIG. 26D, the second selection indicator 1004b is activated. Had the seventeenth user input 1010 corresponded to selection of an already selected selection indicator, e.g. the selection indicator 1004a, the monitor device 20 had deactivated the selection indicator 1004a.

As illustrated, the export menu 1006 comprises an export summary 1006 indicating the number of files and their type, which are about to be exported.

As illustrated the user may select type of export, e.g. DICOM or Basic (e.g. jpg, png, tiff etc.), and may input patient details, such as Patient ID, First Name, Last Name, Date of Birth, etc. In some examples, export via DICOM may be only available for users being authenticated.

As illustrated in FIG. 26D, after having selected the files for export, the user may provide an eighteenth user input 1010 corresponding to selection of the export confirm icon 1008. The monitor device is adapted to detect the eighteenth user input 1010, and in response to detection of the eighteenth user input 1010, the monitor device transmits to an auxiliary device, e.g. a USB drive or a server via a local or wide area network, stored image files corresponding to the selected one or more selection indicators 1004a, 1004b.

As seen, e.g. in FIG. 24F, following the eighth user input 810 corresponding to selection of the session overview icon 807 of FIG. 24E, and in FIG. 25H following the thirteenth user input 908 corresponding to selection of the first stored procedure session 907 of FIG. 25G, other graphical user interfaces may comprise the export icon 932. Providing an input corresponding to selection of the export icon 932 in these situations would result in the graphical user interface as exemplified with FIG. 26B and the associated description, with the modification that none of the selection indicators would be activated, i.e. none of the stored image files are pre-selected for export.

FIGS. 27A-27E schematically illustrate exemplary user interactions with a graphical user interface of a monitor device 20, such as the monitor device 20 of any of the previous figures. The monitor device 20 may have a visualization device connected, or it may not have a visualization device connected. The exemplary graphical user interface of FIG. 27A may follow, e.g., after the exemplary graphical user interfaces of FIGS. 25I, 25J or FIG. 24D. In the illustrated example, the monitor device 20 displays an enlarged representation 1101 of a stored image file. The enlarged representation 1101 may correspond to the enlarged representation 920 of the select stored image file of FIG. 25I, the enlarged representation 928 of the second select stored image file of FIG. 25J, or the enlarged representation 808 of the primary stored image file of FIG. 24D.

A nineteenth user input 948, corresponding to selection of the deletion icon 946, may be received. The monitor device 20 is adapted to detect the nineteenth user input 948, and in response to detection of the nineteenth user input 948, as illustrated in FIG. 27B, the monitor device 20 displays a confirmation dialogue 950 indicative of potential deletion of the stored image file (corresponding to the enlarged representation 1101 displayed when the nineteenth user input 948 was detected).

The user provides a twentieth user input 952 to the conformation dialogue 950. The monitor device is adapted to detect the twentieth user input 952 and determine whether the twentieth user input 952 is indicative of the user confirming deletion of the stored image file or of the user cancelling deletion of the select stored image file.

Figure 27A:
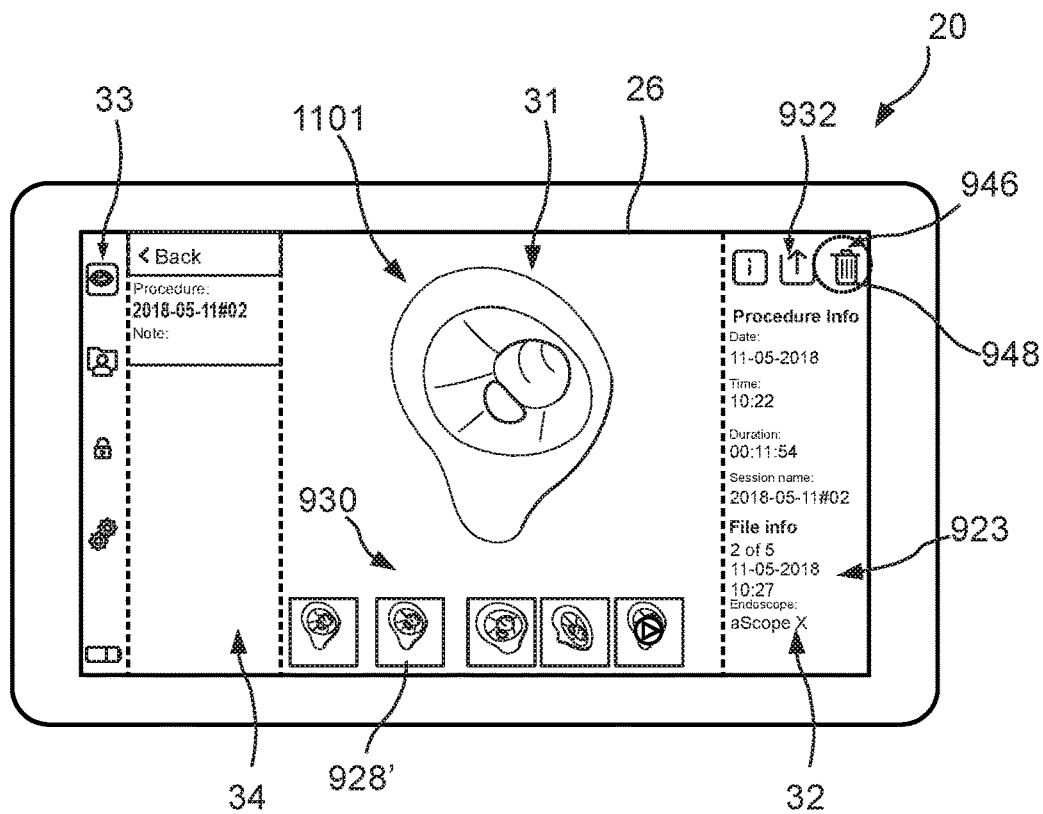
Figure 27B:
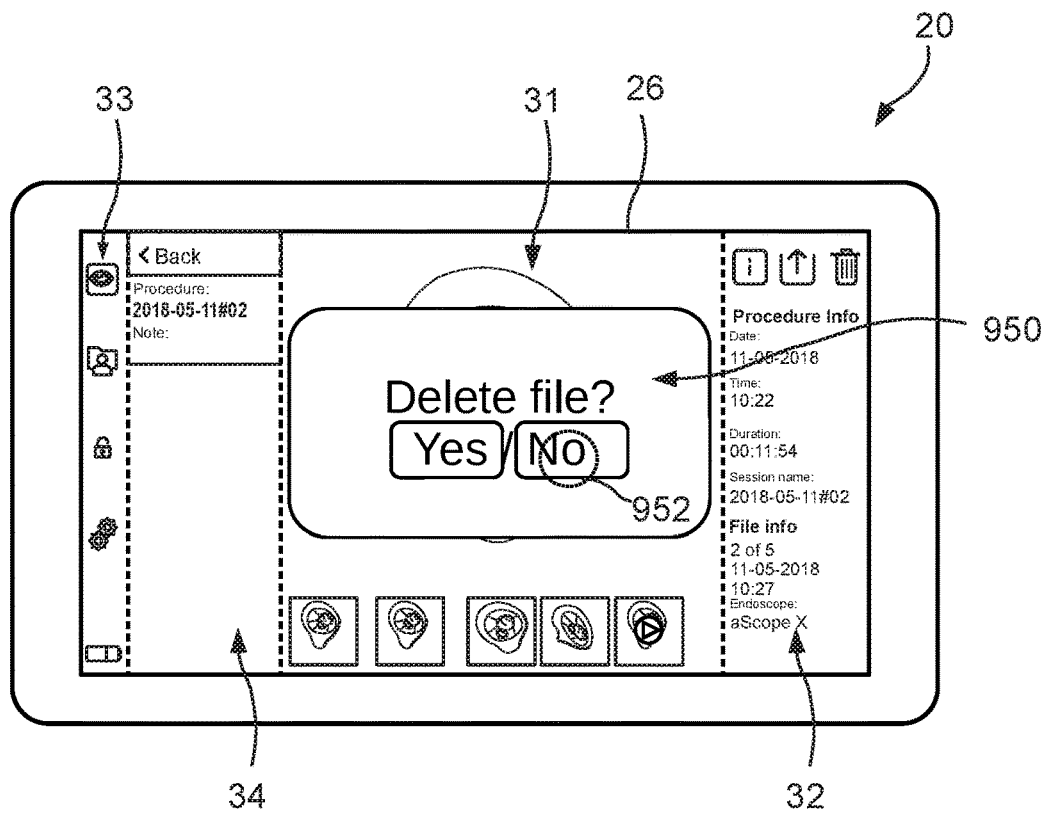
Figure 27C:
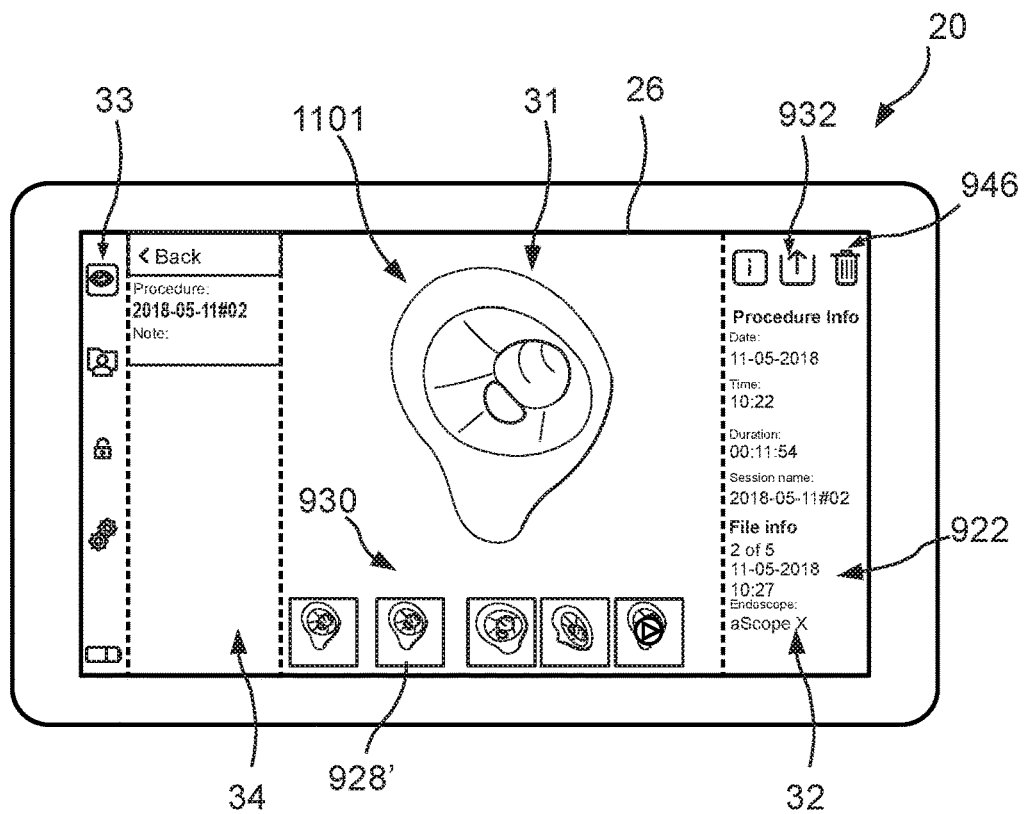

In one example, as illustrated in FIG. 27B, the twentieth user input 952 is indicative of the user cancelling deletion of the select stored image file. The monitor device accordingly foregoes deletion of the select stored image file and maintains display of the enlarged representation 1101 of the stored image file within the first portion 31 of the graphical user interface, as illustrated in FIG. 27C.

Figure 27D:
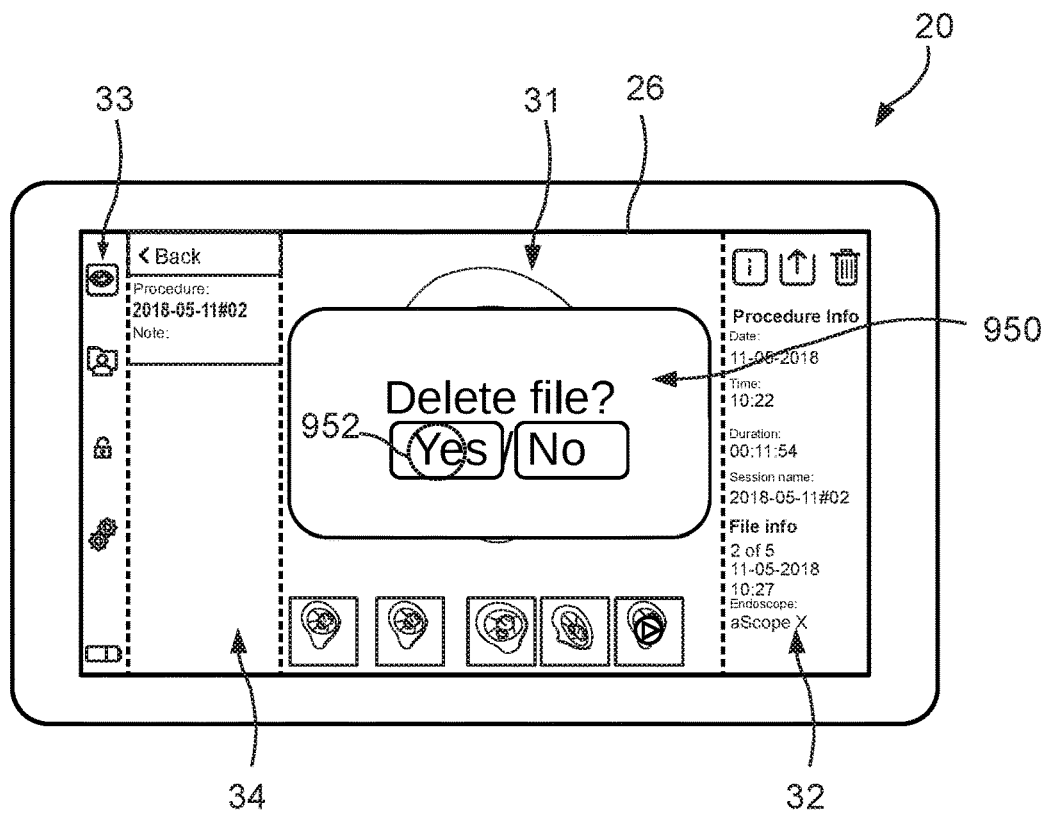
Figure 27E:
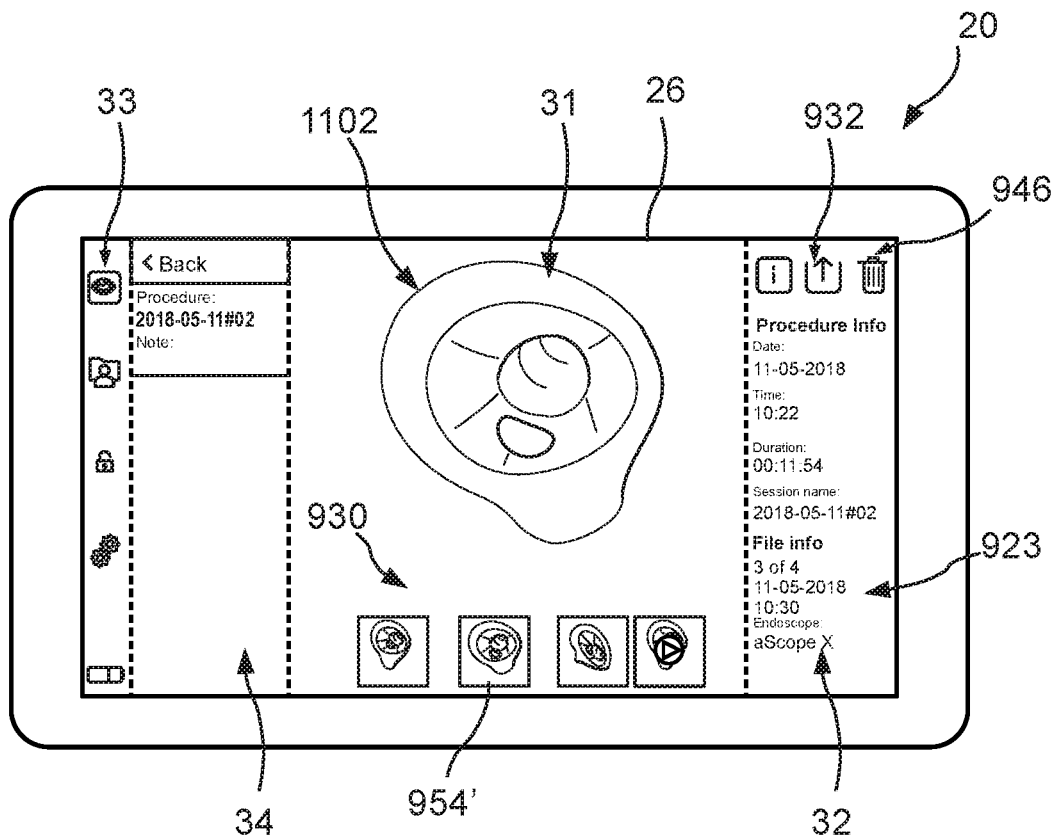

In another example, as illustrated in FIG. 27D, the twentieth user input 952 is indicative of the user confirming deletion of the stored image file. The monitor device accordingly deletes the stored image file, and replaces the display of the enlarged representation 1101 of the stored image file with an enlarged representation 1102 of a second stored image file, as illustrated in FIG. 27E.

As seen, e.g. in FIG. 24F, following the eighth user input 810 corresponding to selection of the session overview icon 807 of FIG. 24E, and in FIG. 25H following the thirteenth user input 908 corresponding to selection of the first stored procedure session 907 of FIG. 25G, graphical user interfaces comprising the selection interface, as explained with respect to FIGS. 26B-26D, may comprise the deletion icon 946. Multiple image files may be selected for deletion in accordance with the selection as explained with respect to FIGS. 26B-26D, and a subsequent user input to the deletion icon 946 will displays a confirmation dialogue similar to the confirmation dialogue 950, indicative of potential deletion of the selected stored image files. A confirmation or cancellation similar to the description with respect to FIGS. 27B and 27D will cause either deletion or cancellation of deletion of the selected stored image files.

Additional exemplary embodiments of the foregoing aspect of the present disclosure are set out in the following items:

1. A medical visualization system comprising a visualization device having an image sensor configured to generate image data indicative of a view from the visualization device, the medical visualization system further comprising a monitor device operable to receive the image data as the image data is being generated by the image sensor, the monitor device comprising a first housing extending in a first direction from a first housing side to a second housing side and in a second direction perpendicular to the first direction from a third housing side to a fourth housing side, the monitor device comprising a touch sensitive display accommodated in the first housing and having a first length in the first direction and a second length in the second direction, the monitor device displays with the touch sensitive display a graphical user interface, wherein the monitor device:
  opens a procedure session;
  displays a live representation of the image data within a first portion of the graphical user interface;
  displays one or more actionable items within a second portion of the graphical user interface, wherein the one or more actionable items comprise an image capture button, the second portion and the first portion being non-overlapping; and
  displays a folder icon within a background portion of the graphical user interface, the background portion and the first portion being non-overlapping,
and wherein the monitor device is further adapted to detect a first user input corresponding to selection of the image capture button, and in response to detection of the first user input, the monitor device:
  stores a first image file corresponding to the image data received when the first user input was detected;
  associates the first image file with the procedure session; and
  displays within the background portion of the graphical user interface a first representation of a still image corresponding to the stored first image file;
after a predetermined delay after detection of the first user input, the monitor device displays an animation of transitioning the first representation to the folder icon.

2. Medical visualization system according to item 1, wherein the monitor device is adapted to establish connection to the visualization device including obtaining device identifier information from a device identifier of the visualization device, and wherein the monitor device opens the procedure session in response to establishing the connection to the visualization device, and the procedure session corresponds to the device identifier information.

3. Medical visualization system according to item 2, wherein the monitor device in opening the procedure session determines, based on the device identifier information, whether the visualization device has been previously connected to the monitor device; and wherein
in accordance with determining that the visualization device has previously been connected to the monitor device, the monitor device reopens the procedure session corresponding to the device identifier information; and
in accordance with determining that the visualization device has not previously been connected to the monitor device, the monitor device creates the procedure session corresponding to the device identifier information.

4. Medical visualization system according to any of the preceding items, wherein the predetermined delay is between 1-5 seconds, such as between 1.5-3 seconds, such as 1.5 seconds or 2 seconds.

5. Medical visualization system according to any of the preceding items, wherein the animation of transitioning the first representation to the folder icon has a duration between 100-1500 ms, such as between 300-1000 ms, such as between 300-600 ms, such as 400 ms or 500 ms.

6. Medical visualization system according to any of the preceding items, wherein the folder icon comprises a visual representation of a count of stored files stored during the procedure session, and wherein the monitor device in response to detection of the first user input, updates display of the visual representation of the count of stored files stored during the procedure session including increasing the count of stored files.

7. Medical visualization system according to any of the preceding items, wherein the monitor device, after detection of the first user input, is further adapted to detect a second user input corresponding to selection of the image capture button, and in response to detection of the second user input the monitor device:
stores a second image file corresponding to the image data received when the second user input was detected;
associates the second image file with the procedure session; and
displays within the background portion of the graphical user interface a second representation of a still image corresponding to the stored second image file;
after the predetermined delay after detection of the second user input, the monitor device displays an animation of transitioning the second representation to the folder icon.

8. Medical visualization system according to any of the preceding items, wherein the monitor device is adapted to establish connection to a second visualization device including obtaining second device identifier information from a second device identifier of the second visualization device, in response to establishing the connection to the second visualization device, the monitor device opens a second procedure session corresponding to the second device identifier information.

9. Medical visualization system according to item 8, wherein the monitor device:
displays a live representation of second image data generated by a second image sensor of the second visualization device;
displays a second folder icon within the background portion of the graphical user interface;
and wherein the monitor device is adapted to detect a third user input corresponding to selection of the image capture button, and in response to detection of the third user input, the monitor device:
stores a third image file corresponding to the second image data received when the third user input was detected; and
associates the third image file with the second procedure session.

10. Medical visualization system according to item 9, wherein in response to detection of the third user input, the monitor device displays within the background portion of the graphical user interface a third representation of a still image corresponding to the stored third image file, after the predetermined delay after detection of the third user input, the monitor device displays an animation of transitioning the third representation to the second folder icon.

11. Medical visualization system according to any of the preceding items, wherein the one or more actionable items comprises a video capture button displayed in a first appearance, and wherein the monitor device is adapted to detect a fourth user input corresponding to selection of the video capture button, and in response to detection of the fourth user input, the monitor device changes the appearance of the video capture button to a second appearance,
after detection of the fourth user input, the monitor device is adapted to detect a fifth user input corresponding to selection of the video capture button, and in response to detection of the fifth user input, the monitor device:

changes the appearance of the video capture button to the first appearance;

stores a first video data file corresponding to the image data received between detection of the fourth user input and the fifth user input;

associates the first video data file with the procedure session; and displays within the background portion of the graphical user interface a fourth representation corresponding to a frame of the stored first video data file, after the predetermined delay after detection of the fifth user input, the monitor device displays an animation transitioning the fourth representation to the folder icon.

12. Medical visualization system according to any of the preceding items wherein the monitor device is adapted to detect a sixth user input corresponding to selection of the folder icon, and in response to detection of the sixth user input, the monitor device displays, within the background portion of the graphical user interface, a first plurality of representations corresponding to a first plurality of stored image files stored during the procedure session.

13. Medical visualization system according to item 12 wherein the monitor device is further adapted to detect a seventh user input corresponding to selection of a primary representation of the first plurality of representations displayed in response to detection of the sixth user input, the primary representation corresponding to a primary stored image file, and in response to detection of the seventh user input the monitor device:

displays an enlarged representation of the primary stored image file within the first portion of the graphical user interface; and displays thumbnail representations of a second plurality of the stored image files stored during the procedure session.

14. Medical visualization system according to any of items 12-13, wherein in response to detection of the sixth user input, the monitor device displays a session overview icon within the background portion of the graphical user interface, the monitor device being adapted to detect an eighth user input corresponding to selection of the session overview icon, and in response to detection of the eighth user input the monitor device:

displays in the first portion of the graphical user interface a third plurality of representations corresponding to a third plurality of stored image files stored during the procedure session;

displays general information of the procedure session; and displays a note field.

15. Medical visualization system according to item 14 wherein the monitor device is further adapted to detect a ninth user input corresponding to selection of the note field, and in response to detection of the ninth user input the monitor device displays a virtual keyboard in the first portion of the graphical user interface and optionally extending into the second portion of the graphical user interface, the virtual keyboard being configured for entering text in the note field, the monitor device being further adapted to:

detect a sequence of keyboard user inputs corresponding to typing of a text using the displayed virtual keyboard; and detect a tenth user input indicative of accept of the text typed using the displayed virtual keyboard, in response to detection of the tenth user input, the monitor device stores and associates the typed text as a note for the procedure session.

16. Medical visualization system according to any of the preceding items wherein in response to disconnection of the visualization device from the monitor device, the monitor device displays, within the background portion of the graphical user interface, a first plurality of representations corresponding to a first plurality of stored image files stored during the procedure session.

17. Medical visualization system according to item 16 wherein in response to disconnection of the visualization device from the monitor device, the monitor device further displays a session overview icon within the background portion of the graphical user interface.

18. Medical visualization system according to any of the preceding items wherein the monitor device displays one or more actionable menu items within a third portion of the graphical user interface, wherein the one or more actionable menu items comprises an archive menu item, the third portion and the first portion being non-overlapping, the monitor device being adapted to detect an eleventh user input corresponding to selection of the archive menu item, and in response to detection of the eleventh user input, the monitor device displays a primary archive menu associated with the archive menu item within a fourth portion of the graphical user interface, wherein the primary archive menu comprises one or more primary actionable archive items including a first primary actionable archive item, the fourth portion and the first portion being non-overlapping, while displaying the primary archive menu, the monitor device is adapted to detect a twelfth user input corresponding to selection of the first primary actionable archive item, and in response to detection of the twelfth user input, the monitor device displays in the first portion of the graphical user interface a secondary archive menu associated with the first primary actionable archive item, in accordance with the monitor device operating in an authorised state, the secondary archive menu comprises a list of stored procedure sessions, in accordance with the monitor device operating in a non-authorised state and a setting to require authorisation is activated, the secondary archive menu comprises an empty list or a list of a subset of the stored procedure sessions, in accordance with the monitor device operating in a non-authorised state and a setting to require authorisation is deactivated, the secondary archive menu comprises the list of stored procedure sessions.

19. Medical visualization system according to item 18 wherein while displaying the secondary archive menu comprising the list of stored procedure sessions or the list of a subset of the stored procedure sessions, the monitor device is adapted to detect a thirteenth user input corresponding to selection of a first stored procedure session of the list of stored procedure sessions or the list of a subset of the stored procedure sessions, and in response to detection of the thirteenth user input the monitor device:

displays in the first portion of the graphical user interface a fourth plurality of representations corresponding to a fourth plurality of stored image files stored during the first stored procedure session;

displays general information of the first stored procedure session; and displays a note field.

20. Medical visualization system according to item 19, wherein the monitor device is further adapted to detect a fourteenth user input, corresponding to selection of a select representation of the fourth plurality of representations, wherein the select representation corresponds to a select stored image file, and in response to detection of the fourteenth user input the monitor device:

displays an enlarged representation of the select stored image file within the first portion of the graphical user interface; and displays thumbnail representations of a fifth plurality of the stored image files stored during the first stored procedure session.

21. Medical visualization system according to item 20, wherein the thumbnail representations comprises a thumbnail representation of the select stored image file.

22. Medical visualization system according to any of items 20-21, wherein in response to detection of the fourteenth user input, the monitor device further displays, within the second portion of the graphical user interface, image information associated with the select stored image file.

23. Medical visualization system according to item 22, wherein the image information associated with the select stored image file comprise information indicative of the visualization device.

24. Medical visualization system according any of items 20-23, wherein the monitor device is further adapted to detect a fifteenth user input, corresponding to selection of a select thumbnail of the displayed thumbnail representations, wherein the select thumbnail corresponds to a second select stored image file, and in response to detection of the fifteenth user input the monitor device:

displays an enlarged representation of the second select stored image file within the first portion of the graphical user interface; and displays thumbnail representations of a sixth plurality of the stored image files stored during the first stored procedure session.

25. Medical visualization system according any of items 20-24, wherein in response to detection of the fourteenth user input, the monitor device further displays an export icon, and wherein the monitor device is further adapted to detect a sixteenth user input, corresponding to selection of the export icon, and in response to detection of the sixteenth user input the monitor device:

displays in the first portion of the graphical user interface the fourth plurality of representations corresponding to the fourth plurality of stored image files, wherein each of the fourth plurality of representations comprises a selection indicator, wherein the selection indicator of the select representation is activated; and displays an export menu comprising an export confirm icon;

26. Medical visualization system according to item 25, wherein the monitor device is further adapted to, after detection of the sixteenth user input, detect a seventeenth user input, corresponding to selection of one or more of the selection indicators of the fourth plurality of representations, and in response to detection of the seventeenth user input, the monitor device activates the selection indicators of the fourth plurality of representations corresponding to the selected one or more selection indicators.

27. Medical visualization system according to any of items 25-26, wherein the monitor device is further adapted to, after detection of the sixteenth user input, detect an eighteenth user input, corresponding to selection of the export confirm icon, and in response to detection of the eighteenth user input, the monitor device transmits to an auxiliary device stored image files corresponding to the selected one or more selection indicators.

28. Medical visualization system according any of items 20-27, wherein in response to detection of the fourteenth user input, the monitor device further displays a deletion icon, and wherein the monitor device is further adapted to detect a nineteenth user input, corresponding to selection of the deletion icon, and in response to detection of the nineteenth user input, the monitor device displays a confirmation dialogue indicative of potential deletion of the select stored image file, the monitor device being adapted to detect a twentieth user input to the confirmation dialogue, and in accordance with the twentieth user input being indicative of the user confirming deletion of the select stored image file the monitor device:

deletes the select stored image file; and replaces the display of the enlarged representation of the select stored image file with an enlarged representation of a second select stored image file, in accordance with the twentieth user input being indicative of the user cancelling deletion of the select stored image file the monitor device:

foregoes deletion of the select stored image file; and maintains display of the enlarged representation of the select stored image file within the first portion of the graphical user interface.

The invention has been described with reference to preferred embodiments. However, the scope of the invention is not limited to the illustrated embodiments, and alterations and modifications can be carried out without deviating from the scope of the invention. The additional exemplary embodiments of an aspect of the present disclosure set out in the form of various items above can be combined in a monitor device, system, or method, with items described with reference to other of the aspects described above.

Throughout the description, the use of the terms "first", "second", "third", "fourth", "primary", "secondary", "tertiary" etc. does not imply any particular order of importance, but are included to identify individual elements. Furthermore, the labelling of a first element does not imply the presence of a second element and vice versa.

LIST OF REFERENCES 2 medical visualization system
4 visualization device
6 handle
7 control button
8 elongated flexible member
9 distal part
10 distal end of elongated flexible member
12 image sensor
14 device cable
16 device connector
20 monitor device
21 first housing side 22 second housing side
23 third housing side
24 fourth housing side
25 first housing
26 touch sensitive display
27 graphical user interface
31 first portion
32 second portion
33 third portion
34 fourth portion
36 actionable item(s)
37 first image direction
38 second image direction
40 connection port(s)
42 actionable menu item(s)
44 invert view button
46 inverted view mode indicator
50 battery indicator
60 processing unit
61 power supply
61a battery
61b power connection
62 memory
64 orientation sensor
66 input/output
68 microphone
70 live representation of image data
x1 first direction
x2 second direction
L1 first length
L2 second length

We claim:

1. A medical visualisation system comprising:
a visualisation device having a distal end and an image sensor configured to generate image data indicative of a view from the distal end, the visualisation device comprising a handle and an elongated flexible member extending from the handle, the handle including a control button adapted to receive an input in a first input direction and adapted to cause a distal portion of the elongated flexible member to bend in a first bending direction responsive to receipt of the input; and
a monitor device operable to receive the image data as the image data is being generated by the image sensor, the monitor device including:
  a first housing extending in a first direction from a first housing side to a second housing side and in a second direction perpendicular to the first direction from a third housing side to a fourth housing side;
  a touch sensitive display accommodated in the first housing and having a first length in the first direction and a second length in the second direction; and
  a graphical user interface comprising a plurality of non-overlapping portions including a first portion and a second portion,
wherein the monitor device displays the graphical user interface with the touch sensitive display,
wherein the monitor device displays with the touch sensitive display one or more actionable items within the second portion of the graphical user interface and displays a live representation of the image data within the first portion of the graphical user interface,
wherein the first bending direction corresponds to a first image direction of the live representation, and wherein the first image direction is parallel to the first direction,
wherein the monitor device has a first interface orientation mode and a second interface orientation mode, wherein in the first interface orientation mode, the second portion is arranged between the fourth housing side and the first portion and the first image direction and the first direction are the same, and wherein in the second interface orientation mode, the second portion is arranged between the third housing side and the first portion and the first image direction and the first direction are opposite,
wherein the monitor device comprises a default view mode and an inverted view mode,
wherein in the default view mode, in the first interface orientation mode the first image direction and the first direction are the same and in the second interface orientation mode the first image direction and the first direction are opposite, and
wherein in the inverted view mode, in the first interface orientation mode the first image direction and the first direction are opposite and in the second interface orientation mode the first image direction and the first direction are the same.

2. The medical visualisation system of claim 1, wherein the monitor device comprises an orientation sensor, wherein the monitor device operates in the first interface orientation mode when a signal of the orientation sensor is indicative of the first housing being oriented in a first orientation, and wherein the monitor device operates in the second interface orientation mode when the signal of the orientation sensor is not indicative of the first housing being in the first orientation.

3. The medical visualisation system of claim 2, wherein the first direction is upwards.

4. The medical visualisation system of claim 1, wherein the monitor device displays with the touch sensitive display an invert interface button, and wherein the monitor device changes between operating in the first interface orientation mode and operating in the second interface orientation mode in response to activation of the invert interface button.

5. The medical visualisation system of claim 1, wherein the visualisation device comprises a connector, and wherein the monitor device comprises one or more connection ports provided on the third housing side and configured to receive the connector of the visualisation device.

6. The medical visualisation system of claim 1, wherein the one or more actionable items comprise an image capture button, and wherein the monitor device stores an image data file corresponding to the image data received when the image capture button is activated.

7. The medical visualisation system of claim 1, wherein the one or more actionable items comprises a video capture button, and wherein the monitor device stores a video sequence of image data corresponding to the image data received responsive to activation of the video capture button.

8. The medical visualisation system of claim 1, wherein the plurality of non-overlapping portions includes a third portion arranged between the third housing side and the first portion in the first interface orientation mode and between the fourth housing side and the first portion in the second interface orientation mode, and wherein the monitor device displays with the touch sensitive display one or more actionable menu items within the third portion.

9. The medical visualisation system of claim 8, wherein the plurality of non-overlapping portions includes a fourth portion, and wherein the fourth portion is arranged between the third portion and the first portion.

10. The medical visualisation system of claim 9, wherein each of the plurality of non-overlapping portions extends substantially throughout the first length in the first direction.

11. The medical visualisation system of claim 1, wherein each of the plurality of non-overlapping portions extends substantially throughout the first length in the first direction.

12. The medical visualisation system of claim 1, wherein the monitor device displays with the touch sensitive display an invert view button, and wherein the monitor device changes between the default view mode and the inverted view mode in response to activation of the invert view button.

13. The medical visualisation system of claim 12, wherein the monitor device comprises a settings menu comprising an option for enabling the inverted view mode, and wherein in accordance with the inverted view mode being enabled, the monitor device displays with the touch sensitive display the invert view button, and in accordance with the inverted view mode not being enabled, the monitor device does not display the invert view button.

14. The medical visualisation system of claim 12, wherein in the default view mode the invert view button is displayed in a first orientation and in the inverted view mode the invert view button is displayed in a second orientation, and wherein the second orientation of the invert view button is rotated compared to the first orientation of the invert view button.

15. The medical visualisation system of claim 14, wherein the invert view button is rotated 180 degrees.

16. The medical visualisation system of claim 1, wherein in the inverted view mode the monitor device displays with the touch sensitive display an inverted view mode indicator in the first portion overlaying a portion of the live representation.

17. The medical visualisation system of claim 1, wherein the one or more actionable items comprise an image capture button, wherein the monitor device stores an image data file corresponding to the image data received when the image capture button is activated, and wherein in the inverted view mode the monitor device stores with the image data file information indicative of the monitor device operating in the inverted view mode when the image capture button was activated.

18. The medical visualisation system of claim 1, wherein the one or more actionable items comprises a video capture button, wherein the monitor device stores a video sequence of image data corresponding to the image data received responsive to activation of the video capture button, and wherein in the inverted view mode the monitor device stores with the video sequence of image data being stored information indicative of the monitor device operating in the inverted view mode when the video capture button was activated.

* * * * *